US 8,703,761 B2

(12) United States Patent
Forster et al.

(10) Patent No.: US 8,703,761 B2
(45) Date of Patent: Apr. 22, 2014

(54) ORGANIC COMPOUNDS

(75) Inventors: Cornelia Jutta Forster, Pelham, NH (US); Young-Shin Kwak, Lexington, MA (US); Katsumasa Nakajima, Winchester, MA (US); Bing Wang, Waltham, MA (US)

(73) Assignee: Novartis AG, Basel (CH)

( * ) Notice: Subject to any disclaimer, the term of this patent is extended or adjusted under 35 U.S.C. 154(b) by 436 days.

(21) Appl. No.: 12/502,669

(22) Filed: Jul. 14, 2009

(65) Prior Publication Data

US 2010/0022513 A1    Jan. 28, 2010

Related U.S. Application Data

(60) Provisional application No. 61/080,913, filed on Jul. 15, 2008.

(51) Int. Cl.
| C07D 249/14 | (2006.01) |
| C07D 401/02 | (2006.01) |
| C07D 405/12 | (2006.01) |
| C07D 413/12 | (2006.01) |
| C07D 403/12 | (2006.01) |

(52) U.S. Cl.
CPC ............ *C07D 249/15* (2013.01); *C07D 401/02* (2013.01); *C07D 405/12* (2013.01); *C07D 413/12* (2013.01); *C07D 403/12* (2013.01)
USPC .................. 514/211.15; 514/255.05; 514/256; 514/383; 548/265.4; 548/236; 546/272.4; 544/333; 544/405; 540/544

(58) Field of Classification Search
None
See application file for complete search history.

(56) References Cited

U.S. PATENT DOCUMENTS

| 2004/0019091 A1 | 1/2004 | Bignon et al. |
| 2006/0069082 A1 | 3/2006 | Priepke et al. |
| 2007/0123504 A1 | 5/2007 | Bolin et al. |

FOREIGN PATENT DOCUMENTS

| CA | 1062260 A | * | 9/1979 |
| CA | 01160234 | | 1/1984 |
| EP | 1845081 A1 | | 10/2007 |
| JP | 2004-067635 | | 3/2004 |
| JP | 2005-206492 | | 8/2005 |
| JP | 2005/206492 A | | 8/2005 |
| JP | 2006-089485 | | 4/2006 |
| JP | 2008-133218 | | 6/2008 |
| WO | 96/39384 | | 12/1996 |
| WO | 98/04277 | | 2/1998 |
| WO | 98/51686 | | 11/1998 |
| WO | 98/51686 A1 | | 11/1998 |
| WO | 00/24392 | | 5/2000 |
| WO | 00/44731 | | 8/2000 |
| WO | 01/74783 | | 10/2001 |
| WO | 03/010141 | | 2/2003 |
| WO | 2004/033434 | | 4/2004 |
| WO | 2004/033439 A1 | | 4/2004 |
| WO | WO 2004089470 A2 | * | 10/2004 |
| WO | 2005/103050 | | 11/2005 |
| WO | 2006/033434 | | 3/2006 |
| WO | 2006/034822 | | 4/2006 |
| WO | 2006/042954 | | 4/2006 |
| WO | 2006/046778 | | 5/2006 |
| WO | 2006/082952 | | 8/2006 |
| WO | 2006/120125 A1 | | 11/2006 |
| WO | 2006/127550 | | 11/2006 |
| WO | 2007/026959 A2 | | 3/2007 |
| WO | 2007/118852 | | 10/2007 |
| WO | 2008/011131 A2 | | 1/2008 |
| WO | 2008/056150 | | 5/2008 |
| WO | 2009/105509 | | 8/2009 |

OTHER PUBLICATIONS

Sharma S. K., et al: "Development of peptidomimetics targeting IAPs" International Journal of Peptide Research and Therapeutics, vol. 12, No. 1, Jan. 1, 2006, pp. 21-32. XP002402669, Springer-Verlag, Dordrecht , NL. ISSN: 1573-3149; compound 31.
Database Registry [Online] Chemical Abstracts Service, Columbus, Ohio, US; XP002551366, retrieved from STN Database accession No. 669724-17-8 (RN) abstract, Apr. 1, 2004.
Database Registry [Online] Chemical Abstracts Service, Columbus, Ohio, US; XP002551367, retrieved from STN Database accession No. 406470-01-7 (RN) abstract, Apr. 22, 2002.
Database Registry [Online] Chemical Abstracts Service, Columbus, Ohio, US; XP002551368, retrieved from STN Database accession No. 402769-98-6 (RN) abstract, Mar. 25, 2002.
Database Registry [Online] Chenical Abstracts Service, Columbus, Ohio, US; XP002551369, retrieved from STN Database accession No. 352565-18-5 (RN) abstract, Aug. 24, 2001.
Database Registry [Online] Chemical Abstracts Service, Columbus, Ohio, US; XP002551370, retrieved from STN Database accession No. 329904-51-0 (RN)abstract, Apr. 4, 2001.
Kitagawa et al., Chem. Pharm. Bull., 49:335-339 (2001).
K. Ekambareswara et al., Chemical Research in Toxicology, 4(2):241-252 (1991).

* cited by examiner

*Primary Examiner* — Michael Barker
(74) *Attorney, Agent, or Firm* — Joshua Roth

(57) ABSTRACT

The invention relates to compounds of formula (I):

$$R^3\diagdown_{(Z)_r}\diagup^{(M)_s}\diagdown\underset{R^4}{N}\diagdown\underset{\underset{O}{\|}}{C}\diagup\underset{R^1\ R^2}{\overset{R^5}{\underset{|}{N}}}\diagdown\underset{A}{\diagup}(R^{10a})_a \atop (R^{10b})_b$$

(I)

where A is an optionally substituted heteroaryl, useful for treating disorders mediated by acyl coA-diacylglycerol acyl transferase 1 (DGAT1), e.g. metabolic disorders. The invention also provides methods of treating such disorders, and compounds and compositions etc. for their treatment.

14 Claims, No Drawings

ORGANIC COMPOUNDS

This application claims benefit under 35 U.S.C. §119(e) of U.S. Provisional Application No. 61/080,913, filed Jul. 15, 2008, the contents of which are incorporated herein by reference in their entirety.

TECHNICAL FIELD

This invention relates to compounds useful for treating disorders mediated by acyl coA-diacylglycerol acyl transferase 1 (DGAT1), e.g. metabolic disorders. The invention also provides methods of treating such disorders, and compounds and compositions etc. for their treatment.

BACKGROUND ART

Although triglycerides (also known as "triacylglycerides") are essential for normal physiology, excess triglyceride accumulation results in obesity and, particularly when it occurs in nonadipose tissues, is associated with insulin resistance. Obesity increases the risk of many common and serious conditions, including coronary heart disease, hypertension, dyslipidemia, atherosclerosis, type-II diabetes, stroke, osteoarthritis, restrictive pulmonary disease, sleep apnoea, certain types of cancers and inflammatory disorders. The standard treatment for obesity is calorific restriction and increase of physical exercise. However, such approaches are rarely successful and pharmaceutical treatments are required to correct these metabolic disorders.

A potential therapy for these conditions therefore involves inhibiting triglyceride synthesis.

Diacylglycerol acyl-transference (DGAT) is an enzyme that catalyzes the last step in triacylglycerol biosynthesis. DGAT catalyzes the coupling of a 1,2-diacylglycerol with a fatty acyl-CoA resulting in Coenzyme A and triacylglycerol. Two enzymes that display DGAT activity have been identified: DGAT1 (acyl coA-diacylglycerol acyl transferase 1) [Cases et al., *Proc. Natl. Acad. Sci.* 1998, 95:13018-13023] and DGAT2 (acyl coA-diacylglycerol acyl transferase 2) [Cases et al., *J. Biol. Chem.* 2001, 276:38870-38876].

DGAT1 and DGAT2 do not share significant protein sequence homology. Importantly, however, DGAT1 knockout mice are protected from high fat diet-induced weight gain and insulin resistance [Smith et al., *Nature Genetics* 2000, 25:87-90]. The phenotype of the DGAT1 knockout mice suggests that DGAT1 inhibitors would be useful for the treatment of obesity and obesity-associated complications [Smith et al., *Nature Genetics* 2000, 25:87-90].

There is therefore a need for compounds which inhibit the activity of DGAT1.

DISCLOSURE OF THE INVENTION

The inventors have found compounds of formula (I) that are useful for inhibiting the activity of DGAT1.

Accordingly, in a first aspect of the invention, there is provided a compound of formula (I):

$$R^3-(Z)_r-(M)_s-N(R^4)-C(R^1)(R^2)-C(O)-N(R^5)-A(R^{10a})_a(R^{10b})_b \quad (I)$$

or a pharmaceutically acceptable derivative thereof, wherein:

$R^3$ is H or optionally substituted $C_{1-10}$alkyl, $C_{1-10}$heteroalkyl, $-(Alk^b)_g-C_{3-10}$cycloalkyl, $-(Alk^b)_g-C_{3-10}$heterocycloalkyl, $C_{2-10}$alkenyl, $C_{2-10}$heteroalkenyl, $-(Alk^b)_g-C_{3-10}$cycloalkenyl, $-(Alk^b)_g-C_{3-10}$heterocycloalkenyl, $C_{2-10}$alkynyl. $C_{2-10}$heteroalkynyl, $-(Alk^b)_g-C_{6-14}$aryl, $-(Alk^b)_g$-heteroaryl (where heteroaryl contains 5-13 ring members), wherein
   $Alk^b$ is optionally substituted $C_{1-6}$alkylene or $C_{1-6}$heteroalkylene,
   g is 0 or 1;

r is 0 or 1;

Z is O or $NR^6$, wherein
   $R^6$ is H or optionally substituted $C_{1-6}$alkyl, $C_{1-6}$heteroalkyl, $C_{3-6}$cycloalkyl, $C_{3-6}$heterocycloalkyl, $C_{2-6}$alkenyl, $C_{2-6}$heteroalkenyl, $C_{3-6}$cycloalkenyl, $C_{3-6}$heterocycloalkenyl, phenyl, or heteroaryl containing 5 or 6 ring members;

s is 0 or 1;

M is —C(O)— or —S(O)$_t$—, wherein
   t is 1 or 2;

$R^4$ is H or optionally substituted $C_{1-6}$alkyl, $C_{1-6}$heteroalkyl, $C_{3-6}$cycloalkyl, $C_{3-6}$heterocycloalkyl, $C_{2-6}$alkenyl, $C_{2-6}$heteroalkenyl, $C_{3-6}$cycloalkenyl, $C_{3-6}$heterocycloalkenyl, phenyl, or heteroaryl containing 5 or 6 ring members;

$R^1$ and $R^2$ are independently H or optionally substituted $C_{1-6}$alkyl, $C_{1-6}$heteroalkyl, $-(Alk^c)_h-C_{3-6}$cycloalkyl, $-(Alk^c)_h-C_{3-6}$heterocycloalkyl, $C_{2-6}$alkenyl, $C_{2-6}$heteroalkenyl, $-(Alk^c)_h-C_{3-6}$cycloalkenyl, $-(Alk^c)_h-C_{3-6}$heterocycloalkenyl, $-(Alk^c)_h$-phenyl, or $-(Alk^c)_h$-heteroaryl (where heteroaryl contains 5 or 6 ring members), where
   $Alk^c$ is independently optionally substituted $C_{1-6}$alkylene or $C_{1-6}$heteroalkylene,
   h is independently 0 or 1;

$R^5$ is H or optionally substituted $C_{1-6}$alkyl, $C_{1-6}$heteroalkyl, $C_{3-6}$cycloalkyl, $C_{3-6}$heterocycloalkyl, $C_{2-6}$alkenyl, $C_{2-6}$heteroalkenyl, $C_{3-6}$cycloalkenyl, $C_{3-6}$heterocycloalkenyl, phenyl, or heteroaryl containing 5 or 6 ring members; or one of:
   $R^1$ and $R^4$ together form optionally substituted $C_{3-5}$alkylene, $C_{3-5}$alkenylene, $C_{3-5}$heteroalkylene, or $C_{3-5}$heteroalkenylene;
   $R^1$ and $R^2$ together form optionally substituted $C_{2-6}$alkylene, $C_{2-6}$-alkenylene, $C_{2-8}$heteroalkylene, or $C_{2-8}$heteroalkenylene; or
   $R^1$ and $R^5$ together form optionally substituted $C_{2-4}$alkylene, $C_{2-4}$alkenylene, $C_{2-4}$heteroalkylene, or $C_{2-4}$heteroalkenylene;

A is optionally substituted heteroaryl containing 5-13 ring members;

a is 0-3;

b is 0-3;

$R^{10a}$ is -Q-$R^{7a}$ and $R^{10b}$ is —$R^{7b}$, wherein

Q is independently optionally substituted $C_{1-6}$-alkylene, $C_{1-6}$heteroalkylene, $C_{2-6}$alkenylene or $C_{2-6}$heteroalkenylene, or O, S, $NR^8$, or —C(O)—, wherein $R^8$ is H or optionally substituted $C_{1-6}$alkyl; and $R^{7a}$ is H or optionally substituted $C_{1-10}$alkyl, $C_{1-10}$heteroalkyl, $C_{3-10}$cycloalkyl, $C_{3-10}$heterocycloalkyl, $C_{6-14}$aryl or heteroaryl containing 5-13 ring members;

$R^{7b}$ is optionally substituted $C_{1-10}$alkyl, $C_{1-10}$heteroalkyl, $C_{3-10}$cycloalkyl, $C_{3-10}$heterocycloalkyl, $C_{6-14}$aryl or heteroaryl containing 5-13 ring members; and provided that at least one of $R^3$ and $R^4$ is not H.

In one embodiment, there is provided a compound of formula (I):

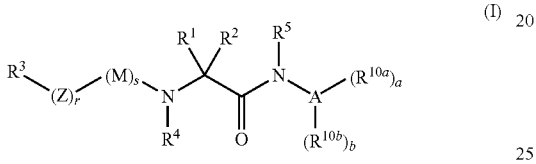

(I)

or a pharmaceutically acceptable derivative thereof, wherein:

$R^3$ is H or optionally substituted $C_{1-10}$alkyl, $C_{1-10}$heteroalkyl, -(Alk$^b$)$_g$-$C_{3-10}$cycloalkyl, -(Alk$^b$)$_g$-$C_{3-10}$heterocycloalkyl, $C_{2-10}$alkenyl, $C_{2-10}$heteroalkenyl, -(Alk$^b$)$_g$-$C_{3-10}$cycloalkenyl, -(Alk$^b$)$_g$-$C_{3-10}$heterocycloalkenyl, $C_{2-10}$alkynyl, $C_{2-10}$heteroalkynyl, -(Alk$^b$)$_g$-$C_{6-14}$aryl, -(Alk$^b$)$_g$-heteroaryl (where heteroaryl contains 5-13 ring members), wherein Alk$^b$ is optionally substituted $C_{1-6}$alkylene or $C_{1-6}$heteroalkylene, g is 0 or 1;

r is 0 or 1;

Z is O or $NR^6$, wherein $R^6$ is H or optionally substituted $C_{1-6}$alkyl, $C_{1-6}$heteroalkyl, $C_{3-6}$cycloalkyl, $C_{3-6}$heterocycloalkyl, $C_{2-6}$alkenyl, $C_{2-6}$heteroalkenyl, $C_{3-6}$cycloalkenyl, $C_{3-6}$heterocycloalkenyl, phenyl, or heteroaryl containing 5 or 6 ring members;

s is 0 or 1;

M is —C(O)— or —S(O)$_t$—, wherein t is 1 or 2;

$R^4$ is H or optionally substituted $C_{1-6}$alkyl, $C_{1-6}$heteroalkyl, $C_{3-6}$cycloalkyl, $C_{3-6}$heterocycloalkyl, $C_{2-6}$alkenyl, $C_{2-6}$heteroalkenyl, $C_{3-6}$cycloalkenyl, $C_{3-6}$heterocycloalkenyl, phenyl, or heteroaryl containing 5 or 6 ring members;

$R^1$ and $R^2$ are independently H or optionally substituted $C_{1-6}$alkyl, $C_{1-6}$heteroalkyl, -(Alk$^c$)$_h$-$C_{3-6}$cycloalkyl, -(Alk$^c$)$_h$-$C_{3-6}$heterocycloalkyl, $C_{2-6}$alkenyl, $C_{2-6}$heteroalkenyl, -(Alk$^c$)$_h$-$C_{3-6}$cycloalkenyl, -(Alk$^c$)$_h$-$C_{3-6}$heterocycloalkenyl, -(Alk$^c$)$_h$-phenyl, or -(Alk$^c$)$_h$-heteroaryl (where heteroaryl contains 5 or 6 ring members), where Alk$^c$ is independently optionally substituted $C_{1-6}$alkylene or $C_{1-6}$heteroalkylene, h is independently 0 or 1;

$R^5$ is H or optionally substituted $C_{1-6}$alkyl, $C_{1-6}$heteroalkyl, $C_{3-6}$cycloalkyl, $C_{3-6}$heterocycloalkyl, $C_{2-6}$alkenyl, $C_{2-6}$heteroalkenyl, $C_{3-6}$cycloalkenyl, $C_{3-6}$heterocycloalkenyl, phenyl, or heteroaryl containing 5 or 6 ring members; or one of:

$R^1$ and $R^4$ together form optionally substituted $C_{3-5}$alkylene, $C_{3-5}$alkenylene, $C_{3-5}$heteroalkylene, or $C_{3-5}$heteroalkenylene;

$R^1$ and $R^2$ together form optionally substituted $C_{2-6}$alkylene, $C_{2-6}$alkenylene, $C_{2-8}$heteroalkylene, or $C_{2-8}$heteroalkenylene; or $R^1$ and $R^5$ together form optionally substituted $C_{2-4}$alkylene, $C_{2-4}$alkenylene, $C_{2-4}$heteroalkylene, or $C_{2-4}$heteroalkenylene;

A is optionally substituted heteroaryl containing 5-13 ring members;

a is 0-3;

b is 0-3;

$R^{10a}$ is -Q-$R^{7a}$ and $R^{10b}$ is —$R^{7b}$, wherein

Q is independently $C_{1-6}$alkylene, $C_{1-6}$heteroalkylene, $C_{2-6}$alkenylene, $C_{2-6}$heteroalkenylene, O, S, $NR^8$, or —C(O)—, wherein $R^8$ is H or optionally substituted $C_{1-6}$alkyl; and $R^{7a}$ is H or optionally substituted $C_{1-10}$alkyl. $C_{1-10}$heteroalkyl, $C_{3-10}$cycloalkyl, $C_{3-10}$heterocycloalkyl, $C_{6-14}$aryl or heteroaryl containing 5-13 ring members;

$R^{7b}$ is optionally substituted $C_{3-10}$cycloalkyl, $C_{3-10}$heterocycloalkyl, $C_{6-14}$aryl or heteroaryl containing 5-13 ring members; and provided that at least one of $R^3$ and $R^4$ is not H.

In a second aspect of the invention, the compound of formula (I) is of formula (II):

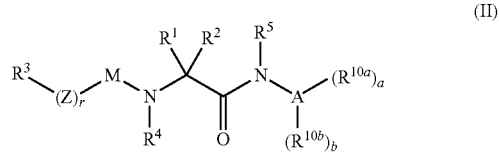

(II)

or a pharmaceutically acceptable derivative thereof. wherein:

$R^3$ is optionally substituted $C_{1-10}$alkyl, $C_{1-10}$heteroalkyl, -(Alk$^b$)$_g$-$C_{3-10}$cycloalkyl, -(Alk$^b$)$_g$-$C_{3-10}$heterocycloalkyl, $C_{2-10}$alkenyl, $C_{2-10}$heteroalkenyl, -(Alk$^b$)$_g$-$C_{3-10}$cycloalkenyl, -(Alk$^b$)$_g$-$C_{3-10}$heterocycloalkenyl, $C_{2-10}$alkynyl, $C_{2-10}$heteroalkynyl, -(Alk$^b$)$_g$-$C_{6-14}$aryl, -(Alk$^b$)$_g$-heteroaryl (where heteroaryl contains 5-13 ring members), wherein Alk$^b$ is optionally substituted $C_{1-6}$alkylene or $C_{1-6}$heteroalkylene, g is 0 or 1;

r is 0 or 1;

Z is O or $NR^6$, wherein $R^6$ is H or optionally substituted $C_{1-6}$alkyl;

M is —C(O)— or —S(O)$_2$—;

$R^4$ is H or optionally substituted $C_{1-6}$alkyl;

$R^1$ and $R^2$ are independently H or optionally substituted $C_{1-6}$alkyl or -(Alk$^c$)$_h$-phenyl, where Alk$^c$ is independently optionally substituted $C_{1-6}$alkylene or $C_{1-6}$heteroalkylene, h is independently 0 or 1;

$R^5$ is H or optionally substituted $C_{1-6}$alkyl; or one of:

$R^1$ and $R^4$ together form optionally substituted $C_{3-5}$alkylene or $C_{3-5}$heteroalkylene;

$R^1$ and $R^2$ together form optionally substituted $C_{2-8}$alkylene or $C_{2-8}$heteroalkylene; or $R^1$ and $R^5$ together form optionally substituted $C_{2-4}$alkylene or $C_{2-4}$heteroalkylene;

A is optionally substituted heteroaryl containing 5, 6, 9 or 10 ring members;

a and b are independently 0-2, provided the sum of a+b=1 or 2; and $R^{10a}$ is -Q-$R^{7a}$ and $R^{10b}$ is —$R^{7b}$, wherein
Q is optionally substituted $C_{1-6}$alkylene or $C_{1-6}$heteroalkylene, O, S, $NR^8$, or —C(O)— wherein
$R^8$ is H or optionally substituted $C_{1-6}$alkyl; and
$R^{7a}$ is H or optionally substituted $C_{1-10}$alkyl, $C_{1-10}$heteroalkyl, $C_{3-10}$cycloalkyl, $C_{3-10}$heterocycloalkyl, phenyl, naphthyl or heteroaryl containing 5, 6, 9 or 10 ring members;
$R^{7b}$ is optionally substituted $C_{1-10}$alkyl, $C_{3-10}$heterocycloalkyl, phenyl, naphthyl or heteroaryl containing 5, 6, 9 or 10 ring members.

In one embodiment, there is provided a compound of formula (II):

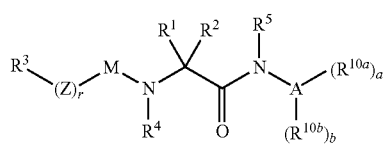

(II)

or a pharmaceutically acceptable derivative thereof,
wherein:
$R^3$ is optionally substituted $C_{1-10}$alkyl, $C_{1-10}$heteroalkyl, -(Alk$^b$)$_g$-$C_{3-10}$cycloalkyl, -(Alk$^b$)$_g$-$C_{3-10}$heterocycloalkyl, $C_{2-10}$alkenyl, $C_{2-10}$heteroalkenyl, -(Alk$^b$)$_g$-$C_{3-10}$cycloalkenyl, -(Alk$^b$)$_g$-$C_{3-10}$heterocycloalkenyl, $C_{2-10}$alkynyl, $C_{2-10}$heteroalkynyl, -(Alk$^b$)$_g$-$C_{6-14}$aryl, -(Alk$^b$)$_g$-heteroaryl (where heteroaryl contains 5-13 ring members), wherein
Alk$^b$ is optionally substituted $C_{1-6}$alkylene or $C_{1-6}$heteroalkylene,
g is 0 or 1;
r is 0 or 1;
Z is O or $NR^6$, wherein
$R^6$ is H or optionally substituted $C_{1-6}$alkyl;
M is —C(O)— or —S(O)$_2$—;
$R^4$ is H or optionally substituted $C_{1-6}$alkyl;
$R^1$ and $R^2$ are independently H or optionally substituted $C_{1-6}$alkyl or -(Alk$^c$)$_h$-phenyl, where
Alk$^c$ is independently optionally substituted $C_{1-6}$alkylene or $C_{1-6}$heteroalkylene,
h is independently 0 or 1;
$R^5$ is H or optionally substituted $C_{1-6}$alkyl; or one of:
$R^1$ and $R^4$ together form optionally substituted $C_{3-5}$alkylene or $C_{3-5}$heteroalkylene;
$R^1$ and $R^2$ together form optionally substituted $C_{2-8}$alkylene or $C_{2-8}$heteroalkylene; or
$R^1$ and $R^5$ together form optionally substituted $C_{2-4}$alkylene or $C_{2-4}$heteroalkylene;

A is optionally substituted heteroaryl containing 5, 6, 9 or 10 ring members;
a and b are independently 0-2, provided the sum of a+b=1 or 2; and
$R^{10a}$ is -Q-$R^{7a}$ and $R^{10b}$ is —$R^{7b}$, wherein
Q is —CH$_2$—, O, S, $NR^8$, or —C(O)— wherein
$R^8$ is H or optionally substituted $C_{1-6}$alkyl; and
$R^{7a}$ is H or optionally substituted $C_{1-10}$alkyl, $C_{1-10}$heteroalkyl, $C_{3-10}$cycloalkyl, $C_{3-10}$heterocycloalkyl, phenyl, naphthyl or heteroaryl containing 5, 6, 9 or 10 ring members;
$R^{7b}$ is optionally substituted $C_{3-10}$heterocycloalkyl, phenyl, naphthyl or heteroaryl containing 5, 6, 9 or 10 ring members.

In a third aspect of the invention, the compound of formula (I) is of formula (III):

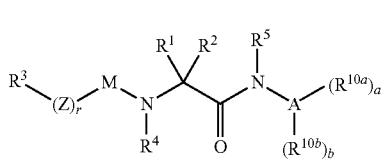

(III)

or a pharmaceutically acceptable derivative thereof,
wherein:
$R^3$ is optionally substituted $C_{1-10}$alkyl, $C_{1-10}$heteroalkyl, -(Alk$^b$)$_g$-$C_{3-10}$cycloalkyl, -(Alk$^b$)$_g$-$C_{3-10}$heterocycloalkyl. -(Alk$^b$)$_g$-$C_{6-14}$aryl, -(Alk$^b$)$_g$-heteroaryl (where heteroaryl contains 5, 6, 9 or 10 ring members), wherein
Alk$^b$ is optionally substituted $C_{1-6}$alkylene,
g is 0 or 1;
r is 0 or 1;
Z is O or $NR^6$, wherein
$R^6$ is H or optionally substituted $C_{1-6}$alkyl;
M is —C(O)— or —S(O)$_2$—;
$R^4$ is H or optionally substituted $C_{1-6}$alkyl;
$R^1$ and $R^2$ are independently optionally substituted $C_{1-6}$alkyl, or $R^1$ is optionally substituted $C_{1-6}$alkyl and $R^2$ is optionally substituted -(Alk$^c$)-phenyl, wherein
Alk$^c$ is optionally substituted $C_{1-6}$alkylene.
$R^5$ is H or optionally substituted $C_{1-6}$alkyl; or one of:
$R^1$ and $R^4$ together form optionally substituted $C_{3-6}$alkylene;
$R^1$ and $R^2$ together form optionally substituted $C_{2-8}$alkylene or $C_{2-8}$heteroalkenylene; or
$R^1$ and $R^5$ together form optionally substituted $C_{2-4}$alkylene;
A is optionally substituted heteroaryl containing 5 ring members;
a and b are independently 0-2, provided the sum of a+b=1 or 2; and
$R^{10a}$ is -Q-$R^{7a}$ and $R^{10b}$ is —$R^{7b}$, wherein
Q is —CH$_2$—, O, S, $NR^8$, or —C(O)—, wherein
$R^8$ is H or optionally substituted $C_{1-6}$alkyl; and
$R^{7a}$ is H or optionally substituted $C_{1-10}$alkyl, $C_{1-10}$heteroalkyl, $C_{3-10}$cycloalkyl, $C_{3-10}$heterocycloalkyl or phenyl.
$R^{7b}$ is optionally substituted phenyl.

In a fourth aspect of the invention, the compound of formula (I) is of formula (IV):

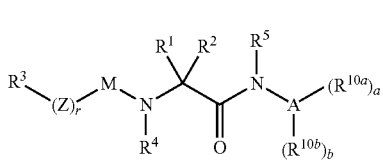

(IV)

or a pharmaceutically acceptable derivative thereof, wherein:
R³ is optionally substituted $C_{1-10}$alkyl, $C_{1-10}$heteroalkyl, -$(Alk^b)_g$-$C_{3-10}$cycloalkyl, -$(Alk^b)_g$-$C_{3-10}$heterocycloalkyl, -$(Alk^b)_g$-$C_{6-14}$aryl, -$(Alk^b)_g$-heteroaryl (where heteroaryl contains 5, 6, 9 or 10 ring members), wherein $Alk^b$ is optionally substituted $C_{1-6}$alkylene,
g is 0 or 1;
r is 0 or 1;
Z is O or $NR^6$, wherein
  $R^6$ is H or optionally substituted $C_{1-6}$alkyl;
M is —C(O)— or —S(O)$_2$—;
$R^4$ is H or optionally substituted $C_{1-6}$alkyl;
$R^1$ and $R^2$ are independently optionally substituted $C_{1-6}$alkyl, or $R^1$ is optionally substituted $C_{1-6}$alkyl and $R^2$ is optionally substituted -$(Alk^c)$-phenyl, wherein $Alk^c$ is optionally substituted $C_{1-6}$alkylene.
$R^5$ is H or optionally substituted $C_{1-6}$alkyl; or one of:
  $R^1$ and $R^4$ together form optionally substituted $C_{3-5}$alkylene;
  $R^1$ and $R^2$ together form optionally substituted $C_{2-8}$alkylene or $C_{2-8}$heteroalkenylene, or
  $R^1$ and $R^5$ together form optionally substituted $C_{2-4}$alkylene;
A is optionally substituted heteroaryl containing 6 ring members;
a and b are independently 0-2, provided the sum of a+b=1 or 2; and
$R^{10a}$ is -Q-$R^{7a}$ and $R^{10b}$ is —$R^{7b}$, wherein
  Q is —CH$_2$—, O, S, NR⁸, or —C(O)—, wherein
    $R^8$ is H or optionally substituted $C_{1-6}$alkyl; and
  $R^{7a}$ is H or optionally substituted $C_{1-10}$alkyl, $C_{1-10}$heteroalkyl, $C_{3-10}$cycloalkyl, $C_{3-10}$heterocycloalkyl or phenyl.
  $R^{7b}$ is optionally substituted phenyl.

Embodiments of Compounds of Formulae (I)-(IV)

General
In one embodiment, at least one of r, s, a or b=1.
In one embodiment, at least one of r or s=1. In another embodiment, at least one of a or b=1.
Various embodiments of the invention are described herein. It will be recognised that features specified in each embodiment may be combined with other specified features to provide further embodiments.
Linkers to $R^3$
In one embodiment, s=1. In a further embodiment, s=1 and r=1. In a further embodiment, s=1 and r=0.
In one embodiment, s=0. In a further embodiment, s=0 and r=0.
In one embodiment M is —C(O)—. In another embodiment, M is —S(O)$_t$—, e.g. wherein t=2.
In one embodiment, s=1 and M is —C(O)—, e.g. wherein r=0.
In one embodiment, $R^6$ is H or optionally substituted $C_{1-6}$alkyl. In a further embodiment, $R^6$ is H.
Group $R^3$
In one embodiment, $R^3$ is optionally substituted $C_{1-10}$alkyl, $C_{1-10}$heteroalkyl, -$(Alk^b)_g$-$C_{3-10}$cycloalkyl, -$(Alk^b)_g$-$C_{3-10}$heterocycloalkyl, $C_{2-10}$alkenyl, $C_{2-10}$heteroalkenyl, -$(Alk^b)_g$-$C_{3-10}$cycloalkenyl, -$(Alk^b)_g$-$C_{3-10}$heterocycloalkenyl, $C_{2-10}$alkynyl, $C_{2-10}$heteroalkynyl, -$(Alk^b)_g$-$C_{6-14}$aryl, -$(Alk^b)_g$-heteroaryl (where heteroaryl contains 5-13 ring members).
In one embodiment, heteroaryl contains 5, 6, 9 or 10 ring members.

In one embodiment, $R^3$ is optionally substituted $C_{1-10}$alkyl, $C_{1-10}$heteroalkyl, -$(Alk^b)_g$-$C_{3-10}$cycloalkyl, -$(Alk^b)_g$-$C_{3-10}$heterocycloalkyl, -$(Alk^b)_g$-$C_{6-14}$aryl, -$(Alk^b)_g$-heteroaryl (where heteroaryl contains 5, 6, 9 or 10 ring members).
In one embodiment, $Alk^b$ is optionally substituted $C_{1-6}$alkylene.
In one embodiment, $Alk^b$ is unsubstituted.
Linear $R^1$, $R^2$, $R^4$ & $R^5$
In one embodiment, $R^4$ is H or optionally substituted $C_{1-6}$alkyl. In one embodiment $R^4$ is H.
In one embodiment, $R^1$ and $R^2$ are independently H or optionally substituted $C_{1-6}$alkyl or -$(Alk^c)_h$-phenyl.
In one embodiment, $R^1$ and $R^2$ are independently optionally substituted $C_{1-6}$alkyl, or $R^1$ is optionally substituted $C_{1-6}$alkyl and $R^2$ is optionally substituted -$(Alk^c)_h$-phenyl.
In one embodiment, $Alk^c$ is optionally substituted $C_{1-6}$alkylene (e.g. unsubstituted $C_{1-6}$alkylene) and h=1.
In one embodiment, $R^1$ and $R^2$ are independently optionally substituted $C_{1-6}$alkyl, e.g. $R^1$ and $R^2$ are both methyl.
In one embodiment, $R^5$ is H or optionally substituted $C_{1-6}$alkyl. In one embodiment, $R^5$ is H.
Cyclic $R^1$-$R^2$, $R^1$-$R^4$, $R^1$-$R^5$
In one embodiment, $R^1$ and $R^4$ together form optionally substituted $C_{3-5}$alkylene, $C_{3-5}$alkenylene, $C_{3-5}$heteroalkylene, or $C_{3-5}$heteroalkenylene. In one embodiment, $R^1$ and $R^4$ together form optionally substituted $C_{3-5}$alkylene (in one embodiment unsubstituted), e.g. $C_3$ or $C_4$ alkylene (to form 5 and 6 membered rings, respectively). In one embodiment, when $R^1$ and $R^4$ together form optionally substituted $C_{3-5}$alkylene, $C_{3-5}$alkenylene, $C_{3-5}$heteroalkylene, or $C_{3-5}$heteroalkenylene, $R^2$ and $R^5$ are independently H or optionally substituted $C_{1-6}$alkyl, in one embodiment H.
In one embodiment, when $R^1$ and $R^4$ together form optionally substituted $C_{3-5}$alkylene, $C_{3-5}$alkenylene, $C_{3-5}$heteroalkylene, or $C_{3-5}$heteroalkenylene, the carbon atom to which $R^2$ is attached has the following stereochemistry in formula (I):

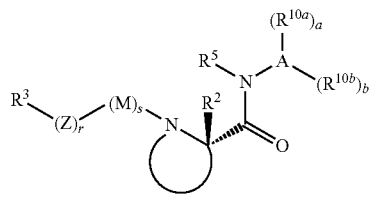

and equivalent stereochemistries in formulae (II) and (III).
In one embodiment, $R^1$ and $R^2$ together form optionally substituted $C_{2-8}$alkylene (e.g. $C_{4-6}$alkylene), $C_{2-8}$alkenylene (e.g. $C_{4-6}$alkenylene), $C_{2-8}$heteroalkylene (e.g. $C_{4-6}$heteroalkylene), or $C_{2-8}$heteroalkenylene (e.g. $C_{4-6}$heteroalkenylene). In one embodiment, $R^1$ and $R^2$ together form optionally substituted $C_{2-8}$alkylene or $C_{2-8}$heteroalkylene (in one embodiment unsubstituted), e.g. $C_4$alkylene (to form a 4 member ring) or —CH$_2$—CH$_2$—O—CH$_2$—CH$_2$— (to form a 5 membered ring). In one embodiment, when $R^1$ and $R^2$ together form optionally substituted $C_{2-8}$alkylene, $C_{2-8}$alkenylene, $C_{2-8}$heteroalkylene, or $C_{2-8}$heteroalkenylene, $R^4$ and $R^5$ are independently H or optionally substituted $C_{1-6}$alkyl, in one embodiment H.
In one embodiment, $R^1$ and $R^5$ together form optionally substituted $C_{2-4}$alkylene, $C_{2-4}$alkenylene, $C_{2-4}$heteroalkylene, or $C_{2-4}$heteroalkenylene. In one embodiment, $R^1$ and $R^5$ together form optionally substituted $C_{2-4}$alkylene (in one embodiment unsubstituted), e.g. $C_2$ alkylene (to form a 5 member ring). In one embodiment, when $R^1$ and $R^5$ together form optionally substituted $C_{2-4}$alkylene, $C_{2-4}$alkenylene, $C_{2-4}$heteroalkylene, or $C_{2-4}$heteroalkenylene, $R^2$ and $R^4$ are independently H or optionally substituted $C_{1-6}$alkyl, in one embodiment H.

Substituents on Groups Other than A

In one embodiment, the optional substituent(s) on groups other than A is/are independently halogen, trihalomethyl, trihaloethyl, —$NO_2$, —CN, —$N^+(C_{1-6}alkyl)_2O^-$, —$CO_2H$, —$CO_2C_{1-6}alkyl$, —$SO_3H$, —$SOC_{1-6}alkyl$, —$SO_2C_{1-6}alkyl$, —$SO_3C_{1-6}alkyl$, —$OC(=O)OC_{1-6}alkyl$, —$C(=O)H$, —$C(=O)C_{1-6}alkyl$, —$OC(=O)C_{1-6}alkyl$, =O, —$N(C_{1-6}alkyl)_2$, —$C(=O)NH_2$, —$C(=O)N(C_{1-6}alkyl)_2$, —$N(C_{1-6}alkyl)C(=O)O(C_{1-6}alkyl)$, —$N(C_{1-6}alkyl)C(=O)N(C_{1-6}alkyl)_2$, —$OC(=O)N(C_{1-6}alkyl)_2$, —$N(C_{1-6}alkyl)C(=O)C_{1-6}alkyl$, —$C(=S)N(C_{1-6}alkyl)_2$, —$N(C_{1-6}alkyl)C(=S)C_{1-6}alkyl$, —$SO_2N(C_{1-6}alkyl)_2$, —$N(C_{1-6}alkyl)SO_2C_{1-6}alkyl$, —$N(C_{1-6}alkyl)C(=S)N(C_{1-6}alkyl)_2$, —$N(C_{1-6}alkyl)SO_2N(C_{1-6}alkyl)_2$, —$C_{1-6}alkyl$, —$C_{1-6}heteroalkyl$, —$C_{3-6}cycloalkyl$, —$C_{3-6}heterocycloalkyl$, —$C_{2-6}alkenyl$, —$C_{2-6}heteroalkenyl$, —$C_{3-6}cycloalkenyl$, —$C_{3-6}heterocycloalkenyl$, —$C_{2-6}alkynyl$, —$C_{2-6}heteroalkynyl$, —$Z^u$—$C_{1-6}alkyl$, —$Z^u$—$C_{3-6}cycloalkyl$, —$Z^u$—$C_{2-6}alkenyl$, —$Z^u$—$C_{3-6}cycloalkenyl$, or —$Z^u$—$C_{2-6}alkynyl$, wherein $Z^u$ is independently O, S, NH or $N(C_{1-6}alkyl)$.

In another embodiment, the optional substituent(s) on groups other than A is/are independently halogen, trihalomethyl, trihaloethyl, —$NO_2$, —CN, —$N^+(C_{1-6}alkyl)_2O^-$, —$CO_2H$, —$SO_3H$, —$SOC_{1-6}alkyl$, —$SO_2C_{1-6}alkyl$, —$C(=O)H$, —$C(=O)C_{1-6}alkyl$, =O, —$N(C_{1-6}alkyl)_2$, —$C(=O)NH_2$, —$C_{1-6}alkyl$, —$C_{3-6}cycloalkyl$, —$C_{3-6}heterocycloalkyl$, —$Z^uC_{1-6}alkyl$ or —$Z^u$—$C_{3-6}cycloalkyl$, wherein $Z^u$ is defined above.

Group A

Where present, the substituents $R^{10a}$ and $R^{10b}$ may be attached, where valency permits, to a carbon atom or a nitrogen atom of the heteroaryl group A.

In one embodiment, A is optionally substituted heteroaryl containing 5 ring members.

In one embodiment, the optionally substituted heteroaryl containing 5 ring members is optionally substituted:

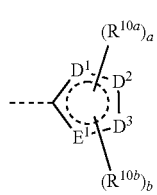

wherein:
$E^1$ is O, S or $NR^{11}$, wherein
$R^{11}$ is H or optionally substituted $C_{1-6}alkyl$; and
$D^1$, $D^2$ and $D^3$ are independently N or optionally substituted CH.

Preferably, at least one of $D^1$, $D^2$ or $D^3$ is optionally substituted CH.

In one embodiment, the group of formula (X) is optionally substituted:

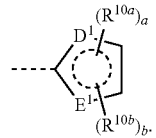

In another embodiment, the group of formula (X) is:

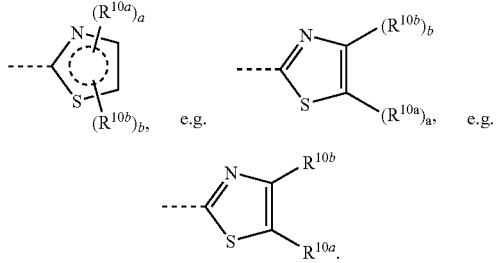

In one embodiment, the group of formula (X) is

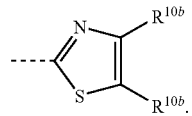

In other embodiments, the group of formula (X) is optionally substituted:

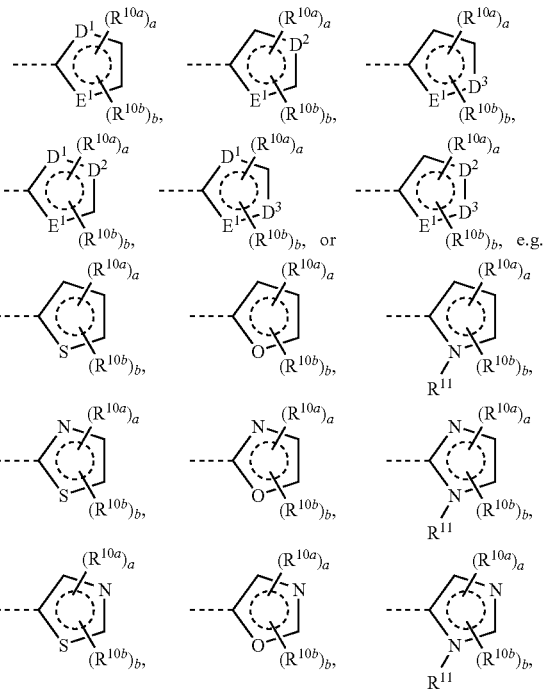

-continued

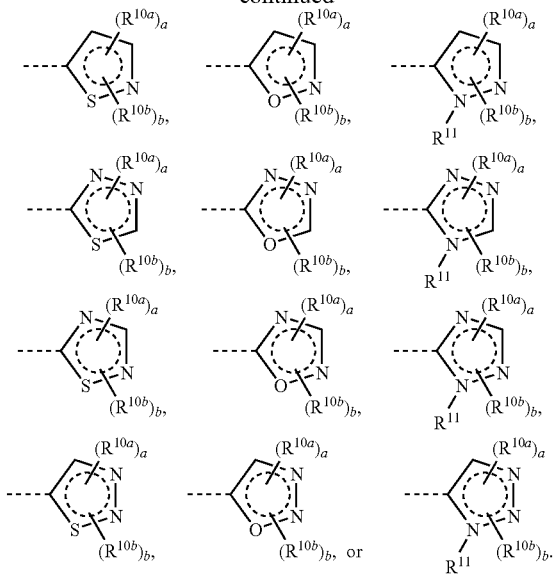

In one embodiment, the group of formula (X) is:

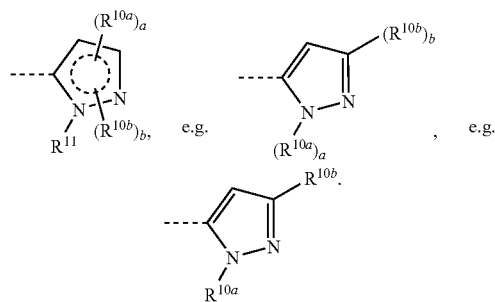

In one embodiment, the group of formula (X) is

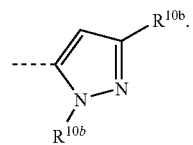

In one embodiment, the optionally substituted heteroaryl containing 5 ring members is optionally substituted:

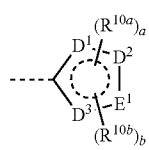

(XI)

wherein:
E$^1$ is O, S or NR$^{11}$, wherein
  R$^{11}$ is H or optionally substituted C$_{1-6}$alkyl; and
D$^1$, D$^2$ and D$^3$ are independently N or optionally substituted CH.

Preferably, at least one of D$^1$, D$^2$ or D$^3$ is optionally substituted CH.

In some embodiments, the group of formula (XI) is optionally substituted:

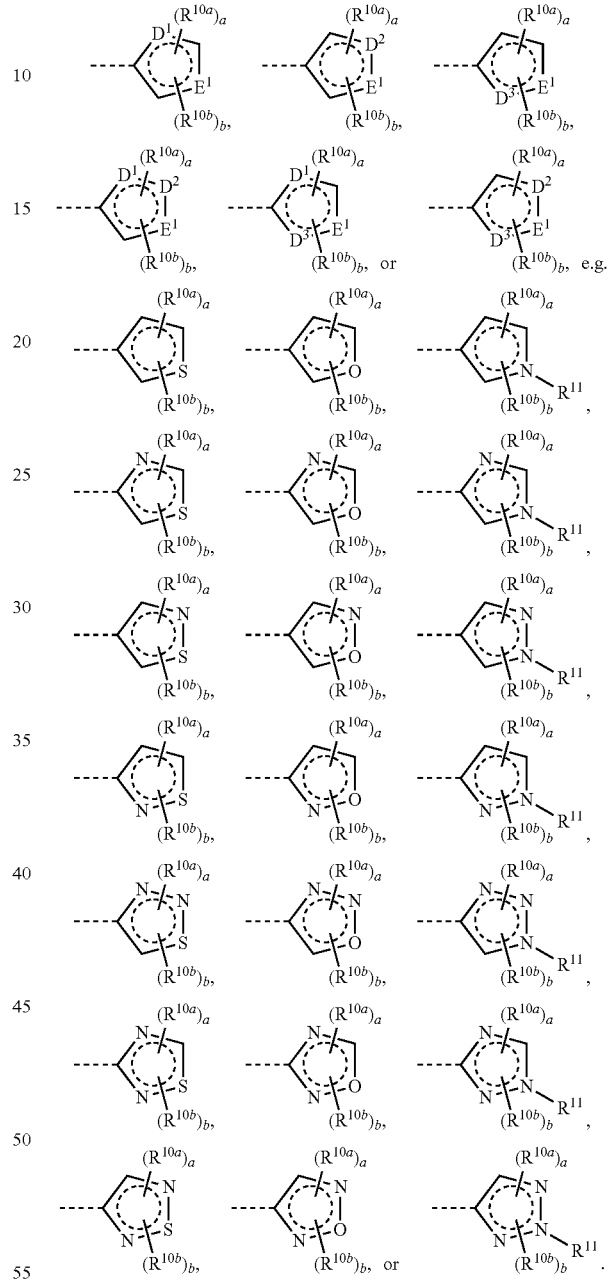

In one embodiment, the group of formula (XI) is

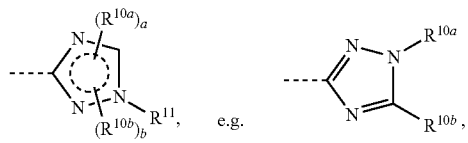

-continued

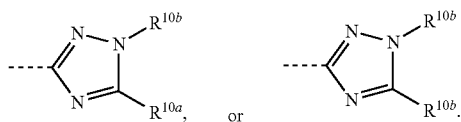

In one embodiment, the optionally substituted heteroaryl containing 5 ring members is optionally substituted:

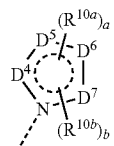

(XII)

wherein:
D$^4$, D$^5$, D$^6$ and D$^7$ are independently N or optionally substituted CH, provided at least one of D$^4$, D$^5$, D$^6$ or D$^7$ is optionally substituted CH.

In one embodiment, at least two of D$^4$, D$^5$, D$^6$ or D$^7$ are optionally substituted CH.

In other embodiments, the group of formula (XII) is optionally substituted:

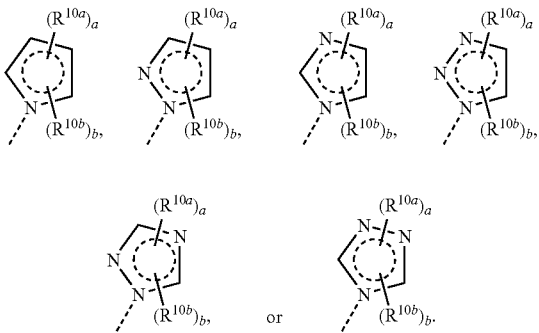

In one embodiment, A is optionally substituted heteroaryl containing 6 ring members. In one embodiment, the optionally substituted heteroaryl containing 6 ring members is optionally substituted:

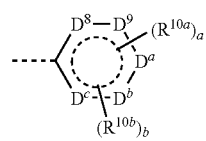

(XIII)

wherein:
D$^8$, D$^9$, D$^a$, D$^b$ and D$^c$ are independently N or optionally substituted CH, provided at least one of D$^8$, D$^9$, D$^a$, D$^b$ or D$^c$ is N and that at least three of D$^8$, D$^9$, D$^a$, D$^b$ or D$^c$ are optionally substituted CH.

In one embodiment, the group of formula (XIII) is optionally substituted:

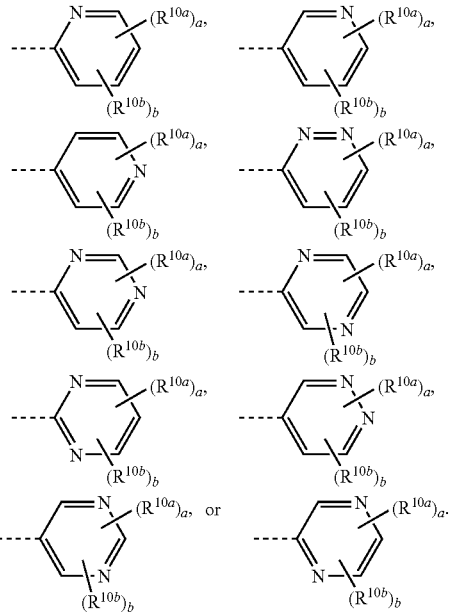

In one embodiment, the group of formula (XIII) is:

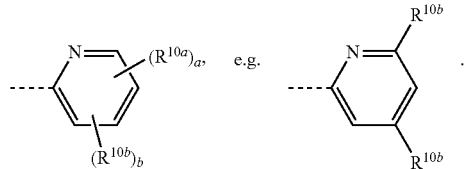

In one embodiment, A is optionally substituted heteroaryl containing 9 ring members. In one embodiment, the optionally substituted heteroaryl containing 9 ring members is optionally substituted:

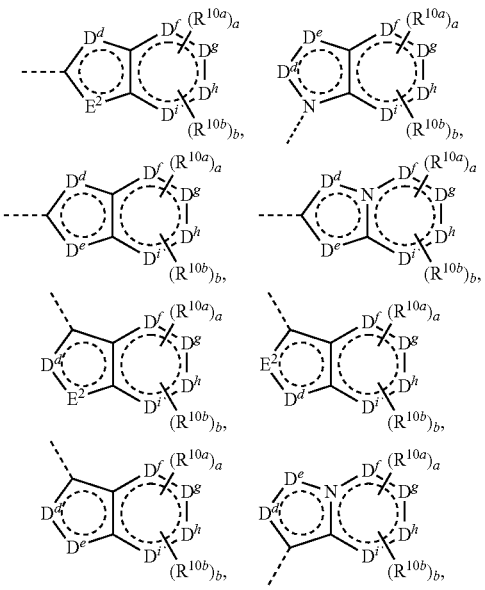

-continued

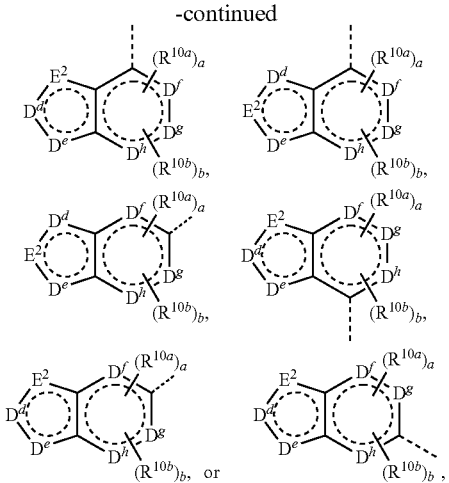

wherein:

E² is O, S or NR¹², wherein

R¹² is H or optionally substituted $C_{1-6}$alkyl; and $D^d$, $D^e$, $D^f$, $D^g$, $D^h$ and $D^i$ are independently N or optionally substituted CH, provided at least two of $D^d$, $D^e$, $D^f$, $D^g$, $D^h$ or $D^i$ are optionally substituted CH.

$R^{10a}$ or $R^{10b}$ may be substituted on either of the rings (i.e. either the 5-membered ring or the 6-membered ring).

In one embodiment, at least one of $D^d$ or $D^e$ is optionally substituted CH and at least one of $D^f$, $D^g$, $D^h$ or $D^i$ (in one embodiment at least two) are optionally substituted CH.

In one embodiment, A is optionally substituted heteroaryl containing 10 ring members. In one embodiment, the optionally substituted heteroaryl containing 10 ring members is optionally substituted:

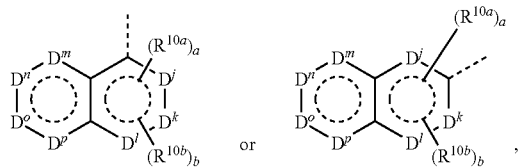

wherein:

$D^j$, $D^k$, $D^l$, $D^m$, $D^n$, $D^o$ and $D^p$ are independently N or optionally substituted CH, provided at least one of $D^j$, $D^k$ or $D^l$, is N and that at least two of $D^m$, $D^n$, $D^o$ and $D^p$ are optionally substituted CH.

$R^{10a}$ or $R^{10b}$ may be substituted on either of the 6-membered rings.

In one embodiment, the optionally substituted heteroaryl containing 10 ring members is optionally substituted:

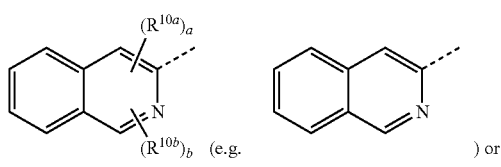

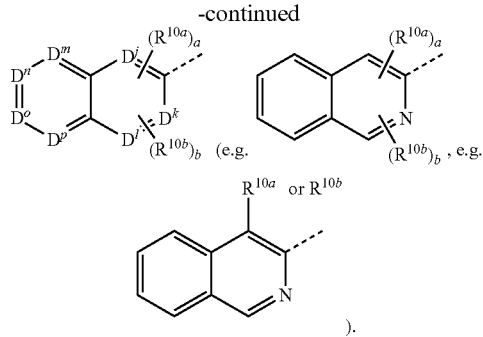

In one embodiment, the optional substituent is halo.

Substituents on A

In one embodiment, any optional substituent(s) on A other than $R^{10a}$ and $R^{10b}$ is/are independently halogen, trihalomethyl (e.g. —CF₃), trihaloethyl (e.g. —CH₂CF₃), —NO₂, —CN, —N⁺($C_{1-6}$alkyl)₂O—, —CO₂H, —CO₂$C_{1-6}$alkyl, —SO₃H, —SO$C_{1-6}$alkyl, —SO₂$C_{1-6}$alkyl, —SO₃$C_{1-6}$alkyl, —OC(=O)O$C_{1-6}$alkyl, —C(=O)H, —C(=O)$C_{1-6}$alkyl, —OC(=O)$C_{1-6}$alkyl, =O, —N($C_{1-6}$alkyl)₂, —C(=O)NH₂, —C(=O)N($C_{1-6}$alkyl)₂, —N($C_{1-6}$alkyl)C(=O)O($C_{1-6}$alkyl), —N($C_{1-6}$alkyl)C(=O)N($C_{1-6}$alkyl)₂, —OC(=O)N($C_{1-6}$alkyl)₂, —N($C_{1-6}$alkyl)C(=O)$C_{1-6}$alkyl, —C(=S)N($C_{1-6}$alkyl)₂, —N($C_{1-6}$alkyl)C(=S)$C_{1-6}$alkyl, —SO₂N($C_{1-6}$alkyl)₂, —N($C_{1-6}$alkyl)SO₂$C_{1-6}$alkyl, —N($C_{1-6}$alkyl)C(=S)N($C_{1-6}$alkyl)₂, —N($C_{1-6}$alkyl)SO₂N($C_{1-6}$alkyl)₂, —$C_{1-6}$alkyl, —$C_{1-6}$heteroalkyl, —$C_{3-6}$cycloalkyl, —$C_{3-6}$heterocycloalkyl, —$C_{2-6}$alkenyl, —$C_{2-6}$heteroalkenyl, —$C_{3-6}$cycloalkenyl, —$C_{3-6}$heterocycloalkenyl, —$C_{2-6}$alkynyl, —$C_{2-6}$heteroalkynyl, —$Z^v$—$C_{1-6}$alkyl, —$Z^v$—$C_{3-6}$cycloalkyl, —$Z^v$—$C_{2-6}$alkenyl, —$Z^v$—$C_{3-6}$cycloalkenyl, or —$Z^v$—$C_{2-6}$alkynyl, wherein $Z^v$ is independently O, S, NH or N($C_{1-6}$alkyl).

In another embodiment, the optional substituent(s) on A other than $R^{10a}$ and $R^{10b}$ is/are independently halogen, trihalomethyl, trihaloethyl, —NO₂, —CN, —N⁺($C_{1-6}$alkyl)₂O—, —CO₂H, —SO₃H, —SO$C_{1-6}$alkyl, —SO₂$C_{1-6}$alkyl, —C(=O)H, —C(=O)$C_{1-6}$alkyl, =O, —N($C_{1-6}$alkyl)₂, —C(=O)NH₂, —$C_{1-6}$alkyl, —$C_{3-6}$cycloalkyl, —$C_{3-6}$heterocycloalkyl, —$Z^v$$C_{1-6}$alkyl or —$Z^v$—$C_{3-6}$cycloalkyl, wherein $Z^v$ is defined above.

In one embodiment (e.g. when A is a 5-membered heterocycle), A is unsubstituted other than by $R^{10a}$ and/or $R^{10b}$.

In one embodiment the sum of a+b>0.

In one embodiment, a and b are independently 0-2, provided the sum of a+b=1 or 2.

In one embodiment (e.g. when A is a 10-membered heterocycle), a=1 and b=0.

In one embodiment, a+b=2. In one embodiment, a=1 and b=1. In another embodiment, a=0 and b=2.

In one embodiment, Q is independently $C_{1-6}$alkylene, $C_{1-6}$heteroalkylene, $C_{2-6}$alkenylene, $C_{2-6}$heteroalkenylene, O, S, NR⁸, or —C(O)—.

In one embodiment Q is independently optionally substituted $C_{1-6}$alkylene or $C_{1-6}$heteroalkylene. In one embodiment, Q is independently optionally substituted $C_{1-6}$heteroalkylene, e.g. —C(O)—NH—CH₂—, —C(O)—NH—CH₂—CH₂— or —CH₂—NH—CH₂—.

In one embodiment, Q is independently —CH₂—, —C(OH)₂—, O, S, NR⁸, or —C(O)—, e.g. —CH₂—, —C(OH)₂—, O, or —C(O)—.

In one embodiment, Q is —CH₂—, O, S, NR⁸, or —C(O)—, e.g. —CH₂—, O, or —C(O)—.

In one embodiment, $R^{7a}$ is H or optionally substituted $C_{1-10}$alkyl, $C_{1-10}$heteroalkyl, $C_{3-10}$cycloalkyl, $C_{3-10}$heterocycloalkyl, phenyl, naphthyl or heteroaryl containing 5, 6, 9 or 10 ring members.

In one embodiment, $R^{7a}$ is $C_{3-10}$cycloalkyl, $C_{3-10}$heterocycloalkyl, phenyl, naphthyl or heteroaryl containing 5, 6, 9 or 10 ring members, except when Q is —C(O)—, $R^{7a}$ is H or optionally substituted $C_{1-10}$alkyl, $C_{1-10}$heteroalkyl, $C_{3-10}$cycloalkyl, $C_{3-10}$heterocycloalkyl, phenyl, naphthyl or heteroaryl containing 5, 6, 9 or 10 ring members.

In one embodiment, $R^{7a}$ is H or optionally substituted $C_{1-10}$alkyl, $C_{1-10}$heteroalkyl, $C_{3-10}$cycloalkyl, $C_{3-10}$heterocycloalkyl or phenyl.

In one embodiment, $R^{7a}$ is optionally substituted $C_{3-10}$heterocycloalkyl, e.g. piperazinyl, morpholinyl, pyrrolidinyl, piperidinyl or tetrahydropyran (e.g. optionally substituted by fluoro, —OMe, —$CH_3$, —OH, =O, —COMe or cyclopropyl).

In one embodiment, $R^{7a}$ is phenyl. In one embodiment, $R^{7a}$ is independently unsubstituted phenyl or phenyl substituted by halo (e.g. fluoro).

In one embodiment, $R^{7b}$ is independently optionally substituted $C_{1-10}$alkyl (e.g. optionally substituted methyl, e.g. trifluoromethyl), $C_{3-10}$cycloalkyl, $C_{3-10}$heterocycloalkyl, $C_{6-14}$aryl or heteroaryl containing 5-13 ring members.

In one embodiment, $R^{7b}$ is independently optionally substituted $C_{3-10}$cycloalkyl, $C_{3-10}$heterocycloalkyl, $C_{6-14}$aryl or heteroaryl containing 5-13 ring members.

In one embodiment, $R^{7b}$ is optionally substituted $C_{3-10}$heterocycloalkyl, phenyl, naphthyl or heteroaryl containing 5, 6, 9 or 10 ring members.

In one embodiment, $R^{7b}$ is optionally substituted phenyl. In one embodiment, $R^{7b}$ is independently unsubstituted phenyl or phenyl substituted by halo (e.g. fluoro).

In one embodiment where b>1, at least one $R^{7b}$ is optionally substituted phenyl, e.g. phenyl substituted by halo (e.g. fluoro).

In one embodiment where b>1, at least one $R^{7b}$ is $C_{1-10}$alkyl (e.g. optionally substituted methyl, e.g. trifluoromethyl), $C_{3-10}$cycloalkyl or $C_{3-10}$heterocycloalkyl (e.g. piperazinyl, morpholinyl, pyrrolidinyl, piperidinyl or tetrahydropyran, e.g. optionally substituted by fluoro, —OMe, —$CH_3$, —OH, =O, —COMe or cyclopropyl).

In one embodiment where b=2, one $R^{7b}$ is optionally substituted phenyl, e.g. phenyl substituted by halo (e.g. fluoro), and the other $R^{7b}$ is $C_{1-10}$alkyl (e.g. optionally substituted methyl, e.g. trifluoromethyl), $C_{3-10}$cycloalkyl or $C_{3-10}$heterocycloalkyl (e.g. piperazinyl, morpholinyl, pyrrolidinyl, piperidinyl or tetrahydropyran, e.g. optionally substituted by fluoro, —OMe, —$CH_3$, —OH, =O, —COMe or cyclopropyl).

Specific Compounds

In another aspect of the invention, there is provided:

N-[1-(5-Benzyl-4-phenyl-thiazol-2-ylcarbamoyl)-1-methyl-ethyl]-3,4-diethoxy-benzamide;
[1-(5-Benzyl-4-phenyl-thiazol-2-ylcarbamoyl)-1-methyl-ethyl]-carbamic acid tert-butyl ester;
2-Amino-N-(5-benzyl-4-phenyl-thiazol-2-yl)-2-methyl-propionamide;
N-[1-(5-Benzyl-4-phenyl-thiazol-2-ylcarbamoyl)-1-methyl-ethyl]-3,5-dimethoxy-benzamide;
N-(5-Benzyl-4-phenyl-thiazol-2-yl)-2-methyl-2-(3-o-tolyl-ureido)-propionamide;
N-(5-Benzyl-4-phenyl-thiazol-2-yl)-2-(4-fluoro-benzenesulfonylamino)-2-methyl-propionamide;
N-[1-(5-Benzyl-4-phenyl-thiazol-2-ylcarbamoyl)-1-methyl-ethyl]-2-methoxy-benzamide;
N-[1-(5-Benzyl-4-phenyl-thiazol-2-ylcarbamoyl)-1-methyl-ethyl]-4-methoxy-benzamide;
N-[1-(5-Benzyl-4-phenyl-thiazol-2-ylcarbamoyl)-1-methyl-ethyl]-4-ethoxy-benzamide;
N-(5-Benzyl-4-phenyl-thiazol-2-yl)-2-[2-(4-methoxy-phenyl)-acetylamino]-2-methyl-propionamide,
Benzo[1,3]dioxole-5-carboxylic acid [1-(5-benzyl-4-phenyl-thiazol-2-ylcarbamoyl)-1-methyl-ethyl]-amide;
N-(5-Benzyl-4-phenyl-thiazol-2-yl)-2-(2-cyclopentyl-acetylamino)-2-methyl-propionamide;
N-(5-Benzyl-4-phenyl-thiazol-2-yl)-2-[3-(2-methoxy-phenyl)-ureido]-2-methyl-propionamide;
N-(5-Benzyl-4-phenyl-thiazol-2-yl)-2-methyl-2-(3-phenyl-propionylamino)-propionamide;
N-[1-(5-Benzyl-4-phenyl-thiazol-2-ylcarbamoyl)-1-methyl-ethyl]-3,4-dimethoxy-benzamide;
N-[1-(5-Benzyl-4-phenyl-thiazol-2-ylcarbamoyl)-1-methyl-ethyl]-3-methoxy-benzamide:
N-[1-(5-Benzyl-4-phenyl-thiazol-2-ylcarbamoyl)-1-methyl-ethyl]-4-dimethylamino-benzamide;
N-(5-Benzyl-4-phenyl-thiazol-2-yl)-2-[3-(2-chloro-phenyl)-ureido]-2-methyl-propionamide;
N-(5-Benzyl-4-phenyl-thiazol-2-yl)-2-[3-(3,4-dihydro-2H-benzo[b][1,4]dioxepin-7-yl)-ureido]-2-methyl-propionamide;
N-(5-Benzyl-4-phenyl-thiazol-2-yl)-2-[3-(2,3-dihydro-benzo[1,4]dioxin-6-yl)-ureido]-2-methyl-propionamide;
N-(5-Benzyl-4-phenyl-thiazol-2-yl)-2-[3-(3-cyclopentyloxy-4-methoxy-phenyl)-ureido]-2-methyl-propionamide;
N-[1-(5-Benzyl-4-phenyl-thiazol-2-ylcarbamoyl)-1-methyl-ethyl]-3-chloro-4-methoxy-benzamide;
2,3-Dihydro-benzo[1,4]dioxine-6-carboxylic acid [1-(5-benzyl-4-phenyl-thiazol-2-ylcarbamoyl)-1-methyl-ethyl]-amide;
N-(5-Benzyl-4-phenyl-thiazol-2-yl)-2-(3-butyl-ureido)-2-methyl-propionamide;
1-Methyl-1H-imidazole-2-carboxylic acid [1-(5-benzyl-4-phenyl-thiazol-2-ylcarbamoyl)-1-methyl 5 ethyl]-amide;
5-tert-Butyl-2-methyl-2H-pyrazole-3-carboxylic acid [1-(5-benzyl-4-phenyl-thiazol-2-ylcarbamoyl)-1-methyl-ethyl]-amide;
Benzofuran-5-carboxylic acid [1-(5-benzyl-4-phenyl-thiazol-2-ylcarbamoyl)-1-methyl-ethyl]-amide;
Pyridine-2-carboxylic acid [1-(5-benzyl-4-phenyl-thiazol-2-ylcarbamoyl)-1-methyl-ethyl]-amide;
1-Methyl-1H-imidazole-4-carboxylic acid [1-(5-benzyl-4-phenyl-thiazol-2-ylcarbamoyl)-1-methyl-ethyl]-amide;
N-[1-(5-Benzyl-4-phenyl-thiazol-2-ylcarbamoyl)-1-methyl-ethyl]-4-morpholin-4-yl-benzamide;
N-[1-(5-Benzyl-4-phenyl-thiazol-2-ylcarbamoyl)-1-methyl-ethyl]-6-trifluoromethyl-nicotinamide;
N-[1-(5-Benzyl-4-phenyl-thiazol-2-ylcarbamoyl)-1-methyl-ethyl]-nicotinamide;
N-(5-Benzyl-4-phenyl-thiazol-2-yl)-2-[3-(4-chloro-3-trifluoromethyl-phenyl)-ureido]-2-methyl-propionamide;
N-(5-Benzyl-4-phenyl-thiazol-2-yl)-2-methyl-2-[3-(4-trifluoromethoxy-phenyl)-ureido]-propionamide;
2,5-Dimethyl-2H-pyrazole-3-carboxylic acid [1-(5-benzyl-4-phenyl-thiazol-2-ylcarbamoyl)-1-methyl-ethyl]-amide;
N-(5-Benzyl-4-phenyl-thiazol-2-yl)-2-methyl-2-[3-(4-trifluoromethyl-phenyl)-ureido]-propionamide;
N-(5-Benzyl-4-phenyl-thiazol-2-yl)-2-(4-methoxy-benzenesulfonylamino)-2-methyl-propionamide;
N-(5-Benzyl-4-phenyl-thiazol-2-yl)-2-methyl-2-(4-trifluoromethyl-benzenesulfonylamino)-propionamide, N-(5-Benzyl-4-phenyl-thiazol-2-yl)-2-(2-fluoro-benzene-sulfonylamino)-2-methyl-propionamide;
N-[1-(5-Benzyl-4-phenyl-thiazol-2-ylcarbamoyl)-1-methyl-ethyl]-3-fluoro-benzamide;
N-[1-(5-Benzyl-4-phenyl-thiazol-2-ylcarbamoyl)-1-methyl-ethyl]-3-fluoro-5-trifluoromethyl-benzamide;
N-[1-(5-Benzyl-4-phenyl-thiazol-2-ylcarbamoyl)-1-methyl-ethyl]-isonicotinamide;
N-[1-(5-Benzyl-4-phenyl-thiazol-2-ylcarbamoyl)-1-methyl-ethyl]-3-fluoro-4-trifluoromethyl-benzamide;
N-[1-(5-Benzyl-4-phenyl-thiazol-2-ylcarbamoyl)-1-methyl-ethyl]-2-fluoro-3-trifluoromethyl-benzamide;
N-[1-(5-Benzyl-4-phenyl-thiazol-2-ylcarbamoyl)-1-methyl-ethyl]-4-trifluoromethoxy-benzamide;
N-(5-Benzyl-4-phenyl-thiazol-2-yl)-2-(3-cyclohexyl-ureido)-2-methyl-propionamide;
N-(5-Benzyl-4-phenyl-thiazol-2-yl)-2-[3-(4-fluoro-3-trifluoromethyl-phenyl)-ureido]-2-methyl-propionamide;
N-(5-Benzyl-4-phenyl-thiazol-2-yl)-2-methyl-2-[3-(3-trifluoromethyl-phenyl)-ureido]-propionamide;
N-[1-(5-Benzyl-4-phenyl-thiazol-2-ylcarbamoyl)-1-methyl-ethyl]-4-trifluoromethyl-benzamide;
Pyridine-2-carboxylic acid [4-(5-benzyl-4-phenyl-thiazol-2-ylcarbamoyl)-tetrahydro-pyran-4-yl]-amide;
Pyrrolidine-1,2-dicarboxylic acid 2-[(5-benzyl-4-phenyl-thiazol-2-yl)-amide]1-o-tolylamide:
N-(5-Benzyl-4-phenyl-thiazol-2-yl)-3-(4-fluoro-phenyl)-2-methyl-2-(3-o-tolyl-ureido)-propionamide;
[1-(5-Benzoyl-4-phenyl-thiazol-2-ylcarbamoyl)-1-methyl-ethyl]-carbamic acid tert-butyl ester;
N-(5-Benzoyl-4-phenyl-thiazol-2-yl)-2-[3-(2-chloro-phenyl)-ureido]-2-methyl-propionamide;
[1-(4,5-Diphenyl-thiazol-2-ylcarbamoyl)-1-methyl-ethyl]-carbamic acid tert-butyl ester;
N-(5-Benzoyl-4-phenyl-thiazol-2-yl)-2-(2-cyclopentyl-acetylamino)-2-methyl-propionamide;
2-(2-Cyclopentyl-acetylamino)-N-(4,5-diphenyl-thiazol-2-yl)-2-methyl-propionamide;
N-(5-Benzoyl-4-phenyl-thiazol-2-yl)-2-(2,2-dimethyl-propionylamino)-2-methyl-propionamide;
2-(2,2-Dimethyl-propionylamino)-N-(4,5-diphenyl-thiazol-2-yl)-2-methyl-propionamide;
Cyclopentanecarboxylic acid [1-(4,5-diphenyl-thiazol-2-ylcarbamoyl)-1-methyl-ethyl]-amide;
Cyclopentanecarboxylic acid [1-(5-benzoyl-4-phenyl-thiazol-2-ylcarbamoyl)-1-methyl-ethyl]-amide;
Pyridine-2-carboxylic acid {1-[1-chloro-4-(4-fluoro-phenyl)-isoquinolin-3-ylcarbamoyl]-1-methyl-ethyl}-amide;
N-(1-Bromo-isoquinolin-3-yl)-2-[3-(2-chloro-phenyl)-ureido]-2-methyl-propionamide;
N-(4-Benzyl-1-chloro-isoquinolin-3-yl)-2-[3-(2-chloro-phenyl)-ureido]-2-methyl-propionamide;
N-(2-Benzyl-5-phenyl-2H-pyrazol-3-yl)-2-[3-(2-chloro-phenyl)-ureido]-2-methyl-propionamide;
1-(Pyridine-2-carbonyl)-pyrrolidine-2-carboxylic acid (5-benzyl-4-phenyl-thiazol-2-yl)-amide;
Pyrrolidine-1,2-dicarboxylic acid 2-[(5-benzyl-4-phenyl-thiazol-2-yl)-amide]1-o-tolylamide;
1-(4-Trifluoromethoxy-benzoyl)-pyrrolidine-2-carboxylic acid (5-benzyl-4-phenyl-thiazol-2-yl)-amide;
(S)-Pyrrolidine-1,2-dicarboxylic acid 2-[(5-benzyl-4-phenyl-thiazol-2-yl)-amide]1-[(2-chloro-phenyl)-amide];
(S)-Pyrrolidine-1,2-dicarboxylic acid 2-[(5-benzyl-4-phenyl-thiazol-2-yl)-amide]1-[(2-isopropyl-phenyl)-amide];
(S)-Pyrrolidine-1,2-dicarboxylic acid 2-[(5-benzyl-4-phenyl-thiazol-2-yl)-amide]1-[(2,4-difluoro-phenyl)-amide];
(S)-1-(2-Cyclopentyl-acetyl)-pyrrolidine-2-carboxylic acid (5-benzyl-4-phenyl-thiazol-2-yl)-amide;
(S)-Pyrrolidine-1,2-dicarboxylic acid 2-[(5-benzyl-4-phenyl-thiazol-2-yl)-amide]1-[(2-fluoro-4-trifluoromethyl-phenyl)-amide];
(S)-Pyrrolidine-1,2-dicarboxylic acid 2-[(5-benzyl-4-phenyl-thiazol-2-yl)-amide]1-[(2-trifluoromethyl-phenyl)-amide].
(S)-2-Methyl-pyrrolidine-1,2-dicarboxylic acid 2-[(5-benzyl-4-phenyl-thiazol-2-yl)-amide]1-[(2-chloro-phenyl)-amide];
(2S,4R)-1-(2-Cyclopentyl-acetyl)-4-fluoro-pyrrolidine-2-carboxylic acid (5-benzyl-4-phenyl-thiazol-2-yl)-amide;
(S)-1-(2-Cyclopentyl-acetyl)-4,4-difluoro-pyrrolidine-2-carboxylic acid (5-benzyl-4-phenyl-thiazol-2-yl)-amide;
(S)-1-(2-Cyclopentyl-acetyl)-pyrrolidine-2-carboxylic acid [5-(4-fluoro-phenoxy)-4-(4-fluoro-phenyl)-thiazol-2-yl]-amide;
(S)-2-(5-Benzoyl-4-phenyl-thiazol-2-ylcarbamoyl)-pyrrolidine-1-carboxylic acid tert-butyl ester;
(S)-1-(Pyridine-2-carbonyl)-piperidine-2-carboxylic acid (5-benzyl-4-phenyl-thiazol-2-yl)-amide;
(S)-1-(2-Cyclopentyl-acetyl)-piperidine-2-carboxylic acid (5-benzyl-4-phenyl-thiazol-2-yl)-amide;
N-{1-[5-(4-Fluoro-phenoxy)-4-(4-fluoro-phenyl)-thiazol-2-ylcarbamoyl]-1-methyl-ethyl}-4-trifluoromethoxybenzamide;
Morpholine-4-carboxylic acid {1-[5-(4-fluoro-phenoxy)-4-(4-fluoro-phenyl)-thiazol-2-ylcarbamoyl]-1-methyl-ethyl}-amide;
Pyridine-2-carboxylic acid {1-[5-(4-fluoro-phenoxy)-4-(4-fluoro-phenyl)-thiazol-2-ylcarbamoyl]-1-methyl-ethyl}-amide;
N-{1-[5-(4-Fluoro-phenoxy)-4-(4-fluoro-phenyl)-thiazol-2-ylcarbamoyl]-1-methyl-ethyl}-isophthalamic acid;
Pyrimidine-4-carboxylic acid {1-[5-(4-fluoro-phenoxy)-4-(4-fluoro-phenyl)-thiazol-2-ylcarbamoyl]-1-methyl-ethyl}-amide;
N-[5-(4-Fluoro-phenoxy)-4-(4-fluoro-phenyl)-thiazol-2-yl]-2-methyl-2-(3,3,3-trifluoro-propionylamino)-propionamide;
2-(3-Cyclopropyl-ureido)-N-[5-(4-fluoro-phenoxy)-4-(4-fluoro-phenyl)-thiazol-2-yl]-2-methyl-propionamide;
N-{1-[5-(4-Fluoro-phenoxy)-4-(4-fluoro-phenyl)-thiazol-2-ylcarbamoyl]-1-methyl-ethyl}-nicotinamide;
Thiazole-5-carboxylic acid {1-[5-(4-fluoro-phenoxy)-4-(4-fluoro-phenyl)-thiazol-2-ylcarbamoyl]-1-methyl-ethyl}-amide;
(S)-1-(2-Cyclopentyl-acetyl)-pyrrolidine-2-carboxylic acid (4-phenyl-quinolin-2-yl)-amide;
(S)-2-(6-Phenyl-4-p-tolyl-pyridin-2-ylcarbamoyl)-pyrrolidine-1-carboxylic acid tert-butyl ester;
{1-[5-(4-Fluoro-phenoxy)-4-(4-fluoro-phenyl)-thiazol-2-yl]-2-oxo-pyrrolidin-3-yl}-carbamic acid tert-butyl ester;
Morpholine-4-carboxylic acid {1-[5-(4-fluoro-phenoxy)-4-(4-fluoro-phenyl)-thiazol-2-yl]-2-oxo-pyrrolidin-3-yl}-amide;
Pyridine-2-carboxylic acid {1-[5-(4-fluoro-phenoxy)-4-(4-fluoro-phenyl)-thiazol-2-yl]-2-oxo-pyrrolidin-3-yl}-amide;
(S)-1-Benzooxazol-2-yl-pyrrolidine-2-carboxylic acid (5-benzyl-4-phenyl-thiazol-2-yl)-amide;
(S)—N-(5-Benzyl-4-phenyl-thiazol-2-yl)-2-(2-cyclopentyl-acetylamino)-3-(4-fluoro-phenyl)-2-methyl-propionamide;
Pyridine-2-carboxylic acid [1-(5-benzyl-thiazol-2-ylcarbamoyl)-1-methyl-ethyl]-amide;

2-Benzylamino-N-(5-benzyl-4-phenyl-thiazol-2-yl)-2-methyl-propionamide;
Tetrahydro-furan-3-carboxylic acid [1-(5-benzoyl-4-phenyl-thiazol-2-ylcarbamoyl)-1-methyl-ethyl]-amide;
(2S,4R)-4-Fluoro-1-(pyridine-2-carbonyl)-pyrrolidine-2-carboxylic acid (5-benzyl-4-phenyl-thiazol-2-yl)-amide;
Pyridine-2-carboxylic acid {1-[4-(4-fluoro-phenyl)-thiazol-2-ylcarbamoyl]-1-methyl-ethyl}-amide;
Pyridine-2-carboxylic acid [1-(4-benzyl-1-chloro-isoquinolin-3-ylcarbamoyl)-1-methyl-ethyl]-amide;
(R)-1-(2-Cyclopentyl-acetyl)-pyrrolidine-2-carboxylic acid (5-benzyl-4-phenyl-thiazol-2-yl)-amide;
(R)-Pyrrolidine-1,2-dicarboxylic acid 2-[(5-benzyl-4-phenyl-thiazol-2-yl)-amide]1-[(2-chloro-phenyl)-amide];
(R)-1-(Pyridine-2-carbonyl)-piperidine-2-carboxylic acid (5-benzyl-4-phenyl-thiazol-2-yl)-amide;
(R)-1-(2-Cyclopentyl-acetyl)-piperidine-2-carboxylic acid (5-benzyl-4-phenyl-thiazol-2-yl)-amide;
2-(2-Cyclopentyl-acetylamino)-2-methyl-N-(4-phenyl-quinolin-2-yl)-propionamide;
N-[4-(4-Chloro-phenyl)-quinolin-2-yl]-2-(2-cyclopentyl-acetylamino)-2-methyl-propionamide;
2-(2-Cyclopentyl-acetylamino)-2-methyl-N-(4-pyridin-2-yl-quinolin-2-yl)-propionamide;
2-(2-Cyclopentyl-acetylamino)-2-methyl-N-(4-pyridin-4-yl-quinolin-2-yl)-propionamide;
2-(2-Cyclopentyl-acetylamino)-2-methyl-N-(6-phenyl-4-p-tolyl-pyridin-2-yl)-propionamide;
N-{1-[5-(4-Fluoro-phenoxy)-4-(4-fluoro-phenyl)-thiazol-2-ylcarbamoyl]-1-methyl-ethyl}-3-hydroxy-benzamide;
2-Cyano-N-{1-[5-(4-fluoro-phenoxy)-4-(4-fluoro-phenyl)-thiazol-2-ylcarbamoyl]-1-methyl-ethyl}-benzamide;
2-Chloro-N-{1-[5-(4-fluoro-phenoxy)-4-(4-fluoro-phenyl)-thiazol-2-ylcarbamoyl]-1-methyl-ethyl}-benzamide;
N-{1-[5-(4-Fluoro-phenoxy)-4-(4-fluoro-phenyl)-thiazol-2-ylcarbamoyl]-1-methyl-ethyl}-benzamide;
2-Fluoro-N-{1-[5-(4-fluoro-phenoxy)-4-(4-fluoro-phenyl)-thiazol-2-ylcarbamoyl]-1-methyl-ethyl}-benzamide;
N-{1-[5-(4-Fluoro-phenoxy)-4-(4-fluoro-phenyl)-thiazol-2-ylcarbamoyl]-1-methyl-ethyl}-4-methoxy-benzamide;
4-Fluoro-N-{1-[5-(4-fluoro-phenoxy)-4-(4-fluoro-phenyl)-thiazol-2-ylcarbamoyl]-1-methyl-ethyl}-N-methyl-benzamide;
N-[5-(4-Fluoro-phenoxy)-4-(4-fluoro-phenyl)-thiazol-2-yl]-2-methyl-2-(2-methyl-2-morpholin-4-yl-propionylamino)-propionamide;
2-((R)-2-Amino-2-phenyl-acetylamino)-N-[5-(4-fluoro-phenoxy)-4-(4-fluoro-phenyl)-thiazol-2-yl]-2-methyl-propionamide;
4-Fluoro-N-{1-[4-(4-fluoro-phenyl)-5-(pyridin-3-yloxy)-thiazol-2-ylcarbamoyl]-1-methyl-ethyl}-benzamide;
Morpholine-4-carboxylic acid {1-[4-(4-fluoro-phenyl)-5-(pyridin-3-yloxy)-thiazol-2-ylcarbamoyl]-1-methyl-ethyl}-amide;
4-Fluoro-N-{1-methyl-1-[4-phenyl-5-(piperazine-1-carbonyl)-thiazol-2-ylcarbamoyl]-ethyl}-benzamide;
4-Methyl-piperidine-4-carboxylic acid {1-[5-(4-fluoro-phenoxy)-4-(4-fluoro-phenyl)-thiazol-2-ylcarbamoyl]-1-methyl-ethyl}-amide;
4-Fluoro-N-[1-methyl-1-(4-phenyl-5-piperazin-1-ylmethyl-thiazol-2-ylcarbamoyl)-ethyl]-benzamide;
{1-[4-(4-Fluoro-phenyl)-5-morpholin-4-yl-thiazol-2-ylcarbamoyl]-1-methyl-ethyl}-carbamic acid tert-butyl ester;
{1-[4-(4-Fluoro-phenyl)-5-piperidin-1-yl-thiazol-2-ylcarbamoyl]-1-methyl-ethyl}-carbamic acid tert-butyl ester;
Pyridine-2-carboxylic acid {1-[4-(4-fluoro-phenyl)-5-piperidin-1-yl-thiazol-2-ylcarbamoyl]-1-methyl-ethyl}-amide;
4-Fluoro-N-{1-[4-(4-fluoro-phenyl)-5-piperidin-1-yl-thiazol-2-ylcarbamoyl]-1-methyl-ethyl}-benzamide;
Pyridine-2-carboxylic acid {1-[4-(4-fluoro-phenyl)-5-morpholin-4-yl-thiazol-2-ylcarbamoyl]-1-methyl-ethyl}-amide;
4-Fluoro-N-{1-[4-(4-fluoro-phenyl)-5-morpholin-4-yl-thiazol-2-ylcarbamoyl]-1-methyl-ethyl}-benzamide;
(R)-3-Hydroxy-pyrrolidine-1-carboxylic acid {1-[5-(4-fluoro-phenoxy)-4-(4-fluoro-phenyl)-thiazol-2-ylcarbamoyl]-1-methyl-ethyl}-amide;
(1-{4-(4-Fluoro-phenyl)-5-[methyl-(tetrahydro-pyran-4-yl)-amino]-thiazol-2-ylcarbamoyl}-1-methyl-ethyl)-carbamic acid tert-butyl ester;
Pyrrolidine-2-carboxylic acid {1-[5-(4-fluoro-phenoxy)-4-(4-fluoro-phenyl)-thiazol-2-ylcarbamoyl]-1-methyl-ethyl}-amide;
Piperidine-2-carboxylic acid {1-[5-(4-fluoro-phenoxy)-4-(4-fluoro-phenyl)-thiazol-2-ylcarbamoyl]-1-methyl-ethyl}-amide;
N-[5-(4-Fluoro-phenoxy)-4-(4-fluoro-phenyl)-thiazol-2-yl]-2-methyl-2-(2-methyl-2-pyrrolidin-1-yl-propionylamino)-propionamide;
4-Fluoro-N-[1-methyl-1-(5-morpholin-4-ylmethyl-4-phenyl-thiazol-2-ylcarbamoyl)-ethyl]-benzamide;
4-Fluoro-N-[1-methyl-1-(4-phenyl-5-pyrrolidin-1-ylmethyl-thiazol-2-ylcarbamoyl)-ethyl]-benzamide;
N-[5-(4-Fluoro-phenoxy)-4-(4-fluoro-phenyl)-thiazol-2-yl]-2-methyl-2-(2-pyrrolidin-1-yl-20 acetylamino)-propionamide;
2-Methyl-pyrrolidine-2-carboxylic acid {1-[5-(4-fluoro-phenoxy)-4-(4-fluoro-phenyl)-thiazol-2-ylcarbamoyl]-1-methyl-ethyl}-amide;
Pyridine-2-carboxylic acid (1-{4-(4-fluoro-phenyl)-5-[methyl-(tetrahydro-pyran-4-yl)-amino]-thiazol-2-ylcarbamoyl}-1-methyl-ethyl)-amide;
4-Fluoro-N-(1-{4-(4-fluoro-phenyl)-5-[methyl-(tetrahydro-pyran-4-yl)-amino]-thiazol-2-ylcarbamoyl}-1-methyl-ethyl)-benzamide;
2-(3-Cyclohexyl-ureido)-N-{4-(4-fluoro-phenyl)-5-[methyl-(tetrahydro-pyran-4-yl)-amino]-thiazol-2-yl}-2-methyl-propionamide;
2-(2-Cyclopentyl-acetylamino)-N-[4-(4-fluoro-phenyl)-5-morpholin-4-yl-thiazol-2-yl]-2-methyl-propionamide;
2-(3-Cyclohexyl-ureido)-N-[4-(4-fluoro-phenyl)-5-morpholin-4-yl-thiazol-2-yl]-2-methyl-propionamide;
(R)-3-Hydroxy-pyrrolidine-1-carboxylic acid {1-[4-cyclopropyl-5-(4-fluoro-phenoxy)-thiazol-2-ylcarbamoyl]-1-methyl-ethyl}-amide;
Morpholine-4-carboxylic acid {1-[4-cyclopropyl-5-(4-fluoro-phenoxy)-thiazol-2-ylcarbamoyl]-1-methyl-ethyl}-amide;
(S)-3-Hydroxy-pyrrolidine-1-carboxylic acid {1-[5-(4-fluoro-phenoxy)-4-(4-fluoro-phenyl)-thiazol-2-ylcarbamoyl]-1-methyl-ethyl}-amide;
(3R,4R)-3,4-Dihydroxy-pyrrolidine-1-carboxylic acid {1-[5-(4-fluoro-phenoxy)-4-(4-fluoro-phenyl)-thiazol-2-ylcarbamoyl]-1-methyl-ethyl}-amide;
N-{1-[4-Cyclopropyl-5-(4-fluoro-phenoxy)-thiazol-2-ylcarbamoyl]-1-methyl-ethyl}-4-fluoro-benzamide;
3,5-Difluoro-pyridine-2-carboxylic acid {1-[4-cyclopropyl-5-(4-fluoro-phenoxy)-thiazol-2-ylcarbamoyl]-1-methyl-ethyl}-amide;

{1-[5-(5-Chloro-pyridin-2-yloxy)-4-(4-fluoro-phenyl)-thiazol-2-ylcarbamoyl]-1-methyl-ethyl}-carbamic acid tert-butyl ester;

(S)-2-[5-(5-Chloro-pyridin-2-yloxy)-4-(4-fluoro-phenyl)-thiazol-2-ylcarbamoyl]-pyrrolidine-1-carboxylic acid tert-butyl ester;

{1-[5-Cyclohexyloxy-4-(4-fluoro-phenyl)-thiazol-2-ylcarbamoyl]-1-methyl-ethyl}-carbamic acid tert-butyl ester;

1-Trifluoromethyl-cyclopentanecarboxylic acid {1-[4-(4-fluoro-phenyl)-5-morpholin-4-yl-thiazol-2-ylcarbamoyl]-1-methyl-ethyl}-amide;

(S)-1-Isopropyl-piperidine-2-carboxylic acid {1-[4-(4-fluoro-phenyl)-5-morpholin-4-yl-thiazol-2-ylcarbamoyl]-1-methyl-ethyl}-amide;

1-Trifluoromethyl-cyclobutanecarboxylic acid {1-[4-(4-fluoro-phenyl)-5-morpholin-4-yl-thiazol-2-ylcarbamoyl]-1-methyl-ethyl}-amide;

3,5-Difluoro-pyridine-2-carboxylic acid {1-[4-(4-fluoro-phenyl)-5-morpholin-4-yl-thiazol-2-ylcarbamoyl]-1-methyl-ethyl}-amide;

N-[4-(4-Fluoro-phenyl)-5-morpholin-4-yl-thiazol-2-yl]-2-methyl-2-((S)-2-tetrahydro-furan-3-yl-acetylamino)-propionamide;

N-[4-(4-Fluoro-phenyl)-5-morpholin-4-yl-thiazol-2-yl]-2-methyl-2-(2-tetrahydro-pyran-4-yl-acetylamino)-propionamide;

4-Fluoro-N-{1-methyl-1-[4-phenyl-5-(piperidine-1-carbonyl)-thiazol-2-ylcarbamoyl]-ethyl}-benzamide;

4-Fluoro-N-{1-methyl-1-[4-phenyl-5-(pyrrolidine-1-carbonyl)-thiazol-2-ylcarbamoyl]-ethyl}-benzamide;

N-{1-[5-(3,3-Difluoro-pyrrolidine-1-carbonyl)-4-phenyl-thiazol-2-ylcarbamoyl]-1-methyl-ethyl}-4-fluoro-benzamide;

4-Fluoro-N-{1-[5-(4-fluoro-phenoxy)-4-(tetrahydro-pyran-4-yl)-thiazol-2-ylcarbamoyl]-1-methyl-ethyl}-benzamide;

3,5-Difluoro-pyridine-2-carboxylic acid {1-[5-(4-fluoro-phenoxy)-4-(tetrahydro-pyran-4-yl)-thiazol-2-ylcarbamoyl]-1-methyl-ethyl}-amide;

N-{1-[5-Cyclohexyloxy-4-(4-fluoro-phenyl)-thiazol-2-ylcarbamoyl]-1-methyl-ethyl}-4-fluoro-benzamide;

3,5-Difluoro-pyridine-2-carboxylic acid {1-[5-cyclohexyloxy-4-(4-fluoro-phenyl)-thiazol-2-ylcarbamoyl]-1-methyl-ethyl}-amide;

Pyridine-2-carboxylic acid {1-[5-cyclohexyloxy-4-(4-fluoro-phenyl)-thiazol-2-ylcarbamoyl]-1-methyl-ethyl}-amide;

2-Methyl-pyrrolidine-2-carboxylic acid {1-[5-(4-fluoro-phenoxy)-4-(tetrahydro-pyran-4-yl)-thiazol-2-ylcarbamoyl]-1-methyl-ethyl}-amide;

4-Fluoro-N-[1-methyl-1-(4-phenyl-5-piperidin-1-ylmethyl-thiazol-2-ylcarbamoyl)-ethyl]-benzamide;

4-Fluoro-N-{1-[5-(3-methoxy-pyrrolidin-1-ylmethyl)-4-phenyl-thiazol-2-ylcarbamoyl]-1-methyl-ethyl}-benzamide;

N-{1-[5-(3,3-Difluoro-pyrrolidin-1-ylmethyl)-4-phenyl-thiazol-2-ylcarbamoyl]-1-methyl-ethyl}-4-fluoro-benzamide;

N-{1-[5-((2R,6S)-2,6-Dimethyl-morpholin-4-ylmethyl)-4-phenyl-thiazol-2-ylcarbamoyl]-1-methyl-ethyl}-4-fluoro-benzamide;

4-Fluoro-N-{1-[5-((S)-3-hydroxy-pyrrolidin-1-ylmethyl)-4-phenyl-thiazol-2-ylcarbamoyl]-1-methyl-ethyl}-benzamide;

Morpholine-3-carboxylic acid {1-[5-(4-fluoro-phenoxy)-4-(4-fluoro-phenyl)-thiazol-2-ylcarbamoyl]-1-methyl-ethyl}-amide;

{1-[5-((2R,6S)-2,6-Dimethyl-morpholin-4-yl)-4-(4-fluoro-phenyl)-thiazol-2-ylcarbamoyl]-1-methyl-ethyl}-carbamic acid tert-butyl ester;

Morpholine-4-carboxylic acid {1-[5-(4-fluoro-benzoyl)-4-trifluoromethyl-thiazol-2-ylcarbamoyl]-1-methyl-ethyl}-amide;

1-Methyl-cyclopropanecarboxylic acid {1-[5-(4-fluoro-benzoyl)-4-trifluoromethyl-thiazol-2-ylcarbamoyl]-1-methyl-ethyl}-amide.

Tetrahydro-furan-2-carboxylic acid {1-[5-(4-fluoro-benzoyl)-4-trifluoromethyl-thiazol-2-ylcarbamoyl]-1-methyl-ethyl}-amide;

2-[2-(4-Fluoro-benzoylamino)-2-methyl-propionylamino]-4-(4-fluoro-phenyl)-thiazole-5-carboxylic acid ethyl ester;

2-[2-(4-Fluoro-benzoylamino)-2-methyl-propionylamino]-4-(4-fluoro-phenyl)-thiazole-5-carboxylic acid 4-fluoro-benzylamide;

Morpholine-4-carboxylic acid {1-[5-(4-fluoro-benzoyl)-4-(1-fluoro-1-methyl-ethyl)-thiazol-2-ylcarbamoyl]-1-methyl-ethyl}-amide;

N-{1-[5-(5-Cyclopropyl-[1,3,4]oxadiazol-2-yl)-4-(4-fluoro-phenyl)-thiazol-2-ylcarbamoyl]-1-methyl-ethyl}-4-fluoro-benzamide;

2-[2-(4-Fluoro-benzoylamino)-2-methyl-propionylamino]-4-(4-fluoro-phenyl)-thiazole-5-carboxylic acid [2-(4-fluoro-phenyl)-ethyl]-amide;

Morpholine-4-carboxylic acid {1-[5-(3,3-difluoro-pyrrolidin-1-ylmethyl)-4-(4-fluoro-phenyl)-thiazol-2-ylcarbamoyl]-1-methyl-ethyl}-amide;

N-[1-(1-Benzyl-5-phenyl-1H-[1,2,4]triazol-3-ylcarbamoyl)-1-methyl-ethyl]-4-fluoro-benzamide;

N-{1-[5-(4-Acetyl-piperazin-1-yl methyl)-4-phenyl-thiazol-2-ylcarbamoyl]-1-methyl-ethyl}-4-fluoro-benzamide;

4-Fluoro-N-{1-methyl-1-[5-(3-oxo-piperazin-1-ylmethyl)-4-phenyl-thiazol-2-ylcarbamoyl]-ethyl}-benzamide;

3,5-Difluoro-pyridine-2-carboxylic acid {1-[5-(dideuteromorpholin-4-yl-methyl)-4-phenyl-thiazol-2-ylcarbamoyl]-1-methyl-ethyl}-amide;

Pyrimidine-4-carboxylic acid {1-[5-(dideutero-morpholin-4-yl-methyl)-4-phenyl-thiazol-2-ylcarbamoyl]-1-methyl-ethyl}-amide;

1-Methyl-cyclopropanecarboxylic acid {1-[5-(dideutero-morpholin-4-yl-methyl)-4-phenyl-thiazol-2-ylcarbamoyl]-1-methyl-ethyl}-amide;

N-{1-[1-(4-Chloro-benzyl)-5-(4-chloro-phenyl)-1H-[1,2,4]triazol-3-ylcarbamoyl]-1-methyl-ethyl}-4-fluoro-benzamide;

N-{1-[5-(4-Chloro-benzyl)-1-phenyl-1H-[1,2,4]triazol-3-ylcarbamoyl]-1-methyl-ethyl}-4-fluoro-benzamide;

N-{1-[1-Benzyl-5-(4-fluoro-phenyl)-1H-[1,2,4]triazol-3-ylcarbamoyl]-1-methyl-ethyl}-4-fluoro-benzamide;

(S)-2-Methyl-pyrrolidine-2-carboxylic acid {1-[5-(4-fluoro-benzoyl)-4-(4-fluoro-phenyl)-thiazol-2-ylcarbamoyl]-1-methyl-ethyl}-amide;

N-{1-[5-((3R,5S)-3,5-Dimethyl-piperazin-1-ylmethyl)-4-phenyl-thiazol-2-ylcarbamoyl]-1-methyl-ethyl}-4-fluoro-benzamide;

N-{1-[5-(4-Cyclopropyl-piperazin-1-ylmethyl)-4-phenyl-thiazol-2-ylcarbamoyl]-1-methyl-ethyl}-4-fluoro-benzamide;

N-(1-{5-[(Cyclopropylmethyl-amino)-methyl]-4-phenyl-thiazol-2-ylcarbamoyl}-1-methyl-ethyl)-4-fluoro-benzamide;

N-{1-[1-Benzyl-5-(4-fluoro-phenyl)-1H-[1,2,4]triazol-3-ylcarbamoyl]-1-methyl-ethyl}-4-chloro-benzamide;

N-{1-[1-Benzyl-5-(4-fluoro-phenyl)-1H-[1,2,4]triazol-3-yl-carbamoyl]-1-methyl-ethyl}-4-trifluoromethyl-benzamide;

N-{1-[5-(4-Acetyl-piperazin-1-ylmethyl)-4-trifluoromethyl-thiazol-2-ylcarbamoyl]-1-methyl-ethyl}-4-fluoro-benzamide;

N-{1-[5-(4-Cyclopropyl-piperazin-1-ylmethyl)-4-trifluoromethyl-thiazol-2-ylcarbamoyl]-1-methyl-ethyl}-4-fluoro-benzamide;

4-Fluoro-N-[1-methyl-1-(5-[1,4]oxazepan-4-ylmethyl-4-trifluoromethyl-thiazol-2-ylcarbamoyl)-ethyl]-benzamide;

4-Fluoro-N-(1-{5-[4-(4-fluoro-phenyl)-piperazin-1-ylmethyl]-4-trifluoromethyl-thiazol-2-ylcarbamoyl}-1-methyl-ethyl)-benzamide;

[1,4]Oxazepane-4-carboxylic acid {1-[5-(4-fluoro-benzoyl)-4-trifluoromethyl-thiazol-2-ylcarbamoyl]-1-methyl-ethyl}-amide;

N-{1-[1-Benzyl-5-(2-fluoro-phenyl)-1H-[1,2,4]triazol-3-yl-carbamoyl]-1-methyl-ethyl}-4-fluoro-benzamide;

N-{1-[1-Benzyl-5-(2-chloro-phenyl)-1H-[1,2,4]triazol-3-ylcarbamoyl]-1-methyl-ethyl}-4-fluoro-benzamide;

N-{1-[1,5-Bis-(4-fluoro-phenyl)-1H-pyrazol-3-ylcarbamoyl]-1-methyl-ethyl}-4-fluoro-benzamide;

N-{1-[1-Benzyl-5-(4-fluoro-phenyl)-1H-pyrazol-3-ylcarbamoyl]-1-methyl-ethyl}-4-fluoro-benzamide;

4-Fluoro-N-{1-[5-(4-fluoro-phenyl)-1-(2,2,2-trifluoro-ethyl)-1H-pyrazol-3-ylcarbamoyl]-1-methyl-ethyl}-benzamide;

{1-[1-Benzyl-5-(4-fluoro-phenyl)-1H-[1,2,4]triazol-3-yl-carbamoyl]-1-methyl-ethyl}-carbamic acid benzyl ester;

4-Fluoro-N-{1-[5-(4-fluoro-phenyl)-4-trifluoromethyl-thiazol-2-ylcarbamoyl]-1-methyl-ethyl}-benzamide;

4-(4-Fluoro-benzoylamino)-tetrahydro-pyran-4-carboxylic acid [1-benzyl-5-(4-fluoro-phenyl)-1H-[1,2,4]triazol-3-yl]-amide;

4-Fluoro-N-{1-[4-(4-fluoro-phenyl)-5-morpholin-4-ylmethyl-thiazol-2-ylcarbamoyl]-1-methyl-ethyl}-benzamide;

Pyridine-2-carboxylic acid {1-[1-benzyl-5-(4-fluoro-phenyl)-1H-[1,2,4]triazol-3-ylcarbamoyl]-1-methyl-ethyl}-amide;

2-Benzylamino-N-[1-benzyl-5-(4-fluoro-phenyl)-1H-[1,2,4]triazol-3-yl]-2-methyl-propionamide;

4-Chloro-pyridine-2-carboxylic acid {1-[1-benzyl-5-(4-fluoro-phenyl)-1H-[1,2,4]triazol-3-ylcarbamoyl]-1-methyl-ethyl}-amide;

N-[1-Benzyl-5-(4-fluoro-phenyl)-1H-[1,2,4]triazol-3-yl]-2-(2-cyclopentyl-acetylamino)-2-methyl-propionamide;

1-Methyl-cyclopropanecarboxylic acid {1-[1-benzyl-5-(4-fluoro-phenyl)-1H-[1,2,4]triazol-3-ylcarbamoyl]-1-methyl-ethyl}-amide;

N-[1-Benzyl-5-(4-fluoro-phenyl)-1H-[1,2,4]triazol-3-yl]-2-methyl-2-phenylacetylamino-propionamide;

N-[1-Benzyl-5-(4-fluoro-phenyl)-1H-[1,2,4]triazol-3-yl]-2-(3-cyclopentyl-ureido)-2-methyl-propionamide;

(S)-3-Phenyl-pyrrolidine-1-carboxylic acid {1-[5-(4-fluoro-benzoyl)-4-trifluoromethyl-thiazol-2-ylcarbamoyl]-1-methyl-ethyl}-amide;

(R)-3-Phenyl-pyrrolidine-1-carboxylic acid {1-[5-(4-fluoro-benzoyl)-4-trifluoromethyl-thiazol-2-ylcarbamoyl]-1-methyl-ethyl}-amide;

N-[1-Benzyl-5-(4-fluoro-phenyl)-1H-[1,2,4]triazol-3-yl]-2-(3-cyclohexyl-ureido)-2-methyl-propionamide;

Tetrahydro-pyran-4-carboxylic acid {1-[1-benzyl-5-(4-fluoro-phenyl)-1H-[1,2,4]triazol-3-ylcarbamoyl]-1-methyl-ethyl}-amide;

2-(3-Cyclohexyl-ureido)-N-[5-(4-fluoro-benzoyl)-4-trifluoromethyl-thiazol-2-yl]-2-methyl-propionamide;

2-(3-Cyclopentyl-ureido)-N-[5-(4-fluoro-benzoyl)-4-trifluoromethyl-thiazol-2-yl]-2-methyl-propionamide;

(S)-1-Methyl-pyrrolidine-2-carboxylic acid {1-[1-benzyl-5-(4-fluoro-phenyl)-1H-[1,2,4]triazol-3-ylcarbamoyl]-1-methyl-ethyl}-amide;

N-[5-(4-Fluoro-benzoyl)-4-trifluoromethyl-thiazol-2-yl]-2-methyl-2-phenylacetylamino-propionamide;

2-(2-Cyclopentyl-acetylamino)-N-[5-(4-fluoro-benzoyl)-4-trifluoromethyl-thiazol-2-yl]-2-methyl-propionamide;

[1,4]Oxazepane-4-carboxylic acid {1-[1-benzyl-5-(4-fluoro-phenyl)-1H-[1,2,4]triazol-3-ylcarbamoyl]-1-methyl-ethyl}-amide;

(R)-3-Phenyl-pyrrolidine-1-carboxylic acid {1-[1-benzyl-5-(4-fluoro-phenyl)-1H-[1,2,4]triazol-3-ylcarbamoyl]-1-methyl-ethyl}-amide;

2-Methyl-2H-pyrazole-3-carboxylic acid {1-[1-benzyl-5-(4-fluoro-phenyl)-1H-[1,2,4]triazol-3-ylcarbamoyl]-1-methyl-ethyl}-amide;

Oxazole-4-carboxylic acid {1-[1-benzyl-5-(4-fluoro-phenyl)-1H-[1,2,4]triazol-3-ylcarbamoyl]-1-methyl-ethyl}-amide;

[1,4]Oxazepane-4-carboxylic acid {1-methyl-1-[5-(4-methyl-benzoyl)-4-trifluoromethyl-thiazol-2-ylcarbamoyl]-ethyl}-amide;

Oxazole-5-carboxylic acid {1-[1-benzyl-5-(4-fluoro-phenyl)-1H-[1,2,4]triazol-3-ylcarbamoyl]-1-methyl-ethyl}-amide;

Isoxazole-5-carboxylic acid {1-[1-benzyl-5-(4-fluoro-phenyl)-1H-[1,2,4]triazol-3-ylcarbamoyl]-1-methyl-ethyl}-amide;

4-Fluoro-N-{1-[5-(4-fluoro-benzoyl)-4-trifluoromethyl-thiazol-2-ylcarbamoyl]-1-methyl-ethyl}-benzamide;

(S)-1-(Pyridine-2-carbonyl)-pyrrolidine-2-carboxylic acid [1-benzyl-5-(4-fluoro-phenyl)-1H-[1,2,4]triazol-3-yl]-amide;

(R)-2-Methoxymethyl-pyrrolidine-1-carboxylic acid {1-[1-benzyl-5-(4-fluoro-phenyl)-1H-[1,2,4]triazol-3-ylcarbamoyl]-1-methyl-ethyl}-amide;

(S)-2-Methoxymethyl-pyrrolidine-1-carboxylic acid {1-[5-(4-fluoro-benzoyl)-4-trifluoromethyl-thiazol-2-ylcarbamoyl]-1-methyl-ethyl}-amide;

(R)-2-Methoxymethyl-pyrrolidine-1-carboxylic acid {1-[5-(4-fluoro-benzoyl)-4-trifluoromethyl-thiazol-2-ylcarbamoyl]-1-methyl-ethyl}-amide;

(R)-2-Methoxymethyl-pyrrolidine-1-carboxylic acid {1-methyl-1-[5-(4-methyl-benzoyl)-4-trifluoromethyl-thiazol-2-ylcarbamoyl]-ethyl}-amide;

(S)-2-Methoxymethyl-pyrrolidine-1-carboxylic acid {1-methyl-1-[5-(4-methyl-benzoyl)-4-trifluoromethyl-thiazol-2-ylcarbamoyl]-ethyl}-amide;

1-Methyl-1H-pyrrole-2-carboxylic acid {1-[1-benzyl-5-(4-fluoro-phenyl)-1H-[1,2,4]triazol-3-ylcarbamoyl]-1-methyl-ethyl}-amide;

5-Methyl-isoxazole-3-carboxylic acid {1-[1-benzyl-5-(4-fluoro-phenyl)-1H-[1,2,4]triazol-3-ylcarbamoyl]-1-methyl-ethyl}-amide;

4-Methyl-oxazole-5-carboxylic acid {1-[1-benzyl-5-(4-fluoro-phenyl)-1H-[1,2,4]triazol-3-ylcarbamoyl]-1-methyl-ethyl}-amide;

2-Oxa-7-aza-spiro[3.5]nonane-7-carboxylic acid {1-methyl-1-[5-(4-methyl-benzoyl)-4-trifluoromethyl-thiazol-2-ylcarbamoyl]-ethyl}-amide;

1-Methoxymethyl-cyclopropanecarboxylic acid {1-[5-(4-fluoro-benzoyl)-4-trifluoromethyl-thiazol-2-ylcarbamoyl]-1-methyl-ethyl}-amide;

N-{1-[5-Benzyl-1-(4-fluoro-phenyl)-1H-[1,2,4]triazol-3-yl-carbamoyl]-1-methyl-ethyl}-4-fluoro-benzamide;
6-Methyl-pyridine-2-carboxylic acid {1-[1-benzyl-5-(4-fluoro-phenyl)-1H-[1,2,4]triazol-3-ylcarbamoyl]-1-methyl-ethyl}-amide;
4-Methyl-pyridine-2-carboxylic acid {1-[1-benzyl-5-(4-fluoro-phenyl)-1H-[1,2,4]triazol-3-ylcarbamoyl]-1-methyl-ethyl}-amide;
4-Methoxy-pyridine-2-carboxylic acid {1-[1-benzyl-5-(4-fluoro-phenyl)-1H-[1,2,4]triazol-3-ylcarbamoyl]-1-methyl-ethyl}-amide;
6-Methoxy-pyridine-2-carboxylic acid {1-[1-benzyl-5-(4-fluoro-phenyl)-1H-[1,2,4]triazol-3-ylcarbamoyl]-1-methyl-ethyl}-amide;
4-(5-Trifluoromethyl-pyridin-2-yl)-[1,4]diazepane-1-carboxylic acid {1-[5-(4-fluoro-benzoyl)-4-trifluoromethyl-thiazol-2-ylcarbamoyl]-1-methyl-ethyl}-amide;
4-Methyl-tetrahydro-pyran-4-carboxylic acid {1-[5-(4-fluoro-benzoyl)-4-trifluoromethyl-thiazol-2-ylcarbamoyl]-1-methyl-ethyl}-amide;
(R)-1-Methyl-piperidine-2-carboxylic acid {1-[1-benzyl-5-(4-fluoro-phenyl)-1H-[1,2,4]triazol-3-ylcarbamoyl]-1-methyl-ethyl}-amide;
(S)-1-Methyl-piperidine-2-carboxylic acid {1-[1-benzyl-5-(4-fluoro-phenyl)-1H-[1,2,4]triazol-3-ylcarbamoyl]-1-methyl-ethyl}-amide;
(R)-1-Methyl-pyrrolidine-2-carboxylic acid {1-[1-benzyl-5-(4-fluoro-phenyl)-1H-[1,2,4]triazol-3-ylcarbamoyl]-1-methyl-ethyl}-amide;
(R)-1-Isopropyl-pyrrolidine-2-carboxylic acid {1-[1-benzyl-5-(4-fluoro-phenyl)-1H-[1,2,4]triazol-3-ylcarbamoyl]-1-methyl-ethyl}-amide;
(S)-1-Isopropyl-pyrrolidine-2-carboxylic acid {1-[1-benzyl-5-(4-fluoro-phenyl)-1H-[1,2,4]triazol-3-ylcarbamoyl]-1-methyl-ethyl}-amide;
3-Methyl-pyridine-2-carboxylic acid {1-[1-benzyl-5-(4-fluoro-phenyl)-1H-[1,2,4]triazol-3-ylcarbamoyl]-1-methyl-ethyl}-amide;
Pyrimidine-4-carboxylic acid {1-[1-benzyl-5-(4-fluoro-phenyl)-1H-[1,2,4]triazol-3-ylcarbamoyl]-1-methyl-ethyl}-amide;
Pyrazine-2-carboxylic acid {1-[1-benzyl-5-(4-fluoro-phenyl)-1H-[1,2,4]triazol-3-ylcarbamoyl]-1-methyl-ethyl}-amide;
1-Methyl-1H-imidazole-2-carboxylic acid {1-[1-benzyl-5-(4-fluoro-phenyl)-1H-[1,2,4]triazol-3-ylcarbamoyl]-1-methyl-ethyl}-amide;
Pyrimidine-2-carboxylic acid {1-[1-benzyl-5-(4-fluoro-phenyl)-1H-[1,2,4]triazol-3-ylcarbamoyl]-1-methyl-ethyl}-amide;
1-Isopropyl-1H-pyrazole-4-carboxylic acid {1-[1-benzyl-5-(4-fluoro-phenyl)-1H-[1,2,4]triazol-3-ylcarbamoyl]-1-methyl-ethyl}-amide;
(S)-1-Benzooxazol-2-yl-pyrrolidine-2-carboxylic acid [4-(4-fluoro-phenyl)-5-propyl-thiazol-2-yl]-amide;
(S)-1-Benzooxazol-2-yl-pyrrolidine-2-carboxylic acid [4-(4-fluoro-phenyl)-5-morpholin-4-yl-thiazol-2-yl]-amide;
N-[1-Benzyl-5-(4-fluoro-phenyl)-1H-[1,2,4]triazol-3-yl]-2-(3,3-dimethyl-2,5-dioxo-pyrrolidin-1-yl)-isobutyramide;
or a pharmaceutically acceptable derivative thereof.

Optional Disclaimers

Certain compounds of formula (I) are known in the art for various purposes unrelated to the invention. Optionally, therefore, the following compounds may be disclaimed from certain embodiments of the invention:

The compounds listed in Annexe A

The compounds disclosed in WO2004/033439, e.g. those of Tables 1-3 of WO2004/033439. In one embodiment, compounds of formula (A) or pharmaceutically acceptable derivatives thereof are disclaimed:

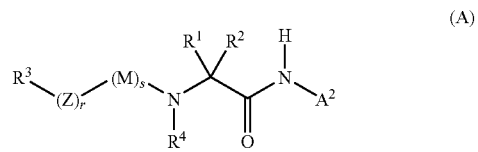

(A)

wherein:
A$^2$ is optionally substituted

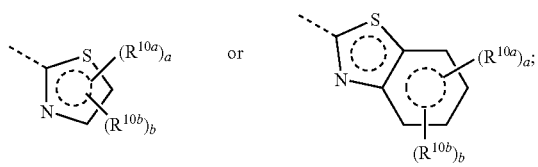

and
all other groups are as defined in formula (I) except R$^4$ may not form a group together with R$^1$.

The compounds disclosed in WO2004/033434, e.g. those of Tables 1-3 of WO2004/033434. In one embodiment, compounds of formula (B) or pharmaceutically acceptable derivatives thereof are disclaimed:

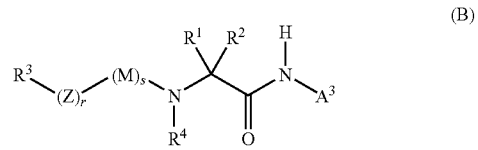

(B)

wherein:
A$^3$ is optionally substituted

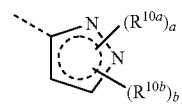

or a bis-fused benzene derivative thereof; and
all other groups are as defined in formula (I) except R$^4$ may not form a group together with R$^1$.

The compounds disclosed in WO01/74783, e.g. those of formula (I) disclosed in WO01/74783. In one embodiment, compounds of formula (I) of the invention where R$^1$ and R$^5$ together form a group; r=0, and R$^3$ is optionally substituted —C$_{3-10}$cycloalkyl, —C$_{3-10}$heterocloalkyl, —C$_{3-10}$cycloalkenyl or C$_{3-10}$heterocycloalkenyl are disclaimed.

The compounds disclosed in US2006/0069082, e.g. those of formula (I) disclosed in US2006/0069082. In one embodiment, compounds of Formula (I) of the invention where R$^3$ is

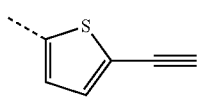

are disclaimed.

The compounds disclosed in WO03/10141, e.g. those of formula (I) disclosed in WO03/101401. In one embodiment, compounds of formula (I) of the invention where $R^3$ is an optionally substituted 9-membered heteroaryl group containing 2 or more ring nitrogen atoms are disclaimed.

Compounds of Formula (I)-(IV) etc. and Derivatives Thereof

As used herein, the terms "compounds of the invention" and "compound of formula (I)" etc. include pharmaceutically acceptable derivatives thereof and polymorphs, isomers and isotopically labelled variants thereof. Furthermore, the term "compounds of the invention" and "compound of formula (I)" etc include compounds of formula (II), (III) and (IV), and the embodiments thereof disclosed herein.

Pharmaceutically Acceptable Derivatives

The term "pharmaceutically acceptable derivative" includes any pharmaceutically acceptable salt, solvate, hydrate or prodrug of a compound of formula (I). In one embodiment, the pharmaceutically acceptable derivatives are pharmaceutically acceptable salts, solvates or hydrates of a compound of formula (I).

Pharmaceutically Acceptable Salts

The term "pharmaceutically acceptable salt" includes a salt prepared from pharmaceutically acceptable non-toxic acids or bases including inorganic or organic acids and bases.

Compounds of formula (I) which contain basic, e.g. amino, groups are capable of forming pharmaceutically acceptable salts with acids. In one embodiment, pharmaceutically acceptable acid addition salts of the compounds of formula (I) include, but are not limited to, those of inorganic acids such as hydrohalic acids (e.g. hydrochloric, hydrobromic and hydriodic acid), sulfuric acid, nitric acid, and phosphoric acids. In one embodiment, pharmaceutically acceptable acid addition salts of the compounds of formula (I) include, but are not limited to, those of organic acids such as aliphatic, aromatic, carboxylic and sulfonic classes of organic acids, examples of which include: aliphatic monocarboxylic acids such as formic acid, acetic acid, propionic acid or butyric acid; aliphatic hydroxy acids such as lactic acid, citric acid, tartaric acid or malic acid; dicarboxylic acids such as maleic acid or succinic acid; aromatic carboxylic acids such as benzoic acid, p-chlorobenzoic acid, phenylacetic acid, diphenylacetic acid or triphenylacetic acid; aromatic hydroxyl acids such as o-hydroxybenzoic acid, p-hydroxybenzoic acid, 1-hydroxynaphthalene-2-carboxylic acid or 3-hydroxynaphthalene-2-carboxylic acid; and sulfonic acids such as methanesulfonic acid, ethanesulfonic acid or benzenesulfonic acid. Other pharmaceutically acceptable acid addition salts of the compounds of formula (I) include, but are not limited to, those of glycolic acid, glucuronic acid, furoic acid, glutamic acid, anthranilic acid, salicylic acid, mandelic acid, embonic (pamoic) acid, pantothenic acid, stearic acid, sulfanilic acid, algenic acid, and galacturonic acid.

Compounds of formula (I) which contain acidic, e.g. carboxyl, groups are capable of forming pharmaceutically acceptable salts with bases. In one embodiment, pharmaceutically acceptable basic salts of the compounds of formula (I) include, but are not limited to, metal salts such as alkali metal or alkaline earth metal salts (e.g. sodium, potassium, magnesium or calcium salts) and zinc or aluminium salts. In one embodiment, pharmaceutically acceptable basic salts of the compounds of formula (I) include, but are not limited to, salts formed with ammonia or pharmaceutically acceptable organic amines or heterocyclic bases such as ethanolamines (e.g. diethanolamine), benzylamines, N-methyl-glucamine, amino acids (e.g. lysine) or pyridine.

Hemisalts of acids and bases may also be formed, e.g. hemisulphate salts.

Pharmaceutically acceptable salts of compounds of formula (I) may be prepared by methods well-known in the art.

For a review of pharmaceutically acceptable salts, see Stahl and Wermuth, Handbook of Pharmaceutical Salts: Properties. Selection and Use (Wiley-VCH, Weinheim, Germany, 2002).

Solvates & Hydrates

The compounds of the invention may exist in both unsolvated and solvated forms. The term "solvate" includes molecular complexes comprising a compound of the invention and one or more pharmaceutically acceptable solvent molecules such as water or $C_{1-6}$ alcohols. e.g. ethanol. The term "hydrate" means a "solvate" where the solvent is water.

Prodrugs

The invention includes prodrugs of the compounds of formula (I). Prodrugs are derivatives of compounds of formula (I) (which may have little or no pharmacological activity themselves), which can, when administered in vivo, be converted into compounds of formula (I).

Prodrugs can, for example, be produced by replacing functionalities present in the compounds of formula (I) with appropriate moieties which are metabolized in vivo to form a compound of formula (I). The design of prodrugs is well-known in the art, as discussed in Bundgaard, *Design of Prodrugs* 1985 (Elsevier), *The Practice of Medicinal Chemistry* 2003, $2^{nd}$ Ed, 561-585 and Leinweber, *Drug Metab. Res.* 1987, 18: 379.

Examples of prodrugs of compounds of formula (I) are esters and amides of the compounds of formula (I). For example, where the compound of formula (I) contains a carboxylic acid group (—COOH), the hydrogen atom of the carboxylic acid group may be replaced in order to form an ester (e.g. the hydrogen atom may be replaced by $C_{1-6}$alkyl). Where the compound of formula (I) contains an alcohol group (—OH), the hydrogen atom of the alcohol group may be replaced in order to form an ester (e.g. the hydrogen atom may be replaced by —C(O)$C_{1-6}$alkyl. Where the compound of formula (I) contains a primary or secondary amino group, one or more hydrogen atoms of the amino group may be replaced in order to form an amide (e.g. one or more hydrogen atoms may be replaced by —C(O)$C_{1-6}$alkyl).

Amorphous & Crystalline Forms

The compounds of the invention may exist in solid states from amorphous through to crystalline forms. All such solid forms are included within the invention.

Isomeric Forms

Compounds of the invention may exist in one or more geometrical, optical, enantiomeric, diastereomeric and tautomeric forms, including but not limited to cis- and trans-forms, E- and Z-forms, R-, S- and meso-forms, keto-, and enol-forms. All such isomeric forms are included within the invention. The isomeric forms may be in isomerically pure or enriched form, as well as in mixtures of isomers (e.g. racemic or diastereomeric mixtures).

Accordingly, the invention provides:
stereoisomeric mixtures of compounds of formula (I);
a diastereomerically enriched or diastereomerically pure isomer of a compound of formula (I); or an enantiomerically enriched or enantiomerically pure isomer of a compound of formula (I).

Where appropriate isomers can be separated from their mixtures by the application or adaptation of known methods (e.g. chromatographic techniques and recrystallisation techniques). Where appropriate isomers can be prepared by the application or adaptation of known methods (e.g. asymmetric synthesis).

Isotopic Labeling

The invention includes pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of formula (I), for example, those incorporating a radioactive isotope, are useful in drug and/or substrate tissue distribution studies. The radioactive isotopes $^3$H and $^{14}$C are particularly useful for this purpose in view of their ease of incorporation and ready means of detection.

Substitution with positron emitting isotopes, such as $^{11}$C., $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described herein using an appropriate isotopically-labelled reagent in place of the non-labelled reagent previously employed.

Treatment of Diseases and Conditions

Compounds of formula (I) have been found to be inhibitors of DGAT1.

The invention provides a compound of formula (I) for use in therapy. The invention further provides a pharmaceutical composition comprising a compound of formula (I) in combination with a pharmaceutically acceptable excipient.

The invention further provides a method for the treatment of a disease or condition mediated by DGAT1, comprising the step of administering a therapeutically effective amount of a compound of formula (I) to a patient. The invention also provides the use of a compound of formula (I) in the manufacture of a medicament for the treatment of a disease or condition mediated by DGAT1. The invention also provides a compound of formula (I) for use in treating a disease or condition mediated by DGAT1.

The invention also provides a crystal of DGAT1 and a compound of formula (I). Such crystals can be used for X-ray diffraction studies of DGAT1 inhibition, e.g. to provide atomic structural information in order to aid rational design of further DGAT1 inhibitors.

The DGAT1 inhibitory activity of the compounds of the invention may be demonstrated by the DGAT1 assay disclosed herein (see "DGAT1 Inhibition Assay"). Preferred compounds of the invention have an $IC_{50}$ in the DGAT1 Inhibition Assay of <100 µM, in one embodiment <10 µM, in another embodiment <1 µM, in another embodiment <100 nM, and in another embodiment <10 nM.

Diseases and Conditions Mediated by DGAT1

The invention is useful for the treatment of a disease or condition mediated by DGAT1. Diseases and conditions mediated by DGAT1 include: metabolic disorders such as obesity, diabetes (e.g. Type II diabetes), anorexia nervosa, bulimia, cachexia, syndrome X, insulin resistance, glucose tolerance, hypoglycemia, hyperglycemia, hyperuricemia, hyperinsulinemia, hypercholesterolemia, hyperlipidemia, dyslipidemia, mixed dyslipidemia, hypertriglyceridemia, pancreatitis, and nonalcoholic fatty liver disease; cardiovascular diseases, such as atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, and vascular stenosis; neoplastic diseases, such as solid tumors, skin cancer, melanoma, lymphoma, and endothelial cancers, for example, breast cancer, lung cancer, colorectal cancer, stomach cancer, other cancers of the gastrointestinal tract (e.g. esophageal cancer and pancreatic cancer), prostate cancer, kidney cancer, liver cancer, bladder cancer, cervical cancer, uterine cancer, testicular cancer, and ovarian cancer; dermatological conditions, such as acne vulgaris.

One embodiment, the disease or condition mediated by DGAT1 is impaired glucose tolerance (IGT), Type II diabetes or obesity.

As used herein a patient is suffering from "obesity" if the patient exhibits at least one of:
  a body mass index (BMI), i.e. the patient's mass (in kg) divided by the square of the patient's height (in m), of 30 or more;
  an absolute waist circumference of >102 cm in men or >88 cm in women;
  a waist-to-hip ratio >0.9 in men or >0.85 in women; or
  a percent body fat >25% in men or >30% in women.

As used herein a patient is suffering from "Type II diabetes" if they meet the World Health Organisation criteria for Diabetes diagnosis (Definition and diagnosis of diabetes mellitus and intermediate hyperglycaemia, WHO, 2006), i.e. the patient exhibits at least one of:
  a fasting plasma glucose ≥7.0 mmol/l (126 mg/dl); or
  a venous plasma glucose ≥11.1 mmol/l (200 mg/dl) 2 hours after ingestion of 75 g oral glucose load.

As used herein a patient is suffering from "IGT" if they meet the World Health Organisation criteria for IGT diagnosis (Definition and diagnosis of diabetes mellitus and intermediate hyperglycaemia, WHO, 2006), i.e. the patient exhibits both of:
  a fasting plasma glucose <7.0 mmol/l (126 mg/dl); and
  a venous plasma glucose ≥7.8 and <11.1 mmol/l (200 mg/dl) 2 hours after ingestion of 75 g oral glucose load.

In yet another aspect, the invention is useful as an anorectic.

Therapeutic Definitions

As used herein, "treatment" includes curative and prophylactic treatment. As used herein, a "patient" means an animal, preferably a mammal, preferably a human, in need of treatment.

The amount of the compound of the invention administered should be a therapeutically effective amount where the compound or derivative is used for the treatment of a disease or condition and a prophylactically effective amount where the compound or derivative is used for the prevention of a disease or condition.

The term "therapeutically effective amount" used herein refers to the amount of compound needed to treat or ameliorate a targeted disease or condition. The term "prophylactically effective amount" used herein refers to the amount of compound needed to prevent a targeted disease or condition. The exact dosage will generally be dependent on the patient's status at the time of administration. Factors that may be taken into consideration when determining dosage include the severity of the disease state in the patient, the general health of the patient, the age, weight, gender, diet, time, frequency and route of administration, drug combinations, reaction sensitivities and the patient's tolerance or response to therapy. The precise amount can be determined by routine experimentation, but may ultimately lie with the judgement of the clinician. Generally, an effective dose will be from 0.01 mg/kg/day (mass of drug compared to mass of patient) to 1000 mg/kg/day, e.g. 1 mg/kg/day to 100 mg/kg/day. Compositions may be administered individually to a patient or may be administered in combination with other agents, drugs or hormones.

Administration & Formulation

General

For pharmaceutical use, the compounds of the invention may be administered as a medicament by enteral or parenteral routes, including intravenous, intramuscular, subcutaneous, transdermal, airway (aerosol), oral, intranasal, rectal, vaginal and topical (including buccal and sublingual) administration. The compounds of formula (I) should be assessed for their biopharmaceutical properties, such as solubility and solution stability (across pH), permeability, etc., in order to select the most appropriate dosage form and route of administration for treatment of the proposed indication.

The compounds of the invention may be administered as crystalline or amorphous products. The compounds of the invention may be administered alone or in combination with one or more other compounds of the invention or in combination with one or more other drugs (or as any combination thereof). Generally, they will be administered as a formulation in association with one or more pharmaceutically acceptable excipients. The term "excipient" includes any ingredient other than the compound(s) of the invention which may impart either a functional (e.g. drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form. Typical pharmaceutically acceptable excipients include:

diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

A thorough discussion of pharmaceutically acceptable excipients is available in Gennaro, *Remington: The Science and Practice of Pharmacy* 2000, 20th edition (ISBN: 0683306472).

Accordingly, in one embodiment, the present invention provides a pharmaceutical composition comprising a compound of formula (I) and a pharmaceutically acceptable excipient.

Oral Administration

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

Formulations suitable for oral administration may also be designed to deliver the compounds of formula (I) in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, *Expert Opinion in Therapelutic Patents* 2001, 11(6): 981-986.

The formulation of tablets is discussed in H. Lieberman and L. Lachman, *Pharmaceutical Dosage Forms: Tablets* 1980, vol. 1 (Marcel Dekker, New York).

Parenteral Administration

The compounds of the invention can be administered parenterally.

The compounds of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of co-solvents and/or solubility-enhancing agents such as surfactants, micelle structures and cyclodextrins.

Inhalation & Intranasal Administration

The compounds of the invention can be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, for example, PGLA. Modified release formulations include delayed-, sustained-, pulsed-, controlled-, targeted and programmed release.

Transdermal Administration

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Combination Therapy

The compound of formula (I) may be administered alone, or may be administered in combination with another therapeutic agent (i.e. a different agent to the compound of formula (I)). Preferably, the compound of the invention and the other therapeutic agent are administered in a therapeutically effective amount.

The compound of the present invention may be administered either simultaneously with, or before or after, the other therapeutic agent. The compound of the present invention may be administered separately, by the same or different route of administration, or together in the same pharmaceutical composition.

In one embodiment, the invention provides a product comprising a compound of formula (I) and another therapeutic agent as a combined preparation for simultaneous, separate or sequential use in therapy. In one embodiment, the therapy is the treatment of a disease or condition mediated by DGAT1. Products provided as a combined preparation include a composition comprising the compound of formula (I) and the other therapeutic agent together in the same pharmaceutical composition, or the compound of formula (I) and the other therapeutic agent in separate form, e.g. in the form of a kit.

In one embodiment, the invention provides a pharmaceutical composition comprising a compound of formula (I) and another therapeutic agent. Optionally, the pharmaceutical composition may comprise a pharmaceutically acceptable excipient, as described above in "Administration & Formulation".

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) in the manufacture of a medicament for treating a disease or condition mediated by DGAT1, wherein the medicament is prepared for administration with another therapeutic agent. The invention also provides the use of a another therapeutic agent in the manufacture of medicament for treating a disease or condition mediated by DGAT1, wherein the medicament is prepared for administration with a compound of formula (I).

The invention also provides a compound of formula (I) for use in a method of treating a disease or condition mediated by DGAT1,wherein the compound of formula (I) is prepared for administration with another therapeutic agent. The invention also provides another therapeutic agent for use in a method of treating a disease or condition mediated by DGAT1, wherein the other therapeutic agent is prepared for administration with a compound of formula (I). The invention also provides a compound of formula (I) for use in a method of treating a disease or condition mediated by DGAT1, wherein the compound of formula (I) is administered with another therapeutic agent. The invention also provides another therapeutic agent for use in a method of treating a disease or condition mediated by DGAT1,wherein the other therapeutic agent is administered with a compound of formula (I).

The invention also provides the use of a compound of formula (I) in the manufacture of a medicament for treating a disease or condition mediated by DGAT1,wherein the patient has previously (e.g. within 24 hours) been treated with another therapeutic agent. The invention also provides the use of another therapeutic agent in the manufacture of a medicament for treating a disease or condition mediated by DGAT1, wherein the patient has previously (e.g. within 24 hours) been treated with a compound of formula (I).

In one embodiment, the other therapeutic agent is selected from:
antidiabetic agents, such as insulin, insulin derivatives and mimetics; insulin secretagogues such as the sulfonylureas, e.g. Glipizide, glyburide and Amaryl; insulinotropic sulfonylurea receptor ligands such as meglitinides, e.g. nateglinide and repaglinide; protein tyrosine phosphatase-1B (PTP-1B) inhibitors such as PTP-112; Cholesteryl ester transfer protein (CETP) inhibitors such as torcetrapib, GSK3 (glycogen synthase kinase-3) inhibitors such as SB-517955, SB-4195052, SB-216763, NN-57-05441 and NN-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as vildagliptin;
hypolipidemic agents such as 3-hydroxy-3-methyl-glutaryl coenzyme A (HMG-CoA) reductase inhibitors, e.g. lovastatin, pitavastatin, simvastatin, pravastatin, cerivastatin, mevastatin, velostatin, fluvastatin, dalvastatin, atorvastatin, rosuvastatin and rivastatin, squalene synthase inhibitors; FXR (farnesoid X receptor) and LXR (liver X receptor) ligands; cholestyramine; fibrates; nicotinic acid and aspirin;
anti-obesity agents such as orlistat or rimonabant;
anti-hypertensive agents, e.g. loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as ditekiren, zankiren, terlakiren, aliskiren, RO 66-1132 and RO-66-1168; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors;
agonists of peroxisome proliferator-activator receptors, such as fenofibrate, pioglitazone, rosiglitazone, tesaglitazar, BMS-298585, L-796449, the compounds specifically described in the patent application WO 2004/103995 i.e. compounds of examples 1 to 35 or compounds specifically listed in claim 21, or the compounds specifically described in the patent application WO 03/043985 i.e. compounds of examples 1 to 7 or compounds specifically listed in claim 19 and especially (R)-1-{4-[5-methyl-2-(4-trifluoromethyl-phenyl)-oxazol-4-ylmethoxy]-benzenesulfonyl}-2,3-dihydro-1H-indole-2-carboxylic or a salt thereof; and
the specific anti-diabetic compounds described in *Expert Opin Investig Drugs* 2003, 12(4): 623-633, FIGS. 1 to 7.

General Methods of Preparation

Specific methods for the preparation of the compounds of the invention are disclosed in detail below in the Examples.

In general compounds of formula (I) may be prepared by the reaction schemes described below.

In Scheme 1, compounds of formula (3) are assembled from carboxylic acids (1) and amino esters (2) by amide bond formation, followed by ester hydrolysis. Compounds of formula (5) are then obtained from acylamino acids (3) and aromatic amines (4) by amide bond formation. Conditions for amide bond formation include, but not limited to, HATU/DIET in a suitable solvent such as, but not limited to, DMF. Conditions for ester hydrolysis include, but not limited to, LiOH in a suitable solvent such as, but not limited to, THF/water.

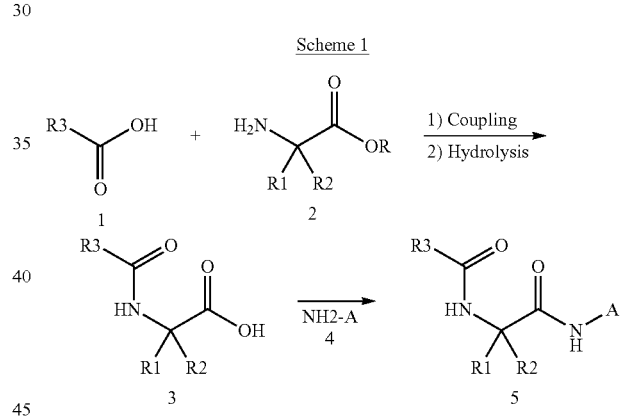

Scheme 1

In Scheme 2, compounds of formula (7) are assembled from N-protected amino acid (PG=protecting group) (X=OH) (6) or hydrochloride salt of amino acid chloride ($R_3$=H, X=Cl) (6) and aromatic amines (4), followed by removal of PG group by standard deprotection conditions. Coupling of compounds (7) with carboxylic acids (X=OH) (9) or acid chloride (X=Cl) (9) by standard conditions for amide bond formation as described in Scheme 1 provides compounds of formula (10). Coupling of compounds (7) with sulfonyl chloride (11) by standard conditions for sulfonamide bond formation such as, but not limited to, $Et_3N$ in a suitable solvent such as, but not limited to, dichloromethane provides compounds of formula (12). Coupling of compounds (7) with isocyanates (13) by standard conditions for urea bond formation in a suitable solvent such as, but not limited to, dichloromethane provides compounds of formula (15). Compounds of formula (15) are alternatively obtained by isocyanate formation from amines (7) to compounds (8) using reagents such as, but not limited to, triphosgene/$K_2CO_3$ in a suitable solvent such as, but not limited to, dichloromethane/water, followed by addition of amines (14) to isocyanates (8) in a suitable solvent such as, but not limited to, pyridine.

Scheme 2

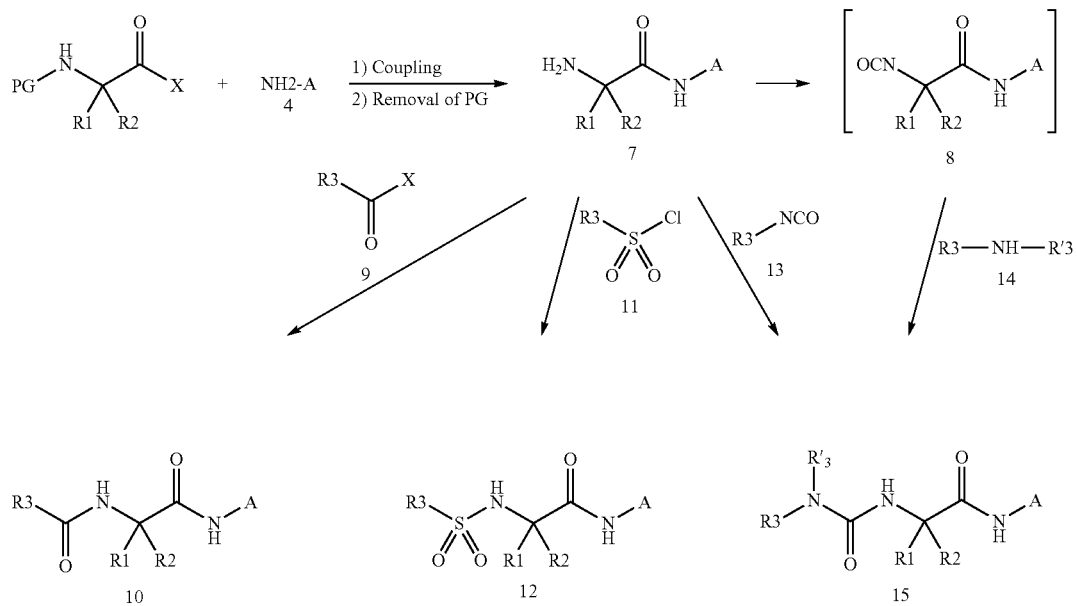

In Scheme 3, compounds of formula (17) are assembled from N-protected amino acid (PG=protecting group) (16) and aromatic amines (4), followed by removal of PG group by standard deprotection conditions. Coupling of compounds (17) with carboxylic acids (X=OH) (9) or acid chloride (X=Cl) (9) by standard conditions for amide bond formation as described in Scheme 1 provides compounds of formula (18). Coupling of compounds (17) with isocyanates (10) by standard conditions for urea bond formation in a suitable solvent such as, but not limited to, dichloromethane provides compounds of formula (19).

In Scheme 4, following a literature procedure for general method of β-lactam formation with aromatic amines [*Tetrahedron Lett.* 2000, 41, 1141] compounds of formula (21) are assembled from lactone (20) and aromatic amines (4). Deprotection of lactams (21) with TFA provides amines (22). Coupling of compounds (22) with carboxylic acids (X=OH) (9) or acid chloride (X=Cl) (9) by standard conditions for amide bond formation as described in Scheme 1 provides compounds of formula (23). Compounds of formula (24) are obtained from amines (22) by standard conditions for urea bond formation as described in Scheme 1.

Scheme 3

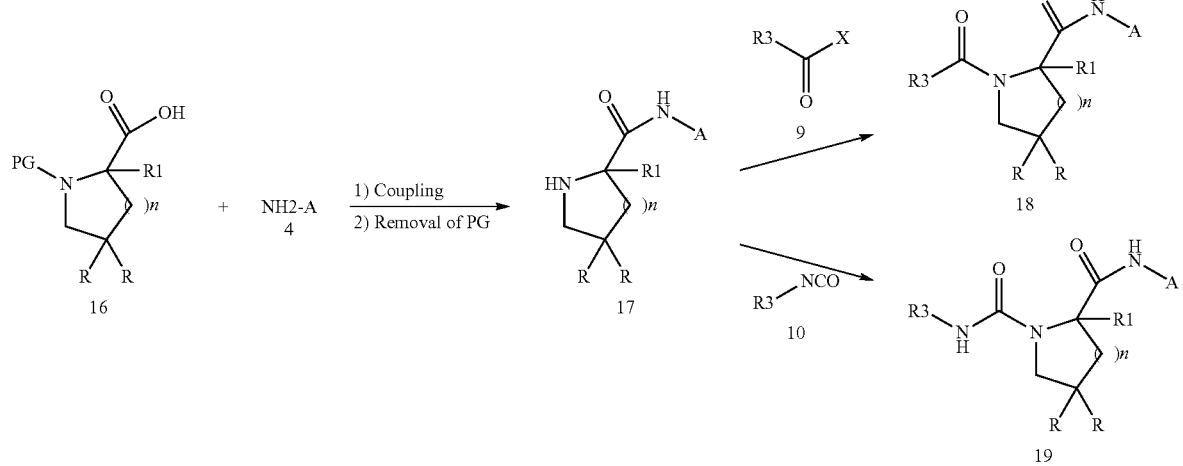

Scheme 4

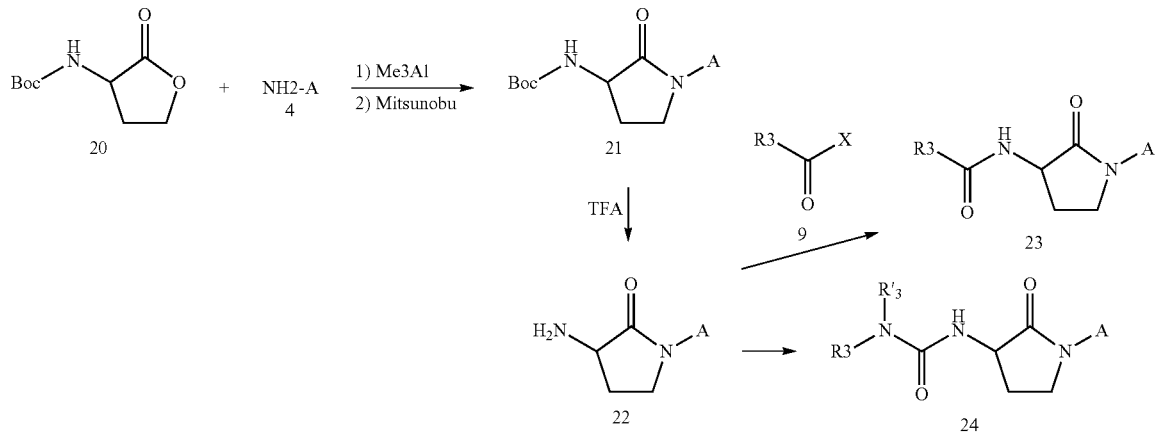

Compounds of formula (I) may be prepared from other compounds of formula (I) by well-known methods.

Chemical Groups

Halo

The term "halogen" (or "halo") includes fluorine, chlorine, bromine and iodine.

Alkyl, alkylene, alkenyl, alkynyl, cycloalkyl etc.

The terms "alkyl", "alkylene", "alkenyl", or "alkynyl" are used herein to refer to both straight and branched chain acyclic forms. Cyclic analogues thereof are referred to as cycloalkyl, etc.

The term "alkyl" includes monovalent, straight or branched, saturated, acyclic hydrocarbyl groups. In one embodiment alkyl is $C_{1-10}$alkyl, in another embodiment $C_{1-6}$alkyl, in another embodiment $C_{1-4}$alkyl, such as methyl, ethyl, n-propyl, i-propyl or t-butyl groups.

The term "cycloalkyl" includes monovalent, saturated, cyclic hydrocarbyl groups. In one embodiment cycloalkyl is $C_{3-10}$cycloalkyl, in another embodiment $C_{3-6}$cycloalkyl such as cyclopentyl and cyclohexyl.

The term "alkoxy" means alkyl-O—.

The term "alkenyl" includes monovalent, straight or branched, unsaturated, acyclic hydrocarbyl groups having at least one carbon-carbon double bond and, in one embodiment, no carbon-carbon triple bonds. In one embodiment alkenyl is $C_{2-10}$alkenyl, in another embodiment $C_{2-6}$alkenyl, in another embodiment $C_{2-4}$alkenyl.

The term "cycloalkenyl" includes monovalent, partially unsaturated, cyclic hydrocarbyl groups having at least one carbon-carbon double bond and, in one embodiment, no carbon-carbon triple bonds. In one embodiment cycloalkenyl is $C_{3-10}$cycloalkenyl, in another embodiment $C_{5-10}$cycloalkenyl, e.g. cyclohexenyl or benzocyclohexyl.

The term "alkynyl" includes monovalent, straight or branched, unsaturated, acyclic hydrocarbyl groups having at least one carbon-carbon triple bond and, in one embodiment, no carbon-carbon double bonds. In one embodiment, alkynyl is $C_{2-10}$alkynyl, in another embodiment $C_{2-6}$alkynyl, in another embodiment $C_{2-4}$alkynyl.

The term "alkylene" includes divalent, straight or branched, saturated, acyclic hydrocarbyl groups. In one embodiment alkylene is $C_{1-10}$alkylene, in another embodiment $C_{1-6}$alkylene, in another embodiment $C_{1-4}$alkylene, such as methylene, ethylene, n-propylene, i-propylene or t-butylene groups.

The term "alkenylene" includes divalent, straight or branched, unsaturated, acyclic hydrocarbyl groups having at least one carbon-carbon double bond and, in one embodiment, no carbon-carbon triple bonds. In one embodiment alkenylene is $C_{2-10}$alkenylene, in another embodiment $C_{2-6}$alkenylene, in another embodiment $C_{2-4}$alkenylene.

Heteroalkyl etc.

The term "heteroalkyl" includes alkyl groups in which up to three carbon atoms, in one embodiment up to two carbon atoms, in another embodiment one carbon atom, are each replaced independently by O, $S(O)_q$ or N, provided at least one of the alkyl carbon atoms remains. The heteroalkyl group may be C-linked or hetero-linked, i.e. it may be linked to the remainder of the molecule through a carbon atom or through O, $S(O)_q$ or N.

The term "heterocycloalkyl" includes cycloalkyl groups in which up to three carbon atoms, in one embodiment up to two carbon atoms, in another embodiment one carbon atom, are each replaced independently by O, $S(O)_q$ or N, provided at least one of the cycloalkyl carbon atoms remains. Examples of heterocycloalkyl groups include oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl and 1,4-diazepanyl. The heterocycloalkyl group may be C-linked or N-linked, i.e. it may be linked to the remainder of the molecule through a carbon atom or through a nitrogen atom.

The term "heteroalkenyl" includes alkenyl groups in which up to three carbon atoms, in one embodiment up to two carbon atoms, in another embodiment one carbon atom, are each replaced independently by O, $S(O)_q$ or N, provided at least one of the alkenyl carbon atoms remains. The heteroalkenyl group may be C-linked or hetero-linked, i.e. it may be linked to the remainder of the molecule through a carbon atom or through O, $S(O)_q$ or N.

The term "heterocycloalkenyl" includes cycloalkenyl groups in which up to three carbon atoms, in one embodiment up to two carbon atoms, in another embodiment one carbon atom, are each replaced independently by O, $S(O)_q$ or N, provided at least one of the cycloalkenyl carbon atoms remains. Examples of heterocycloalkenyl groups include 3,4- dihydro-2H-pyranyl, 5-6-dihydro-2H-pyranyl, 2H-pyranyl, 1,2,3,4-tetrahydropyridinyl and 1,2,5,6-tetrahydropyridinyl. The heterocycloalkenyl group may be C-linked or N-linked, i.e. it may be linked to the remainder of the molecule through a carbon atom or through a nitrogen atom.

The term "heteroalkynyl" includes alkynyl groups in which up to three carbon atoms, in one embodiment up to two carbon atoms, in another embodiment one carbon atom, are each replaced independently by O, $S(O)_q$ or N, provided at least one of the alkynyl carbon atoms remains. The heteroalkynyl group may be C-linked or hetero-linked, i.e. it may be linked to the remainder of the molecule through a carbon atom or through O, $S(O)_q$ or N.

The term "heteroalkylene" includes alkylene groups in which up to three carbon atoms, in one embodiment up to two carbon atoms, in another embodiment one carbon atom, are each replaced independently by O, $S(O)_q$ or N, provided at least one of the alkylene carbon atoms remains.

The term "heteroalkenylene" includes alkenylene groups in which up to three carbon atoms, in one embodiment up to two carbon atoms, in another embodiment one carbon atom, are each replaced independently by O, $S(O)_q$ or N, provided at least one of the alkenylene carbon atoms remains.

Aryl

The term "aryl" includes monovalent, aromatic, cyclic hydrocarbyl groups, such as phenyl or naphthyl (e.g. 1-naphthyl or 2-naphthyl). In general, the aryl groups may be monocyclic or polycyclic fused ring aromatic groups. Preferred aryl are $C_6$-$C_{14}$aryl.

Other examples of aryl groups are monovalent derivatives of aceanthrylene, acenaphthylene, acephenanthrylene, anthracene, azulene, chrysene, coronene, fluoranthene, fluorene, as-indacene, s-indacene, indene, naphthalene, ovalene, perylene, phenalene, phenanthrene, picene, pleiadene, pyrene, pyranthrene and rubicene.

The term "arylalkyl" means alkyl substituted with an aryl group, e.g. benzyl.

Heteroaryl

The term "heteroaryl" includes monovalent, heteroaromatic, cyclic hydrocarbyl groups additionally containing one or more heteroatoms independently selected from O, S, N and $NR^N$, where $R^N$ is defined below (and in one embodiment is H or alkyl (e.g. $C_{1-6}$alkyl)).

In general, the heteroaryl groups may be monocyclic or polycyclic (e.g. bicyclic) fused ring heteroaromatic groups. In one embodiment, heteroaryl groups contain 5-13 ring members (preferably 5-10 members) and 1, 2, 3 or 4 ring heteroatoms independently selected from O, S, N and $NR^N$. In one embodiment, a heteroaryl group may be 5, 6, 9 or 10 membered, e.g. 5-membered monocyclic, 6-membered monocyclic, 9-membered fused-ring bicyclic or 10-membered fused-ring bicyclic.

Monocyclic heteroaromatic groups include heteroaromatic groups containing 5-6 ring members and 1, 2, 3 or 4 heteroatoms selected from O, S, N or $NR^N$.

In one embodiment, 5-membered monocyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 5 ring members are carbon atoms).

Examples of 5-membered monocyclic lieteroaryl groups are pyrrolyl, furanyl, thiophenyl, pyrazolyl, imidazolyl, isoxazolyl, oxazolyl, isothiazolyl, thiazolyl, 1,2,3 triazolyl, 1,2,4 triazolyl, 1,2,3 oxadiazolyl, 1,2,4 oxadiazolyl, 1,2,5 oxadiazolyl, 1,3,4 oxadiazolyl, 1,3,4 thiadiazolyl, pyridyl, pyrimidinyl, pyridazinyl, pyrazinyl, 1,3,5 triazinyl, 1,2,4 triazinyl, 1,2,3 triazinyl and tetrazolyl.

Examples of 6-membered monocyclic heteroaryl groups are pyridinyl, pyridazinyl, pyrimidinyl and pyrazinyl.

In one embodiment, 6-membered monocyclic heteroaryl groups contain 1 or 2 ring members which are =N— atoms (where the remainder of the 6 ring members are carbon atoms).

Bicyclic heteroaromatic groups include fused-ring heteroaromatic groups containing 9-13 ring members and 1, 2, 3, 4 or more heteroatoms selected from O, S, N or $NR^N$.

In one embodiment, 9-membered bicyclic heteroaryl groups contain 1 ring member which is an —$NR^N$— group, an —O— atom or an —S— atom and, optionally, 1-3 ring members (e.g. 1 or 2 ring members) which are =N— atoms (where the remainder of the 9 ring members are carbon atoms).

Examples of 9-membered fused-ring bicyclic heteroaryl groups are benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolininyl, imidazo[1,2-a]pyridinyl, imidazo[1,5-a]pyridinyl, pyrazolo[1,2-a]pyridinyl, pyrrolo[1,2-b]pyridazinyl and imidazo[1,2-c]pyrimidinyl.

In one embodiment, 10-membered bicyclic heteroaryl groups contain 1-3 ring members which are =N— atoms (where the remainder of the 10 ring members are carbon atoms).

Examples of 10-membered fused-ring bicyclic heteroaryl groups are quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl and pyrimido[4,5-d]pyrimidinyl.

The term "heteroarylalkyl" means alkyl substituted with a heteroaryl group.

General

Unless indicated explicitly otherwise, where combinations of groups are referred to herein as one moiety, e.g. arylalkyl, the last mentioned group contains the atom by which the moiety is attached to the rest of the molecule.

Where reference is made to a carbon atom of an alkyl group or other group being replaced by O, $S(O)_q$ or N, what is intended is that:

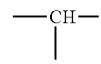

is replaced by

—CH= is replaced by —N=.
=C—H is replaced by =N; or

—CH$_2$— is replaced by —O—, —S(O)$_q$— or —NR$^N$—, where R$^N$ is H, alkyl, cycloalkyl, aryl, heteroaryl, —C(O)-alkyl, —C(O)-aryl, —C(O)-heteroaryl, —S(O)$_q$-alkyl, —S(O)$_q$-aryl or —S(O)$_q$-heteroaryl. R$^N$ is preferably H, alkyl (e.g. C$_{1-6}$alkyl) or cycloalkyl (e.g. C$_{3-6}$cycloalkyl). q is independently 0, 1 or 2. In one embodiment, q is 0.

By way of clarification, in relation to the above mentioned heteroatom containing groups (such as heteroalkyl etc.), where a numerical of carbon atoms is given, for instance C$_{3-6}$heteroalkyl, what is intended is a group based on C$_{3-6}$alkyl in which one of more of the 3-6 chain carbon atoms is replaced by O, S(O)$_q$ or N. Accordingly, a C$_{3-6}$heteroalkyl group, for example, will contain less than 3-6 chain carbon atoms.

Substitution

Groups of the compounds of the invention (e.g. alkyl, cycloalkyl, alkoxy, alkenyl, cycloalkenyl, alkynyl, alkylene, alkenylene, heteroalkyl, heterocycloalkyl, heteroalkenyl, heterocycloalkenyl, heteroalkynyl, heteroalkylene, heteroalkenylene aryl, arylalkyl, arylheteroalkyl, heteroaryl, heteroarylalkyl or heteroarylheteroalkyl groups etc.) may be substituted or unsubstituted, in one embodiment unsubstituted. Typically, substitution involves the notional replacement of a hydrogen atom with a substituent group, or two hydrogen atoms in the case of substitution by =O.

Where substituted, there will generally be 1 to 5 substituents on each group, in one embodiment 1 to 3 substituents, in one embodiment 1 or 2 substituents, in one embodiment 1 substituent.

In one embodiment, the substituent(s) is/are independently Sub$^1$ or Sub$^2$ (in one embodiment Sub$^2$) wherein:

Sub$^1$ is independently halogen, trihalomethyl, trihaloethyl, —NO$_2$, —CN, —N$^+$(R$^s$)$_2$O$^-$, —CO$_2$H, —CO$_2$R$^s$, —SO$_3$H, —SOR$^s$, —SO$_2$R$^s$, —SO$_3$R$^s$, —OC(=O)OR$^s$, —C(=O)H, —C(=O)R$^s$, —OC(=O)R$^s$, =O, —NR$^s_2$, —C(=O)NH$_2$, —C(=O)NR$^s_2$, —N(R$^s$)C(=O)OR$^s$, —N(R$^s$)C(=O)NR$^s_2$, —OC(=O)NR$^s_2$, —N(RS)C(=O)R$^s$, —C(=S)NR$^s_2$, —NR$^s$C(=S)R$^s$, —SO$_2$NR$^s_2$, —NR$^s$SO$_2$R$^s$, —N(R$^s$)C(=S)NR$^s_2$, —N(R$^s$)SO$_2$NR$^s_2$, —R$^s$ or —Z$^s$R$^s$, wherein;

Z$^s$ is independently O, S or NR$^s$;

R$^s$ is independently H or C$_{1-6}$alkyl, C$_{1-6}$heteroalkyl, -(Alk$^a$)$_f$-C$_{3-6}$cycloalkyl, -(Alk$^a$)$_f$-C$_{3-6}$heterocycloalkyl, C$_{2-6}$alkenyl, C$_{2-6}$heteroalkenyl, -(Alk$^a$)$_f$-C$_{3-6}$cycloalkenyl, -(Alk$^a$)$_f$-C$_{3-6}$heterocycloalkenyl, C$_{2-6}$alkynyl, C$_{2-6}$heteroalkynyl, -(Alk$^a$)$_f$-C$_{6-14}$aryl, -(Alk$^a$)$_f$-C$_{6-14}$aryl or -(Alk$^a$)$_f$-heteroaryl (where heteroaryl contains 5-13 ring members), where f is 0 or 1;

Alk$^a$ is C$_{1-6}$alkylene or C$_{1-6}$heteroalkylene; and

R$^s$ is optionally substituted itself (in one embodiment unsubstituted) by 1 to 3 substituents Sub$^2$;

Sub$^2$ is independently halogen, trihalomethyl, trihaloethyl, —NO$_2$, —CN, —N$^+$(C$_{1-6}$alkyl)$_2$O$^-$, —CO$_2$H, —CO$_2$C$_{1-6}$alkyl, —SO$_3$H, —SOC$_{1-6}$alkyl, —SO$_2$C$_{1-6}$alkyl, —SO$_3$C$_{1-6}$alkyl, —OC(=O)OC$_{1-6}$alkyl, —C(=O)H, —C(=O)C$_{1-6}$alkyl, —OC(=O)C$_{1-6}$alkyl, =O, —N(C$_{1-6}$alkyl)$_2$, —C(=O)NH$_2$, —C(=O)N(C$_{1-6}$alkyl)$_2$, —N(C$_{1-6}$alkyl)C(=O)O(C$_{1-6}$alkyl), —N(C$_{1-6}$alkyl)C(=O)N(C$_{1-6}$alkyl)$_2$, —OC(=O)N(C$_{1-6}$alkyl)$_2$, —N(C$_{1-6}$alkyl)C(=O)C$_{1-6}$alkyl, —C(=S)N(C$_{1-6}$alkyl)$_2$, —N(C$_{1-6}$alkyl)C(=S)C$_{1-6}$alkyl, —SO$_2$N(C$_{1-6}$alkyl)$_2$, —N(C$_{1-6}$alkyl)SO$_2$C$_{1-6}$alkyl, —N(C$_{1-6}$alkyl)C(=S)N(C$_{1-6}$alkyl)$_2$, —N(C$_{1-6}$alkyl)SO$_2$N(C$_{1-6}$alkyl)$_2$, —C$_{1-6}$alkyl, —C$_{1-6}$heteroalkyl, —C$_{3-6}$cycloalkyl, —C$_{3-6}$heterocycloalkyl, —C$_{2-6}$alkenyl, —C$_{2-6}$heteroalkenyl, —C$_{3-6}$cycloalkenyl, —C$_{3-6}$heterocycloalkenyl, —C$_{2-6}$alkynyl, —C$_{2-6}$heteroalkynyl, —Z$^t$—C$_{1-6}$alkyl, —Z$^t$—C$_{3-6}$cycloalkyl, —Z$^t$—C$_{2-6}$alkenyl, —Z$^t$—C$_{3-6}$cycloalkenyl, or —Z$^t$—C$_{2-6}$alkynyl; and Z$^t$ is independently O, S, NH or N(C$_{1-6}$alkyl).

While R$^s$ in Sub$^1$ can be optionally substituted by 1 to 3 substituents Sub$^2$, Sub$^2$ is unsubstituted. However, in one embodiment, R$^s$ is unsubstituted.

In one embodiment, R$^s$ is H or C$_{1-6}$alkyl, optionally substituted by 1 to 3 substituents Sub$^2$.

In one embodiment, Sub$^2$ is independently halogen, trihalomethyl, trihaloethyl, —NO$_2$, —CN, —N$^+$(C$_{1-6}$alkyl)$_2$O$^-$, —CO$_2$H, —SO$_3$H, —SOC$_{1-6}$alkyl, —SO$_2$C$_{1-6}$alkyl, —C(=O)H, —C(=O)C$_{1-6}$alkyl, =O, —N(C$_{1-6}$alkyl)$_2$, —C(=O)NH$_2$, —C$_{1-6}$alkyl, —C$_{3-6}$cycloalkyl, —C$_{3-6}$heterocycloalkyl. —Z$^t$—C$_{1-6}$alkyl or —Z$^t$—C$_{3-6}$cycloalkyl.

In one embodiment, where the substituted group is acyclic (e.g. alkyl, heteroalkyl, alkenyl etc.), Sub$^1$ is not —R$^s$ and Sub$^2$ is not —C$_{1-6}$alkyl, —C$_{1-6}$heteroalkyl, —C$_{2-6}$alkenyl, —C$_{2-6}$heteroalkenyl, —C$_{2-6}$alkynyl or —C$_{2-6}$heteroalkynyl.

Where a group has at least 2 positions which may be substituted, the group may be substituted by both ends of an alkylene or heteroalkylene chain to form a cyclic moiety.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

MODES FOR CARRYING OUT THE INVENTION

The following Examples are intended to illustrate the invention and are not to be construed as being limitations thereon. If not mentioned otherwise, all evaporations are performed under reduced pressure, between about 50 mmHg and 100 mmHg. The structure of final products, intermediates and starting materials is confirmed by standard analytical methods, e.g., microanalysis, melting point (m.p.) and spectroscopic characteristics, e.g. MS, IR and NMR. Abbreviations used are those conventional in the art.

The structural formulae of the examples are shown in Annexe B.

HPLC Conditions:

A: Inertsil 4.6 mm×5 cm C8-3 column, 10-90% acetonitrile in 5 mM ammonium formate, 2 min gradient, 4 mL/min, 50 degrees centigrade or Inertsil 3 mm×3.3 cm C8-3 column, 10-90% acetonitrile in 5 mM ammonium formate, 2.2 min gradient, 2 mL/min, 40 degrees centigrade.

B: Atlantis C18 (Water Inc.) 15 cm×4.6 mm×5 μM, column temperature-ambient, 150 mm C18 column, 40-95% acetonitrile (with 0.05% TFA) in water (with 0.1% TFA) over 20 min.

Example 1-1

N-[1-(5-Benzyl-4-phenyl-thiazol-2-ylcarbamoyl)-1-methyl-ethyl]-3,4-diethoxy-benzamide

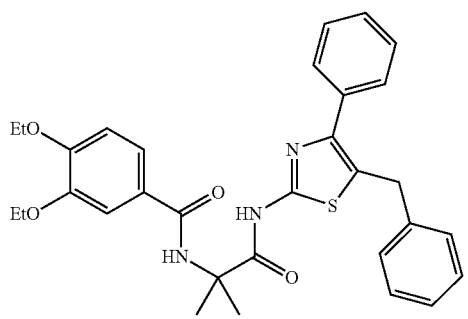 [SMILES: CCOc1ccc(C(=O)NC(C)(C)C(=O)Nc2nc(-c3ccccc3)c(Cc3ccccc3)s2)cc1OCC]

A. 2-(3,4-Diethoxy-benzoylamino)-2-methyl-propionic acid 210 mg of 3,4-diethoxybenzoic acid and 160 mg of methyl aminoisobutyrate were stirred in 3 ml of DMF at room temperature. It was treated with 440 mg of HATU and 0.4 ml of DIEA at the same temperature and the reaction was stirred for 2 days. The reaction was monitored by LC-MS, which indicated complete consumption of the starting materials. Product LC-MS (m/z 310.1). This crude reaction mixture was then diluted with 3 ml of water followed by an addition of 250 mg of LiOH. The reaction mixture was stirred at room temperature overnight and the LC-MS analysis indicated the reaction was completed. The reaction mixture was neutralized by 6N-HCl and the resulting creamy precipitates were collected by filtration and washed with water (50 ml). Drying the filter cake yielded the title compound. m/z 296.1 (MH+).

B. N-[1-(5-Benzyl-4-phenyl-thiazol-2-ylcarbamoyl)-1-methyl-ethyl]-3,4-diethoxy-benzamide 150 mg of 2-(3,4-Diethoxy-benzoylamino)-2-methyl-propionic acid and 130 mg of 5-Benzyl-4-phenyl-thiazol-2-ylamine (WO2006082952) were stirred in 2 ml of acetonitrile at room temperature. 120 mg of EDCl and 100 mg of HOBT were added and the reaction mixture was stirred at 50° C. for 2 days and cooled to room temperature. It was diluted with water and the resulting precipitates were collected by filtration followed by washing with water. The filter cake was then purified by column chromatography (heptane/ethyl acetate=3/1) to provide the title compound. $^1$H NMR (400 MHz. CD$_3$OD) δ 1.34-1.54 (m, 3H) 1.44 (d, J=5.31 Hz, 3H) 1.65 (s, 7H) 4.14 (qd, J=6.95, 2.53 Hz, 4H) 4.23 (s, 2H) 7.01 (d, J=8.46 Hz, 1H) 7.16-7.26 (m, 3H) 7.26-7.45 (m, 6H) 7.47-7.67 (m, 4H). m/z 545.1 (MH+).

Example 1-2

[1-(5-Benzyl-4-phenyl-thiazol-2-ylcarbamoyl)-1-methyl-ethyl]-carbamic acid tert-butyl ester

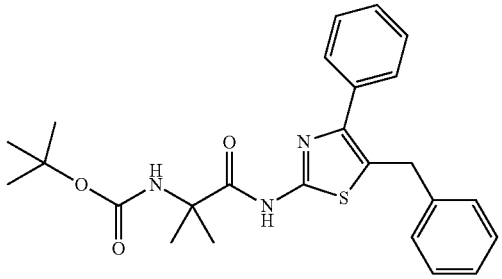 [SMILES: CC(C)(C)OC(=O)NC(C)(C)C(=O)Nc1nc(-c2ccccc2)c(Cc2ccccc2)s1]

The title compound was prepared analogously to Example 1-1. 1H NMR (400 MHz, DMSO-D6) δ 1.28-1.39 (m, 15H) 4.22 (s, 2H) 7.17-7.26 (m, 3H) 7.33 (dt, J=12.98, 7.34 Hz, 3H) 7.43 (t, J=7.52 Hz, 2H) 7.57-7.64 (m, 2H). m/z 452.2 (MH+).

Example 1-3

2-Amino-N-(5-benzyl-4-phenyl-thiazol-2-yl)-2-methyl-propionamide

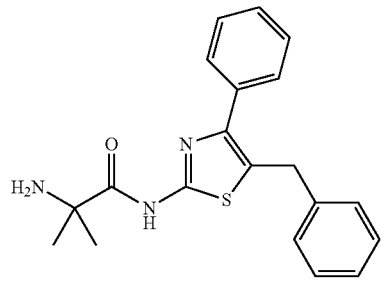 [SMILES: CC(C)(N)C(=O)Nc1nc(-c2ccccc2)c(Cc2ccccc2)s1]

[1-(5-Benzyl-4-phenyl-thiazol-2-ylcarbamoyl)-1-methyl-ethyl]-carbamic acid tert-butyl ester (6.4 g) was stirred overnight in freshly prepared HCl (g)/EtOAc solution (150 mL). Evaporation of the solvent gave the title compound as the hydrochloride salt. 1H NMR (400 MHz, DMSO-D6) δ 1.62 (s, 6H) 4.24 (s, 2H) 7.16-7.25 (m, 3H) 7.30 (d, J=7.58 Hz, 2H) 7.37 (s, 1H) 7.41-7.47 (m, 2H) 7.58-7.63 (m, 2H) 8.64 (s, 3H). m/z 352.1 (MH+).

Example 1-4

N-[1-(5-Benzyl-4-phenyl-thiazol-2-ylcarbamoyl)-1-methyl-ethyl]-3,5-dimethoxy-benzamide

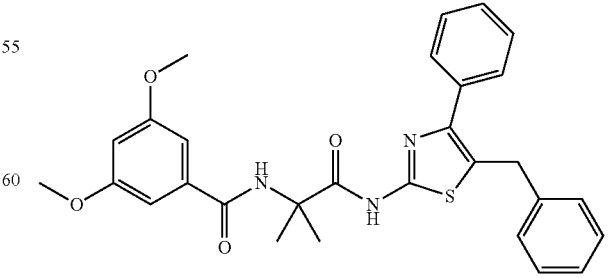

2-Amino-N-(benzyl-4-phenyl-thiazol-2-yl)-2-methyl-propionamide (100 mg, 0.3 mmol), 3,5-dimethoxy benzyl C: Atlantis C18 (Water Inc.) 15 cm×4.6 mm×5 µM, column temperature-ambient, 0-95% acetonitrile (with 0.05% TFA) in water (with 0.1% TFA) over 19 min and 1.8 min hold. Flow rate 1.4 mL/min.

chloride (54 mg, 0.3 mmol) and triethyl amine (73 µL, 1 mmol) were stirred as a solution in DCM (5 mL). Purification via HPLC afforded the title compound. 1H NMR (400 MHz, DMSO-D6) δ 1.48 (s, 6H) 3.78 (s, 6H) 4.20 (s, 2H) 5.75 (s, 1H) 6.61-6.67 (m, 1H) 7.10 (d, J=2.27 Hz, 2H) 7.28-7.35 (m, 3H) 7.37-7.42 (m, 2H) 7.53-7.58 (m, 2H) 8.42 (s, 1H) 11.94 (s, 1H). m/z 516.2 (MH$^+$).

Example 1-5

N-(5-Benzyl-4-phenyl-thiazol-2-yl)-2-methyl-2-(3-o-tolyl-ureido)-propionamide

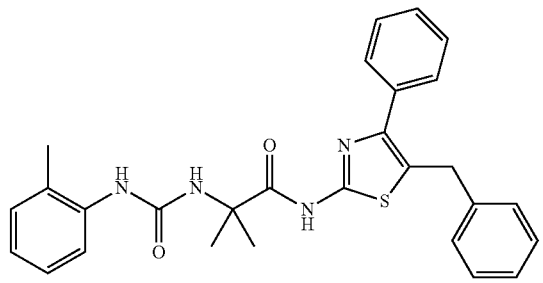 [SMILES: Cc1ccccc1NC(=O)NC(C)(C)C(=O)Nc1nc(-c2ccccc2)c(Cc2ccccc2)s1]

2-Amino-N-(benzyl-4-phenyl-thiazol-2-yl)-2-methyl-propionamide (100 mg, 0.3 mmol) and o-tolyl isocyanate (36 mg, 0.3 mmol) were stirred as a solution in DCM (5 mL). Purification via HPLC afforded the title compound. 1H NMR (400 MHz, CHLOROFORM-D) δ 1.58 (s, 6H) 2.22 (s, 3H) 4.13 (s, 2H) 5.76 (s, 1H) 7.15, (s, 5H) 7.32 (s, 4H) 7.50 (s, 6H). m/z 485.2 (MH$^+$).

Example 1-6

N-(5-Benzyl-4-phenyl-thiazol-2-yl)-2-(4-fluoro-benzenesulfonylamino)-2-methyl-propionamide

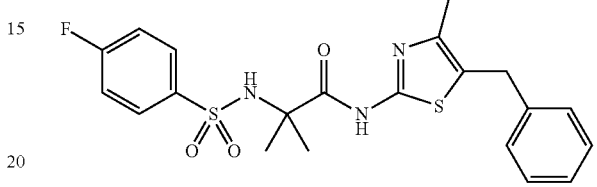

2-Amino-N-(benzyl-4-phenyl-thiazol-2-yl)-2-methyl-propionamide (100 mg, 0.3 mmol), 4-Fluoro-benzensulfonyl chloride (80 mg, 0.4 mmol) and triethyl amine (85 µL, 1 mmol) were stirred a solution in DMF (5 mL). Purification via HPLC afforded the title compound. 1H NMR (400 MHz, DMSO-D6) δ 1.31 (s, 6H) 4.21 (s, 2H) 7.20-7.26 (m, 3H) 7.28-7.39 (m, 5H) 7.45 (s, 2H) 7.62 (d, J=7.07 Hz, 2H) 7.85 (s, 2H) 7.95 (s, 1H) 11.80 (s, 1H). m/z 510.1 (MH$^+$).

Examples 1-7 to 1-66

The following compounds were prepared using similar procedures described above.

| Ex. | Name | LC rt | Method | (M + H)+ |
|---|---|---|---|---|
| 1-7 | N-[1-(5-Benzyl-4-phenyl-thiazol-2-ylcarbamoyl)-1-methyl-ethyl]-3,4-diethoxy-benzamide | 13.6 | C | 570.0 |
| 1-8 | N-[1-(5-Benzyl-4-phenyl-thiazol-2-ylcarbamoyl)-1-methyl-ethyl]-2-methoxy-benzamide | 1.8 | A | 486.2 |
| 1-9 | N-[1-(5-Benzyl-4-phenyl-thiazol-2-ylcarbamoyl)-1-methyl-ethyl]-4-methoxy-benzamide | 1.7 | A | 486.2 |
| 1-10 | N-[1-(5-Benzyl-4-phenyl-thiazol-2-ylcarbamoyl)-1-methyl-ethyl]-4-ethoxy-benzamide | 1.8 | A | 500.2 |
| 1-11 | N-(5-Benzyl-4-phenyl-thiazol-2-yl)-2-[2-(4-methoxy-phenyl)-acetylamino]-2-methyl-propionamide | 1.7 | A | 500.2 |
| 1-12 | Benzo[1,3]dioxole-5-carboxylic acid [1-(5-benzyl-4-phenyl-thiazol-2-ylcarbamoyl)-1-methyl-ethyl]-amide | 1.7 | A | 500.2 |
| 1-13 | N-(5-Benzyl-4-phenyl-thiazol-2-yl)-2-(2-cyclopentyl-acetylamino)-2-methyl-propionamide | 1.8 | A | 462.2 |
| 1-14 | N-(5-Benzyl-4-phenyl-thiazol-2-yl)-2-[3-(2-methoxy-phenyl)-ureido]-2-methyl-propionamide | 1.8 | A | 501.1 |
| 1-15 | N-(5-Benzyl-4-phenyl-thiazol-2-yl)-2-methyl-2-(3-phenyl-propionylamino)-propionamide | 1.8 | A | 484.1 |
| 1-16 | N-[1-(5-Benzyl-4-phenyl-thiazol-2-ylcarbamoyl)-1-methyl-ethyl]-3,4-dimethoxy-benzamide | 1.6 | A | 516.2 |
| 1-17 | N-[1-(5-Benzyl-4-phenyl-thiazol-2-ylcarbamoyl)-1-methyl-ethyl]-3-methoxy-benzamide | 1.7 | A | 486.2 |
| 1-18 | N-[1-(5-Benzyl-4-phenyl-thiazol-2-ylcarbamoyl)-1-methyl-ethyl]-4-dimethylamino-benzamide | 1.7 | A | 499.2 |
| 1-19 | N-(5-Benzyl-4-phenyl-thiazol-2-yl)-2-[3-(2-chloro-phenyl)-ureido]-2-methyl-propionamide | 1.8 | A | 505.1 |
| 1-20 | N-(5-Benzyl-4-phenyl-thiazol-2-yl)-2-[3-(3,4-dihydro-2H-benzo[b][1,4]dioxepin-7-yl)-ureido]-2-methyl-propionamide | 1.6 | A | 543.3 |

| Ex. | Name | LC rt | Method | (M + H)+ |
|---|---|---|---|---|
| 1-21 | N-(5-Benzyl-4-phenyl-thiazol-2-yl)-2-[3-(2,3-dihydro-benzo[1,4]dioxin-6-yl)-ureido]-2-methyl-propionamide | 1.7 | A | 529.2 |
| 1-22 | N-(5-Benzyl-4-phenyl-thiazol-2-yl)-2-[3-(3-cyclopentyloxy-4-methoxy-phenyl)-ureido]-2-methyl-propionamide | 1.8 | A | 585.3 |
| 1-23 | N-[1-(5-Benzyl-4-phenyl-thiazol-2-ylcarbamoyl)-1-methyl-ethyl]-3-chloro-4-methoxy-benzamide | 1.7 | A | 520.1 |
| 1-24 | 2,3-Dihydro-benzo[1,4]dioxine-6-carboxylic acid [1-(5-benzyl-4-phenyl-thiazol-2-ylcarbamoyl)-1-methyl-ethyl]-amide | 1.6 | A | 514.2 |
| 1-25 | N-(5-Benzyl-4-phenyl-thiazol-2-yl)-2-(3-butyl-ureido)-2-methyl-propionamide | 1.7 | A | 451.2 |
| 1-26 | 1-Methyl-1H-imidazole-2-carboxylic acid [1-(5-benzyl-4-phenyl-thiazol-2-ylcarbamoyl)-1-methyl-ethyl]-amide | 1.5 | A | 460.2 |
| 1-27 | 5-tert-Butyl-2-methyl-2H-pyrazole-3-carboxylic acid [1-(5-benzyl-4-phenyl-thiazol-2-ylcarbamoyl)-1-methyl-ethyl]-amide | 1.8 | A | 516.3 |
| 1-28 | Benzofuran-5-carboxylic acid [1-(5-benzyl-4-phenyl-thiazol-2-ylcarbamoyl)-1-methyl-ethyl]-amide | 1.7 | A | 496.2 |
| 1-29 | Pyridine-2-carboxylic acid [1-(5-benzyl-4-phenyl-thiazol-2-ylcarbamoyl)-1-methyl-ethyl]-amide | 1.7 | A | 457.2 |
| 1-30 | 1-Methyl-1H-imidazole-4-carboxylic acid [1-(5-benzyl-4-phenyl-thiazol-2-ylcarbamoyl)-1-methyl-ethyl]-amide | 1.5 | A | 460.2 |
| 1-31 | N-[1-(5-Benzyl-4-phenyl-thiazol-2-ylcarbamoyl)-1-methyl-ethyl]-4-morpholin-4-yl-benzamide | 1.6 | A | 541.2 |
| 1-32 | N-[1-(5-Benzyl-4-phenyl-thiazol-2-ylcarbamoyl)-1-methyl-ethyl]-6-trifluoromethyl-nicotinamide | 1.7 | A | 525.2 |
| 1-33 | N-[1-(5-Benzyl-4-phenyl-thiazol-2-ylcarbamoyl)-1-methyl-ethyl]-nicotinamide | 1.5 | A | 457.2 |
| 1-34 | N-(5-Benzyl-4-phenyl-thiazol-2-yl)-2-[3-(4-chloro-3-trifluoromethyl-phenyl)-ureido]-2-methyl-propionamide | 1.8 | A | 573.1 |
| 1-35 | N-(5-Benzyl-4-phenyl-thiazol-2-yl)-2-methyl-2-[3-(4-trifluoromethoxy-phenyl)-ureido]-propionamide | 1.8 | A | 555.2 |
| 1-36 | 2,5-Dimethyl-2H-pyrazole-3-carboxylic acid [1-(5-benzyl-4-phenyl-thiazol-2-ylcarbamoyl)-1-methyl-ethyl]-amide | 1.6 | A | 474.2 |
| 1-37 | N-(5-Benzyl-4-phenyl-thiazol-2-yl)-2-methyl-2-[3-(4-trifluoromethyl-phenyl)-ureido]-propionamide | 1.7 | A | 539.2 |
| 1-38 | N-(5-Benzyl-4-phenyl-thiazol-2-yl)-2-(4-methoxy-benzenesulfonylamino)-2-methyl-propionamide | 1.7 | A | 522.2 |
| 1-39 | N-(5-Benzyl-4-phenyl-thiazol-2-yl)-2-methyl-2-(4-trifluoromethyl-benzenesulfonylamino)-propionamide | 1.8 | A | 560.1 |
| 1-40 | N-(5-Benzyl-4-phenyl-thiazol-2-yl)-2-(2-fluoro-benzenesulfonylamino)-2-methyl-propionamide | 1.7 | A | 474.2 |
| 1-41 | N-[1-(5-Benzyl-4-phenyl-thiazol-2-ylcarbamoyl)-1-methyl-ethyl]-3-fluoro-benzamide | 1.7 | A | 474.2 |
| 1-42 | N-[1-(5-Benzyl-4-phenyl-thiazol-2-ylcarbamoyl)-1-methyl-ethyl]-3-fluoro-5-trifluoromethyl-benzamide | 1.8 | A | 542.2 |
| 1-43 | N-[1-(5-Benzyl-4-phenyl-thiazol-2-ylcarbamoyl)-1-methyl-ethyl]-isonicotinamide | 1.5 | A | 457.2 |
| 1-44 | N-[1-(5-Benzyl-4-phenyl-thiazol-2-ylcarbamoyl)-1-methyl-ethyl]-3-fluoro-4-trifluoromethyl-benzamide | 1.8 | A | 542.2 |
| 1-45 | N-[1-(5-Benzyl-4-phenyl-thiazol-2-ylcarbamoyl)-1-methyl-ethyl]-2-fluoro-3-trifluoromethyl-benzamide | 1.8 | A | 542.2 |
| 1-46 | N-[1-(5-Benzyl-4-phenyl-thiazol-2-ylcarbamoyl)-1-methyl-ethyl]-4-trifluoromethoxy-benzamide | 1.8 | A | 540.2 |
| 1-47 | N-(5-Benzyl-4-phenyl-thiazol-2-yl)-2-(3-cyclohexyl-ureido)-2-methyl-propionamide | 1.7 | A | 477.2 |
| 1-48 | N-(5-Benzyl-4-phenyl-thiazol-2-yl)-2-[3-(4-fluoro-3-trifluoromethyl-phenyl)-ureido]-2-methyl-propionamide | 1.8 | A | 557.2 |
| 1-49 | N-(5-Benzyl-4-phenyl-thiazol-2-yl)-2-methyl-2-[3-(3-trifluoromethyl-phenyl)-ureido]-propionamide | 1.8 | A | 539.2 |
| 1-50 | N-[1-(5-Benzyl-4-phenyl-thiazol-2-ylcarbamoyl)-1-methyl-ethyl]-4-trifluoromethyl-benzamide | 1.8 | A | 524.2 |
| 1-51 | Pyridine-2-carboxylic acid [4-(5-benzyl-4-phenyl-thiazol-2-ylcarbamoyl)-tetrahydro-pyran-4-yl]-amide | 9.9 | B | 499.2 |
| 1-52 | Pyrrolidine-1,2-dicarboxylic acid 2-[(5-benzyl-4-phenyl-thiazol-2-yl)-amide] 1-o-tolylamide | 13.6 | B | 551.2 |
| 1-53 | N-(5-Benzyl-4-phenyl-thiazol-2-yl)-3-(4-fluoro-phenyl)-2-methyl-2-(3-o-tolyl-ureido)-propionamide | 14 | B | 579.2 |

| Ex. | Name | LC rt | Method | (M + H)+ |
|---|---|---|---|---|
| 1-54 | [1-(5-Benzoyl-4-phenyl-thiazol-2-ylcarbamoyl)-1-methyl-ethyl]-carbamic acid tert-butyl ester | 1.6 | A | 466.2 |
| 1-55 | N-(5-Benzoyl-4-phenyl-thiazol-2-yl)-2-[3-(2-chloro-phenyl)-ureido]-2-methyl-propionamide | 1.7 | A | 519.1 |
| 1-56 | (S)-N-(5-Benzyl-4-phenyl-thiazol-2-yl)-2-(2-cyclopentyl-acetylamino)-3-(4-fluoro-phenyl)-2-methyl-propionamide | 13.8 | B | 556.2 |
| 1-57 | Pyridine-2-carboxylic acid {1-[4-(4-fluoro-phenyl)-thiazol-2-ylcarbamoyl]-1-methyl-ethyl}-amide | 1.4 | A | 384.8 |
| 1-58 | Pyridine-2-carboxylic acid [1-(5-benzyl-thiazol-2-ylcarbamoyl)-1-methyl-ethyl]-amide | 1.5 | A | 381.1 |
| 1-59 | [1-(4,5-Diphenyl-thiazol-2-ylcarbamoyl)-1-methyl-ethyl]-carbamic acid tert-butyl ester | 1.7 | A | 438.1 |
| 1-60 | N-(5-Benzoyl-4-phenyl-thiazol-2-yl)-2-(2-cyclopentyl-acetylamino)-2-methyl-propionamide | 1.5 | A | 476.2 |
| 1-61 | 2-(2-Cyclopentyl-acetylamino)-N-(4,5-diphenyl-thiazol-2-yl)-2-methyl-propionamide | 1.3 | A | 448.2 |
| 1-62 | Tetrahydro-furan-3-carboxylic acid [1-(5-benzoyl-4-phenyl-thiazol-2-ylcarbamoyl)-1-methyl-ethyl]-amide | 1.3 | A | 464.1 |
| 1-63 | N-(5-Benzoyl-4-phenyl-thiazol-2-yl)-2-(2,2-dimethyl-propionylamino)-2-methyl-propionamide | 1.4 | A | 450.1 |
| 1-64 | 2-(2,2-Dimethyl-propionylamino)-N-(4,5-diphenyl-thiazol-2-yl)-2-methyl-propionamide | 1.5 | A | 422.1 |
| 1-65 | Cyclopentanecarboxylic acid [1-(4,5-diphenyl-thiazol-2-ylcarbamoyl)-1-methyl-ethyl]-amide | 1.5 | A | 434.1 |
| 1-66 | Cyclopentanecarboxylic acid [1-(5-benzoyl-4-phenyl-thiazol-2-ylcarbamoyl)-1-methyl-ethyl]-amide | 1.4 | A | 462.1 |

Example 2-1

Pyridine-2-carboxylic acid {1-[1-chloro-4-(4-fluoro-phenyl)-isoquinolin-3-ylcarbamoyl]-1-methyl-ethyl}-amide

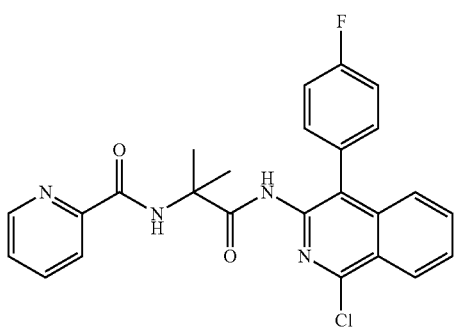 [SMILES: CC(C)(NC(=O)c1ccccn1)C(=O)Nc1nc(Cl)c2ccccc2c1-c1ccc(F)cc1]

A. {1-[1-chloro-4-(4-fluoro-phenyl)-isoquinolin-3-ylcarbamoyl]-1-methyl-ethyl}-amide Hydrochloride salt of 2-Amino-2-methyl-proprionic acid (1.8 g, 13 mmol) and phosphorous pentachloride (3.2 g, 15 mmol) were stirred at room temperature as a suspension in acetonitrile (50 mL) for 5 hours. Filtered and dried precipitate over vacuum to afford 2-amino-2-methyl-propionyl chloride as hydrochloride salt (1.8 g). 115 mg of 2-amino-2-methyl-propionyl chloride hydrochloride in 3 mL $CH_2Cl_2$ was rapidly treated with a mixture of 192 mg of 1-chloro-4-(4-fluoro-phenyl)-isoquinolin-3-ylamine, 0.05 mL of pyridine and 3 mL of $CH_2Cl_2$. The thick yellow suspension was stirred at room temperature for 24 h. The reaction was diluted with $CH_2Cl_2$, washed with 1N NaOH and $NaHCO_3$, was dried ($Na_2SO_4$) and evaporated to provide a golden-yellow semi-solid. m/z 357.8/359.7 ($MH^+$).

B. Pyridine-2-carboxylic acid {1-[1-chloro-4-(4-fluoro-isoquinolin-3-ylcarbamoyl]-1-methyl-ethyl}-amide The title compound was prepared using a similar procedure described above. $^1$H NMR (400 MHz, CHLOROFORM-D) δ 1.58 (s, 5H) 6.97 (t, J=8.65 Hz, 2H) 7.19-7.32 (m, 3H) 7.38-7.52 (m, 2H) 7.55-7.66 (m, 2H) 7.88 (dt, J=7.71, 1.64 Hz, 1H) 8.04 (d, J=7.83 Hz, 1H) 8.23 (s, 1H) 8.30-8.40 (m, 1H) 8.54 (d, J=4.80 Hz, 1H) 9.35 (s, 1H). m/z 462.9 ($MH^+$).

The following compounds were prepared using similar procedures described above.

| Ex. | Name | LC rt | Method | (M + H)+ |
|---|---|---|---|---|
| 2-2 | N-(1-Bromo-isoquinolin-3-yl)-2-[3-(2-chloro-phenyl)-ureido]-2-methyl-propionamide | 1.6 | A | 461.1 |
| 2-3 | N-(4-Benzyl-1-chloro-isoquinolin-3-yl)-2-[3-(2-chloro-phenyl)-ureido]-2-methyl-propionamide | 15.4 | C | 506.7 |

Example 3-1

N-(2-Benzyl-5-phenyl-2H-pyrazol-3-yl)-2-[3-(2-chloro-phenyl)-ureido]-2-methyl-propionamide

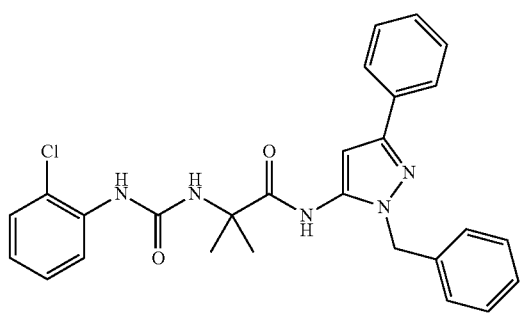 [SMILES: CC(C)(NC(=O)Nc1ccccc1Cl)C(=O)Nc1cc(-c2ccccc2)nn1Cc1ccccc1]

2-Amino-2-methyl-propionyl chloride hydrochloride (150 mg, 1.2 mmol) and 2-benzyl-5-phenyl-2H-pyrazol-3-ylamine (200 mg, 0.8 mmol) were stirred in DCM (5 mL) containing triethyl amine (100 μL, 0.8 mmol). After two hours, 2-chlorophenyl isocyanate (220 mg, 0.9 mmol) and triethyl amine (100 μL, 0.8 mmol) were added. Purification by silica gel chromatography gave the title compound. 1H NMR (400 MHz, DMSO-D6) δ 1.44 (s, 6H) 5.23 (s, 2H) 6.54 (s, 1H) 6.92 (s, 1H) 7.17 (s, 4H) 7.24 (s, 3H) 7.36 (s, 3H) 7.55 (s, 1H) 7.74 (s, 2H) 8.04 (s, 1H) 8.15 (s, 1H) 9.81 (s, 1H). m/z 488.0 (MH+).

The following compounds were prepared using similar procedures described above.

| Ex. | Name | LC rt | Method | (M + H)+ |
|---|---|---|---|---|
| 3-2 | 2-[3-(2-Chloro-phenyl)-ureido]-N-(2,5-diphenyl-2H-pyrazol-3-yl)-2-methyl-propionamide | 1.6 | A | 474.1 |

Example 4-1

1-(Pyridine-2-carbonyl)-pyrrolidine-2-carboxylic acid (5-benzyl-4-phenyl-thiazol-2-yl)-amide

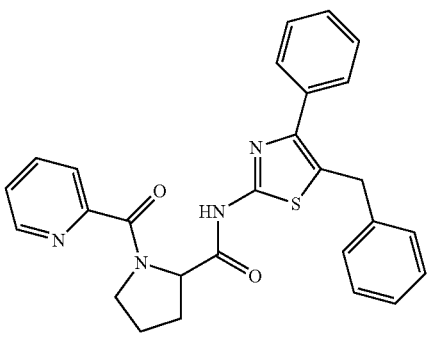 [SMILES: O=C(Nc1nc(-c2ccccc2)c(Cc2ccccc2)s1)C1CCCN1C(=O)c1ccccn1]

A. tert-Butyl-carbamoyl-pyrrolidine-2-carboxylic acid (5-benzyl-4-phenyl-thiazol-2-yl)-amide 281 mg of (S)—BOC-proline, 346 mg of 5-benzyl-4-phenyl-thiazol-2-ylamine, 0.68 mL of DIEA and 542 mg of HATU was stirred in 5 mL $CH_2Cl_2$ at room temperature for 24 h. The reaction was evaporated and purified by chromatography ($SiO_2$, EtOAc/heptane) to provide the title compound as a pale yellow foam. m/z 464.1 (MH+).

B. 1-(Pyridine-2-carbonyl)-pyrrolidine-2-carboxylic acid (5-benzyl-4-phenyl-thiazol-2-yl)-amide The title compound was prepared using similar procedures described above. $^1$H NMR (400 MHz, CHLOROFORM-D) δ 1.83-2.18 (m, 3H) 2.27-2.49 (m, 1H) 3.66-4.10 (m, 2H) 4.20 (s, 2H) 4.88-5.03 (m, 1H) 7.15-7.24 (m, J=7.14, 7.14 Hz, 3H) 7.25-7.31 (m, 2H) 7.31-7.44 (m, 4H) 7.56 (d, J=7.33 Hz, 2H) 7.80 (dt, J=7.77, 1.39 Hz, 1H) 7.94 (d, J=7.33 Hz, 0.5H) 8.05 (d, J=7.45 Hz, 0.5H) 8.50 (s, 0.5H) 8.58 (s, 0.5H) 10.74 (s, 0.5H) 11.34 (s, 0.5H). m/z 469.2 (MH+).

The following compounds were prepared using similar procedures described above.

| Ex. | Name | LC rt | Method | (M + H)+ |
|---|---|---|---|---|
| 4-2 | Pyrrolidine-1,2-dicarboxylic acid 2-[(5-benzyl-4-phenyl-thiazol-2-yl)-amide] 1-o-tolylamide | 11.3 | B | 497.2 |
| 4-3 | 1-(4-Trifluoromethoxy-benzoyl)-pyrrolidine-2-carboxylic acid (5-benzyl-4-phenyl-thiazol-2-yl)-amide | 12.3 | B | 552.2 |
| 4-4 | (2S,4R)-4-Fluoro-pyrrolidine-1,2-dicarboxylic acid 2-[(5-benzyl-4-phenyl-thiazol-2-yl)-amide] 1-[(2-chloro-phenyl)-amide] | 10.8 | B | 535.1 |
| 4-5 | (S)-Pyrrolidine-1,2-dicarboxylic acid 2-[(5-benzyl-4-phenyl-thiazol-2-yl)-amide] 1-[(2-chloro-phenyl)-amide] | 11.9 | B | 517.1 |
| 4-6 | (S)-Pyrrolidine-1,2-dicarboxylic acid 2-[(5-benzyl-4-phenyl-thiazol-2-yl)-amide] 1-[(2-isopropyl-phenyl)-amide] | 12.1 | B | 525.2 |
| 4-7 | (S)-Pyrrolidine-1,2-dicarboxylic acid 2-[(5-benzyl-4-phenyl-thiazol-2-yl)-amide] 1-[(2,4-difluoro-phenyl)-amide] | 10.7 | B | 519.2 |
| 4-8 | (S)-1-(2-Cyclopentyl-acetyl)-pyrrolidine-2-carboxylic acid (5-benzyl-4-phenyl-thiazol-2-yl)-amide | 12.1 | B | 474.2 |
| 4-9 | (S)-Pyrrolidine-1,2-dicarboxylic acid 2-[(5-benzyl-4-phenyl-thiazol-2-yl)-amide] 1-[(2-fluoro-4-trifluoromethyl-phenyl)-amide] | 11.6 | B | 569.2 |

-continued

| Ex. | Name | LC rt | Method | (M + H)+ |
|---|---|---|---|---|
| 4-10 | (S)-Pyrrolidine-1,2-dicarboxylic acid 2-[(5-benzyl-4-phenyl-thiazol-2-yl)-amide] 1-[(2-trifluoromethyl-phenyl)-amide] | 11.7 | B | 551.2 |
| 4-11 | (2S,4R)-4-Fluoro-1-(pyridine-2-carbonyl)-pyrrolidine-2-carboxylic acid (5-benzyl-4-phenyl-thiazol-2-yl)-amide | 8.6 | B | 487.2 |
| 4-12 | (S)-2-Methyl-pyrrolidine-1,2-dicarboxylic acid 2-[(5-benzyl-4-phenyl-thiazol-2-yl)-amide] 1-[(2-chloro-phenyl)-amide] | 13 | B | 531.2 |
| 4-13 | (R)-1-(2-Cyclopentyl-acetyl)-pyrrolidine-2-carboxylic acid (5-benzyl-4-phenyl-thiazol-2-yl)-amide | 12 | B | 474.2 |
| 4-14 | (2S,4R)-1-(2-Cyclopentyl-acetyl)-4-fluoro-pyrrolidine-2-carboxylic acid (5-benzyl-4-phenyl-thiazol-2-yl)-amide | 11.2 | B | 492.2 |
| 4-15 | (R)-Pyrrolidine-1,2-dicarboxylic acid 2-[(5-benzyl-4-phenyl-thiazol-2-yl)-amide] 1-[(2-chloro-phenyl)-amide] | 11.9 | B | 517.1 |
| 4-16 | (S)-1-(2-Cyclopentyl-acetyl)-4,4-difluoro-pyrrolidine-2-carboxylic acid (5-benzyl-4-phenyl-thiazol-2-yl)-amide | 1.8 | B | 510.2 |
| 4-17 | (S)-1-(2-Cyclopentyl-acetyl)-pyrrolidine-2-carboxylic acid [5-(4-fluoro-phenoxy)-4-(4-fluoro-phenyl)-thiazol-2-yl]-amide | 17.3 | C | 512.2 |
| 4-18 | (S)-2-(5-Benzoyl-4-phenyl-thiazol-2-ylcarbamoyl)-pyrrolidine-1-carboxylic acid tert-butyl ester | 1.5 | A | 478.2 |
| 4-19 | (S)-1-(Pyridine-2-carbonyl)-piperidine-2-carboxylic acid (5-benzyl-4-phenyl-thiazol-2-yl)-amide | 10.9 | TFA non-polar | 483.2 |
| 4-20 | (R)-1-(Pyridine-2-carbonyl)-piperidine-2-carboxylic acid (5-benzyl-4-phenyl-thiazol-2-yl)-amide | 10.9 | B | 483.2 |
| 4-21 | (S)-1-(2-Cyclopentyl-acetyl)-piperidine-2-carboxylic acid (5-benzyl-4-phenyl-thiazol-2-yl)-amide | 13.7 | B | 488.2 |
| 4-22 | (R)-1-(2-Cyclopentyl-acetyl)-piperidine-2-carboxylic acid (5-benzyl-4-phenyl-thiazol-2-yl)-amide | 13.7 | B | 488.2 |
| 4-23 | (S)-1-(2-Cyclopentyl-acetyl)-pyrrolidine-2-carboxylic acid (5-benzoyl-4-phenyl-thiazol-2-yl)-amide | 1.5 | A | 488.1 |
| 4-24 | (S)-1-(2,2-Dimethyl-propionyl)-pyrrolidine-2-carboxylic acid (5-benzoyl-4-phenyl-thiazol-2-yl)-amide | 1.5 | A | 462.1 |
| 4-25 | (S)-Pyrrolidine-1,2-dicarboxylic acid 2-[(5-benzoyl-4-phenyl-thiazol-2-yl)-amide] 1-isopropylamide | 1.4 | A | 463.1 |
| 4-26 | (S)-1-(Pyridine-2-carbonyl)-pyrrolidine-2-carboxylic acid [5-(4-fluoro-phenoxy)-4-(4-fluoro-phenyl)-thiazol-2-yl]-amide | 9.4 | B | 507.1 |

Example 5-1

(S)-1-(2,2-Dimethyl-propionyl)-pyrrolidine-2-carboxylic acid (4-phenyl-pyrimidin-2-yl)-amide

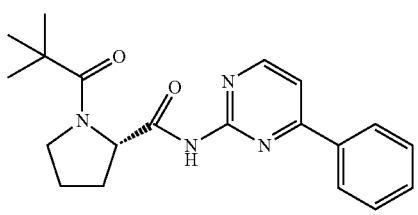 [SMILES: CC(C)(C)C(=O)N1CCC[C@H]1C(=O)Nc1nccc(-c2ccccc2)n1]

A. (S)-2-(4-Phenyl-pyrimidin-2-ylcarbamoyl)-pyrrolidine-1-carboxylic acid tert-butyl ester 4-Phenyl-pyrimidin-2-ylamine (200 mg, 1 mmol), Boc-L-Pro-OH (327 mg, 1.3 mmol) and TFFH (Fluoro-N,N,N'-tetramethylformamidinium hexafluorophosphate; 463 mg, 1.3 mmol) were stirred as a solution in DCM (10 mL) containing triethyl amine (300 mL, 2 mmol). Purification by silica gel chromatography gave the title compound. m/z 369.1 (MH$^+$).

B. (S)-1-(2,2-Dimethyl-propionyl)-pyrrolidine-2-carboxylic acid (4-phenyl-pyrimidin-2-yl)-amide The title compound was prepared using similar procedures described above. 1H NMR (400 MHz, CHLOROFORM-D) δ 1.20-1.28 (m, 3H) 1.30 (s, 9H) 2.22 (dd, J=7.20, 3.03 Hz, 1H) 2.26-2.36 (m, 1H) 3.72-3.83 (m, 2H) 5.10 (s, 1H) 7.38 (d, J=5.31 Hz, 1H) 7.45-7.51 (m, 3H) 8.03-8.09 (m, 2H) 8.63 (d, J=5.31 Hz, 1H). m/z 353.1 (MH$^+$).

The following compounds were prepared using similar procedures described above.

| Ex. | Name | LC rt | Method | (M + H)+ |
|---|---|---|---|---|
| 5-2 | (S)-1-(2-Cyclopentyl-acetyl)-pyrrolidine-2-carboxylic acid (4-phenyl-pyrimidin-2-yl)-amide | 1.6 | A | 474.1 |

Example 6-1

N-{1-[5-(4-Fluoro-phenoxy)-4-(4-fluoro-phenyl)-thiazol-2-ylcarbamoyl]-1-methyl-ethyl}-4-trifluoromethoxybenzamide

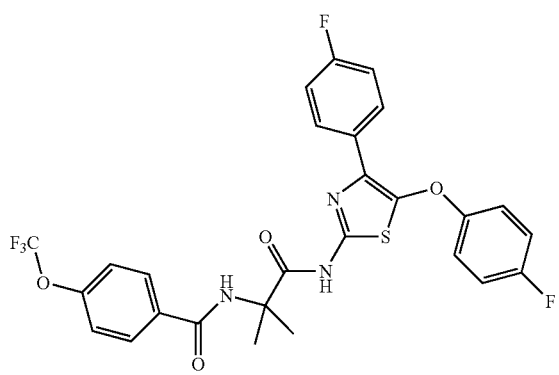 [SMILES: CC(C)(NC(=O)c1ccc(OC(F)(F)F)cc1)C(=O)Nc1nc(-c2ccc(F)cc2)c(Oc2ccc(F)cc2)s1]

A. 5-(4-Fluoro-phenoxy)-4-(4-fluoro-phenyl)-thiazol-2-ylamine

Bromine was added to a solution of 4-(4-fluoro-phenyl)-thiazol-2-ylamine (12 g, 62 mmol) in acetic acid at room temperature. The mixture was stirred at room temperature for 30 sec and solidified. The mixture was diluted with water and poured to ice-water. The light grey suspension was filtered. The solid obtained was taken up in EtOAc and carefully basified with aqueous $K_2CO_3$ (pH was adjusted to 8~9). The EtOAc extract was dried over MgSO4 and concentrated to give crude 5-bromo-4-(4-fluoro-phenyl)-thiazol-2-ylamine (15.15 g). This was then mixed with 4-fluorophenol (6.9 g, 62 mmol) and Cs2CO3 (22 g, 68 mmol) in acetonitrile (120 mL) and heated at 70° C. for 2 h and concentrated. The residue was partitioned between EtOAc and water. The organic extract was dried over MgSO4, concentrated and chromatographed to give the title compound with some impurities. m/z 305.1 (MH+).

B. {1-[5-(4-Fluoro-phenoxy)-4-(4-fluoro-phenyl)-thiazol-2-ylcarbamoyl]-1-methyl-ethyl}-carbamic acid benzyl ester A mixture of 2-benzyloxycarbonylamino-2-methyl-propionic acid (10.5 g, 44.2 mmol), HBTU (16.8 g, 44.3 mmol) and Et3N (6.2 mL, 45 mmol) in DMF (50 mL) was stirred at room temperature for 2 h. To this was added a solution of 5-(4-Fluoro-phenoxy)-4-(4-fluoro-phenyl)-thiazol-2-ylamine (9.62 g, ca. 32 mmol with some impurities present) in DMF (50 mL). The mixture was heated at 85° C. for 18 h and partitioned between EtOAc and, sequentially, 3M HCl and aqueous KOH. The organic extract was dried over MgSO4, concentrated and chromatographed to give the title compound. m/z 524.2 (MH+).

C. 2-Amino-N-[5-(4-fluoro-phenoxy)-4-(4-fluoro-phenyl)-thiazol-2-yl]-2-methyl-propionamide 33% HBr (100 mL) was added to a solution of {1-[5-(4-Fluoro-phenoxy)-4-(4-fluoro-phenyl)-thiazol-2-ylcarbamoyl]-1-methyl-ethyl}-carbamic acid benzyl ester (12 g, 23 mmol) in acetic acid (50 mL). The mixture was stirred at room temperature for 18 h. Most of acetic acid was removed by evaporation under vacuum. The mixture was basified with 1M NaOH, and the product was extracted with dichloromethane. The dichloromethane extract was washed with brine, dried over Na2SO4 and concentrated. The residue was chromatographed to give the title compound. m/z 390.9 (MH+).

D. N-{1-[5-(4-Fluoro-phenoxy)-4-(4-fluoro-phenyl)-thiazol-2-ylcarbamoyl]-1-methyl-ethyl}-4-trifluoromethoxybenzamide The title compound was prepared using a similar procedure described above. 1H NMR (400 MHz, $CD_3OD$) δ 1.64 (s, 6H), 7.37 (d, J=8 Hz, 2H), 7.91-7.01 (m, 6H), 8.03 (d, J=8 Hz, 2H). m/z 578.0 (MH+).

Example 6-2

Morpholine-4-carboxylic acid {1-[5-(4-fluoro-phenoxy)-4-(4-fluoro-phenyl)-thiazol-2-ylcarbamoyl]-1-methyl-ethyl}-amide

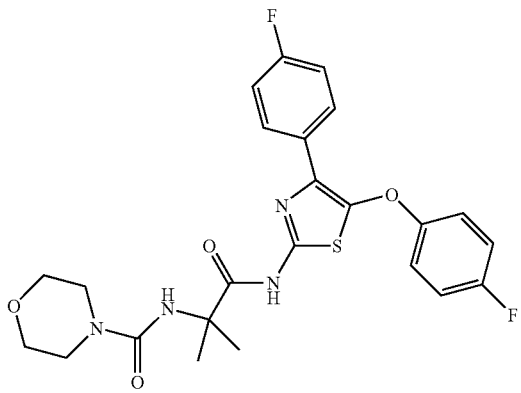 [SMILES: CC(C)(NC(=O)N1CCOCC1)C(=O)Nc1nc(-c2ccc(F)cc2)c(Oc2ccc(F)cc2)s1]

A solution of triphosgene 46 mg, 0.15 mmol) in dichloromethane (1 mL) was added to a mixture of 2-Amino-N-[5-(4-fluoro-phenoxy)-4-(4-fluoro-phenyl)-thiazol-2-yl]-2-methyl-propionamide (56 mg, 0.14 mmol) in dichloromethane (2 mL) and aqueous $K_2CO_3$ (120 mg of $K_2CO_3$ was predissolved in 1 mL of water). The mixture was vigorously stirred at room temperature for 1 h. The dichloromethane layer was separated, dried and concentrated. The residue was taken up in pyridine (3 mL), and morpholine (310 μL) was added. The mixture was heated at 85° C. for 4 h, partitioned between EtOAc and 3M HCl. The organic extract was dried over MgSO4, concentrated and purified by HPLC (0.1% TFA-acetonitrile/0.1% TFA-water as eluent) to give the title compound. 1H NMR (400 MHz, $CDCl_3$) δ 1.61 (s, 6H), 3.39 (br s, 4H), 3.70 (br s, 4H), 6.95-7.15 (m, 6H), 7.79-7.90 (m, 2H). m/z 503.1 (MH+).

The following compounds were prepared using similar procedures described above.

| Ex. | Name | LC rt | Method | (M + H)+ |
|---|---|---|---|---|
| 6-3 | Pyridine-2-carboxylic acid {1-[5-(4-fluoro-phenoxy)-4-(4-fluoro-phenyl)-thiazol-2-ylcarbamoyl]-1-methyl-ethyl}-amide | 1.8 | A | 495.9 |
| 6-4 | N-{1-[5-(4-Fluoro-phenoxy)-4-(4-fluoro-phenyl)-thiazol-2-ylcarbamoyl]-1-methyl-ethyl}-isophthalamic acid | 1.4 | A | 537.8 |
| 6-5 | 4-(3,3,3-Trifluoro-propionylamino)-tetrahydro-pyran-4-carboxylic acid [5-(4-fluoro-phenoxy)-4-(4-fluoro-phenyl)-thiazol-2-yl]-amide | 1.6 | A | 542 |
| 6-6 | Pyrimidine-4-carboxylic acid {1-[5-(4-fluoro-phenoxy)-4-(4-fluoro-phenyl)-thiazol-2-ylcarbamoyl]-1-methyl-ethyl}-amide | 1.6 | A | 496.1 |
| 6-7 | N-[5-(4-Fluoro-phenoxy)-4-(4-fluoro-phenyl)-thiazol-2-yl]-2-methyl-2-(3,3,3-trifluoro-propionylamino)-propionamide | 1.7 | A | 500 |
| 6-8 | 2-(3-Cyclopropyl-ureido)-N-[5-(4-fluoro-phenoxy)-4-(4-fluoro-phenyl)-thiazol-2-yl]-2-methyl-propionamide | 1.4 | A | 473.1 |
| 6-9 | N-{1-[5-(4-Fluoro-phenoxy)-4-(4-fluoro-phenyl)-thiazol-2-ylcarbamoyl]-1-methyl-ethyl}-nicotinamide | 1.4 | A | 495.1 |
| 6-10 | N-{1-[5-(4-Fluoro-phenoxy)-4-(4-fluoro-phenyl)-thiazol-2-ylcarbamoyl]-1-methyl-ethyl}-isonicotinamide | 1.4 | A | 495.1 |
| 6-11 | 3,5-Difluoro-pyridine-2-carboxylic acid {1-[5-(4-fluoro-phenoxy)-4-(4-fluoro-phenyl)-thiazol-2-ylcarbamoyl]-1-methyl-ethyl}-amide | 1.6 | A | 531.1 |
| 6-12 | Pyridazine-4-carboxylic acid {1-[5-(4-fluoro-phenoxy)-4-(4-fluoro-phenyl)-thiazol-2-ylcarbamoyl]-1-methyl-ethyl}-amide | 1.4 | A | 496.1 |
| 6-13 | Pyrimidine-5-carboxylic acid {1-[5-(4-fluoro-phenoxy)-4-(4-fluoro-phenyl)-thiazol-2-ylcarbamoyl]-1-methyl-ethyl}-amide | 1.4 | A | 496.1 |
| 6-14 | Thiazole-5-carboxylic acid {1-[5-(4-fluoro-phenoxy)-4-(4-fluoro-phenyl)-thiazol-2-ylcarbamoyl]-1-methyl-ethyl}-amide | 1.5 | A | 501.1 |
| 6-15 | 5-Hydroxy-pyridine-2-carboxylic acid {1-[5-(4-fluoro-phenoxy)-4-(4-fluoro-phenyl)-thiazol-2-ylcarbamoyl]-1-methyl-ethyl}-amide | 1.5 | A | 511.1 |
| 6-16 | 2-(2-Cyclopentyl-acetylamino)-N-[5-(4-fluoro-phenoxy)-4-(4-fluoro-phenyl)-thiazol-2-yl]-2-methyl-propionamide | 1.6 | A | 500.1 |
| 6-17 | 2-(2-Cyano-acetylamino)-N-[5-(4-fluoro-phenoxy)-4-(4-fluoro-phenyl)-thiazol-2-yl]-2-methyl-propionamide | 1.5 | A | 457 |
| 6-18 | N-[5-(4-Fluoro-phenoxy)-4-(4-fluoro-phenyl)-thiazol-2-yl]-2-[3-(2-methoxy-ethyl)-ureido]-2-methyl-propionamide | 1.5 | A | 491.1 |
| 6-19 | 6-Methyl-pyridine-2-carboxylic acid-{1-[5-(4-fluoro-phenoxy)-4-(4-fluoro-phenyl)-thiazol-2-ylcarbamoyl]-1-methyl-ethyl}-amide | 1.7 | A | 509.2 |
| 6-20 | 2-(2,2-Dimethyl-propionylamino)-N-[5-(4-fluoro-phenoxy)-4-(4-fluoro-phenyl)-thiazol-2-yl]-2-methyl-propionamide | 1.6 | A | 474.2 |
| 6-21 | 3-Fluoro-N-{1-[5-(4-fluoro-phenoxy)-4-(4-fluoro-phenyl)-thiazol-2-ylcarbamoyl]-1-methyl-ethyl}-benzamide | 1.6 | A | 512.2 |
| 6-22 | 2-Cyano-N-{1-[5-(4-fluoro-phenoxy)-4-(4-fluoro-phenyl)-thiazol-2-ylcarbamoyl]-1-methyl-ethyl}-2,2-dimethyl-acetamide | 1.5 | A | 485.1 |
| 6-23 | 2-(2-Fluoro-2-methyl-propionylamino)-N-[5-(4-fluoro-phenoxy)-4-(4-fluoro-phenyl)-thiazol-2-yl]-2-methyl-propionamide | 1.6 | A | 478.1 |
| 6-24 | 1-Cyano-cyclopropanecarboxylic acid {1-[5-(4-fluoro-phenoxy)-4-(4-fluoro-phenyl)-thiazol-2-ylcarbamoyl]-1-methyl-ethyl}-amide | 1.6 | A | 483.2 |
| 6-25 | 2-(2-Cyclopropyl-acetylamino)-N-[5-(4-fluoro-phenoxy)-4-(4-fluoro-phenyl)-thiazol-2-yl]-2-methyl-propionamide | 1.6 | A | 472.2 |
| 6-26 | Cyclobutanecarboxylic acid {1-[5-(4-fluoro-phenoxy)-4-(4-fluoro-phenyl)-thiazol-2-ylcarbamoyl]-1-methyl-ethyl}-amide | 1.6 | A | 472.1 |
| 6-27 | Tetrahydro-pyran-4-carboxylic acid {1-[5-(4-fluoro-phenoxy)-4-(4-fluoro-phenyl)-thiazol-2-ylcarbamoyl]-1-methyl-ethyl}-amide | 1.4 | A | 502.2 |
| 6-28 | 3,3,3-Trifluoro-N-{1-[5-(4-fluoro-phenoxy)-4-(4-fluoro-phenyl)-thiazol-2-ylcarbamoyl]-1-methyl-ethyl}-2-hydroxy-2-methyl-propionamide | 1.5 | A | 530.2 |

| Ex. | Name | LC rt | Method | (M + H)+ |
|---|---|---|---|---|
| 6-29 | 3-Chloro-N-{1-[5-(4-fluoro-phenoxy)-4-(4-fluoro-phenyl)-thiazol-2-ylcarbamoyl]-1-methyl-ethyl}-benzamide | 1.6 | A | 528.1 |
| 6-30 | {1-[5-(4-fluoro-phenoxy)-4-(4-fluoro-phenyl)-thiazol-2-ylcarbamoyl]-1-methyl-ethyl}-amide | 1.6 | A | 538.1 |
| 6-31 | 4-Fluoro-N-{1-[5-(4-fluoro-phenoxy)-4-(4-fluoro-phenyl)-thiazol-2-ylcarbamoyl]-1-methyl-ethyl}-benzamide | 1.6 | A | 512.1 |
| 6-32 | 3-Cyano-N-{1-[5-(4-fluoro-phenoxy)-4-(4-fluoro-phenyl)-thiazol-2-ylcarbamoyl]-1-methyl-ethyl}-benzamide | 1.6 | A | 519.1 |
| 6-33 | 1-Trifluoromethyl-cyclopropanecarboxylic acid {1-[5-(4-fluoro-phenoxy)-4-(4-fluoro-phenyl)-thiazol-2-ylcarbamoyl]-1-methyl-ethyl}-amide | 1.7 | A | 526.2 |
| 6-34 | 1-Trifluoromethyl-cyclobutanecarboxylic acid {1-[5-(4-fluoro-phenoxy)-4-(4-fluoro-phenyl)-thiazol-2-ylcarbamoyl]-1-methyl-ethyl}-amide | 1.7 | A | 540.2 |
| 6-35 | 2-(4-Chloro-phenoxy)-N-{1-[5-(4-fluoro-phenoxy)-4-(4-fluoro-phenyl)-thiazol-2-ylcarbamoyl]-1-methyl-ethyl)}-2-methyl-propionamide | 1.8 | A | 586.2 |
| 6-36 | 4-Cyano-N-{1-[5-(4-fluoro-phenoxy)-4-(4-fluoro-phenyl)-thiazol-2-ylcarbamoyl]-1-methyl-ethyl}-benzamide | 1.5 | A | 519.1 |
| 6-37 | N-{1-[5-(4-Fluoro-phenoxy)-4-(4-fluoro-phenyl)-thiazol-2-ylcarbamoyl]-1-methyl-ethyl}-2-hydroxy-benzamide | 1.7 | A | 510.1 |
| 6-38 | N-{1-[5-(4-Fluoro-phenoxy)-4-(4-fluoro-phenyl)-thiazol-2-ylcarbamoyl]-1-methyl-ethyl}-4-hydroxy-benzamide | 1.5 | A | 510.1 |

Example 7-1

N-{1-[5-(4-Cyano-phenoxy)-4-cyclopropyl-thiazol-2-ylcarbamoyl]-1-methyl-ethyl}-isonicotinamide

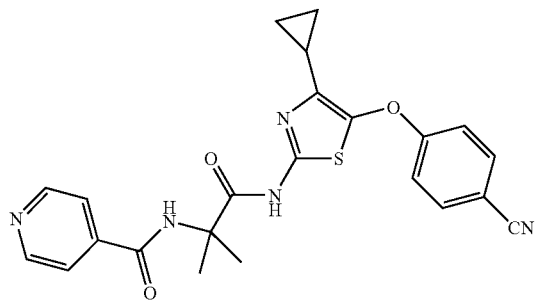 [SMILES: CC(C)(NC(=O)c1ccncc1)C(=O)Nc1nc(C2CC2)c(Oc2ccc(C#N)cc2)s1]

A. 4-(2-Amino-4-cyclopropyl-thiazol-5-yloxy)-benzonitrile

The title compound was prepared by analogous procedure to Example 6-1 A using 4-cyclopropyl-thiazol-2-ylamine (WO2005110980) and 4-cyanophenol. m/z 258.1 (MH$^+$).

B. {1-[5-(4-Cyano-phenoxy)-4-cyclopropyl-thiazol-2-ylcarbamoyl]-1-methyl-ethyl}-carbamic acid benzyl ester A mixture of 2-Benzyloxycarbonylamino-2-methyl-propionic acid (360 mg, 1.52 mmol), HBTU (576 mg, 1.52 mmol) and Et3N (0.21 mL, 1.5 mmol) in DMF (4 mL) was stirred at room temperature for 30 min. To this was added a solution of 4-(2-Amino-4-cyclopropyl-thiazol-5-yloxy)-benzonitrile (260 mg, 1.01 mmol) in DMF (4 mL). The mixture was heated at 85° C. for 18 h and partitioned between EtOAc and 3M HCl. The organic extract was dried over MgSO4, concentrated and chromatographed to give the title compound. m/z 477.1 (MH$^+$).

C. N-{1-[5-(4-Cyano-phenoxy)-4-cyclopropyl-thiazol-2-ylcarbamoyl]-1-methyl-ethyl}-isonicotinamide The title compound was prepared using similar procedures described above. 1H NMR (400 MHz, CDCl$_3$) δ 0.70-0.85 (m, 4H), 1.70-1.80 (m, 1H), 1.78 (s, 6H), 6.67 (br s, 1H), 7.13 (d, J=8.0 Hz, 2H), 7.63 (d, J=8.0 Hz, 2H), 7.65 (d, J=8.0 Hz, 2H), 8.80 (d, J=8.0 Hz, 2H), 9.63 (br s, 1H). m/z 448.1 (MH$^+$).

The following compounds were prepared using similar procedures described above.

| Ex. | Name | LC rt | Method | (M + H)+ |
|---|---|---|---|---|
| 7-2 | N-{1-[5-(4-Cyano-phenoxy)-4-cyclopropyl-thiazol-2-ylcarbamoyl]-1-methyl-ethyl}-2-fluoro-benzamide | 1.1 | A | 465.1 |
| 7-3 | Morpholine-4-carboxylic acid {1-[5-(4-cyano-phenoxy)-4-cyclopropyl-thiazol-2-ylcarbamoyl]-1-methyl-ethyl}-amide | 1.3 | A | 456.2 |

Example 8-1

(S)-1-(2-Cyclopentyl-acetyl)-pyrrolidine-2-carboxylic acid (4-phenyl-quinolin-2-yl)-amide

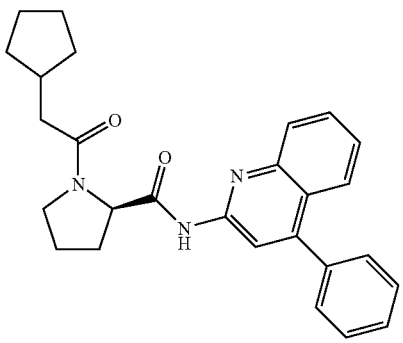 [SMILES: O=C(Nc1cc(-c2ccccc2)c2ccccc2n1)[C@H]1CCCN1C(=O)CC1CCCC1]

A. tert-Butyl-carbamoyl-pyrrolidine-2-carboxylic acid (4-phenyl-quinolin-2-yl)-amide 281 mg of (S)—BOC-proline, 284 mg of 4-phenyl-quinolin-2-ylamine (WO 2006082952 A1). 0.68 mL of DIEA and 540 mg of HATU was stirred in 5 mL CH$_2$Cl$_2$ at room temperature for 24 h. The reaction was evaporated and purified by chromatography (SiO$_2$, EtOAc/heptane) to provide the title compound as an off-white solid. m/z 418.2 (MH$^+$).

B. (S)-1-(2-Cyclopentyl-acetyl)-pyrrolidine-2-carboxylic acid (4-phenyl-quinolin-2-yl)-amide The title compound was prepared using similar procedures described above. $^1$H NMR (400 MHz, CHLOROFORM-D) δ 1.10-1.28 (m, 2H) 1.45-1.74 (m, 4H) 1.75-2.24 (m, 5H) 2.24-2.53 (m, 4H) 3.50 (dt, J=9.35, 7.20 Hz, 1H) 3.64 (dt, 1H) 4.84 (dd, 1H) 7.36 (dt, 1H) 7.40-7.56 (m, 5H) 7.63 (dt, 1H) 7.81 (d, J=8.34 Hz, 1H) 7.92 (d, J=8.46 Hz, 1H) 8.32 (s, 1H) 9.79 (s, 1H). m/z 428.2 (MH$^+$).

The following compounds were prepared using similar procedures described above.

| Ex. | Name | LC rt | Method | (M + H)+ |
|---|---|---|---|---|
| 8-2 | (S)-2-(6-Phenyl-4-p-tolyl-pyridin-2-ylcarbamoyl)-pyrrolidine-1-carboxylic acid tert-butyl ester | 1.7 | A | 458.2 |
| 8-3 | (S)-1-(2-Cyclopentyl-acetyl)-pyrrolidine-2-carboxylic acid (6-phenyl-4-p-tolyl-pyridin-2-yl)-amide | 1.8 | A | 468.2 |
| 8-4 | (S)-1-(2,2-Dimethyl-propionyl)-pyrrolidine-2-carboxylic acid (6-phenyl-4-p-tolyl-pyridin-2-yl)-amide | 1.7 | A | 442.2 |
| 8-5 | (S)-Pyrrolidine-1,2-dicarboxylic acid 1-isopropylamide 2-[(6-phenyl-4-p-tolyl-pyridin-2-yl)-amide] | 1.6 | A | 443.2 |

Example 9-1

{1-[5-(4-Fluoro-phenoxy)-4-(4-fluoro-phenyl)-thiazol-2-yl]-2-oxo-pyrrolidin-3-yl}-carbamic acid tert-butyl ester

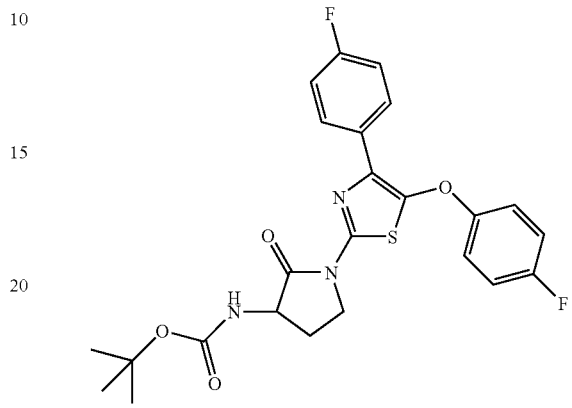

A. {-[1-5-(4-Fluoro-phenoxy)-4-(4-fluoro-phenyl)-thiazol-2-ylcarbamoyl]-3-hydroxy-propyl}-carbamic acid tert-butyl ester Trimethylaluminum (2M in toluene, 0.63 mL, 1.3 mmol) was added to a solution of 5-(4-Fluoro-phenoxy)-4-(4-fluorophenyl)-thiazol-2-ylamine (382 mg, 1.26 mmol) in dichloromethane (3 mL) at room temperature. The mixture was stirred at room temperature for 10 min. To this was added a solution of (2-Oxo-tetrahydro-furan-3-yl)-carbamic acid tert-butyl ester (253 mg, 1.26 mmol) in dichloromethane (3 mL) at room temperature, and the mixture was stirred at this temperature for 18 h. Aqueous ammonium chloride was added. The resulting emulsion was filtered through Celite. The filtrate was partitioned between dichloromethane and aqueous ammonium chloride. The organic extract was dried over MgSO$_4$, concentrated and chromatographed to give the title compound. m/z 506.1 (MH$^+$).

B. {1-[5-(4-Fluoro-phenoxy)-4-(4-fluoro-phenyl)-thiazol-2-yl]-2-oxo-pyrrolidin-3-yl}-carbamic acid tert-butyl ester DIAD (0.22 mL, 1.1 mmol) was added to a solution of PPh$_3$ (300 mg, 1.15 mmol) in THF (5 mL) at room temperature. The mixture was stirred at room temperature for 5 min. To this was added a solution of {1-[5-(4-Fluoro-phenoxy)-4-(4-fluoro-phenyl)-thiazol-2-ylcarbamoyl]-3-hydroxy-propyl}-carbamic acid tert-butyl ester (438 mg, 0.867 mmol) in THF (15 mL). The mixture was stirred at room temperature for 30 min and partitioned between EtOAc and aqueous K$_2$CO$_3$. The organic extract was dried over MgSO$_4$, concentrated and chromatographed to give the title compound. 1H NMR (400 MHz, CDCl$_3$) δ 1.47 (s, 9H), 2.10-2.20 (m, 1H), 2.79-2.87 (m, 1H), 3.87-3.95 (m, 1H), 4.35-4.41 (m, 1H), 4.45-4.52 (m, 1H), 5.08-5.13 (m, 1H), 6.95-7.08 (m, 6H), 7.90-7.95 (m, 2H). m/z 488.1 (MH$^+$).

The following compounds were prepared using similar procedures described above.

| Ex. | Name | LC rt | Method | (M + H)+ |
|---|---|---|---|---|
| 9-2 | 3,3,3-Trifluoro-N-{1-[5-(4-fluoro-phenoxy)-4-(4-fluoro-phenyl)-thiazol-2-yl]-2-oxo-pyrrolidin-3-yl}-propionamide | 1.6 | A | 498 |
| 9-3 | Morpholine-4-carboxylic acid {1-[5-(4-fluoro-phenoxy)-4-(4-fluoro-phenyl)-thiazol-2-yl]-2-oxo-pyrrolidin-3-yl}-amide | 1.4 | A | 501.1 |
| 9-4 | Pyridine-2-carboxylic acid {1-[5-(4-fluoro-phenoxy)-4-(4-fluoro-phenyl)-thiazol-2-yl]-2-oxo-pyrrolidin-3-yl}-amide | 1.6 | A | 493.1 |

Example 10-1

[1-(4,5-Diphenyl-oxazol-2-ylcarbamoyl)-1-methyl-ethyl]-carbamic acid tert-butyl ester

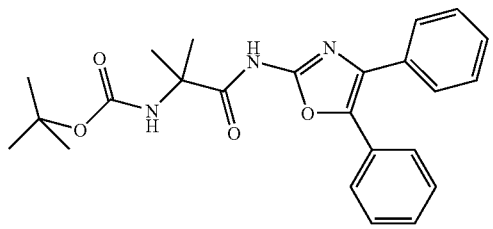 [SMILES: CC(C)(C)OC(=O)NC(C)(C)C(=O)Nc1nc(-c2ccccc2)c(-c2ccccc2)o1]

2-tert-Butoxycarbonylamino-2-methyl-propionic acid (540 mg, 3 mmol), 5-benzyl-4-phenyl-thiazol-2-ylamine (500 mg, 2 mmol) and TFFH (fluoro-N,N,N'-tetramethylformamidinium hexafluorophosphate; 783 mg, 3 mmol) were stirred as a solution in DCM (20 mL) containing triethyl amine (524 ml, 6 mmol) at reflux. Purification by silica gel chromatography afforded the title compound. 1H NMR (400 MHz, CHLOROFORM-D) δ 1.38 (s, 10H) 1.42-1.52 (m, 6H) 7.21-7.31 (m, 6H), 7.53 (dd, J=11.87, 7.45 Hz, 4H). m/z 422.2 (MH+).

The following compounds were prepared using similar procedures described above.

| Ex. | Name | LC rt | Method | (M + H)+ |
|---|---|---|---|---|
| 10-2 | (S)-1-(2,2-Dimethyl-propionyl)-pyrrolidine-2-carboxylic acid (4,5-diphenyl-oxazol-2-yl)-amide | 1.4 | A | 418.3 |
| 10-3 | (S)-2-(4,5-Diphenyl-oxazol-2-ylcarbamoyl)-pyrrolidine-1-carboxylic acid tert-butyl ester | 1.5 | A | 434.1 |
| 10-4 | {1-[7-(4-Fluoro-phenyl)-benzooxazol-2-ylcarbamoyl]-1-methyl-ethyl}-carbamic acid tert-butyl ester | 1.4 | A | 414.2 |

Example 11-1

2-(2-Cyclopentyl-acetylamino)-N-[4-(4-fluoro-phenyl)-5-morpholin-4-yl-thiazol-2-yl]-2-methyl-propionamide

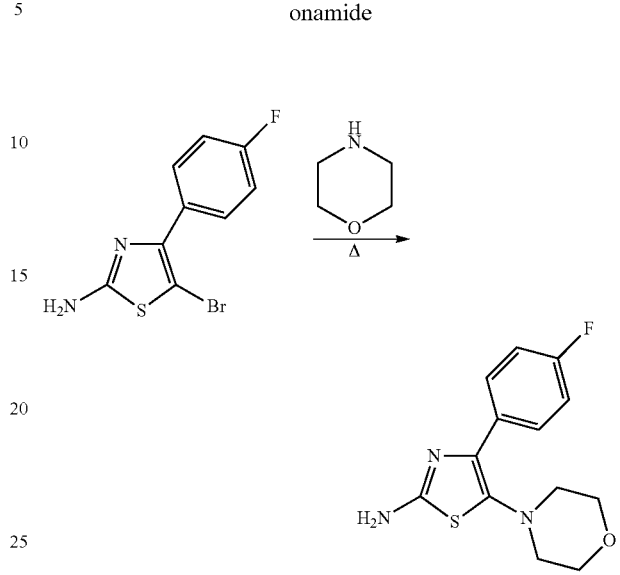

Step A: 5-Bromo-4-(4-fluoro-phenyl)-thiazole-2-ylamine and morpholine (6 eq) were stirred for 30 minutes at 120° C. using microwave heating. The reaction mixture was triturated with ethyl acetate/n-Heptane solvent mixture (1:2 ratio) to afford desired product: LCMS Method 10 Rt=1.14 (M+1=280.0, M-1=278.1). 1H NMR (400 MHz, DMSO-D6) δ ppm 2.67-2.75 (m, 4H) 3.67-3.74 (m, 4H) 6.87 (s, 2H) 7.14-7.20 (m, 2H) 8.11 (ddd, J=12.41, 5.53, 3.03 Hz, 2H).

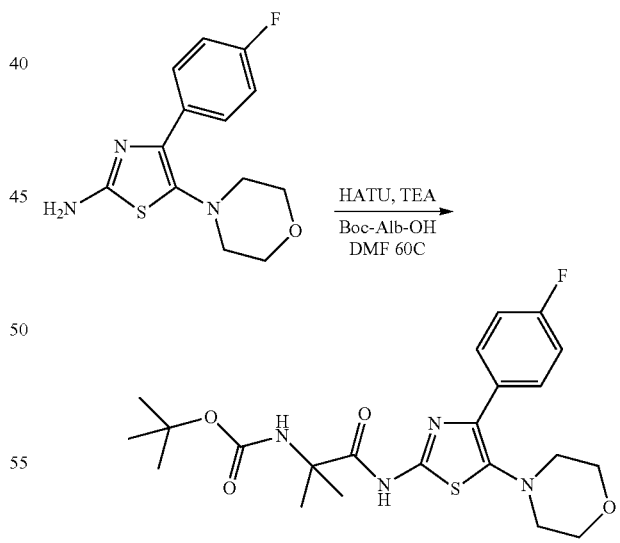

Step B: To a solution of 2-tert-Butoxycarbonylamino-2-methyl-propionic acid (1.5 eq) and 4-(4-Fluoro-phenyl)-5-morpholin-4-yl-thiazol-2-ylamine (1 eq)) in DMF (50 mL) were added HATU (1.5 eq) and TEA (2 eq). Reaction was stirred at 60° C. overnight. Aqueous work up followed by silica gel chromatography afforded desired product. LCMS Method 10 Rt=1.51 (M+1=465.1. M-1=463.1). 1H NMR (400 MHz, DMSO-D6) δ ppm 1.21 (s, 1H) 1.28-1.40 (m, 14H) 2.80-2.87 (m, 4H) 3.70-3.77 (m, 4H) 7.21-7.27 (m, 2H) 8.10-8.16 (m, 2H) 11.59 (s, 1H).

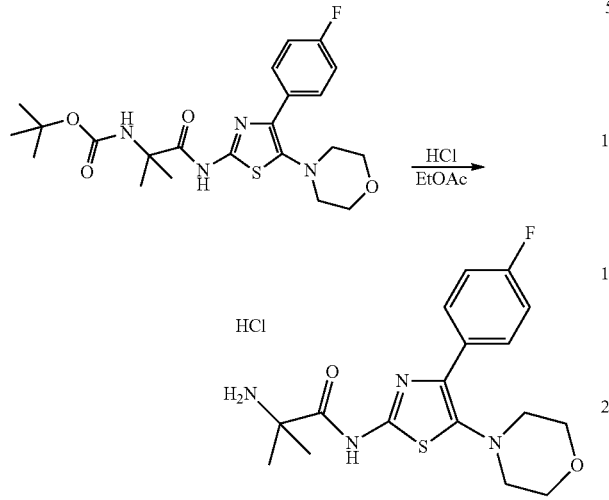

Step C: {1-[4-(4-Fluoro-phenyl)-5-morpholin-4-yl-thiazol-2-ylcarbamoyl]-1-methyl-ethyl}-carbamic acid tert-butyl ester was stirred overnight in freshly prepared HCl (g)/EtOAc solution. Evaporation to dryness afforded the desired product as the hydrochloride salt. 1H NMR (400 MHz, DMSO-D6) 1.63 (s, 6H) 2.81-2.89 (m, 4H) 3.70-3.78 (m, 4H) 7.23-7.29 (m, 2H) 8.10-8.16 (m, 2H) 8.62 (s, 3H) 12.46 (s, 1H).

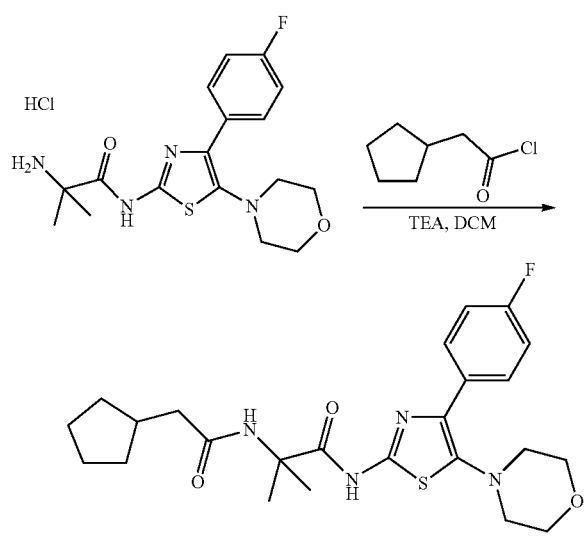

Step D: 2-Amino-N-[4-(4-fluoro-phenyl)-5-morpholin-4-yl-thiazol-2-yl]-2-methyl-propionamide (1 eq), cyclopentyl acetyl chloride (1.05 eq) and triethyl amine (3 eq) were stirred as a solution in DCM (5 mL). Desired product was isolated from reaction mixture by silica gel chromatography. LCMS Method 10 Rt=1.48 (M+1=475.1, M−1=473.1), HRMS; expected=474.2101, found=474.2116. 1H NMR (400 MHz, DMSO-D6) 1.07-1.18 (m, 2H) 1.38 (s, 5H) 1.42-1.51 (m, 2H) 1.52-1.60 (m, 2H) 1.62-1.73 (m, 2H) 2.11 (s, 3H) 2.78-2.88 (m, 4H) 3.69-3.78 (m, 4H) 7.23 (t, J=8.91 Hz, 2H) 8.01 (s, 1H) 8.13 (dd. J=8.59, 5.81 Hz, 2H) 11.45 (s, 1H).

Example 12-1

4-Fluoro-N-{1-methyl-1-[4-phenyl-5-(piperazine-1-carbonyl)-thiazol-2-ylcarbamoyl]-ethyl}-benzamide

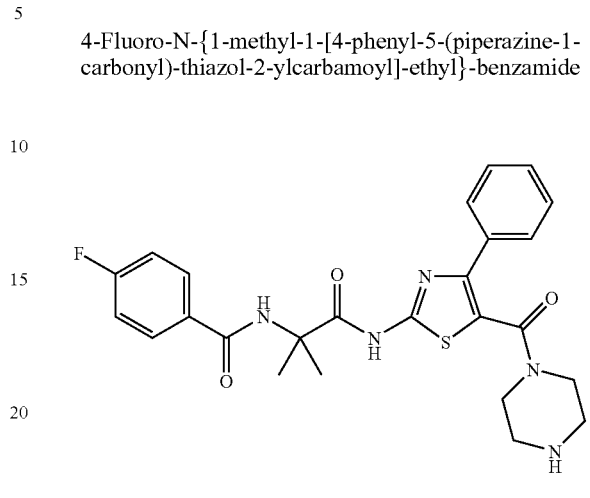

A. 2-(2-Benzyloxycarbonylamino-2-methyl-propionylamino)-4-phenyl-thiazole-5-carboxylic acid ethyl ester A mixture of Cbz-aib-OH (995 mg, 4.20 mmol), ethyl 2-amino-4-phenylthiazoyl-5-carboxylate (1.25 g, 5.04 mmol), HBTU (1.59 g, 4.20 mmol) and triethylamine (880 uL, 6.33 mmol) in DMF was heated at 85° C. for 48 h, cooled to RT and partitioned between ethyl acetate and 3 M HCl. The combined organic extract was dried over MgSO₄, concentrated and chromatographed to give the title compound. m/z 468.3 (MH⁺).

B. 2-(2-Amino-2-methyl-propionylamino)-4-phenyl-thiazole-5-carboxylic acid ethyl ester A mixture of 2-(2-Benzyloxycarbonylamino-2-methyl-propionylamino)-4-phenyl-thiazole-5-carboxylic acid ethyl ester (1.57 g, 3.36 mmol) and 33% HBr (in acetic acid, 8 mL) in acetic acid (7 mL) was stirred at RT for 2 h, basified carefully to pH 7~8 by addition of aqueous KOH, and the product was extracted with ethyl acetate, dried over MgSO₄, concentrated and chromatographed to give the title compound. m/z 334.1 (MH⁺).

C. 2-[2-(4-Fluoro-benzoylamino)-2-methyl-propionylamino]4-phenyl-thiazole-5-carboxylic acid ethyl ester A mixture of 2-(2-Amino-2-methyl-propionylamino)-4-phenyl-thiazole-5-carboxylic acid ethyl ester (249 mg, 0.748 mmol), triethylamine (300 uL. 2.16 mmol) and 4-fluorobenzoyl chloride (135 uL, 1.13 mmol) in dichloromethane (3 mL) was stirred at RT for 2 h and partitioned between ethyl acetate and aq. K₂CO₃. The organic extract was dried over MgSO₄, concentrated and chromatographed to give the title compound. m/z 456.1 (MH⁺).

D. 2-[2-(4-Fluoro-benzoylamino)-2-methyl-propionylamino]-4-phenyl-thiazole-5-carboxylic acid A mixture of 2-[2-(4-Fluoro-benzoylamino)-2-methyl-propionylamino]-4-phenyl-thiazole-5-carboxylic acid ethyl ester (357 mg, 0.785 mmol) and concentrated aqueous KOH (2 mL) in a mixture of THF (3 mL) and ethanol (5 mL) was heated at 65° C. for 2 h, cooled to RT and partitioned between ethyl acetate and 3 M HCl. The combined organic extract was dried and concentrated to give the title compound. m/z 428.1 (MH$^+$).

E. 4-{2-[2-(4-Fluoro-benzoylamino)-2-methyl-propionylamino]-4-phenyl-thiazole-5-carbonyl}-piperazine-1-carboxylic acid tert-butyl ester A mixture of 2-[2-(4-Fluoro-benzoylamino)-2-methyl-propionylamino]-4-phenyl-thiazole-5-carboxylic acid (46 mg, 0.11 mmol), HBTU (50 mg, 0.13 mmol), triethylamine (22 uL, 0.16 mmol) and N-Boc piperazine (27 mg, 0.15 mmol) in DMF (2 mL) was stirred at RT for 18 h and partitioned between ethyl acetate and aq. K$_2$CO$_3$. The organic extract was dried over MgSO$_4$, concentrated and chromatographed to give the title compound. m/z 596.2 (MH$^+$).

F. 4-Fluoro-N-{1-methyl-1-[4-phenyl-5-(piperazine-1-carbonyl)-thiazol-2-ylcarbamoyl]-ethyl}-benzamide A mixture of 4-{2-[2-(4-Fluoro-benzoylamino)-2-methyl-propionylamino]-4-phenyl-thiazole-5-carbonyl}-piperazine-1-carboxylic acid tert-butyl ester (120 mg) and TFA (3 mL) in dichloromethane (3 mL) was stirred at RT for 1 h. The mixture was concentrated, and the residue was partitioned between ethyl acetate and aq. K$_2$CO$_3$. The organic extract was dried over MgSO$_4$ and concentrated. The residue was taken up in dichloromethane-methanol (3:1 v/v), and 2 M HCl (in ether, 100 uL) was added. The mixture was stirred at RT for 10 min and concentrated to give hydrochloride salt of the title compound. LCMS method A, retention time 1.0 min. m/z 496.1 (M+H$^+$).

Example 12-2

4-Fluoro-N-[1-methyl-1-(4-phenyl-5-piperazin-1-ylmethyl-thiazol-2-ylcarbamoyl)-ethyl]-benzamide

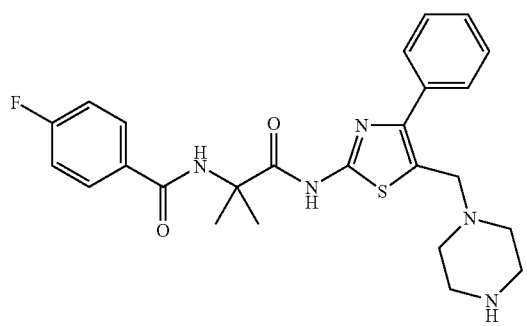 [SMILES: CC(C)(NC(=O)c1ccc(F)cc1)C(=O)Nc1nc(-c2ccccc2)c(CN2CCNCC2)s1]

A. 4-Fluoro-N-[1-(5-hydroxymethyl-4-ph\enyl-thiazol-2-ylcarbamoyl)-1-methyl-ethyl]-benzamide Isobutyl chloroformate (150 uL, 1.15 mmol) was added to a mixture of 2-[2-(4-Fluoro-benzoylamino)-2-methyl-propionylamino]-4-phenyl-thiazole-5-carboxylic acid (225 mg, 0.527 mmol) and triethylamine (200 uL, 1.44 mmol) in THF (5 mL) at RT. The mixture was stirred at RT for 20 min and filtered. The filtrate was concentrated, and the residue was taken up in methanol (10 mL). To this was added NaBH$_4$ (280 mg, 7.41 mmol) in methanol (4 mL) at RT, and the mixture was stirred at RT for 10 min, partitioned between ethyl acetate and aq. K$_2$CO$_3$. The organic extract was dried over MgSO$_4$, concentrated and chromatographed to give the title compound. m/z 414.2 (MH$^+$).

B. 4-{2-[2-(4-Fluoro-benzoylamino)-2-methyl-propionylamino]-4-phenyl-thiazol-5-ylmethyl}-piperazine-1-carboxylic acid tert-butyl ester A mixture of 4-Fluoro-N-[1-(5-hydroxymethyl-4-phenyl-thiazol-2-ylcarbamoyl)-1-methyl-ethyl]-benzamide (82 mg, 0.20 mmol), MsCl (40 uL) and triethylamine (160 uL) in dichloromethane (3 mL) was stirred at RT for 20 min and concentrated. The residue was taken up in MeCN (5 mL), and N-Boc piperazine (120 mg, 0.644 mmol) and triethylamine (160 uL) were added. The mixture was stirred at RT for 20 min and partitioned between ethyl acetate and aq. K$_2$CO$_3$. The combined organic extract was dried over MgSO$_4$, concentrated and chromatographed to give the title compound. m/z 582.2 (MH$^+$).

C. 4-Fluoro-N-[1-methyl-1-(4-phenyl-5-piperazin-1-ylmethyl-thiazol-2-ylcarbamoyl)-ethyl]-benzamide A solution of 4-{2-[2-(4-Fluoro-benzoylamino)-2-methyl-propionylamino]-4-phenyl-thiazol-5-ylmethyl}-piperazine-1-carboxylic acid tert-butyl ester (70 mg) and TFA (1.5 mL) in dichloromethane (3 mL) was stirred at RT for 2 h and concentrated. The residue was partitioned between dichloromethane and aq. K$_2$CO$_3$. The organic extract was dried over MgSO$_4$, concentrated and purified by HPLC to give the title compound. m/z 482.2 (MH$^+$). $^1$H NMR (CD$_3$OD) 7.98-7.96 (m, 2H), 7.57 (d, J=8 Hz, 2H), 7.41 (t, J=8 Hz, 2H), 7.35 (d, J=8 Hz, 2H), 7.21 (t, J=8 Hz, 2H), 3.75 (s, 2H), 2.88-2.85 (m, 4H), 2.55-2.45 (m, 4H).

<Method A, Retention Time 1.13 min>

Example 12-3

1-Methyl-cyclopropanecarboxylic acid {1-[5-(4-fluoro-benzoyl)-4-trifluoromethyl-thiazol-2-ylcarbamoyl]-1-methyl-ethyl}-amide

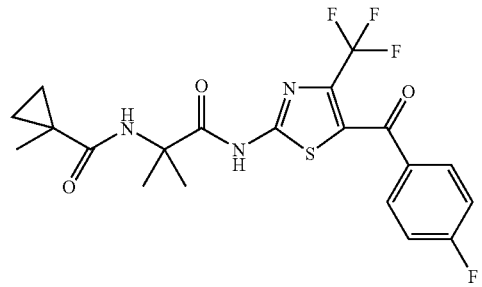 [SMILES: CC1(C(=O)NC(C)(C)C(=O)Nc2nc(C(F)(F)F)c(C(=O)c3ccc(F)cc3)s2)CC1]

A. (2-Amino-4-trifluoromethyl-thiazol-5-yl)-(4-fluoro-phenyl)-methanone

A mixture of 4,4,4-Trifluoro-1-(4-fluoro-phenyl)-butane-1,3-dione (15 g, 64 mmol) and NBS (11.4 g, 64.1 mmol) was ground together at RT, which incited to give a homogeneous mixture and then solidified to give crude brominated product. Water was added to rinse the solid. The solid was taken up in ethanol (50 mL), and thiourea (4.9 g, 64 mmol) was added. The mixture was heated at 85° C. for 4 h, cooled to RT and partitioned between ethyl acetate and aq. K$_2$CO$_3$. The organic extract was dried over MgSO₄, concentrated and chromatographed to give the title compound. m/z 291.0 (MH⁺).

B. {1-[5-(4-Fluoro-benzoyl)-4-trifluoromethyl-thiazol-2-ylcarbamoyl]-1-methyl-ethyl}-carbamic acid benzyl ester A mixture of N-Cbz 2-aminoisobutylic acid (1.52 g, 6.41 mmol), HBTU (2.45 g, 6.60 mmol) and triethylamine (900 uL, 6.46 mmol) in DMF (8 mL) was stirred at RT for 5 min. To this was added (2-Amino-4-trifluoromethyl-thiazol-5-yl)-(4-fluoro-phenyl)-methanone (1.01 g, 3.48 mmol), and the mixture was heated at 85° C. for 3 h, cooled to RT, and triethylamine (1 mL, 7.2 mmol) was added. The mixture was continued to be heated at 85° C. for 16 h, cooled to RT and partitioned between ethyl acetate and, sequentially, 3 M HCl and aqueous KOH. The combined organic extract was dried over MgSO₄, concentrated and chromatographed to give the title compound. m/z 509.9 (MH⁺)

C. 2-Amino-N-[5-(4-fluoro-benzoyl)-4-trifluoromethyl-thiazol-2-yl]-2-methyl-propionamide A mixture of {1-[5-(4-Fluoro-benzoyl)-4-trifluoromethyl-thiazol-2-ylcarbamoyl]-1-methyl-ethyl}-carbamic acid benzyl ester (1.42 g, 2.79 mmol) and 33% HBr (in acetic acid, 5 mL, 92 mmol) in acetic acid (10 mL) was stirred at RT for 1 h, diluted with aqueous KOH carefully to make pH=8-9, and the product was extracted with ethyl acetate, dried over MgSO₄ and concentrated. Chromatography gave the title compound. m/z 376.1 (MH⁺).

D. 1-Methyl-cyclopropanecarboxylic acid {1-[5-(4-fluoro-benzoyl)-4-trifluoromethyl-thiazol-2-ylcarbamoyl]-1-methyl-ethyl}-amide A mixture of 2-Amino-N-[5-(4-fluoro-benzoyl)-4-trifluoromethyl-thiazol-2-yl]-2-methyl-propionamide (150 mg, 0.400 mmol), 1-methylcyclopropyl carboxylic acid (80 mg, 0.80 mmol), triethylamine (140 uL, 1.00 mmol) and HBTU (300 mg, 0.809 mmol) was stirred at RT for 18 h, partitioned between ethyl acetate and, sequentially, 3 M HCl and aqueous KOH. The organic extract was dried over MgSO₄, concentrated and purified by HPLC to give the title compound. m/z 458.3 (MH⁺). ¹H NMR (CDCl₃) δ 7.91 (dd, J=8, 4 Hz, 2H), 7.16 (t, J=8 Hz, 2H), 6.04 (br s, 1H), 1.63 (s, 6H), 1.38 (s, 3H), 1.30-1.25 (m, 2H), 0.70-0.65 (m, 2H), retention time 1.42 min (method A).

Example 12-4

[1,4]Oxazepane-4-carboxylic acid {1-[5-(4-fluoro-benzoyl)-4-trifluoromethyl-thiazol-2-ylcarbamoyl]-1-methyl-ethyl}-amide

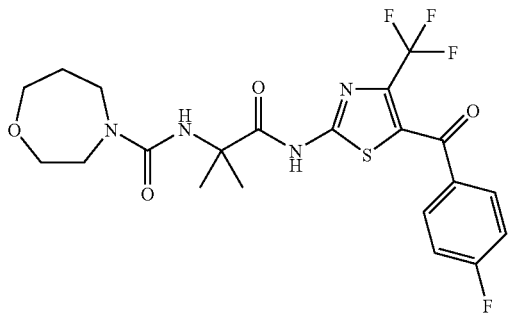 [SMILES: CC(C)(NC(=O)N1CCCOCC1)C(=O)Nc1nc(C(F)(F)F)c(C(=O)c2ccc(F)cc2)s1]

A mixture of triphosgene (79 mg, 0.27 mmol) and 2-Amino-N-[5-(4-fluoro-benzoyl)-4-trifluoromethyl-thiazol-2-yl]-2-methyl-propionamide (100 mg, 0.266 mmol), K₂CO₃ (147 mg, 1.07 mmol) in water (3 mL) and dichloromethane (3 mL) was stirred at RT for 1 h, and water layer was separated, and dichloromethane layer was dried over Na₂SO₄ and concentrated to give the crude intermediate, which was taken up in pyridine (10 mL). Homomorpholine HCl salt (269 mg, 2.66 mmol) was basified by partitioning between ethyl acetate and aqueous KOH, and after evaporation of the solvent, it was added to the intermediate above. The mixture was heated at 80° C. for 18 h, and most of pyridine was removed under vacuum, and the mixture was partitioned between ethyl acetate and 1 M HCl. The combined organic extract was dried over Na₂SO₄, concentrated and chromatographed to give the title compound. m/z 503.0 (MH⁺), ¹H NMR (CDCl₃) δ 11.4 (s, 1H), 7.92 (dd, J=8, 4 Hz, 2H), 7.16 (t, J=8 Hz, 2H), 4.64 (s, 1H), 3.80-3.75 (m, 4H), 3.60-3.50 (m, 4H), 2.02-1.93 (m, 2H), 1.63 (s, 6H). Retention time 1.31 min (method A).

Intermediate 4 (For Examples Similar to 12-28)

[2-Amino-4-(1-fluoro-1-methyl-ethyl)-thiazol-5-yl]-(4-fluoro-phenyl)-methanone

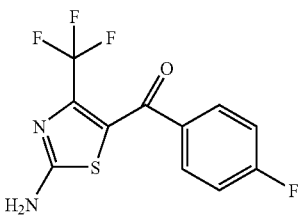 [SMILES: Nc1nc(C(F)(F)F)c(C(=O)c2ccc(F)cc2)s1]

A. 4-Fluoro-1-(4-fluoro-phenyl)-4-methyl-pentane-1,3-dione 1-(4-Fluorophenyl)ethanone (1.2 mL) was added to a solution of 1M NaHMDS (10 mL in THF) in THF (30 mL) at RT. The mixture was stirred at RT for 15 min. To this was added ethyl 2-fluoroisobutylate, and the mixture was stirred at RT for 2 h. The mixture was partitioned between ethyl acetate and 3 M HCl. The organic extract was dried over MgSO₄, concentrated and chromatographed to give the title compound. m/z 227.3 (MH⁺).

B. [2-Amino-4-(1-fluoro-1-methyl-ethyl)-thiazol-5-yl]-(4-fluoro-phenyl)-methanone A mixture of 4-Fluoro-1-(4-fluoro-phenyl)-4-methyl-pentane-1,3-dione (900 mg) and Koser's reagent (4.2 g) in MeCN (20 mL) was heated at 80° C. for 50 min. The mixture was cooled to RT, and thiourea (820 mg) was added. The mixture was heated at 80° C. for 3 h., cooled to RT and partitioned between ethyl acetate and aq. KOH. The organic extract was dried over MgSO₄, concentrated and chromatographed to give the title compound. m/z 283.2 (MH⁺). ¹H NMR (DMSO-d₆) 7.81 (dd, J=8, 4 Hz, 2H), 7.73 (s, 2H), 7.32 (t, J=8 Hz, 2H), 1.61 (d, J=20 Hz, 6H).

Intermediate 5 (For Examples Similar to 12-36)

(2-Amino-4-trifluoromethyl-thiazol-5-yl)-p-tolyl-methanone

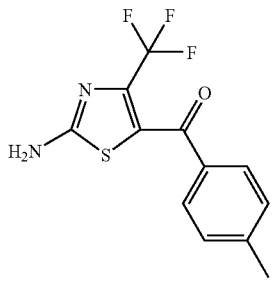 [SMILES: Cc1ccc(C(=O)c2sc(N)nc2C(F)(F)F)cc1]

4,4,4-trifluoro-1-p-tolylbutane-1,3-dione (4 g, 17.4 mmol) in 100 mL dichloromethane at 0° C. under N₂ was treated in portions with 3.09 g (17.4 mmol) N-bromosuccinimide. A white precipitate gradually formed. After 4.5 h solids were filtered off, the filtrate was washed with water and brine and dried over Na₂SO₄, then evaporated. The residue was taken up in 100 mL EtOH, treated with 1.32 g (17.4 mmol)thiourea and 1.04 g (17.4 mmol) silica and heated at 70° C. overnight. The reaction was cooled, filtered and evaporated. The crude was taken up in EtOAc, washed with NaHCO₃ and brine, dried over Na₂SO₄ and evaporated. Trituration with Et₂O: heptane provided 1.31 g desired as a yellow solid, still containing impurities. Chromatography (SiO2, EtOAc: dichloromethane) provided the title compound. The filtrate from the trituration also contained desired material and was similarly purified to provide the title compound. LCMS (method A) 287.1 (M+H), 285.2 (M−H). ¹H-NMR (400 MHz, Chloroform-d) ppm 2.45 (s, 3H), 5.68 (br s, 2H), 7.29 (d, J=7.96 Hz, 2H), 7.77 (d, J=8.21 Hz, 2H).

Intermediate 6 (For Examples Similar to 12-44)

[2-Amino-4-(4-fluoro-phenyl)-thiazol-5-yl]-(4-fluoro-phenyl)-methanone

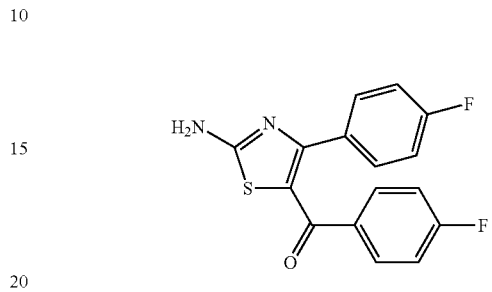

1,3-Bis-(4-fluoro-phenyl)-propane-1,3-dione and NBS (1.05 eq) were heated neat at 60° C. for 10 minutes then cooled. The resulting mixture was dissolved in ethanol (0.2 M) and treated with thiourea (1.5 eq). It was heated at reflux for 15 hours and cooled to room temperature. It was evaporated to dryness and the residue was partioned between EtOAc and saturated NaHCO3. Organic fraction was dried over MgSO4, filtered and concentrated. The title compound was collected by trituration with heptanes. ¹H NMR (400 MHz, DMSO-d6) 6.86-7.01 (m, 4H) 7.22-7.32 (m, 2H) 7.35-7.45 (m, 2H) 8.11 (br. s., 2H). LCMS Method A Rt=1.18 m/z 317.0 (M+1), 315 (M−1).

The following compounds were prepared using similar procedures described above.

| structure | Ex. | Names | LC rt | Method | (M + 1)+ |
|---|---|---|---|---|---|
| 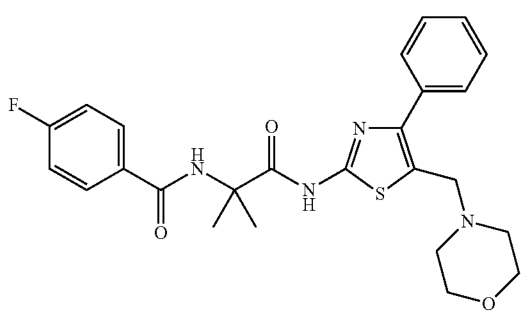 [SMILES: CC(C)(NC(=O)c1ccc(F)cc1)C(=O)Nc1nc(-c2ccccc2)c(CN2CCOCC2)s1] | 12-5 | 4-Fluoro-N-[1-methyl-1-(5-morpholin-4-ylmethyl-4-phenyl-thiazol-2-ylcarbamoyl)-ethyl]-benzamide | 1.33 | A | 483.1 |
| 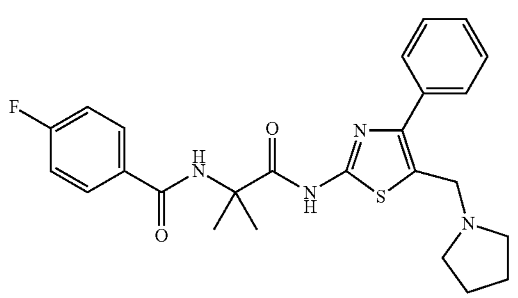 [SMILES: CC(C)(NC(=O)c1ccc(F)cc1)C(=O)Nc1nc(-c2ccccc2)c(CN2CCCC2)s1] | 12-6 | 4-Fluoro-N-[1-methyl-1-(4-phenyl-5-pyrrolidin-1-ylmethyl thiazol-2-ylcarbamoyl)-ethyl]-benzamide | 1.19 | A | 467.1 |

-continued

| structure | Ex. | Names | LC rt | Method | (M + 1)+ |
|---|---|---|---|---|---|
| 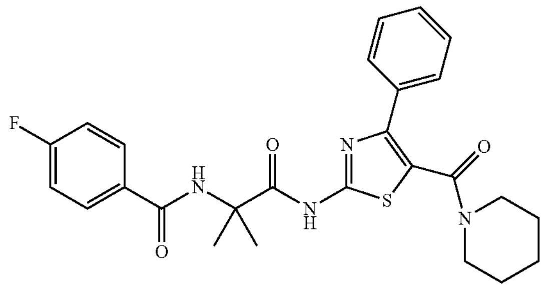 [SMILES: CC(C)(NC(=O)c1ccc(F)cc1)C(=O)Nc1nc(-c2ccccc2)c(C(=O)N2CCCCC2)s1] | 12-7 | 4-Fluoro-N-{1-methyl-1-[4-phenyl-5-(piperidine-1-carbonyl)-thiazol-2-ylcarbamoyl]-ethyl}-benzamide | 1.35 | A | 495.1 |
| 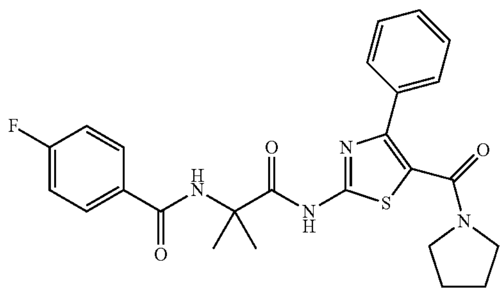 [SMILES: CC(C)(NC(=O)c1ccc(F)cc1)C(=O)Nc1nc(-c2ccccc2)c(C(=O)N2CCCC2)s1] | 12-8 | 4-Fluoro-N-{1-methyl-1-[4-phenyl-5-(pyrrolidine-1-carbonyl)-thiazol-2-ylcarbamoyl]-ethyl}-benzamide | 1.26 | A | 481.0 |
| 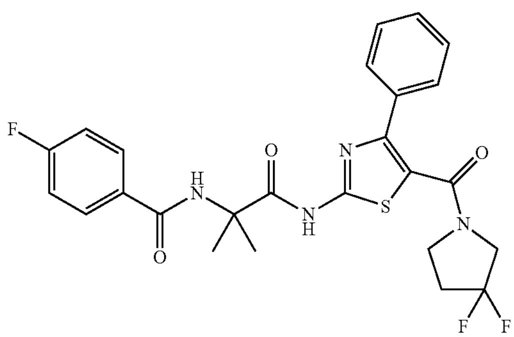 [SMILES: CC(C)(NC(=O)c1ccc(F)cc1)C(=O)Nc1nc(-c2ccccc2)c(C(=O)N2CCC(F)(F)C2)s1] | 12-9 | N-{1-[5-(3,3-Difluoro-pyrrolidine-1-carbonyl)-4-phenyl-thiazol-2-ylcarbamoyl]-1-methyl-ethyl}-4-fluoro-benzamide | 1.32 | A | 517.0 |
| 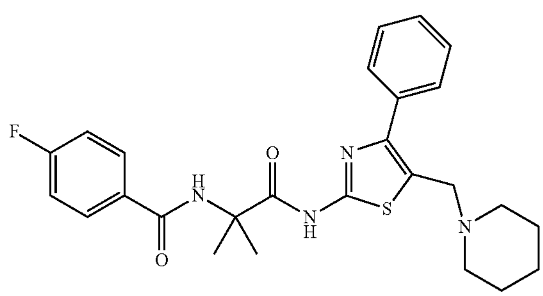 [SMILES: CC(C)(NC(=O)c1ccc(F)cc1)C(=O)Nc1nc(-c2ccccc2)c(CN2CCCCC2)s1] | 12-10 | 4-Fluoro-N-[1-methyl-1-(4-phenyl-5-piperidin-1-ylmethyl-thiazol-2-ylcarbamoyl)-ethyl]-benzamide | 1.29 | A | 481.2 |
| 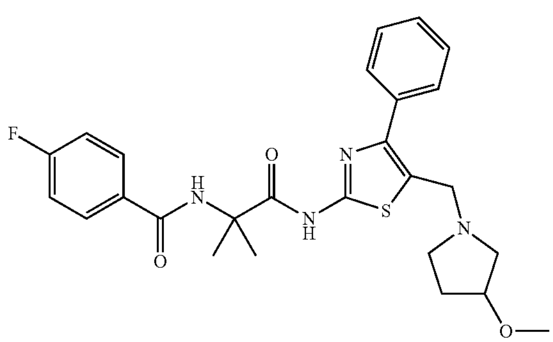 [SMILES: COC1CCN(Cc2sc(NC(=O)C(C)(C)NC(=O)c3ccc(F)cc3)nc2-c2ccccc2)C1] | 12-11 | 4-Fluoro-N-{1-[5-(3-methoxy-pyrrolidin-1-ylmethyl)-4-phenyl-thiazol-2-ylcarbamoyl]-1-methyl-ethyl)-benzamide | 1.27 | A | 497.2 |

-continued

| structure | Ex. | Names | LC rt | Method | (M + 1)+ |
|---|---|---|---|---|---|
| 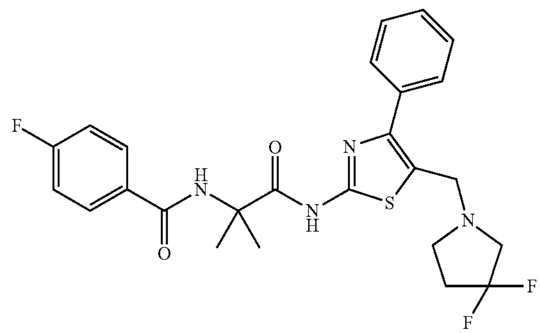 [SMILES: CC(C)(NC(=O)c1ccc(F)cc1)C(=O)Nc1nc(-c2ccccc2)c(CN2CCC(F)(F)C2)s1] | 12-12 | N-{1-[5-(3,3-Difluoro-pyrrolidin-1-ylmethyl)-4-phenyl-thiazol-2-ylcarbamoyl]-1-methyl-ethyl}-4-fluoro-benzamide | 1.47 | A | 503.1 |
| 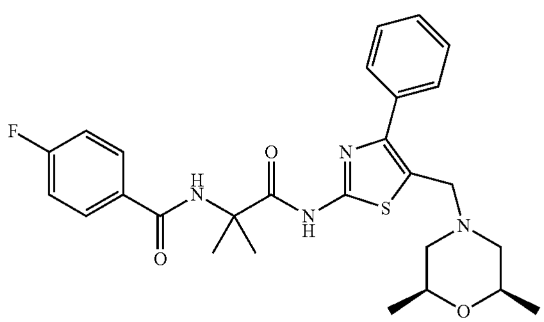 [SMILES: C[C@@H]1CN(Cc2sc(NC(=O)C(C)(C)NC(=O)c3ccc(F)cc3)nc2-c2ccccc2)C[C@H](C)O1] | 12-13 | N-{1-[5-((2R,6S)-2,6-Dimethyl-morpholin-4-ylmethyl)-4-phenyl-thiazol-2-ylcarbamoyl]-1-methyl-ethyl}-4-fluoro-benzamide | 1.45 | A | 511.2 |
| 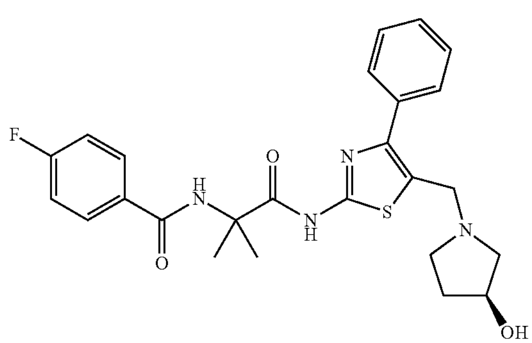 [SMILES: CC(C)(NC(=O)c1ccc(F)cc1)C(=O)Nc1nc(-c2ccccc2)c(CN2CC[C@H](O)C2)s1] | 12-14 | 4-Fluoro-N-{1-[5-((S)-3-hydroxy-pyrrolidin-1-ylmethyl)-4-phenyl-thiazol-2-ylcarbamoyl]-1-methyl-ethyl}-benzamide | 1.06 | A | 483.2 |
| 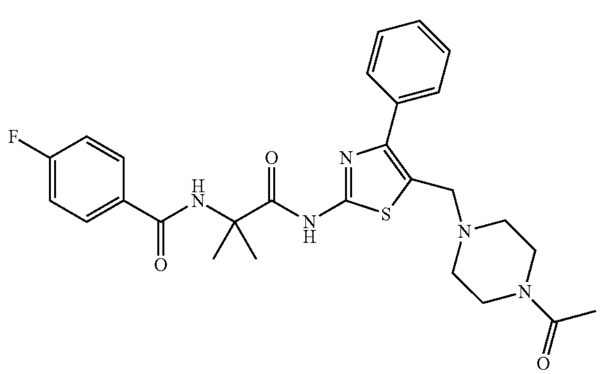 [SMILES: CC(=O)N1CCN(Cc2sc(NC(=O)C(C)(C)NC(=O)c3ccc(F)cc3)nc2-c2ccccc2)CC1] | 12-15 | N-{1-[5-(4-Acetyl-piperazin-1-ylmethyl)-4-phenyl-thiazol-2-ylcarbamoyl]-1-methyl-ethyl}-4-fluorobenzamide | 1.19 | A | 524.1 |

-continued

| structure | Ex. | Names | LC rt | Method | (M + 1)+ |
|---|---|---|---|---|---|
| 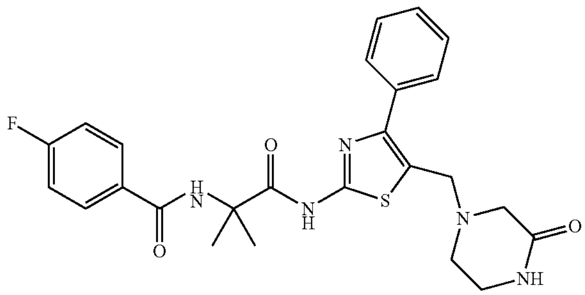 [SMILES: CC(C)(NC(=O)c1ccc(F)cc1)C(=O)Nc1nc(-c2ccccc2)c(CN2CCNC(=O)C2)s1] | 12-16 | 4-Fluoro-N-{1-methyl-1-[5-(3-oxo-piperazin-1-ylmethyl)-4-phenyl-thiazol-2-ylcarbamoyl]-ethyl}-benzamide | 1.09 | A | 496.1 |
| 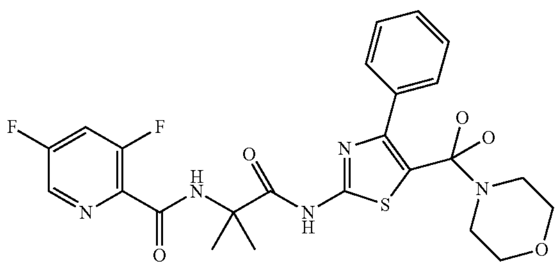 [SMILES: CC(C)(NC(=O)c1ncc(F)cc1F)C(=O)Nc1nc(-c2ccccc2)c(C(O)(O)N2CCOCC2)s1] | 12-17 | 3,5-Difluoro-pyridine-2-carboxylic acid {1-[5-(dideutero-morpholin-4-yl-methyl)-4-phenyl-thiazol-2-ylcarbamoyl]-1-methyl-ethyl}-amide | 1.27 | A | 504.3 |
| 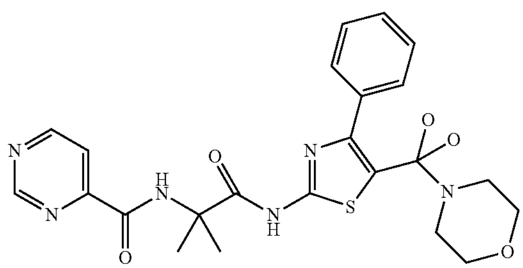 [SMILES: CC(C)(NC(=O)c1ccncn1)C(=O)Nc1nc(-c2ccccc2)c(C(O)(O)N2CCOCC2)s1] | 12-18 | Pyrimidine-4-carboxylic acid {1-[5-(dideutero-morpholin-4-yl-methyl)-4-phenyl-thiazol-2-ylcarbamoyl]-1-methyl-ethyl}-amide | 1.15 | A | 469.3 |
| 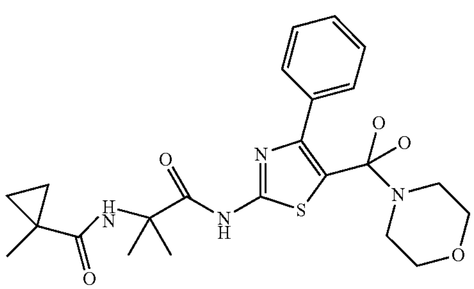 [SMILES: CC1(C(=O)NC(C)(C)C(=O)Nc2nc(-c3ccccc3)c(C(O)(O)N3CCOCC3)s2)CC1] | 12-19 | 1-Methyl-cyclopropanecarboxylic acid {1-[5-(dideutero-morpholin-4-yl-methyl)-4-phenyl-thiazol-2-ylcarbamoyl]-1-methyl-ethyl}-amide | 1.25 | A | 445.4 |
| 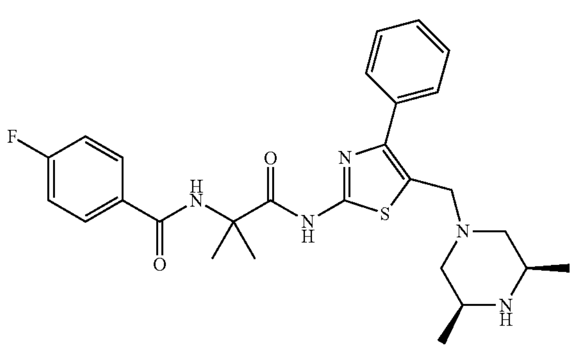 [SMILES: C[C@@H]1CN(Cc2sc(NC(=O)C(C)(C)NC(=O)c3ccc(F)cc3)nc2-c2ccccc2)C[C@H](C)N1] | 12-20 | N-{1-[5-((3R,5S)-3,5-Dimethyl-piperazin-1-ylmethyl)-4-phenyl-thiazol-2-ylcarbamoyl]-1-methyl-ethyl}-4-fluoro-benzamide | 1 | A | 510.1 |

-continued

| structure | Ex. | Names | LC rt | Method | (M + 1)+ |
|---|---|---|---|---|---|
| 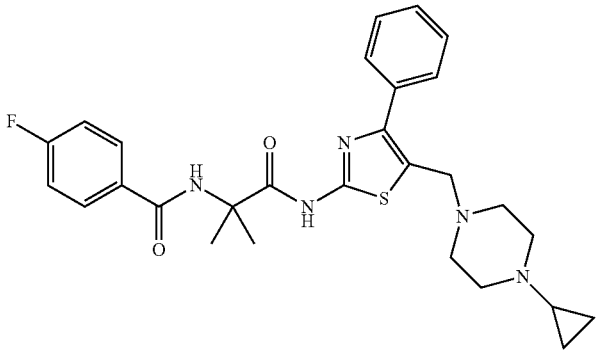 [SMILES: CC(C)(NC(=O)c1ccc(F)cc1)C(=O)Nc1nc(-c2ccccc2)c(CN2CCN(C3CC3)CC2)s1] | 12-21 | N-{1-[5-(4-Cyclopropyl-piperazin-1-ylmethyl)-4-phenyl-thiazol-2-ylcarbamoyl]-1-methyl-ethyl}-4-fluoro-benzamide | 1.37 | A | 522.2 |
| 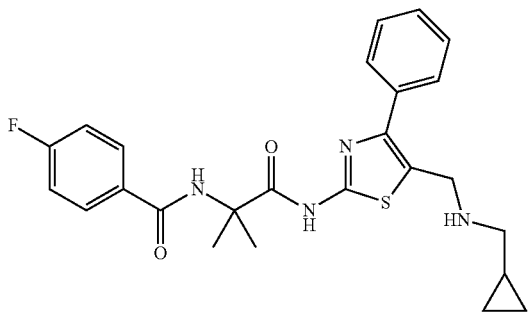 [SMILES: CC(C)(NC(=O)c1ccc(F)cc1)C(=O)Nc1nc(-c2ccccc2)c(CNCC2CC2)s1] | 12-22 | N-(1-{5-[(Cyclopropylmethyl-amino)-methyl]-4-phenyl-thiazol-2-ylcarbamoyl}-1-methyl-ethyl)-4-fluoro-benzamide | 1.11 | A | 467.1 |
| 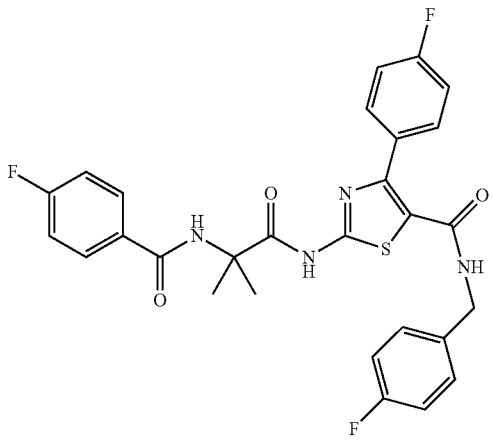 [SMILES: CC(C)(NC(=O)c1ccc(F)cc1)C(=O)Nc1nc(-c2ccc(F)cc2)c(C(=O)NCc2ccc(F)cc2)s1] | 12-23 | 2-[2-(4-Fluoro-benzoylamino)-2-methyl-propionylamino]-4-(4-fluoro-phenyl)-thiazole-5-carboxylic acid 4-fluoro-benzylamide | 1.35 | A | 553.1 |
| 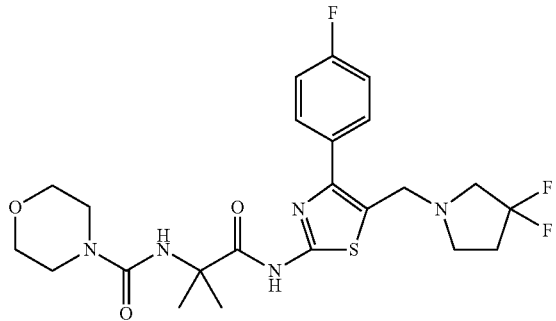 [SMILES: CC(C)(NC(=O)N1CCOCC1)C(=O)Nc1nc(-c2ccc(F)cc2)c(CN2CCC(F)(F)C2)s1] | 12-24 | Morpholine-4-carboxylic acid {1-[5-(3,3-difluoro-pyrrolidin-1-ylmethyl)-4-(4-fluoro-phenyl)-thiazol-2-ylcarbamoyl]-1-methyl-ethyl}-amide | 1.33 | A | 512.3 |

-continued

| structure | Ex. | Names | LC rt | Method | (M + 1)+ |
|---|---|---|---|---|---|
| 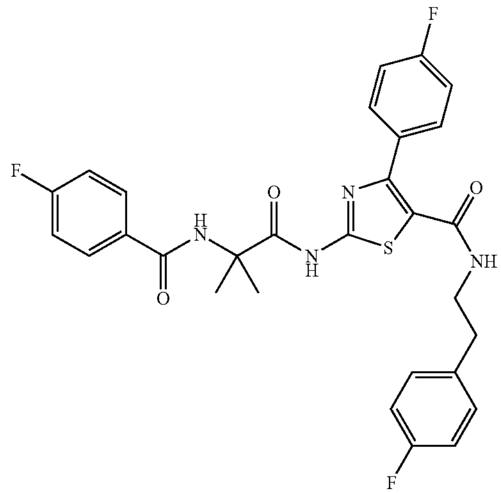 [SMILES: CC(C)(NC(=O)c1ccc(F)cc1)C(=O)Nc1nc(-c2ccc(F)cc2)c(C(=O)NCCc2ccc(F)cc2)s1] | 12-25 | 2-[2-(4-Fluoro-benzoylamino)-2-methyl-propionylamino]-4-(4-fluoro-phenyl)-thiazole-5-carboxylic acid [2-(4-fluoro-phenyl)-ethyl]-amide | 1.41 | A | 567.1 |
| 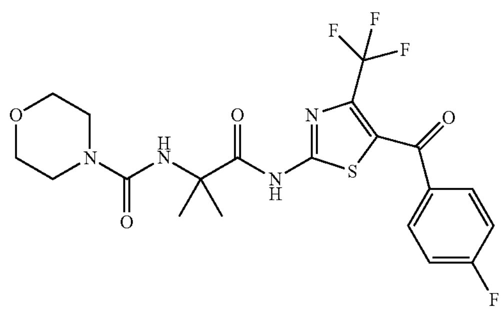 [SMILES: CC(C)(NC(=O)N1CCOCC1)C(=O)Nc1nc(C(F)(F)F)c(C(=O)c2ccc(F)cc2)s1] | 12-26 | Morpholine-4-carboxylic acid {1-[5-(4-fluoro-benzoyl)-4-trifluoromethyl-thiazol-2-ylcarbamoyl]-1-methyl-ethyl}-amide | 1.27 | A | 489 |
| 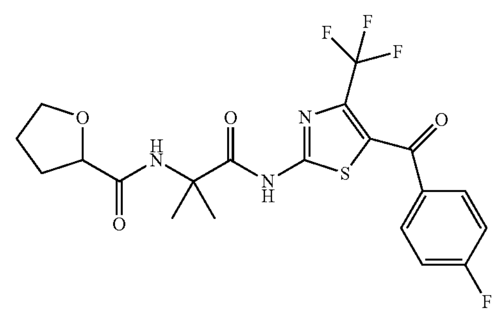 [SMILES: CC(C)(NC(=O)C1CCCO1)C(=O)Nc1nc(C(F)(F)F)c(C(=O)c2ccc(F)cc2)s1] | 12-27 | Tetrahydro-furan-2-carboxylic acid {1-[5-(4-fluoro-benzoyl)-4-trifluoromethyl-thiazol-2-ylcarbamoyl]-1-methyl-ethyl}-amide | 1.35 | A | 473.9 |
| 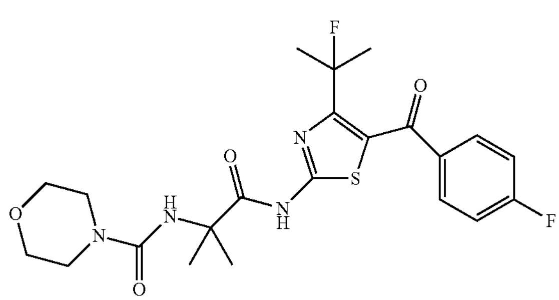 [SMILES: CC(C)(NC(=O)N1CCOCC1)C(=O)Nc1nc(C(C)(C)F)c(C(=O)c2ccc(F)cc2)s1] | 12-28 | Morpholine-4-carboxylic acid {1-[5-(4-fluoro-benzoyl)-4-(1-fluoro-1-methyl-ethyl)-thiazol-2-ylcarbamoyl]-1-methyl-ethyl}-amide | 1.23 | A | 481.1 |

-continued

| structure | Ex. | Names | LC rt | Method | (M + 1)+ |
|---|---|---|---|---|---|
| 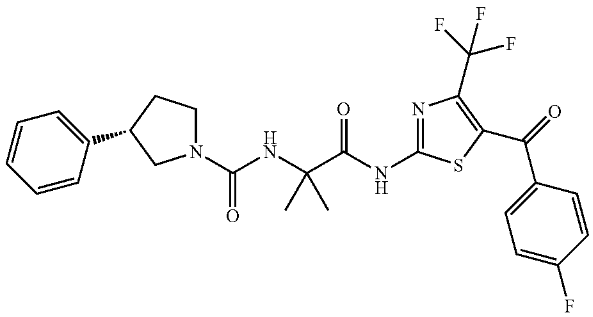 [SMILES: CC(C)(NC(=O)N1CC[C@@H](c2ccccc2)C1)C(=O)Nc1nc(C(F)(F)F)c(C(=O)c2ccc(F)cc2)s1] | 12-30 | (S)-3-Phenyl-pyrrolidine-1-carboxylic acid {1-[5-(4-fluoro-benzoyl)-4-trifluoromethyl-thiazol-2-ylcarbamoyl]-1-methyl-ethyl}-amide | 1.95 | A | 549.1 |
| 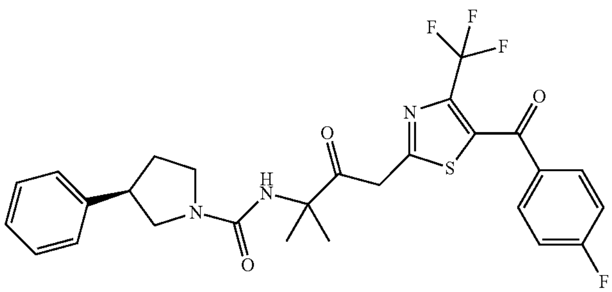 [SMILES: CC(C)(NC(=O)N1CC[C@H](c2ccccc2)C1)C(=O)Cc1nc(C(F)(F)F)c(C(=O)c2ccc(F)cc2)s1] | 12-31 | (R)-3-Phenyl-pyrrolidine-1-carboxylic acid {1-[5-(4-fluoro-benzoyl)-4-trifluoromethyl-thiazol-2-ylcarbamoyl]-1-methyl-ethyl}-amide | 1.93 | A | 549.2 |
| 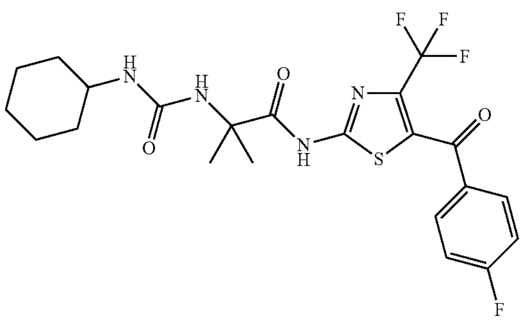 [SMILES: CC(C)(NC(=O)NC1CCCCC1)C(=O)Nc1nc(C(F)(F)F)c(C(=O)c2ccc(F)cc2)s1] | 12-32 | 2-(3-Cyclohexyl-ureido)-N-[5-(4-fluoro-benzoyl)-4-trifluoromethyl-thiazol-2-yl]-2-methyl-propionamide | 1.36 | A | 481.2 |
| 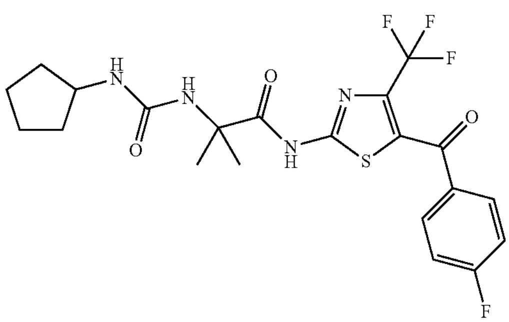 [SMILES: CC(C)(NC(=O)NC1CCCC1)C(=O)Nc1nc(C(F)(F)F)c(C(=O)c2ccc(F)cc2)s1] | 12-33 | 2-(3-Cyclopentyl-ureido)-N-[5-(4-fluoro-benzoyl)-4-trifluoromethyl-thiazol-2-yl]-2-methyl-propionamide | 1.58 | A | 486.9 |
| 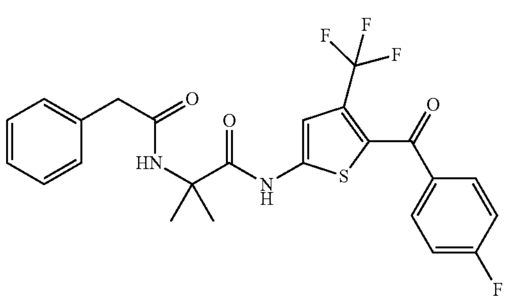 [SMILES: CC(C)(NC(=O)Cc1ccccc1)C(=O)Nc1cc(C(F)(F)F)c(C(=O)c2ccc(F)cc2)s1] | 12-34 | N-[5-(4-Fluoro-benzoyl)-4-trifluoromethyl-thiazol-2-yl]-2-methyl-2-phenylacetylamino-propionamide | 1.73 | A | 493.9 |

-continued

| structure | Ex. | Names | LC rt | Method | (M + 1)+ |
|---|---|---|---|---|---|
| 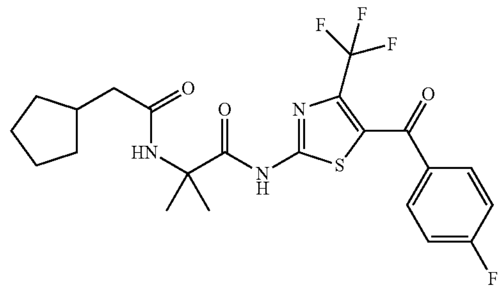 [SMILES: CC(C)(NC(=O)CC1CCCC1)C(=O)Nc1nc(C(F)(F)F)c(C(=O)c2ccc(F)cc2)s1] | 12-35 | 2-(2-Cyclopentyl-acetylamino)-N-[5-(4-fluoro-benzoyl)-4-trifluoromethyl-thiazol-2-yl]-2-methyl-propionamide | 1.78 | A | 485.9 |
| 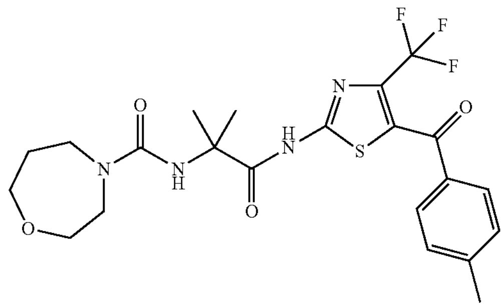 [SMILES: Cc1ccc(C(=O)c2sc(NC(=O)C(C)(C)NC(=O)N3CCCOCC3)nc2C(F)(F)F)cc1] | 12-36 | [1,4]Oxazepane-4-carboxylic acid {1-methyl-1-[5-(4-methyl-benzoyl)-4-trifluoromethyl-thiazol-2-ylcarbamoyl]-ethyl}-amide | 1.48 | A | 499.0 |
| 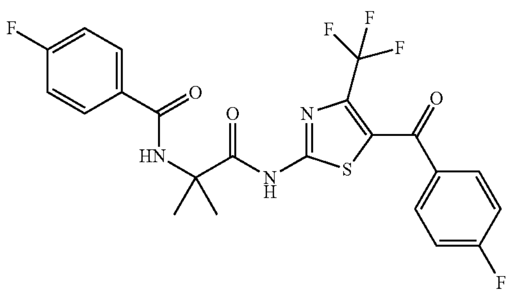 [SMILES: CC(C)(NC(=O)c1ccc(F)cc1)C(=O)Nc1nc(C(F)(F)F)c(C(=O)c2ccc(F)cc2)s1] | 12-37 | 4-Fluoro-N-{1-[5-(4-fluoro-benzoyl)-4-trifluoromethyl-thiazol-2-ylcarbamoyl]-1-methyl-ethyl}-benzamide | 1.73 | A | 498 |
| 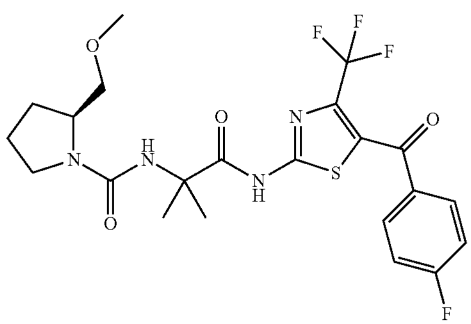 [SMILES: COC[C@@H]1CCCN1C(=O)NC(C)(C)C(=O)Nc1nc(C(F)(F)F)c(C(=O)c2ccc(F)cc2)s1] | 12-38 | (S)-2-Methoxymethyl-pyrrolidine-1-carboxylic acid {1-[5-(4-fluoro-benzoyl)-4-trifluoromethyl-thiazol-2-ylcarbamoyl]-1-methyl-ethyl}-amide | 1.6 | A | 517.0 |
| 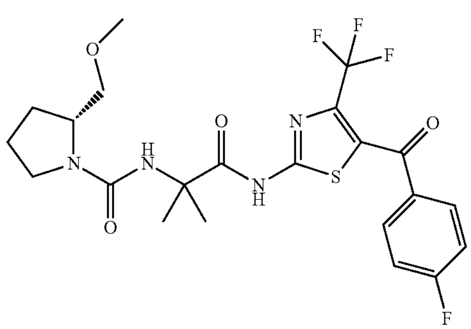 [SMILES: COC[C@H]1CCCN1C(=O)NC(C)(C)C(=O)Nc1nc(C(F)(F)F)c(C(=O)c2ccc(F)cc2)s1] | 12-39 | (R)-2-Methoxymethyl-pyrrolidine-1-carboxylic acid {1-[5-(4-fluoro-benzoyl)-4-trifluoromethyl-thiazol-2-ylcarbamoyl]-1-methyl-ethyl}-amide | 1.59 | A | 516.9 |

| structure | Ex. | Names | LC rt | Method | (M + 1)+ |
|---|---|---|---|---|---|
| 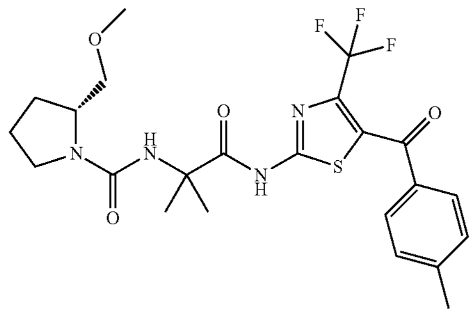 [SMILES: COC[C@H]1CCCN1C(=O)NC(C)(C)C(=O)Nc1nc(C(F)(F)F)c(C(=O)c2ccc(C)cc2)s1] | 12-40 | (R)-2-Methoxymethyl-pyrrolidine-1-carboxylic acid {1-methyl-1-[5-(4-methyl-benzoyl)-4-trifluoromethyl-thiazol-2-ylcarbamoyl]-ethyl}-amide | 1.62 | A | 513.0 |
| 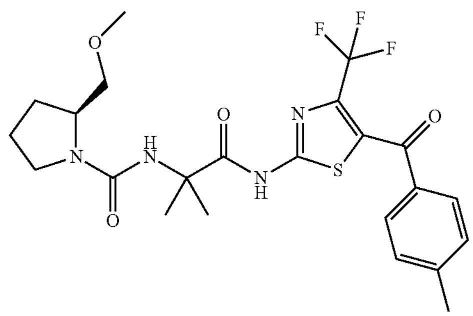 | 12-41 | (S)-2-Methoxymethyl-pyrrolidine-1-carboxylic acid {1-methyl-1-[5-(4-methyl-benzoyl)-4-trifluoromethyl-thiazol-2-ylcarbamoyl]-ethyl}-amide | 1.61 | A | 512.0 |
| 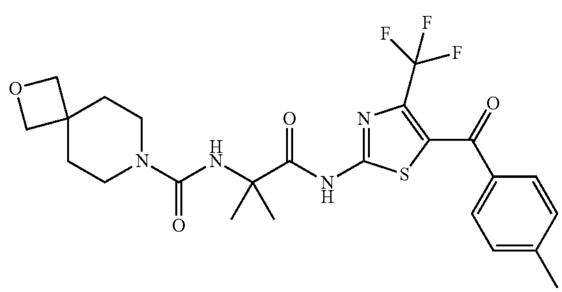 [SMILES: Cc1ccc(C(=O)c2sc(NC(=O)C(C)(C)NC(=O)N3CCC4(CC3)COC4)nc2C(F)(F)F)cc1] | 12-42 | 2-Oxa-7-aza-spiro[3.5]nonane-7-carboxylic acid {1-methyl-1-[5-(4-methyl-benzoyl)-4-trifluoromethyl-thiazol-2-ylcarbamoyl]-ethyl}-amide | 1.58 | A | 525.1 |
| 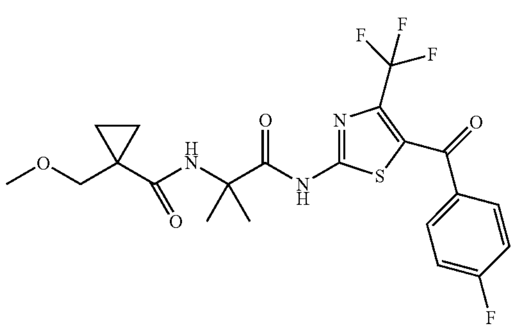 [SMILES: COCC1(C(=O)NC(C)(C)C(=O)Nc2nc(C(F)(F)F)c(C(=O)c3ccc(F)cc3)s2)CC1] | 12-43 | 1-Methoxymethyl-cyclopropanecarboxylic acid {1-[5-(4-fluoro-benzoyl)-4-trifluoromethyl-thiazol-2-ylcarbamoyl]-1-methyl-ethyl}-amide | 1.26 | A | 488.1 |
| 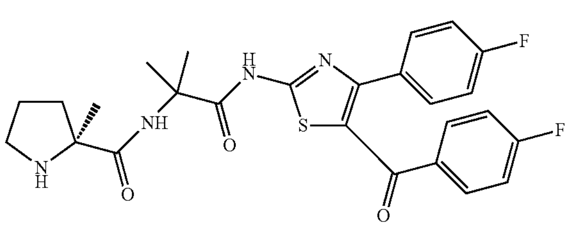 [SMILES: CC(C)(NC(=O)[C@]1(C)CCCN1)C(=O)Nc1nc(-c2ccc(F)cc2)c(C(=O)c2ccc(F)cc2)s1] | 12-44 | (S)-2-Methyl-pyrrolidine-2-carboxylic acid {1-[5-(4-fluoro-benzoyl)-4-(4-fluoro-phenyl)-thiazol-2-ylcarbamoyl]-1-methyl-ethyl}-amide | 1.11 | A | 513.3 |

-continued

| structure | Ex. | Names | LC rt | Method | (M + 1)+ |
|---|---|---|---|---|---|
| 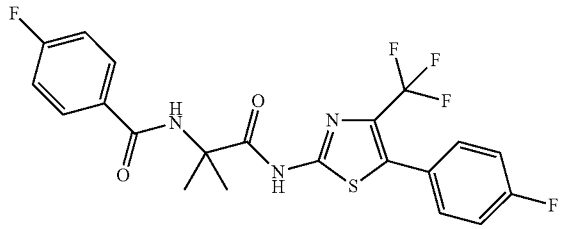 [SMILES: CC(C)(NC(=O)c1ccc(F)cc1)C(=O)Nc1nc(C(F)(F)F)c(-c2ccc(F)cc2)s1] | 12-45 | 4-Fluoro-N-{1-[5-(4-fluoro-phenyl)-4-trifluoromethyl-thiazol-2-ylcarbamoyl]-1-methyl-ethyl}-benzamide | 1.6 | A | 470.1 |
| 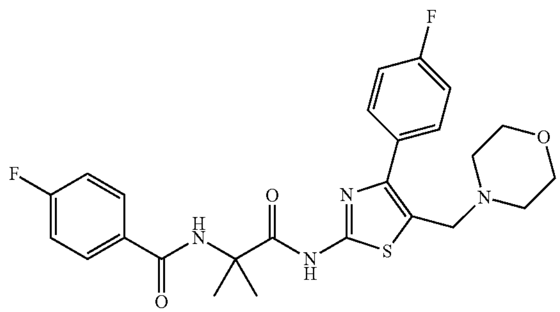 [SMILES: CC(C)(NC(=O)c1ccc(F)cc1)C(=O)Nc1nc(-c2ccc(F)cc2)c(CN2CCOCC2)s1] | 12-46 | 4-Fluoro-N-{1-[4-(4-fluoro-phenyl)-5-morpholin-4-ylmethyl-thiazol-2-ylcarbamoyl]-1-methyl-ethyl}-benzamide | 1.4 | A | 501 |
| 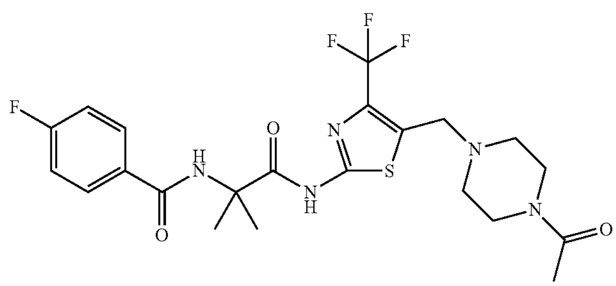 [SMILES: CC(=O)N1CCN(Cc2sc(NC(=O)C(C)(C)NC(=O)c3ccc(F)cc3)nc2C(F)(F)F)CC1] | 12-47 | N-{1-[5-(4-Acetyl-piperazin-1-ylmethyl)-4-trifluoromethyl-thiazol-2-ylcarbamoyl]-1-methyl-ethyl}-4-fluoro-benzamide | 1.21 | A | 516.3 |
| 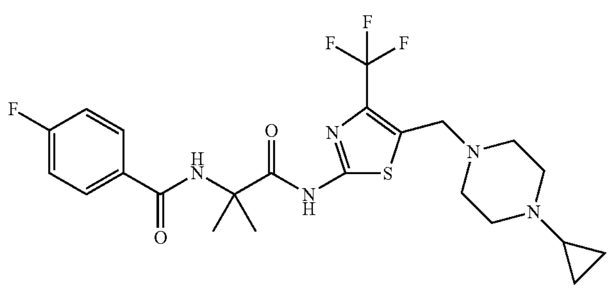 [SMILES: CC(C)(NC(=O)c1ccc(F)cc1)C(=O)Nc1nc(C(F)(F)F)c(CN2CCN(C3CC3)CC2)s1] | 12-48 | N-{1-[5-(4-Cyclopropyl-piperazin-1-ylmethyl)-4-trifluoromethyl-thiazol-2-ylcarbamoyl]-1-methyl-ethyl}-4-fluoro-benzamide | 1.38 | A | 514.2 |
| 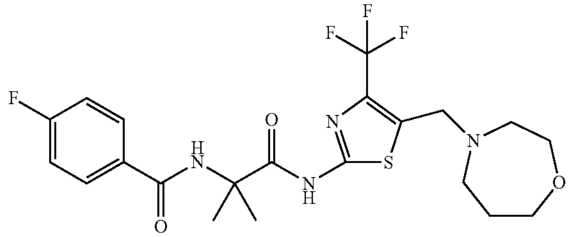 [SMILES: CC(C)(NC(=O)c1ccc(F)cc1)C(=O)Nc1nc(C(F)(F)F)c(CN2CCCOCC2)s1] | 12-49 | 4-Fluoro-N-[1-methyl-1-(5-[1,4]oxazepan-4-ylmethyl-4-trifluoromethyl-thiazol-2-ylcarbamoyl)-ethyl]-benzamide | 1.36 | A | 489.2 |

-continued

| structure | Ex. | Names | LC rt | Method | (M + 1)+ |
|---|---|---|---|---|---|
| 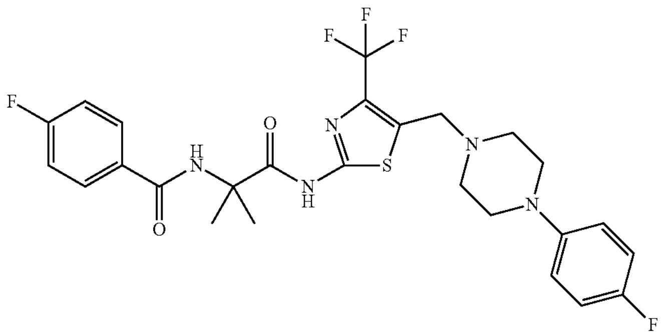 [SMILES: CC(C)(NC(=O)c1ccc(F)cc1)C(=O)Nc1nc(C(F)(F)F)c(CN2CCN(c3ccc(F)cc3)CC2)s1] | 12-50 | 4-Fluoro-N-(1-{5-[4-(4-fluoro-phenyl)-piperazin-1-ylmethyl]-4-trifluoromethyl-thiazol-2-ylcarbamoyl}-1-methyl-ethyl)-benzamide | 1.58 | A | 568.2 |
| 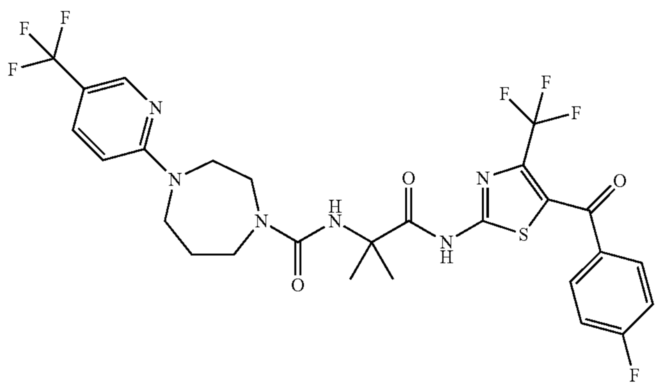 [SMILES: CC(C)(NC(=O)N1CCCN(c2ccc(C(F)(F)F)cn2)CC1)C(=O)Nc1nc(C(F)(F)F)c(C(=O)c2ccc(F)cc2)s1] | 12-51 | 4-(5-Trifluoromethyl-pyridin-2-yl)-[1,4]diazepane-1-carboxylic acid {1-[5-(4-fluoro-benzoyl)-4-trifluoromethyl-thiazol-2-ylcarbamoyl]-1-methyl-ethyl}-amide | 1.43 | A | 647.2 |
| 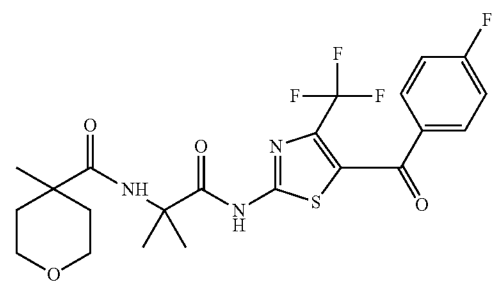 [SMILES: CC1(C(=O)NC(C)(C)C(=O)Nc2nc(C(F)(F)F)c(C(=O)c3ccc(F)cc3)s2)CCOCC1] | 12-52 | 4-Methyl-tetrahydro-pyran-4-carboxylic acid {1-[5-(4-fluoro-benzoyl)-4-trifluoromethyl-thiazol-2-ylcarbamoyl]-1-methyl-ethyl}-amide | 1.68 | A | 502.2 |

Example 13-1

{1-[4-(4-Fluoro-phenyl)-5-morpholin-4-yl-thiazol-2-ylcarbamoyl]-1-methyl-ethyl}carbamic acid tert-butyl ester

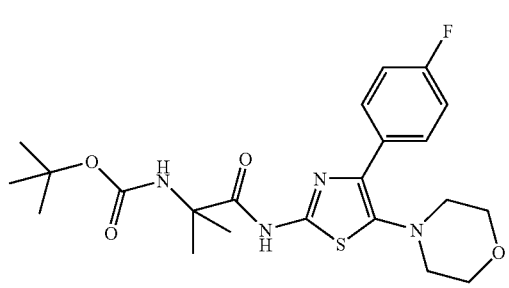 [SMILES: CC(C)(C)OC(=O)NC(C)(C)C(=O)Nc1nc(-c2ccc(F)cc2)c(N2CCOCC2)s1]

A. 4-(4-Fluoro-phenyl)-5-morpholin-4-yl-thiazol-2-ylamine

5-Bromo-4-(4-fluoro-phenyl)-thiazole-2-ylamine and morpholine (6 eq) were stirred for 30 minutes at 120 C, under microwave heat. Triturated with ethyl acetate/n-Heptane solvent mixture (1:2 ratio) to afford the title compound pure. LCMS Method A Rt=1.14 (M+1=280.0, M−1=278.1). $^1$H NMR (400 MHz, DMSO-D6) 2.67-2.75 (m, 4H) 3.67-3.74 (m, 4H) 6.87 (s, 2H) 7.14-7.20 (m, 2H) 8.11 (ddd, J=12.41, 5.53, 3.03 Hz, 2H).

B. {1-[4-(4-Fluoro-phenyl)-5-morpholin-4-yl-thiazol-2-ylcarbamoyl]-1-methyl-ethyl}carbamic acid tert-butyl ester To a solution of 2-tert-Butoxycarbonylamino-2-methyl-propionic acid (1.5 eq) and 4-(4-Fluoro-phenyl)-5-morpholin-4-yl-thiazol-2-ylamine (1 eq)) in DMF (50 mL) were added HATU (1.5 eq) and TEA (2 eq). Reaction was stirred at 60 C over night. Aqueous work up followed by silica gel chromatography afforded the title compound. LCMS Method A Rt=1.51 (M+1=465.1, M−1=463.1). ¹H NMR (400 MHz, DMSO-D6) 1.21 (s, 1H) 1.28-1.40 (m, 14H) 2.80-2.87 (m, 4H) 3.70-3.77 (m, 4H) 7.21-7.27 (m, 2H) 8.10-8.16 (m, 2H) 11.59 (s, 1H).

Example 13-2

4-Fluoro-N-{1-[4-(4-fluoro-phenyl)-5-morpholin-4-yl-thiazol-2-ylcarbamoyl]-1-methyl-ethyl}-benzamide A. 2-Amino-N-[4-(4-fluoro-phenyl)-5-morpholin-4-yl-thiazol-2-yl]-2-methyl-propionamide {1-[4-(4-Fluoro-phenyl)-5-morpholin-4-yl-thiazol-2-yl-carbamoyl]-1-methyl-ethyl}-carbamic acid tert-butyl ester was stirred overnight in freshly prepared HCl (g)/EtOAc solution. Evaporation to dryness afforded the title compound as the hydrochloride salt. ¹H NMR (400 MHz, DMSO-D6) 1.63 (s, 6H) 2.81-2.89 (m, 4H) 3.70-3.78 (m, 4H) 7.23-7.29 (m, 2H) 8.10-8.16 (m, 2H) 8.62 (s, 3H) 12.46 (s, 1H).

B. 4-Fluoro-N-{1-[4-(4-fluoro-phenyl)-5-morpholin-4-yl-thiazol-2-ylcarbamoyl]-1-methyl-ethyl}-benzamide The hydrochloride salt of 2-Amino-N-[4-(f-fluoro-phenyl)-5-morpholin-4-yl-thiazol-2-yl]-2-methyl propionamide, 4-fluorobenzoyl chlorides (1.15 eq) and triethyl amine (3.5 eq) were stirred as a solution in DCM (5 mL) at RT for 2 hours. Evaporation of volitales in vacuo followed by purification via silica gel chromatography (20-30% EtOAc/Hexanes) afforded the title compound. LCMS Method A Rt=1.41 (M+1=487.1, M−1=485.1). ¹H NMR (400 MHz, DMSO-D6) 1.50 (s, 6H) 2.80-2.87 (m, 4H) 3.70-3.77 (m, 4H) 7.16-7.23 (m, 2H) 7.29-7.35 (m, 2H) 7.99-8.04 (m, 2H) 8.06-8.11 (m, 2H) 8.50 (s, 1H) 11.79 (s, 1H)

The following compounds were prepared using similar procedures described above.

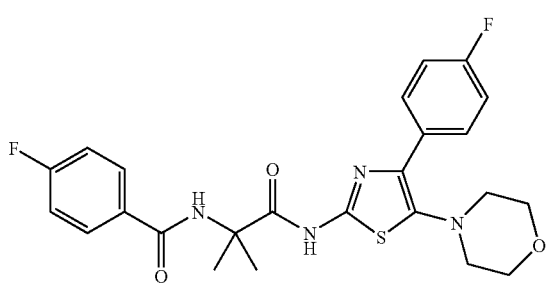 [SMILES: CC(C)(NC(=O)c1ccc(F)cc1)C(=O)Nc1nc(-c2ccc(F)cc2)c(N2CCOCC2)s1]

| structure | Ex. | Names | LC rt | Meth | (M + 1)+ |
|---|---|---|---|---|---|
| 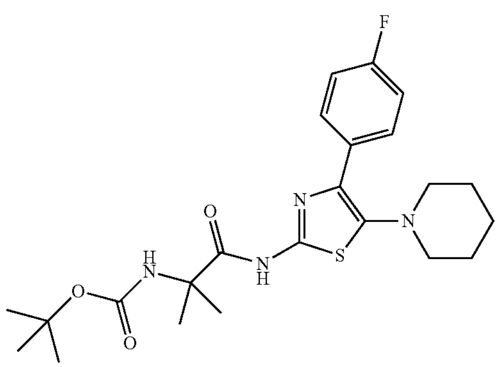 [SMILES: CC(C)(C)OC(=O)NC(C)(C)C(=O)Nc1nc(-c2ccc(F)cc2)c(N2CCCCC2)s1] | 13-3 | {1-[4-(4-Fluoro-phenyl)-5-piperidin-1-yl-thiazol-2-ylcarbamoyl]-1-methyl-ethyl}-carbamic acid tert-butyl ester | 1.74 | A | 463.1 |
| 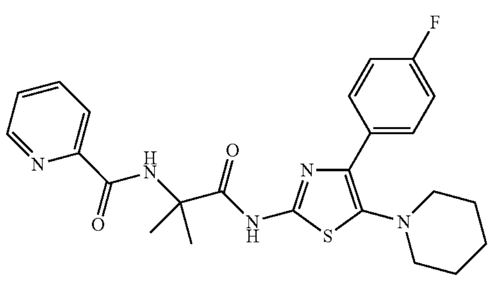 [SMILES: CC(C)(NC(=O)c1ccccn1)C(=O)Nc1nc(-c2ccc(F)cc2)c(N2CCCCC2)s1] | 13-4 | Pyridine-2-carboxylic acid {1-[4-(4-fluoro-phenyl)-5-piperidin-1-yl-thiazol-2-ylcarbamoyl]-1-methyl-ethyl}-amide | 1.63 | A | 468.2 |

-continued

| structure | Ex. | Names | LC rt | Meth | (M + 1)+ |
|---|---|---|---|---|---|
| 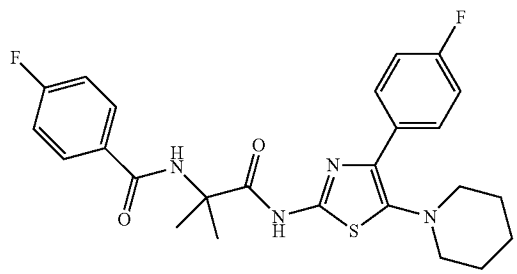 [SMILES: CC(C)(NC(=O)c1ccc(F)cc1)C(=O)Nc1nc(-c2ccc(F)cc2)c(N2CCCCC2)s1] | 13-5 | 4-Fluoro-N-{1-[4-(4-fluoro-phenyl)-5-piperidin-1-yl-thiazol-2-ylcarbamoyl]-1-methyl-ethyl}-benzamide | 1.64 | A | 485.0 |
| 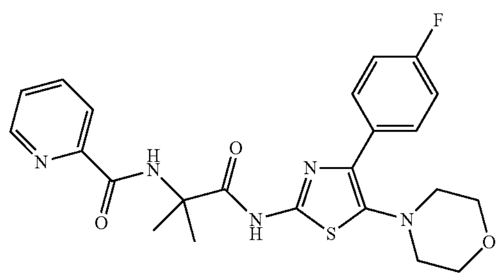 [SMILES: CC(C)(NC(=O)c1ccccn1)C(=O)Nc1nc(-c2ccc(F)cc2)c(N2CCOCC2)s1] | 13-6 | Pyridine-2-carboxylic acid {1-[4-(4-fluoro-phenyl)-5-morpholin-4-yl-thiazol-2-ylcarbamoyl]-1-methyl-ethyl}-amide | 1.4 | A | 470.1 |
| 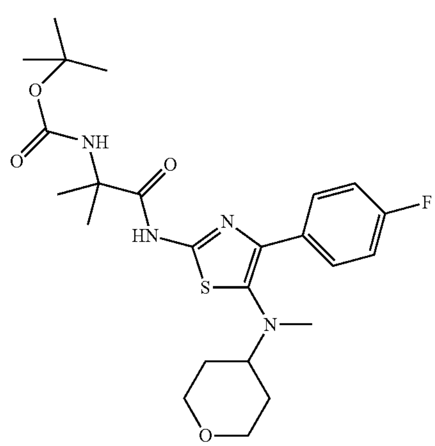 [SMILES: CN(c1sc(NC(=O)C(C)(C)NC(=O)OC(C)(C)C)nc1-c1ccc(F)cc1)C1CCOCC1] | 13-7 | (1-{4-(4-Fluoro-phenyl)-5-[methyl-(tetrahydro-pyran-4-yl)-amino]-thiazol-2-ylcarbamoyl}-1-methyl-ethyl)-carbamic acid tert-butyl ester | 1.5 | A | 493.1 |
| 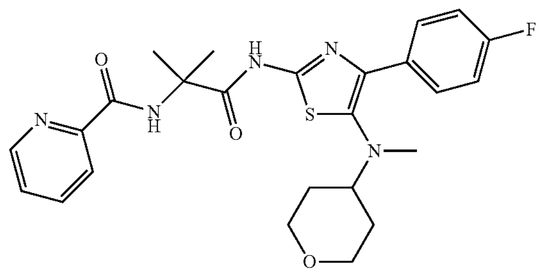 [SMILES: CN(c1sc(NC(=O)C(C)(C)NC(=O)c2ccccn2)nc1-c1ccc(F)cc1)C1CCOCC1] | 13-8 | Pyridine-2-carboxylic acid (1-{4-(4-fluoro-phenyl)-5-[methyl-(tetrahydro-pyran-4-yl)-amino]-thiazol-2-ylcarbamoyl}-1-methyl-ethyl)-amide | 1.44 | A | 498.1 |

| structure | Ex. | Names | LC rt | Meth | (M + 1)+ |
|---|---|---|---|---|---|
| 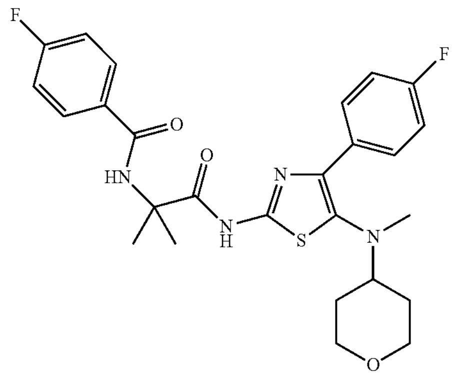 [SMILES: CN(c1sc(NC(=O)C(C)(C)NC(=O)c2ccc(F)cc2)nc1-c1ccc(F)cc1)C1CCOCC1] | 13-9 | 4-Fluoro-N-(1-{4-(4-fluoro-phenyl)-5-[methyl-(tetrahydro-pyran-4-yl)-amino]-thiazol-2-ylcarbamoyl}-1-methyl-ethyl)-benzamide | 1.48 | A | 515.1 |
| 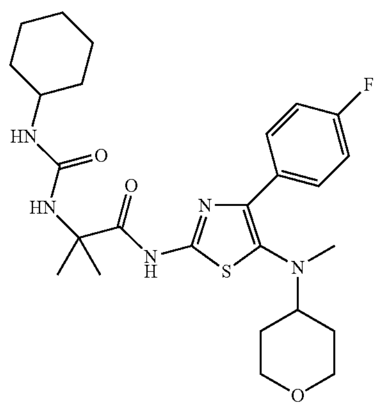 [SMILES: CN(c1sc(NC(=O)C(C)(C)NC(=O)NC2CCCCC2)nc1-c1ccc(F)cc1)C1CCOCC1] | 13-10 | 2-(3-Cyclohexyl-ureido)-N-{4-(4-fluoro-phenyl)-5-[methyl-(tetrahydro-pyran-4-yl)-amino]-thiazol-2-yl}-2-methyl-propionamide | 1.5 | A | 518.1 |
| 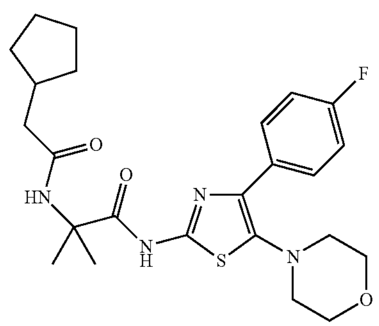 [SMILES: CC(C)(NC(=O)CC1CCCC1)C(=O)Nc1nc(-c2ccc(F)cc2)c(N2CCOCC2)s1] | 13-11 | 2-(2-Cyclopentyl-acetylamino)-N-{4-(4-fluoro-phenyl)-5-morpholin-4-yl-thiazol-2-yl]-2-methyl-propionamide | 1.48 | A | 475.1 |
| 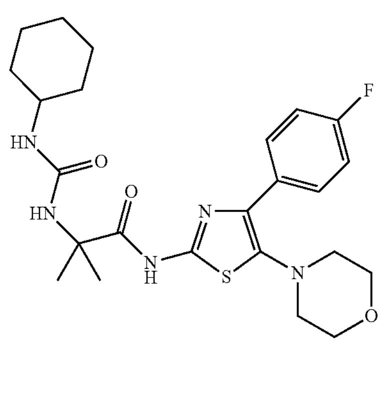 [SMILES: CC(C)(NC(=O)NC1CCCCC1)C(=O)Nc1nc(-c2ccc(F)cc2)c(N2CCOCC2)s1] | 13-12 | 2-(3-Cyclohexyl-ureido)-N-[4-(4-fluoro-phenyl)-5-morpholin-4-yl-thiazol-2-yl]-2-methyl-propionamide | 1.46 | A | 490.2 |

-continued

| structure | Ex. | Names | LC rt | Meth | (M + 1)+ |
|---|---|---|---|---|---|
| 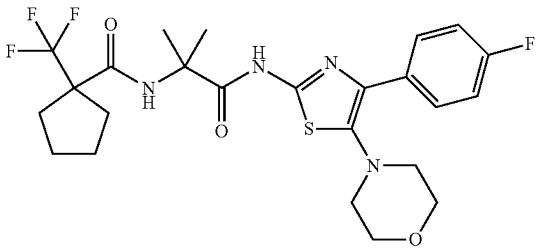 [SMILES: CC(C)(NC(=O)C1(C(F)(F)F)CCCC1)C(=O)Nc1nc(-c2ccc(F)cc2)c(N2CCOCC2)s1] | 13-13 | 1-Trifluoromethyl-cyclopentanecarboxylic acid {1-[4-(4-fluoro-phenyl)-5-morpholin-4-yl-thiazol-2-ylcarbamoyl]-1-methyl-ethyl}-amide | 1.52 | A | 528.9 |
| 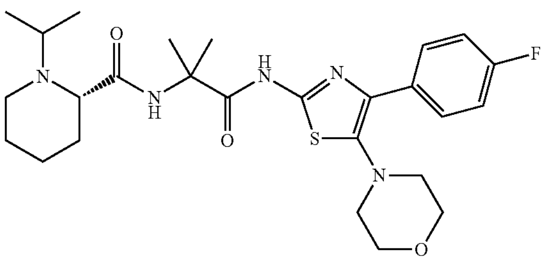 [SMILES: CC(C)N1CCCC[C@H]1C(=O)NC(C)(C)C(=O)Nc1nc(-c2ccc(F)cc2)c(N2CCOCC2)s1] | 13-14 | (S)-1-Isopropyl-piperidine-2-carboxylic acid {1-[4-(4-fluoro-phenyl)-5-morpholin-4-yl-thiazol-2-ylcarbamoyl]-1-methyl-ethyl}-amide | 1.25 | A | 518.0 |
| 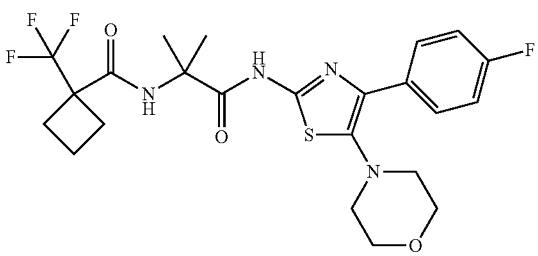 [SMILES: CC(C)(NC(=O)C1(C(F)(F)F)CCC1)C(=O)Nc1nc(-c2ccc(F)cc2)c(N2CCOCC2)s1] | 13-15 | 1-Trifluoromethyl-cyclobutanecarboxylic acid {1-[4-(4-fluoro-phenyl)-5-morpholin-4-yl-thiazol-2-ylcarbamoyl]-1-methyl-ethyl}-amide | 1.45 | A | 514.9 |
| 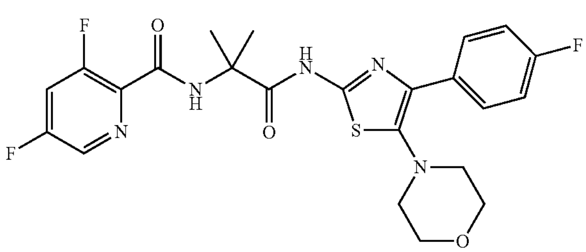 [SMILES: CC(C)(NC(=O)c1ncc(F)cc1F)C(=O)Nc1nc(-c2ccc(F)cc2)c(N2CCOCC2)s1] | 13-16 | 3,5-Difluoro-pyridine-2-carboxylicacid {1-[4-(4-fluoro-phenyl)-5-morpholin-4-yl-thiazol-2ylcarbamoyl]-1-methyl-ethyl}-amide | 1.35 | A | 505.9 |
| 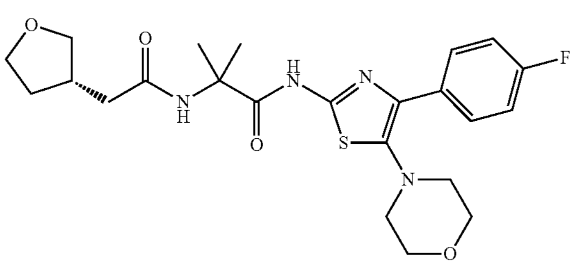 [SMILES: CC(C)(NC(=O)C[C@@H]1CCOC1)C(=O)Nc1nc(-c2ccc(F)cc2)c(N2CCOCC2)s1] | 13-17 | N-[4-(4-Fluoro-phenyl)-5-morpholin-4-yl-thiazol-2-yl]-2-methyl-2-((S)-2-tetrahydro-furan-3-yl-acetylamino)-propionamide | 1.19 | A | 477.0 |
| 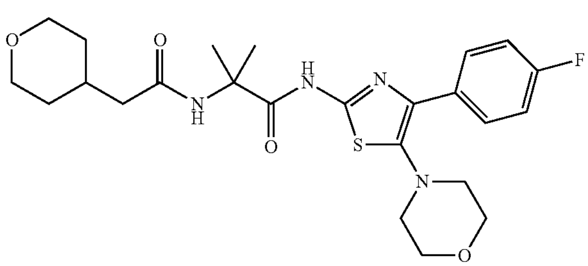 [SMILES: CC(C)(NC(=O)CC1CCOCC1)C(=O)Nc1nc(-c2ccc(F)cc2)c(N2CCOCC2)s1] | 13-18 | N-[4-(4-Fluoro-phenyl)-5-morpholin-4-yl-thiazol-2-yl]-2-methyl-2-(2-tetrahydro-pyran-4-yl-acetylamino)-propionamide | 1.22 | A | 491.0 |

| structure | Ex. | Names | LC rt | Meth | (M + 1)+ |
|---|---|---|---|---|---|
| 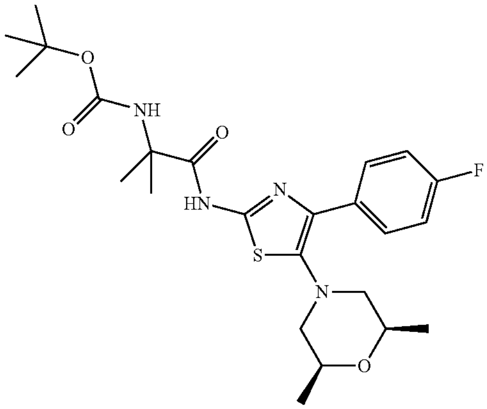 [SMILES: C[C@@H]1CN(c2sc(NC(=O)C(C)(C)NC(=O)OC(C)(C)C)nc2-c2ccc(F)cc2)C[C@H](C)O1] | 13-19 | {1-[5-((2R,6S)-2,6-Dimethyl-morpholin-4-yl)-4-(4-fluoro-phenyl)-thiazol-2-ylcarbamoyl]-1-methyl-ethyl}-carbamic acid tert-butyl ester | 1.6 | A | 470.1 |

Example 14-1

N-{1-[1-Benzyl-5-(4-fluoro-phenyl)-1H-[1,2,4]triazol-3-ylcarbamoyl]-1-methyl-ethyl}-4-fluoro-benzamide

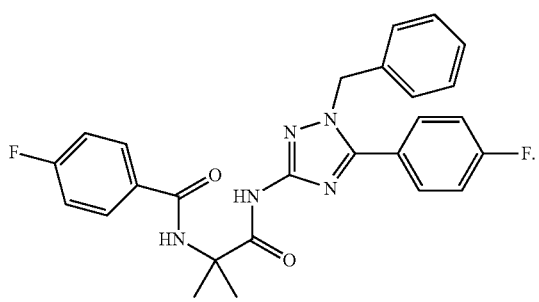 [SMILES: CC(C)(NC(=O)c1ccc(F)cc1)C(=O)Nc1nc(-c2ccc(F)cc2)n(Cc2ccccc2)n1]

A. 2-(4-Fluoro-phenyl)-4,4-dimethyl-4H-oxazol-5-one

A flask containing 2-amino-2-methyl-propionic acid (500 mg, 4.85 mmol) and sodium bicarbonate (1.29 g, 12.12 mmol) in water (10 mL) and acetone (1 mL) was chilled to 5° C. In a dropwise manner 4-fluoro-benzoyl chloride (0.688 mL, 5.82 mmol) was added. After stirring for 1 hr the mixture was allowed to warm to room temperature. After stirring for an additional 16 hr, the reaction was washed with toluene (2 mL). The aqueous portion was removed and the mixture filtered. The filtrate was partitioned and the organic layer removed. The collected solid was solubulized in water (10 mL) and all the aqueous phases combined. The pH of the combined aqueous was adjusted to 3 by slow addition of 1N HCl, and the acidified mixture was extracted with EtOAc (3×30 mL). The combined organics were washed with brine (20 mL) and dried over Na$_2$SO4. Evaporation of the solvent resulted in a white solid. The solid was heated to 50° C. in Ac$_2$O (2.9 mL) and toluene (0.82 mL) for 2 hr. The reaction was concentrated and azeotroped with HEP. The resulting residue was dissolved in Et$_2$O (65 mL) and extracted with NaHCO$_3$ (15 mL) followed by brine (10 mL). After drying over Na$_2$SO$_4$, the solvent was envaporated to afford the title compound as a white solid: R$_t$ (method A)=1.22 min (M+H)$^+$=208.3.

B. N-{1-[1-Benzyl-5-(4-fluoro-phenyl)-1H-[1,2,4]triazol-3-ylcarbamoyl]-1-methyl-ethyl}-4-fluoro-benzamide To a 5 mL Biotage microwave vial were added NMP (1 ml), 1-benzyl-5-(4-fluorophenyl)-1H-1,2,4-triazol-3-amine (150 mg, 0.559 mmol), 2-(4-fluorophenyl)-4,4-dimethyloxazol-5 (4H)-one (116 mg, 0.559 mmol,), under N$_2$. Then it was placed in 100° C. oil bath and stirred for 2.5 h. It was cooled to r.t. and diluted with 2 ml of EtOAc. It was stirred for 10 min that resulted precipitation of the desired product. Then 2 mL of water was added and it was stirred for additional 10 min followed by addition of a couple drops of heptane. The precipitates were collected by filtration and dried under vacuum overnight. This afforded the title compound as a white solid. $^1$H NMR (400 MHz, DMSO-d6) 1.50 (s, 6H) 5.40 (s, 2H) 7.08-7.14 (m, 2H) 7.24-7.39 (m, 7H) 7.63-7.71 (m, 2H) 7.96-8.04 (m, 2H) 8.33 (s, 1H) 10.17 (s, 1H). MS (m/z) 476.2 M(+1), t$_R$=1.36, Method A.

Example 14-2

{1-[1-Benzyl-5-(4-fluoro-phenyl)-1H-[1,2,4]triazol-3-ylcarbamoyl]-1-methyl-ethyl}-carbamic acid benzyl ester

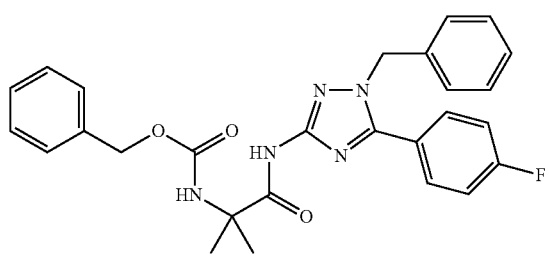 [SMILES: CC(C)(NC(=O)OCc1ccccc1)C(=O)Nc1nc(-c2ccc(F)cc2)n(Cc2ccccc2)n1]

1-Benzyl-5-(4-fluorophenyl)-1H-1,2,4-triazol-3-amine (4.15 g, 15.47 mmol), 2-(benzyloxy)-4,4-dimethyloxazol-5

(4H)-one (4.07 g, 18.56 mmol) were stirred in 5 ml of toluene in a 100 ml prbf. The white suspension was allowed to stir at 50° C. for over weekend. It was then cooled to r.t. The volatiles were removed in vacuo and the resulted solid was dissolved in EtOAc (130 mL) and heptane (50 mL) with heating. It was cooled to r.t. and let sit overnight. The resulted precipitates were collected and dried to afford the title compound. $^1$H NMR (400 MHz, DMSO-d6) 1.41 (s, 6H) 5.01 (s, 2H) 5.43 (s, 2H) 7.12 (d, J=6.82 Hz, 2H) 7.23-7.43 (m, 11H) 7.64-7.74 (m, 2H), 10.05 (br. s., 1H). MS (m/z) 488.1 M(+1), $t_R$=1.60, Method A.

Example 14-3

(S)-1-Methyl-pyrrolidine-2-carboxylic acid {1-[1-benzyl-5-(4-fluoro-phenyl)-1H-[1,2,4]triazol-3-yl-carbamoyl]-1-methyl-ethyl}-amide

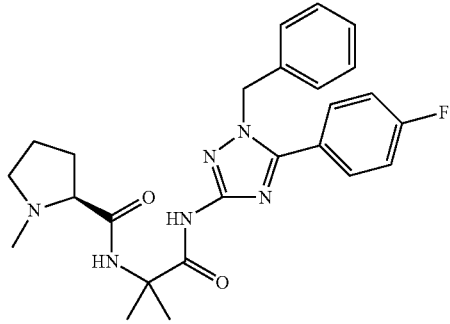 [SMILES: CN1CCC[C@H]1C(=O)NC(C)(C)C(=O)Nc1nc(-c2ccc(F)cc2)n(Cc2ccccc2)n1]

A. 2-amino-N-(1-benzyl-5-(4-fluorophenyl)-1H-1,2,4-triazol-3-yl)-2-methylpropanamide A flask containing {1-[1-Benzyl-5-(4-fluoro-phenyl)-1H-[1,2,4]triazol-3-ylcarbamoyl]-1-methyl-ethyl}-carbamic acid benzyl ester (777 mg, 1.59 mmol) was chilled to 0° C. The solid was dissolved in 48% aqueous HBr (5 mL) and the mixture stirred at 0° C. After 10 min the mixture was allowed to warm to room temp. After 5.5 hr THF (5 mL) was added and the mixture was stirred for 2 days. The reaction was diluted with water (30 mL) and extracted with Et$_2$O (2×50 mL). The pH of the aqueous phase was adjusted to 10 by addition of 4N NaOH. The basic aqueous phase was extracted with Et$_2$O (2×50 mL). The organics from the second extraction were combined and dried with brine (15 mL) followed by Na$_2$SO$_4$. Concentration resulted in a brown oil. The oil was dissolved in EtOAc/MeOH and the solvent evaporated to yield the title compound as a white solid: $^1$H NMR (400 MHz, ACETONITRILE-d$_3$) 1.53 (s, 6H) 5.38 (s, 2H) 7.08-7.19 (m, 2H) 7.19-7.28 (m, 2H) 7.28-7.39 (m, 3H) 7.60-7.69 (m, 2H); R$_t$ (method A)=0.96 min (M+H)$^+$=354.2.

B. (S)-1-Methyl-pyrrolidine-2-carboxylic acid {1-[1-benzyl-5-(4-fluoro-phenyl)-1H-[1,2,4]-triazol-3-ylcarbamoyl]-1-methyl-ethyl}-amide A 100 mL rbf was charged DCM (14.29 ml) followed by addition of 2-amino-N-(1-benzyl-5-(4-fluorophenyl)-1H-1,2,4-triazol-3-yl)-2-methylpropanamide (1.000 g, 2.83 mmol) and (S)-1-methylpyrrolidine-2-carboxylic acid (0.402 g, 3.11 mmol). And it was stirred at room temperature for 10 min, the clear solution save for a couple of particles, was placed in an ice bath at 2° C. Then HATU (2.152 g, 5.66 mmol) and triethylamine (0.789 ml, 5.66 mmol) were added. The yellow semi-solution was allowed to stir at 2° C. for 5 h. It was allowed to warm to room temperature over night. It was diluted with DCM (25 mL) and H$_2$O (30 mL). The white precipitates were collected by filtration and washed with 1:1 water/sat. NaHCO$_3$ solution. (2×60 mL), brine (2×40 mL). This afforded the title compound $^1$H NMR (400 MHz, DMSO-d6) d ppm 1.53 (d, J=1.52 Hz, 6H) 1.66-1.78 (m, 3H) 1.96-2.13 (m, 1H) 2.21-2.29 (m, 1H) 2.30 (s, 3H) 2.61-2.70 (m, 1H) 2.99-3.09 (m, 1H) 5.43 (s, 2H) 7.13 (d, J=6.95 Hz, 2H) 7.26-7.43 (m, 5H) 7.68-7.75 (m, 2H) 7.97 (s, 1H) 10.21 (s, 1H). Theoretical mass 464.23. found 464.23. MS (m/z) 465.00 M (+1), $t_R$=1.23, Meth A. ee: 95%, using 30% EtOH Heptane.

Example 14-4

Pyridine-2-carboxylic acid {1-[1-benzyl-5-(4-fluoro-phenyl)-1H-[1,2,4]triazol-3-ylcarbamoyl]-1-methyl-ethyl}-amide

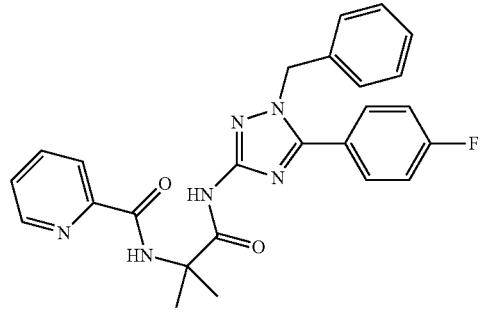 [SMILES: CC(C)(NC(=O)c1ccccn1)C(=O)Nc1nc(-c2ccc(F)cc2)n(Cc2ccccc2)n1]

2-Amino-N-[1-benzyl-5-(4-fluoro-phenyl)-1H-[1,2,4]triazol-3-yl]-2-methyl-propionamide (137 mg, 0.388 mmol), HATU (295 mg, 0.776 mmol), and picolinic acid (72 mg, 0.582 mmol) were stirred in DCM (6 mL). TEA (108 uL, 0.776 mmol) was added to the reaction mixture and it was stirred for 1 day. It was diluted with EtOAc (65 mL) and extracted with water (15 mL), followed by saturated NaHCO$_3$ (15 mL). The organic layer was dried with a brine wash (10 mL) followed by Na$_2$SO$_4$. The solvents were removed in vacuo and the residue was purified by reverse phase HPLC (C18, 45-100% MeOH/H$_2$O+5 mM NH$_4$OH) followed by silica gel chromatography (0-30% ACN/DCM) to afford the title compound as a white solid: $^1$H NMR (400 MHz, DICHLOROMETHANE-d$_2$) δ ppm 1.73 (s, 6H) 5.35 (s, 2H) 7.07-7.22 (m, 4H) 7.26-7.39 (m, 3H) 7.49 (ddd, J=7.61, 4.77, 1.14 Hz, 1H) 7.52-7.61 (m, 2H) 7.90 (td, J=7.74, 1.71 Hz, 1H) 8.19 (dt, J=7.77, 1.04 Hz, 1H) 8.47 (br. s., 1H) 8.58 (ddd, J=4.77, 1.61, 0.95 Hz, 1H) 9.45 (br. s., 1H); Rt (method A)=1.22 min, (M+H)+ 459.0.

Intermediate 7

1-Benzyl-5-phenyl-1H-1,2,4-triazol-3-amine
(General Procedure)

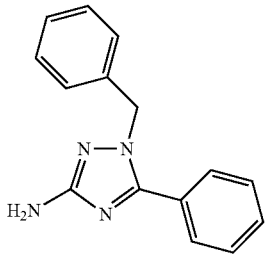 [SMILES: Nc1nc(-c2ccccc2)n(Cc2ccccc2)n1]

Step 1: To a stirred solution of methyl carbamimidothioate (0.901 g, 10 mmol) in 10 ml of THF were added TEA (6.97 ml, 50.0 mmol) and benzoyl chloride (3.48 ml, 30.0 mmol) at r.t. The reaction was stirred for over night. The reaction mixture was diluted with water (20 ml) and the resulting precipitates were collected by filtration. The filter cake was washed with water and heptane. It was dried by suction in air for 4 hours to yield (Z)-methyl N,N'-dibenzoylcarbamimidothioate. After the filtration, it was pure by LCMS. It was carried on to the next step. LCMS method A, (M+H)+299.1, ret T=1.66 min.

Step 2: To a stirred solution of the crude (Z)-methyl N,N'-dibenzoylcarbamimidothioate (0.895 g, 3 mmol) in DMF (8 ml) was added benzylhydrazine (0.367 g, 3.00 mmol) at 40° C. The reaction was stirred for 2 days. The stirred reaction was diluted with water. The resulting precipitates were collected to yield the crude N-(1-benzyl-5-phenyl-1H-1,2,4-triazol-3-yl)benzamide. LCMS method A, (M+H)+355.1, ret T=1.32 min.

Step 3: The crude N-(1-benzyl-5-phenyl-1H-1,2,4-triazol-3-yl)benzamide was dissolved in 5 ml of MeOH. It was stirred and treated with 5 ml of 6N HCl. It was heated at 60° C. for overnight. It was cooled to rt and added to a stirred 4N NaOH (10 ml) in an ice bath. It was extracted with DCM. The combined DCM layer was dried with MgSO$_4$ and rotavapped. The crude was purified by column chromatography with heptane/EtOAc gradient to yield 1-benzyl-5-phenyl-1H-1,2,4-triazol-3-amine (340 mg, 45.3% for 3 steps). $^1$H NMR (400 MHz, MeOD) 5.24 (br. s., 2H) 7.13 (br. s., 2H) 7.30 (br. s., 4H) 7.52 (br. s., 6H), LCMS method A, (M+H)+ 251.1, ret T=1.12 min.

Intermediate 8

1-Benzyl-5-(4-fluorophenyl)-1H-1,2,4-triazol-3-amine

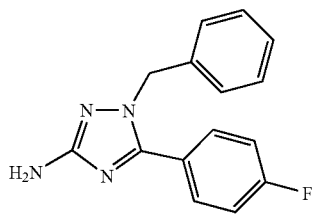 [SMILES: Nc1nc(-c2ccc(F)cc2)n(Cc2ccccc2)n1]

$^1$H NMR (400 MHz, CHLOROFORM-d) 4.12 (s, 2H) 5.22 (s, 2H) 7.14 (s, 4H) 7.33 (br. s., 3H) 7.54 (s, 2H). LCMS method A, (M+H)+ 269.1, ret T=1.15 min.

Intermediate 9 (General Procedure)

5-(4-fluorophenyl)-1-(2,2,2-trifluoroethyl-1H-pyrazole-3-amine

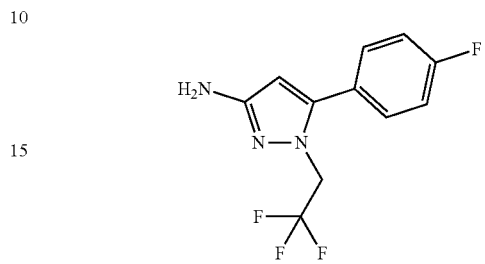

A. Lithium 1-ethoxy-4-(4-fluorophenyl-1,4-dioxobut-2-en-2-olate

Reference: W. V. Murray, J Heterocyclic Chem. (1989), 26, 1389-1392

To a solution of 14.5 mL (14.5 mmol) of 1.0 M LHMDS in THF in 40 mL Et$_2$O at −78° C. under N$_2$ was added over 10 min a solution of 2.00 g (14.5 mmol) of 4-fluorophenyl-acetophenone in 10 mL of Et$_2$O followed after 0.5 h by the addition in one portion of 4.24 g (29.0 mmol) of diethyl oxalate in 10 mL Et$_2$O. The cold bath was removed after 5 min. The reaction was stirred 2 h at room temperature, then allowed to stand without stirring for an additional 2 h at room temperature. The precipitate was filtered, washed with Et$_2$O and stored under N$_2$, providing lithium 1-ethoxy-4-(4-fluorophenyl-1,4-dioxobut-2-en-2-olate as a pale yellow solid. LCMS (method A) 239.2 (M+H), 237.2 (M−H).

B. Ethyl 5-(4-fluorophenyl)-1-(2,2,2-trifluoroethyl)-1H-pyrazole-3-carboxylate

Lithium 1-ethoxy-4-(4-fluorophenyl-1,4-dioxobut-2-en-2-olate (1 g, 4.10 mmol) was added as a solid to a mixture of 0.67 g (4.10 mmol) 2,2,2-trifluoroethyl hydrazine and 4 A molecular sieves in 20 mL ethanol, which had previously been stirring for 10 min. After 3 h no reaction was observed and the mixture was filtered, washing with 20 mL acetic acid. The filtrate was heated at 65° C. for 2 h, then cooled. Solvent was evaporated, the residue was dissolved in methanol/dichloromethane and was washed with NaHCO$_3$ until neutral, then evaporated. Purification by chromatography (SiO$_2$, EtOAc: heptane) provided the desired regioisomer ethyl 5-(4-fluorophenyl)-1-(2,2,2-trifluoroethyl)-1H-pyrazole-3-carboxylate as a major product. LCMS (method A) 317.2 (M+H).

C. 5-(4-fluorophenyl)-1-(2,2,2-trifluoroethyl)-1H-pyrazole-3-carboxylic acid

A mixture of 0.54 g ethyl 5-(4-fluorophenyl)-1-(2,2,2-trifluoroethyl)-1H-pyrazole-3-carboxylate (1.7 mmol) and 0.21 g lithium hydroxide monohydrate (5.09 mmol) in 5 ml THF, 5 ml MeOH, and 2 mL water was stirred at room temperature for 2 h. The reaction was acidified with 1N HCl, was extracted with methanol/dichloromethane, dried over Na$_2$SO$_4$ and evaporated to provide 5-(4-fluorophenyl)-1-(2,2,2-trifluoroethyl)-1H-pyrazole-3-carboxylic acid as a white solid. LCMS (method A) 289.2 (M+H), 287.3 (M−H).

D. tert-Butyl 5-(4-fluorophenyl)-1-(2,2,2-trifluoroethyl)-1H-pyrazol-3-ylcarbamate To a solution of 0.45 g (1.55 mmol) of 5-(4-fluorophenyl)-1-(2,2,2-trifluoroethyl)-1H-pyrazole-3-carboxylic acid and 0.20 mL (1.85 mmol) of 4-methylmorpholine in 10 mL THF at room temperature under $N_2$ was dropwise added 0.21 mL (1.62 mmol) of isobutyl chloroformate. The resulting suspension was stirred for 1 h, then 0.18 g (2.78 mmol) sodium azide was added and the reaction was stirred overnight behind a blast shield. Ice chips were added to the reaction, which was then extracted with three portions of ethyl acetate. The combined organic layers were washed with brine, dried over $Na_2SO_4$ and evaporated. The residue was taken up in 10 mL toluene and 5 mL tert-butanol and heated at 80° C. for 2 days. Solvents were evaporated and purification by chromatography ($SiO_2$, EtOAc:heptane) provided the desired tert-butyl 5-(4-fluorophenyl)-1-(2,2,2-trifluoroethyl)-1H-pyrazol-3-ylcarbamate. LCMS (method A) 360.1 (M+H), 358.0 (M−H).

E. 5-(4-fluorophenyl)-1-(2,2,2-trifluoroethyl-1H-pyrazole-3-amine 0.26 g (0.72 mmol) of tert-butyl 5-(4-fluorophenyl)-1-(2, 2,2-trifluoroethyl)-1H-pyrazol-3-ylcarbamate in 5 mL dichloromethane and 5 mL trifluoroacetic acid was stirred at room temperature 24 h. Solvents were evaporated and the residue was taken up in methanol/dichloromethane, washed with $NaHCO_3$, dried over $Na_2SO_4$ and evaporated to provide the title compound, which was used as is, despite still containing some impurities. LCMS (method A) 260.4 (M+H).

The following compounds were prepared using similar procedures described above.

| Structure | Ex. | Name | LC rt | Meth. | (M + H)+ |
|---|---|---|---|---|---|
| 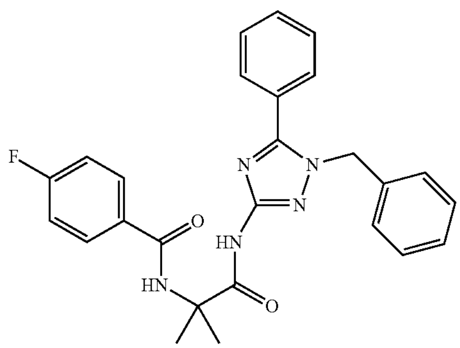 [SMILES: CC(C)(NC(=O)c1ccc(F)cc1)C(=O)Nc1nc(-c2ccccc2)n(Cc2ccccc2)n1] | 14-5 | N-[1-(1-Benzyl-5-phenyl-1H-[1,2,4]-triazol-3-ylcarbamoyl)-1-methyl-ethyl]-4-fluoro-benzamide | 1.36 | A | 458.1 |
| 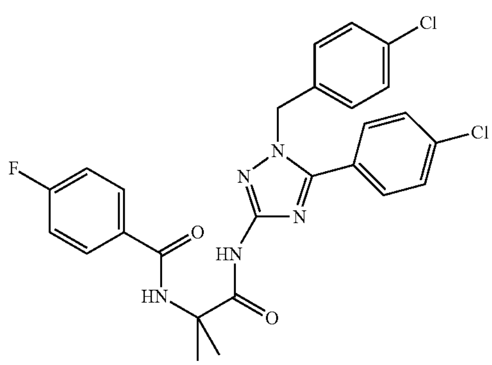 [SMILES: CC(C)(NC(=O)c1ccc(F)cc1)C(=O)Nc1nc(-c2ccc(Cl)cc2)n(Cc2ccc(Cl)cc2)n1] | 14-6 | N-{1-[1-(4-Chloro-benzyl)-5-(4-chloro-phenyl)-1H-[1,2,4]triazol-3-ylcarbamoyl]-1-methyl-ethyl}-4-fluoro-benzamide | 1.49 | A | 526.1 |
| 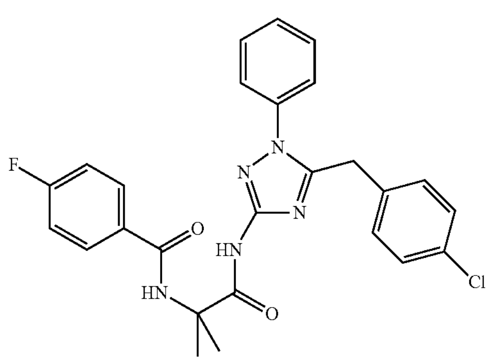 [SMILES: CC(C)(NC(=O)c1ccc(F)cc1)C(=O)Nc1nc(Cc2ccc(Cl)cc2)n(-c2ccccc2)n1] | 14-7 | N-{1-[5-(4-Chloro-benzyl)-1-phenyl-1H-[1,2,4]triazol-3-ylcarbamoyl]-1-methyl-ethyl}-4-fluoro-benzamide | 1.42 | A | 492.2 |

-continued

| Structure | Ex. | Name | LC rt | Meth. | (M + H)+ |
|---|---|---|---|---|---|
| 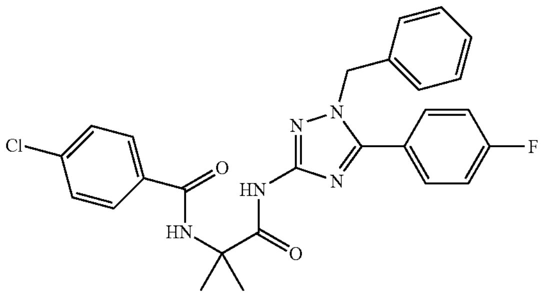 [SMILES: CC(C)(NC(=O)c1ccc(Cl)cc1)C(=O)Nc1nc(-c2ccc(F)cc2)n(Cc2ccccc2)n1] | 14-8 | N-{1-[1-Benzyl-5-(4-fluoro-phenyl)-1H-[1,2,4]triazol-3-ylcarbamoyl]-1-methyl-ethyl}-4-chloro-benzamide | 1.34 | A | 492.3 |
| 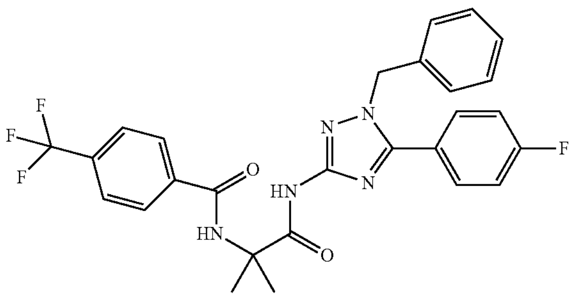 [SMILES: CC(C)(NC(=O)c1ccc(C(F)(F)F)cc1)C(=O)Nc1nc(-c2ccc(F)cc2)n(Cc2ccccc2)n1] | 14-9 | N-{1-[1-Benzyl-5-(4-fluoro-phenyl)-1H-[1,2,4]triazol-3-ylcarbamoyl]-1-methyl-ethyl}-4-trifluoromethyl-benzamide | 1.39 | A | 526.2 |
| 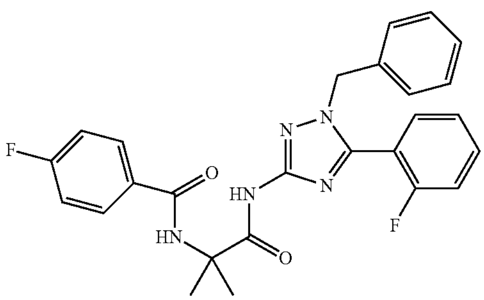 [SMILES: CC(C)(NC(=O)c1ccc(F)cc1)C(=O)Nc1nc(-c2ccccc2F)n(Cc2ccccc2)n1] | 14-10 | N-{1-[1-Benzyl-5-(2-fluoro-phenyl)-1H-[1,2,4]triazol-3-ylcarbamoyl]-1-methyl-ethyl}-4-fluoro-benzamide | 1.35 | A | 476.2 |
| 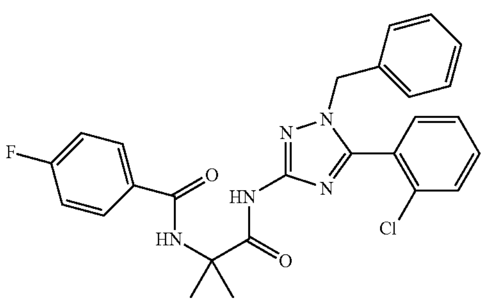 | 14-11 | N-{1-[1-Benzyl-5-(2-chloro-phenyl)-1H-[1,2,4]triazol-3-ylcarbamoyl]-1-methyl-ethyl}-4-fluoro-benzamide | 1.34 | A | 492.2 |
| 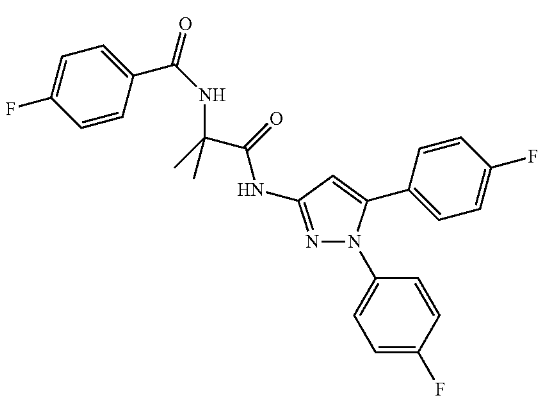 [SMILES: CC(C)(NC(=O)c1ccc(F)cc1)C(=O)Nc1cc(-c2ccc(F)cc2)n(-c2ccc(F)cc2)n1] | 14-12 | N-{1-[1,5-Bis-(4-fluoro-phenyl)-1H-pyrazol-3ylcarbamoyl]-1-methyl-ethyl}-4-fluoro-benzamide | 1.49 | A | 479.1 |

-continued

| Structure | Ex. | Name | LC rt | Meth. | (M + H)+ |
|---|---|---|---|---|---|
| 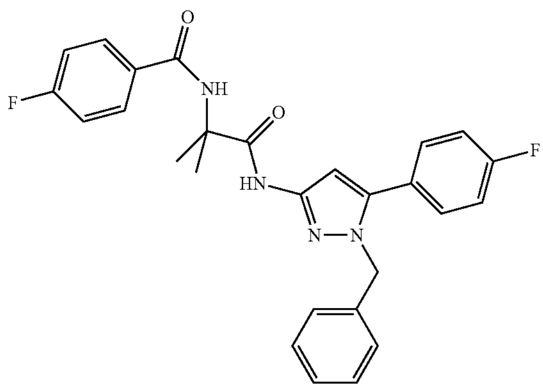 [SMILES: CC(C)(NC(=O)c1ccc(F)cc1)C(=O)Nc1cc(-c2ccc(F)cc2)n(Cc2ccccc2)n1] | 14-13 | N-{1-[1-Benzyl-5-(4-fluoro-phenyl)-1H-pyrazol-3-ylcarbamoyl]-1-methyl-ethyl}-4-fluoro-benzamide | 1.35 | A | 475.3 |
| 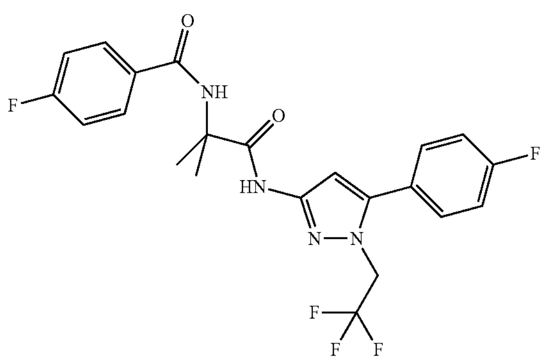 [SMILES: CC(C)(NC(=O)c1ccc(F)cc1)C(=O)Nc1cc(-c2ccc(F)cc2)n(CC(F)(F)F)n1] | 14-14 | 4-Fluoro-N-{1-[5-(4-fluoro-phenyl)-1-(2,2,2-trifluoro-ethyl)-1H-pyrazol-3-ylcarbamoyl]-1-methyl-ethyl}-benzamide | 1.39 | A | 467 |
| 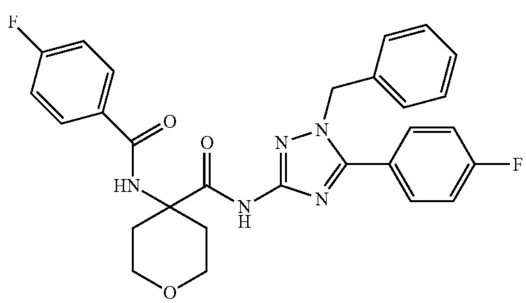 [SMILES: O=C(NC1(C(=O)Nc2nc(-c3ccc(F)cc3)n(Cc3ccccc3)n2)CCOCC1)c1ccc(F)cc1] | 14-15 | 4-(4-Fluoro-benzoylamino)-tetrahydro-pyran-4-carboxylic acid [1-benzyl-5-(4-fluoro-phenyl)-1H-[1,2,4]triazol-3-yl]-amide | 1.29 | A | 518.3 |
| 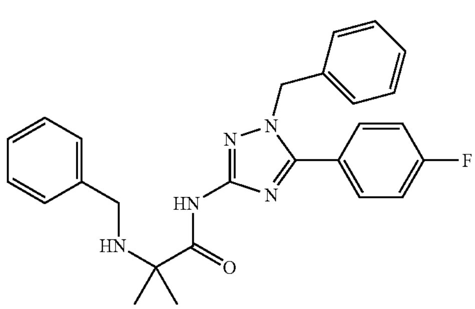 [SMILES: CC(C)(NCc1ccccc1)C(=O)Nc1nc(-c2ccc(F)cc2)n(Cc2ccccc2)n1] | 14-16 | 2-Benzylamino-N-[1-benzyl-5-(4-fluoro-phenyl)-1H-[1,2,4]triazol-3-yl]-2-methyl-propionamide | 1.58 | A | 444.2 |

| Structure | Ex. | Name | LC rt | Meth. | (M + H)+ |
|---|---|---|---|---|---|
| 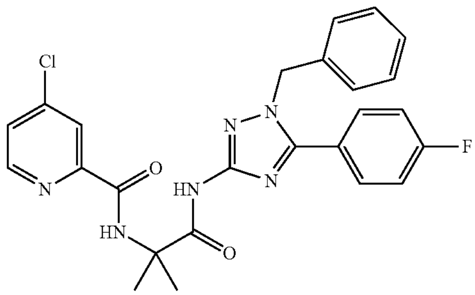 [SMILES: CC(C)(NC(=O)c1cc(Cl)ccn1)C(=O)Nc1nc(-c2ccc(F)cc2)n(Cc2ccccc2)n1] | 14-17 | 4-Chloro-pyridine-2-carboxylic acid {1-[1-benzyl-5-(4-fluoro-phenyl)-1H-[1,2,4]triazol-3-ylcarbamoyl]-1-methyl-ethyl}-amide | 1.47 | A | 493.1 |
| 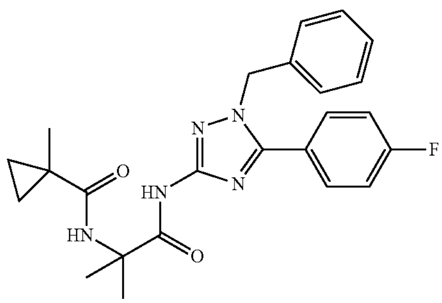 [SMILES: CC1(C(=O)NC(C)(C)C(=O)Nc2nc(-c3ccc(F)cc3)n(Cc3ccccc3)n2)CC1] | 14-18 | 1-Methyl-cyclopropane-carboxylic acid {1-[1-benzyl-5-(4-fluoro-phenyl)-1H-[1,2,4]triazol-3-ylcarbamoyl]-1-methyl-ethyl}-amide | 1.61 | A | 436.3 |
| 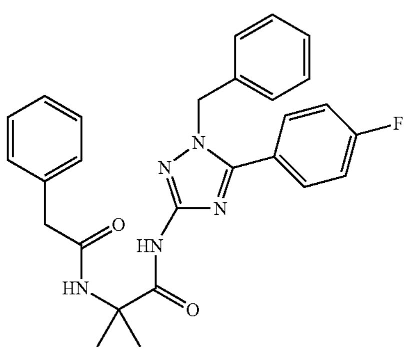 [SMILES: CC(C)(NC(=O)Cc1ccccc1)C(=O)Nc1nc(-c2ccc(F)cc2)n(Cc2ccccc2)n1] | 14-19 | N-[1-Benzyl-5-(4-fluoro-phenyl)-1H-[1,2,4]triazol-3-yl]-2-methyl-2-phenylacetylamino-propionamide | 1.25 | A | 472.0 |
| 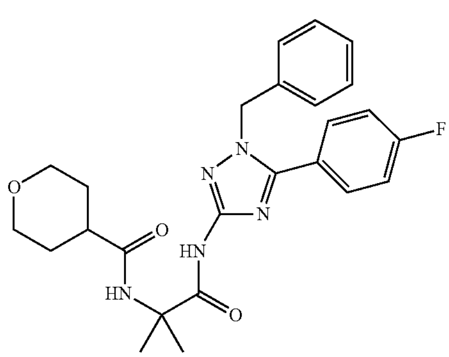 [SMILES: CC(C)(NC(=O)C1CCOCC1)C(=O)Nc1nc(-c2ccc(F)cc2)n(Cc2ccccc2)n1] | 14-20 | Tetrahydro-pyran-4-carboxylic acid {1-[1-benzyl-5-(4-fluoro-phenyl)-1H-[1,2,4]triazol-3-ylcarbamoyl]-1-methyl-ethyl}-amide | 1.27 | A | 466.1 |

| Structure | Ex. | Name | LC rt | Meth. | (M + H)+ |
|---|---|---|---|---|---|
| 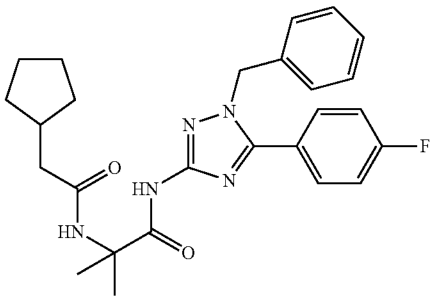 [SMILES: CC(C)(NC(=O)CC1CCCC1)C(=O)Nc1nc(-c2ccc(F)cc2)n(Cc2ccccc2)n1] | 14-21 | N-[1-Benzyl-5-(4-fluoro-phenyl)-1H-[1,2,4]triazol-3-yl]-2-(2-cyclopentyl-acetylamino)-2-methyl-propion-amide | 1.31 | A | 464.1 |
| 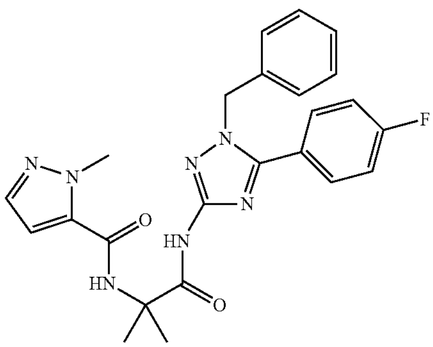 [SMILES: Cn1nccc1C(=O)NC(C)(C)C(=O)Nc1nc(-c2ccc(F)cc2)n(Cc2ccccc2)n1] | 14-22 | 2-Methyl-2H-pyrazole-3-carboxylic acid {1-[1-benzyl-5-(4-fluoro-phenyl)-1H-[1,2,4]triazol-3-ylcarbamoyl]-1-methyl-ethyl}-amide | 1.39 | A | 462.2 |
| 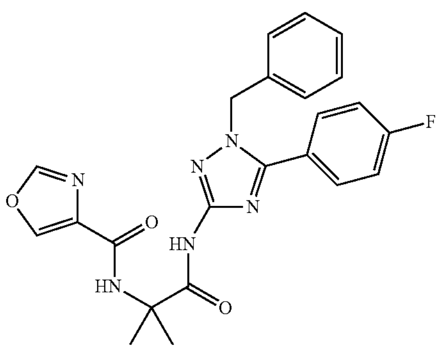 [SMILES: CC(C)(NC(=O)c1cocn1)C(=O)Nc1nc(-c2ccc(F)cc2)n(Cc2ccccc2)n1] | 14-23 | Oxazole-4-carboxylic acid {1-[1-benzyl-5-(4-fluoro-phenyl)-1H-[1,2,4]triazol-3-ylcarbamoyl]-1-methyl-ethyl}-amide | 1.27 | A | 449.0 |
| 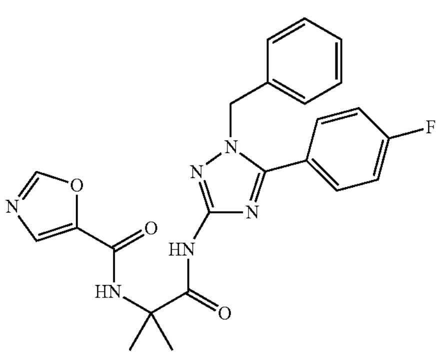 [SMILES: CC(C)(NC(=O)c1cnco1)C(=O)Nc1nc(-c2ccc(F)cc2)n(Cc2ccccc2)n1] | 14-24 | Oxazole-5-carboxylic acid {1-[1-benzyl-5-(4-fluoro-phenyl)-1H-[1,2,4]triazol-3-ylcarbamoyl]-1-methyl-ethyl}-amide | 1.27 | A | 449.0 |

-continued

| Structure | Ex. | Name | LC rt | Meth. | (M + H)+ |
|---|---|---|---|---|---|
| 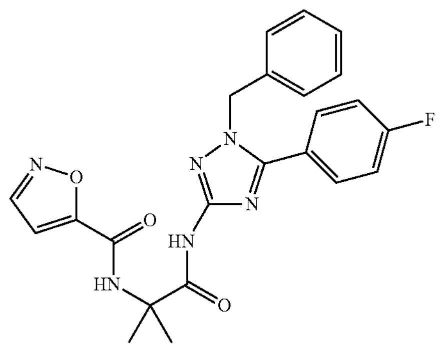 [SMILES: CC(C)(NC(=O)c1ccno1)C(=O)Nc1nc(-c2ccc(F)cc2)n(Cc2ccccc2)n1] | 14-25 | Isoxazole-5-carboxylic acid {1-[1-benzyl-5-(4-fluoro-phenyl)-1H-[1,2,4]triazol-3-ylcarbamoyl]-1-methyl-ethyl}-amide | 1.38 | A | 449.2 |
| 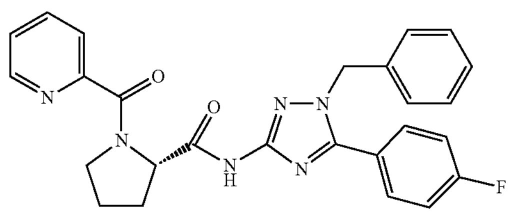 [SMILES: O=C(Nc1nc(-c2ccc(F)cc2)n(Cc2ccccc2)n1)[C@@H]1CCCN1C(=O)c1ccccn1] | 14-26 | (S)-1-(Pyridine-2-carbonyl)-pyrrolidine-2-carboxylic acid [1-benzyl-5-(4-fluoro-phenyl)-1H-[1,2,4]triazol-3-yl]-amide | 1.24 | A | 471.3 |
| 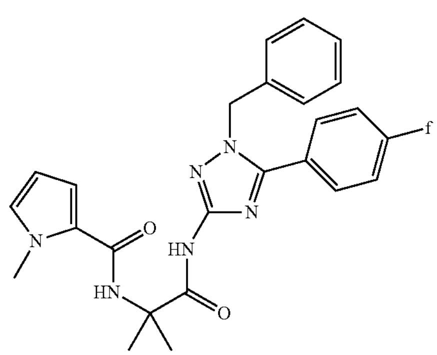 | 14-27 | 1-Methyl-1H-pyrrole-2-carboxylic acid {1-[1-benzyl-5-(4-fluoro-phenyl)-1H-[1,2,4]triazol-3-ylcarbamoyl]-1-methyl-ethyl}-amide | 1.4 | A | 461.0 |
| 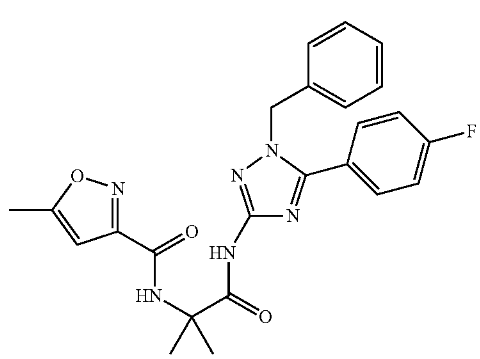 [SMILES: Cc1cc(C(=O)NC(C)(C)C(=O)Nc2nc(-c3ccc(F)cc3)n(Cc3ccccc3)n2)no1] | 14-28 | 5-Methyl-isoxazole-3-carboxylic acid {1-[1-benzyl-5-(4-fluoro-phenyl)-1H-[1,2,4]triazol-3-ylcarbamoyl]-1-methyl-ethyl}-amide | 1.41 | A | 463.0 |

-continued

| Structure | Ex. | Name | LC rt | Meth. | (M + H)+ |
|---|---|---|---|---|---|
| 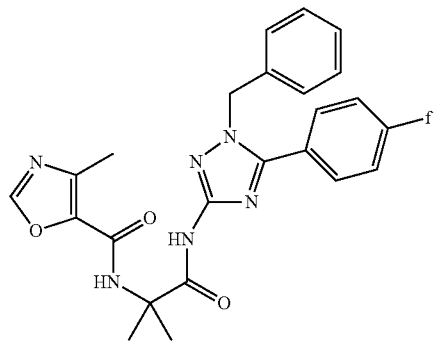 | 14-29 | 4-Methyl-oxazole-5-carboxylic acid {1-[1-benzyl-5-(4-fluoro-phenyl)-1H-[1,2,4]triazol-3-ylcarbamoyl]-1-methyl-ethyl}-amide | 1.32 | A | 463.0 |
| 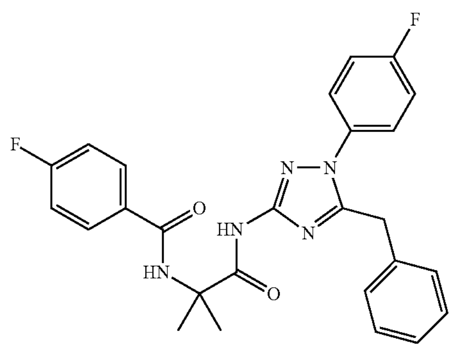 [SMILES: CC(C)(NC(=O)c1ccc(F)cc1)C(=O)Nc1nc(Cc2ccccc2)n(-c2ccc(F)cc2)n1] | 14-30 | N-{1-[5-Benzyl-1-(4-fluoro-phenyl)-1H-[1,2,4]triazol-3-ylcarbamoyl]-1-methyl-ethyl}-4-fluoro-benzamide | 1.44 | A | 476.1 |
| 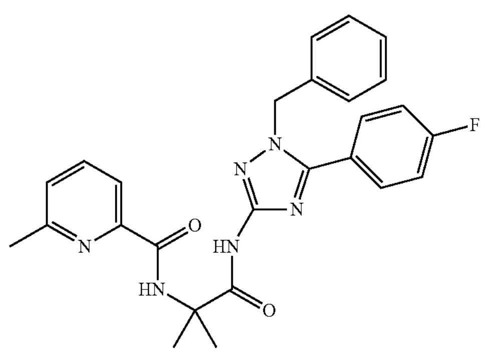 [SMILES: Cc1cccc(C(=O)NC(C)(C)C(=O)Nc2nc(-c3ccc(F)cc3)n(Cc3ccccc3)n2)n1] | 14-31 | 6-Methyl-pyridine-2-carboxylic acid {1-[1-benzyl-5-(4-fluoro-phenyl)-1H-[1,2,4]triazol-3-ylcarbamoyl]-1-methyl-ethyl}-amide | 1.47 | A | 473.3 |
| 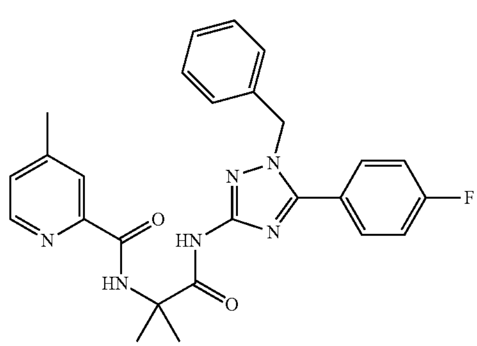 [SMILES: Cc1ccnc(C(=O)NC(C)(C)C(=O)Nc2nc(-c3ccc(F)cc3)n(Cc3ccccc3)n2)c1] | 14-32 | 4-Methyl-pyridine-2-carboxylic acid {1-[1-benzyl-5-(4-fluoro-phenyl)-1H-[1,2,4]triazol-3-ylcarbamoyl]-1-methyl-ethyl}-amide | 1.43 | A | 473.0 |

-continued

| Structure | Ex. | Name | LC rt | Meth. | (M + H)+ |
|---|---|---|---|---|---|
| 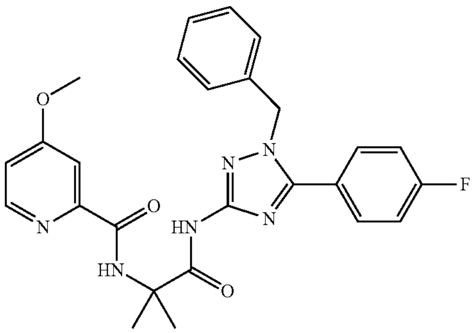 [SMILES: COc1ccnc(C(=O)NC(C)(C)C(=O)Nc2nc(-c3ccc(F)cc3)n(Cc3ccccc3)n2)c1] | 14-33 | 4-Methoxy-pyridine-2-carboxylic acid {1-[1-benzyl-5-(4-fluoro-phenyl)-1H-[1,2,4]triazol-3-ylcarbamoyl]-1-methyl-ethyl}-amide | 1.39 | A | 489.0 |
| 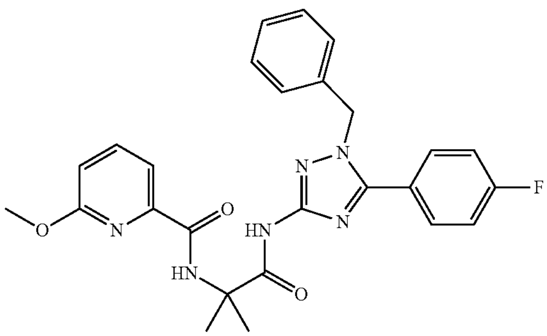 [SMILES: COc1cccc(C(=O)NC(C)(C)C(=O)Nc2nc(-c3ccc(F)cc3)n(Cc3ccccc3)n2)n1] | 14-34 | 6-Methoxy-pyridine-2-carboxylic acid {1-[1-benzyl-5-(4-fluoro-phenyl)-1H-[1,2,4]triazol-3-ylcarbamoyl]-1-methyl-ethyl}-amide | 1.43 | A | 489.2 |
| 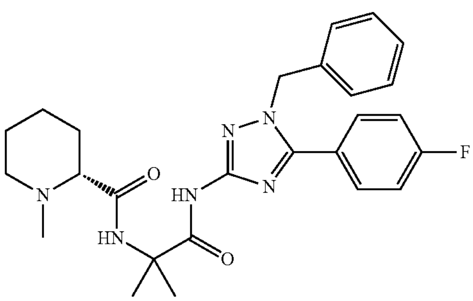 [SMILES: CN1CCCC[C@@H]1C(=O)NC(C)(C)C(=O)Nc1nc(-c2ccc(F)cc2)n(Cc2ccccc2)n1] | 14-35 | (R)-1-Methyl-piperidine-2-carboxylic acid {1-[1-benzyl-5-(4-fluoro-phenyl)-1H-[1,2,4]triazol-3-ylcarbamoyl]-1-methyl-ethyl}-amide | 1.35 | A | 479.2 |
| 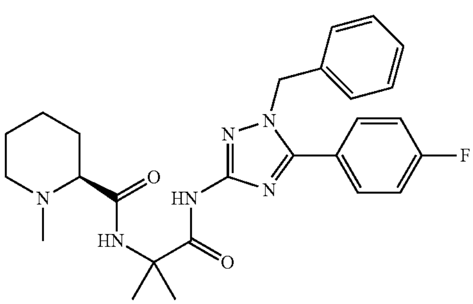 | 14-36 | (S)-1-Methyl-piperidine-2-carboxylic acid {1-[1-benzyl-5-(4-fluoro-phenyl)-1H-[1,2,4]triazol-3-ylcarbamoyl]-1-methyl-ethyl}-amide | 1.35 | A | 479 |
| 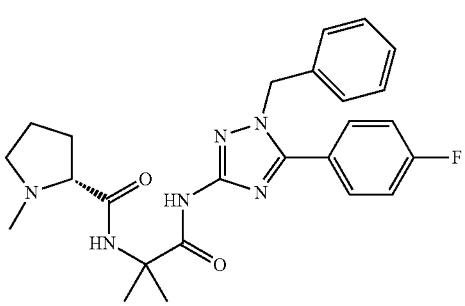 [SMILES: CN1CCC[C@@H]1C(=O)NC(C)(C)C(=O)Nc1nc(-c2ccc(F)cc2)n(Cc2ccccc2)n1] | 14-37 | (R)-1-Methyl-pyrrolidine-2-carboxylic acid {1-[1-benzyl-5-(4-fluoro-phenyl)-1H-[1,2,4]triazol-3-ylcarbamoyl]-1-methyl-ethyl}-amide | 1.3 | A | 465.2 |

-continued

| Structure | Ex. | Name | LC rt | Meth. | (M + H)+ |
|---|---|---|---|---|---|
| 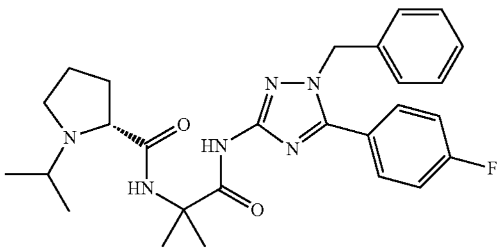 [SMILES: CC(C)N1CCC[C@@H]1C(=O)NC(C)(C)C(=O)Nc1nc(-c2ccc(F)cc2)n(Cc2ccccc2)n1] | 14-38 | (R)-1-Isopropyl-pyrrolidine-2-carboxylic acid {1-[1-benzyl-5-(4-fluoro-phenyl)-1H-[1,2,4]triazol-3-ylcarbamoyl]-1-methyl-ethyl}-amide | 1.26 | A | 493 |
| 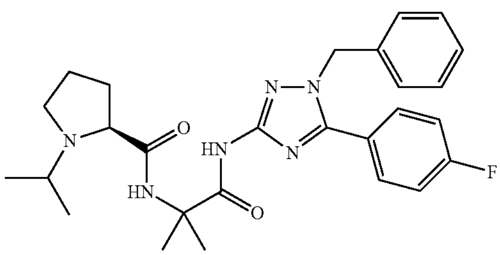 | 14-39 | (S)-1-Isopropyl-pyrrolidine-2-carboxylic acid {1-[1-benzyl-5-(4-fluoro-phenyl)-1H-[1,2,4]triazol-3-ylcarbamoyl]-1-methyl-ethyl}-amide | 1.38 | A | 493 |
| 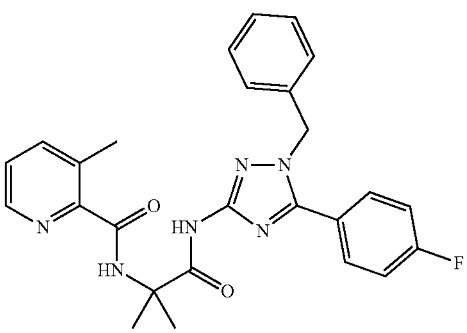 [SMILES: Cc1cccnc1C(=O)NC(C)(C)C(=O)Nc1nc(-c2ccc(F)cc2)n(Cc2ccccc2)n1] | 14-40 | 3-Methyl-pyridine-2-carboxylic acid {1-[1-benzyl-5-(4-fluoro-phenyl)-1H-[1,2,4]triazol-3-ylcarbamoyl]-1-methyl-ethyl}-amide | 1.54 | A | 473.2 |
| 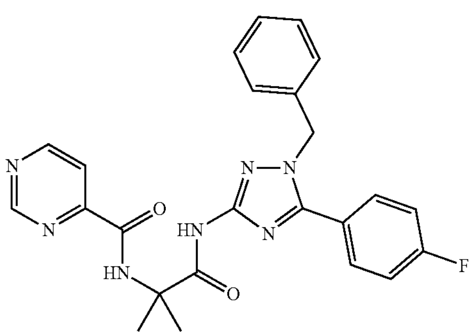 [SMILES: CC(C)(NC(=O)c1ccncn1)C(=O)Nc1nc(-c2ccc(F)cc2)n(Cc2ccccc2)n1] | 14-41 | Pyrimidine-4-carboxylic acid {1-[1-benzyl-5-(4-fluoro-phenyl)-1H-[1,2,4]triazol-3-ylcarbamoyl]-1-methyl-ethyl}-amide | 1.46 | A | 460.2 |
| 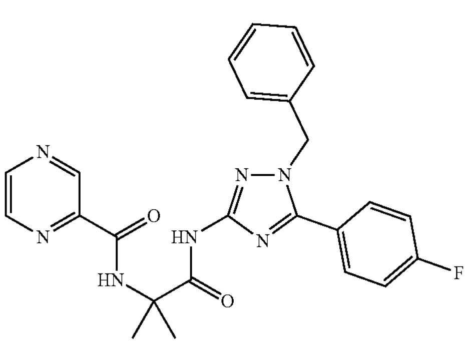 [SMILES: CC(C)(NC(=O)c1cnccn1)C(=O)Nc1nc(-c2ccc(F)cc2)n(Cc2ccccc2)n1] | 14-42 | Pyrazine-2-carboxylic acid {1-[1-benzyl-5-(4-fluoro-phenyl)-1H-[1,2,4]triazol-3-ylcarbamoyl]-1-methyl-ethyl}-amide | 1.46 | A | 460.2 |

-continued

| Structure | Ex. | Name | LC rt | Meth. | (M + H)+ |
|---|---|---|---|---|---|
| 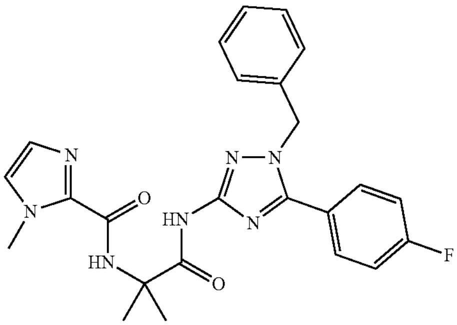 [SMILES: Cn1ccnc1C(=O)NC(C)(C)C(=O)Nc1nc(-c2ccc(F)cc2)n(Cc2ccccc2)n1] | 14-43 | 1-Methyl-1H-imidazole-2-carboxylic acid {1-[1-benzyl-5-(4-fluoro-phenyl)-1H-[1,2,4]triazol-3-ylcarbamoyl]-1-methyl-ethyl}-amide | 1.5 | A | 462.2 |
| 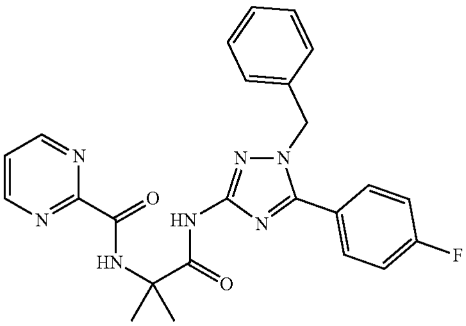 [SMILES: CC(C)(NC(=O)c1ncccn1)C(=O)Nc1nc(-c2ccc(F)cc2)n(Cc2ccccc2)n1] | 14-44 | Pyrimidine-2-carboxylic acid {1-[1-benzyl-5-(4-fluoro-phenyl)-1H-[1,2,4]triazol-3-ylcarbamoyl]-1-methyl-ethyl}-amide | 1.35 | A | 460.2 |
| 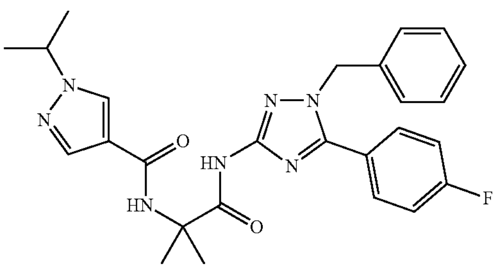 [SMILES: CC(C)n1cc(C(=O)NC(C)(C)C(=O)Nc2nc(-c3ccc(F)cc3)n(Cc3ccccc3)n2)cn1] | 14-45 | 1-Isopropyl-1H-pyrazole-4-carboxylic acid {1-[1-benzyl-5-(4-fluoro-phenyl)-1H-[1,2,4]triazol-3-ylcarbamoyl]-1-methyl-ethyl}-amide | 1.28 | A | 490.4 |

Example 15-1

(R)-3-Phenyl-pyrrolidine-1-carboxylic acid {1-[1-benzyl-5-(4-fluoro-phenyl)-1H-[1,2,4]triazol-3-yl-carbamoyl]-1-methyl-ethyl}-amide

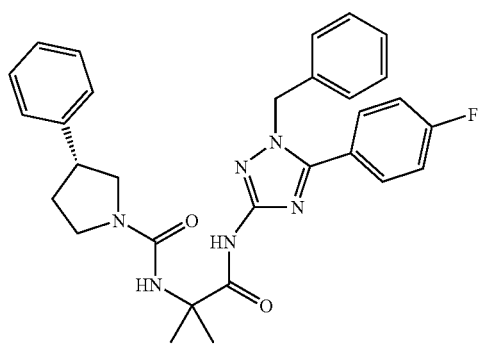 [SMILES: CC(C)(NC(=O)N1CC[C@H](c2ccccc2)C1)C(=O)Nc1nc(-c2ccc(F)cc2)n(Cc2ccccc2)n1]

A. Methyl 2-methyl-2-((4-nitrophenoxy)carbonylamino)propanoate

To a solution of Methyl 2-amino-2-methylpropanoate (5 g, 32 mmol) and N-Methyl morpholine (11 mL, 98 mmol) in DCM (30 mL) was added in one portion 4-nitrophenyl chloroformate (9.8 g, 49 mmol). Diluted reaction with DCM (50 mL) washed with 1N HCl (2×20 mL) and sat. NaHCO3 (2×20 mL), dried organic fraction over magnesium sulfate, filtered and evaporated volatiles in vacuo.

Took up crude solid in DCM and triturated with heptanes to afford the title compound. $^1$H NMR (400 MHz, CHLOROFORM-d) ☐ ppm 1.65 (s, 6H) 3.81 (s, 3H) 5.93 (br. s., 1H) 7.29-7.36 (m, 2H) 8.25 (q, J=5.31 Hz, 1H) 8.25 (d, J=9.22 Hz, 1H).

B. 2-Methyl-2-[((R)-3-phenyl-pyrrolidine-1-carbonyl)-amino]-propionic acid methyl ester Combine 2-methyl-2-(4-nitro-phenoxycarbonylamino)-propionic acid methyl ester (500 mg, 1.77 mmol) and (R)-3-phenyl-pyrrolidine hydrochloride (325 mg, 1.77 mmol) in 1,4-dioxane (5 mL). Add TEA (494 uL, 3.54 mmol) and heat to 130° C. for 5 min by microwave irradiation. Dilute the reaction mixture with DCM (100 mL) and extract with 1 N NaOH (30 mL) followed by 1 N HCl (30 mL). Dry the organic layer over MgSO₄ and concentrate. Purify the concentrate by silica gel chromatography (40-60% EtOAc/HEP) to afford the title compound: $^1$H NMR (400 MHz, DICHLOROMETHANE-$d_2$) 1.51 (d, J=1.77 Hz, 6H) 1.98-2.14 (m, 1H) 2.22-2.38 (m, 1H) 3.31 (t, J=9.28 Hz, 1H) 3.35-3.48 (m, 2H) 3.53-3.65 (m, 1H) 3.70 (s, 3H) 3.80 (dd, J=9.41, 7.52 Hz, 1H) 7.15-7.40 (m, 5H).

C. (R)-3-Phenyl-pyrrolidine-1-carboxylic acid {1-[1-benzyl-5-(4-fluoro-phenyl)-1H-[1,2,4]triazol-3-yl-carbamoyl]-1-methyl-ethyl}-amide THF (3 mL) was added to a flask containing 2-methyl-2-[((R)-3-phenyl-pyrrolidine-1-carbonyl)-amino]-propionic acid methyl ester (100 mg, 0.344 mmol) at 0° C. under N₂. In a dropwise fashion 1 M LiHMDS in THF (344 uL, 0.344 mmol) was added to the flask. Upon complete addition the reaction was allowed to warm to room temp. After 2.5 hr 1-benzyl-5-(4-fluorophenyl)-1H-1,2,4-triazol-3-amine (92 mg, 0.344 mmol) in THF (1 mL) was added to the reaction. The reaction was allowed to stir overnight. The next day more 1 M LiHMDS in THF (172 uL, 0.172 mmol) was added. The reaction was stirred an additional 5.5 hr before being quenched with sat. NH₄Cl (10 mL). The reaction was diluted with EtOAc (60 mL) and extracted with water (5 mL). The organic phase was dried over Na₂SO₄ and the solvent evaporated. The residue was purified by silica gel chromatography (60-100 EtOAc/HEP) followed by HPLC (C18, 50-100% MeOH/H₂O+5 mM NH₄OH) to afford the title compound as a white solid: $^1$H NMR (400 MHz, DICHLOROMETHANE-$d_2$) 1.58 (d, J=3.92 Hz, 6H) 2.01-2.15 (m, 1H) 2.25-2.36 (m, 1H) 3.36 (t, J=9.22 Hz, 1H) 3.40-3.53 (m, 2H) 3.62-3.70 (m, 1H) 3.87 (t, J=8.21 Hz, 1H) 4.74 (br. s., 1H) 5.44 (s, 2H) 7.19-7.36 (m, 9H) 7.36-7.44 (m, 3H) 7.62-7.70 (m, 2H) 10.76 (br. s., 1H); R$_t$ (method A)=1.61 min (M+H)⁺=527.2.

The following compounds were prepared using similar procedures described above.

| Structure | Ex. | Name | LC rt | Method | (M + H)+ |
|---|---|---|---|---|---|
| 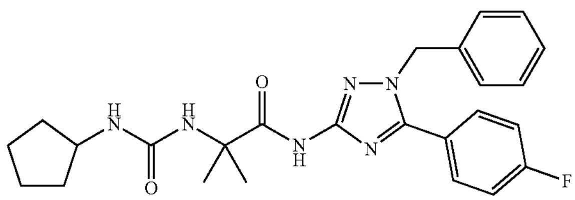 [SMILES: CC(C)(NC(=O)NC1CCCC1)C(=O)Nc1nc(-c2ccc(F)cc2)n(Cc2ccccc2)n1] | 15-2 | N-[1-Benzyl-5-(4-fluoro-phenyl)-1H-[1,2,4]triazol-3-yl]-2-(3-cyclopentyl-ureido)-2-methyl-propionamide | 1.23 | A | 465.0 |
| 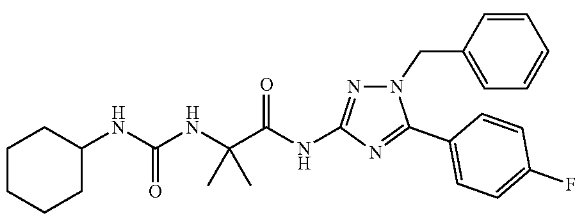 [SMILES: CC(C)(NC(=O)NC1CCCCC1)C(=O)Nc1nc(-c2ccc(F)cc2)n(Cc2ccccc2)n1] | 15-3 | N-[1-Benzyl-5-(4-fluoro-phenyl)-1H-[1,2,4]triazol-3-yl]-2-(3-cyclohexyl-ureido)-2-methyl-propionamide | 1.29 | A | 479.0 |
| 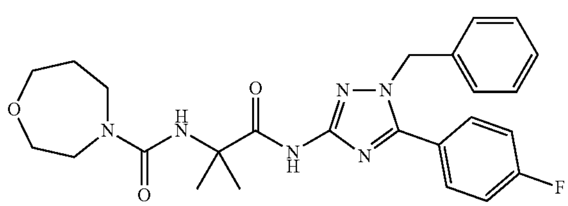 [SMILES: CC(C)(NC(=O)N1CCCOCC1)C(=O)Nc1nc(-c2ccc(F)cc2)n(Cc2ccccc2)n1] | 15-4 | [1,4]Oxazepane-4-carboxylic acid {1-[1-benzyl-5-(4-fluoro-phenyl)-1H-[1,2,4]triazol-3-ylcarbamoyl]-1-methyl-ethyl}-amide | 1.36 | A | 481.2 |
| 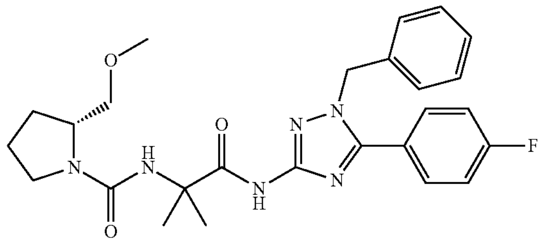 [SMILES: COC[C@H]1CCCN1C(=O)NC(C)(C)C(=O)Nc1nc(-c2ccc(F)cc2)n(Cc2ccccc2)n1] | 15-5 | (R)-2-Methoxymethyl-pyrrolidine-1-carboxylic acid {1-[1-benzyl-5-(4-fluoro-phenyl)-1H-[1,2,4]triazol-3-ylcarbamoyl]-1-methyl-ethyl}-amide | 1.43 | A | 495.1 |

Example 16-1

N-{1-[5-(5-Cyclopropyl-[1,3,4]oxadiazol-2-yl)-4-(4-fluoro-phenyl)-thiazol-2-ylcarbamoyl]-1-methyl-ethyl}-4-fluoro-benzamide

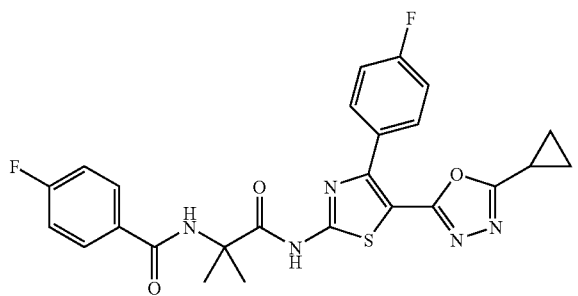 [SMILES: CC(C)(NC(=O)c1ccc(F)cc1)C(=O)Nc1nc(-c2ccc(F)cc2)c(-c2nnc(C3CC3)o2)s1]

A. 2-(2-(4-fluorobenzamido)-2-methylpropanamido)-4-(4-fluorophenyl)thiazole-5-carboxylic acid To a solution of Ethyl-2-(2-(4-fluorobenzamido)-2-methylpropanamido)-4-(4-fluorophenyl)thiazole-5-carboxylate (4.3 g, 9 mmol) in EtOH (25 mL) was added KOH (1 eq) in water (25 mL). The reaction was stirred at 65 C for 15 hours followed by stirring at room temperature over 3 days. It was then acidified with 1 N HCl and the resulting precipitates were collected by filtration and dried to afford the title compound. $^1$H NMR (400 MHz, DMSO-d6) ☐ ppm 1.53 (s, 6H) 7.20 (t, J=8.97 Hz, 2H) 7.32 (t, J=8.84 Hz, 2H) 7.70 (dd, J=8.72, 5.68 Hz, 2H) 8.03 (dd, J=8.72, 5.56 Hz, 2H) 8.64 (s, 1H) 12.43 (s, 1H) 12.94 (br. s., 1H). MS m/z 446 (M+H), 444 (M−1).

B. N-{1-[5-(5-Cyclopropyl-[1,3,4]oxadiazol-2-yl)-4-(4-fluoro-phenyl)-thiazol-2-ylcarbamoyl]-1-methyl-ethyl}-4-fluoro-benzamide To a stirred solution of 2-(2-(4-Fluorobenzamido)-2-methylpropanamido)-4-(4-fluorophenyl)thiazole-5-carboxylic acid (100 mg, 0.224 mmol) and cyclopropanecarbohydrazide (27 mg, 0.27 mmol) were added HATU (128 mg, 0.34 mmol) and TEA (78 uL, 0.56 mmol). Volatiles were removed in vacuo. The residue was taken up in EtOAc and washed with 1N HCl (2×10 mL) followed by sat. NaHCO3 (2×10 mL). Organic layer was dried over magnesium sulfate and filtered. The filtrate was concentrated to dryness to afford a solid. The solid was dissolved in THF (5 mL) and treated with Burgess reagent (68 mg, 0.28 mmol) and heated in microwave at 150° C. for 30 minutes. Purification by silica gel chromatography (30-45% EtOAc/Heptanes) gave the title compound. $^1$H NMR (400 MHz, DMSO-d6) 0.82 (dd, J=4.74, 2.59 Hz, 3H) 1.08 (dd, J=8.34, 2.78 Hz, 3H) 2.19 (s, 1H) 7.33 (t, J=8.91 Hz, 3H) 7.25 (t, J=8.91 Hz, 3H) 7.71 (dd, J=8.84, 5.56 Hz, 3H) 8.03 (dd, J=8.78, 5.62 Hz, 3H) 8.65 (s, 1H) 12.61 (s, 1H). MS m/z 510.4 (M+H), 508.4 (M−1). HRMS cald for C25H18N2O4S=509.1333, found=509.1334. (M+H)+ 510.4, Rt=1.37 min, method A.

Example 17-1

(S)-1-Benzooxazol-2-yl-pyrrolidine-2-carboxylic acid [4-(4-fluoro-phenyl)-5-propyl-thiazol-2-yl]-amide

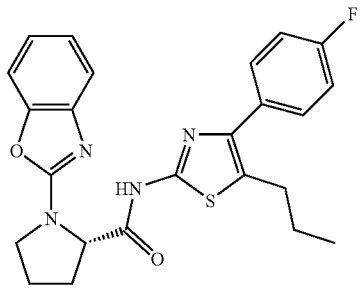 [SMILES: CCCc1sc(NC(=O)[C@@H]2CCCN2c2nc3ccccc3o2)nc1-c1ccc(F)cc1]

A. 4-(4-Fluoro-phenyl)-5-propyl-thiazol-2-ylamine

To 1.525 G of 1-(4-fluoro-phenyl)-butan-1-one and 0.20 mL of acetic acid in 60 mL of chloroform at room temperature was added a solution of 0.455 mL bromine in 10 mL of chloroform in rapid drops. After 2 h the then colorless reaction was washed with saturated NaHCO$_3$, was dried over Na$_2$SO$_4$ and was evaporated. Half of this material was then added to a solution of 0.65 g of thiourea in 30 mL of EtOH and refluxed overnight. After cooling, the solvent was evaporated and the crude material was purified by chromatography (SiO$_2$, MeOH/CH$_2$Cl$_2$) to provide the title compound. m/z 237.2 (MH$^+$).

B. (S)-1-Benzooxazol-2-yl-pyrrolidine-2-carboxylic acid

A mixture of 1.66 G (S)-pyrrolidine-2-carboxylic acid methyl ester, hydrochloride salt and 1.15 mL of 2-chlorobenzoxazole in 6 mL CH$_2$Cl$_2$ was subjected to microwave heating at 120° C. for 0.5 h. Solvent was evaporated. Purification by chromatography (SiO$_2$, EtOAc/heptane) provided 2.283 g (93% yield) of (S)-1-benzooxazol-2-yl-pyrrolidine-2-carboxylic acid, methyl ester as a waxy white solid, m/z 247.16 (MH$^+$). A mixture of 2.0 g of (S)-1-benzooxazol-2-yl-pyrrolidine-2-carboxylic acid, methyl ester and 1.02 G LiOH H$_2$O in 15 mL MeOH and 15 mL water was stirred overnight at room temperature. The reaction was acidified with 1N HCl, was extracted three times with MeOH/CH$_2$Cl$_2$, was dried over Na$_2$SO$_4$ and was evaporated to provide the title compound. m/z 233.17 (MH$^+$).

C. (S)-1-Benzooxazol-2-yl-pyrrolidine-2-carboxylic acid [4-(4-fluoro-phenyl)-5-propyl-thiazol-2-yl]-amide A mixture of 70 mg of (S)-1-benzooxazol-2-yl-pyrrolidine-2-carboxylic acid (intermediate 2), 71 mg of 4-(4-fluoro-phenyl)-5-propyl-thiazol-2-ylamine (intermediate 1), 128 mg of HATU and 0.16 mL of DIEA in CH$_2$Cl$_2$ was stirred at room temperature overnight. Solvent was evaporated and crude material was purified by chromatography (C-18, CH$_3$CN/H$_2$O) to provide the title compound. $^1$H NMR (400

MHz, CHLOROFORM-d) ☐ ppm 0.98 (t, J=7.33 Hz, 3H) 1.62-1.81 (m, 2H) 2.03-2.37 (m, 4H) 2.52-2.68 (m, 1H) 2.82 (t, 2H) 3.76 (q, J=8.84 Hz, 1H) 3.92 (br. s., 1H) 4.88 (br. s., 1H) 7.02-7.14 (m, 3H) 7.22 (t, J=7.71 Hz, 1H) 7.32 (d, J=7.96 Hz, 1H) 7.41-7.58 (m, 3H). MS m/z 451.0 (M+H), 449.1 (M−H). HRMS calcd for $C_{24}H_{23}FN_4O_2S$=450.15257, found=450.15235. HPLC (0-95% ACN in 20 min using 0.1% TFA on 150 mm Atlantis $C_{18}$ column) Rt=15.36.

The following compounds were prepared using similar procedures described above.

| structure | Ex. | Names | LC rt | Method | (M + 1)+ |
|---|---|---|---|---|---|
| 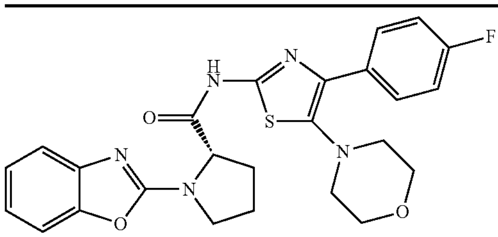 | 17-2 | (S)-1-Benzooxazol-2-yl-pyrrolidine-2-carboxylic acid [4-(4-fluoro-phenyl)-5-morpholin-4-yl-thiazol-2-yl]-amide | 1.45 | A | 494.1 |

Example 18-1

N-[1-Benzyl-5-(4-fuoro-phenyl)-1H-[1,2,4]triazol-3-yl]-2-(3,3-dimethyl-2,5-dioxo-pyrrolidin-1-yl)-isobutyramide

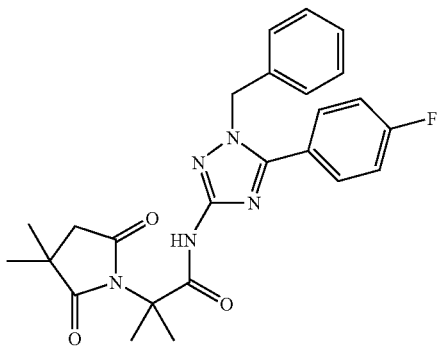 [SMILES: CC1(C)CC(=O)N(C(C)(C)C(=O)Nc2nc(-c3ccc(F)cc3)n(Cc3ccccc3)n2)C1=O]

An open vial charged with 2-amino-N-[1-benzyl-5-(4-fluoro-phenyl)-1H-[1,2,4]triazol-3-yl]-2-methyl-propionamide (100 mg, 0.283 mmol) and 3,3-dimethyl-dihydro-furan-2,5-dione (54 mg, 0.424 mmol) was heated to 185° C. for 40 min. The resulting solid was purified by silica gel chromatography (50-100% EtOAc/HEP) to afford the title compound as a white solid: 1H NMR (400 MHz, DMSO-$d_6$) 1.20 (s, 6H) 1.61 (s, 6H) 5.42 (s, 2H) 7.06-7.18 (m, 2H) 7.24-7.44 (m, 5H) 7.63-7.75 (m, 2H) 10.41 (s, 1H); $R_t$(method A)=1.39 min (M+H)$^+$=464.2.

HPLC Conditions:

A: Inertsil 4.6 mm×5 cm C8-3 column, 10-90% acetonitrile in 5 mM ammonium formate, 2 min gradient, 4 mL/min, 50 degrees centigrade or Inertsil 3 mm×3.3 cm C8-3 column, 10-90% acetonitrile in 5 mM ammonium formate, 2.2 min gradient, 2 mL/min, 40 degrees centigrade.

B: Atlantis C18 (Water Inc.) 15 cm×4.6 mm×5 uM, column temperature-ambient, 150 mm C18 column, 40-95% acetonitrile (with 0.05% TFA) in water (with 0.1% TFA) over 20 min.

C: Atlantis C18 (Water Inc.) 15 cm×4.6 mm×5 uM, column temperature-ambient, 0-95% acetonitrile (with 0.05% TFA) in water (with 0.1% TFA) over 19 min and 1.8 min hold. Flow rate 1.4 mL/min.

Biological Assays

The activity of compounds according to the invention can be assessed by the following inhibition assay.

DGAT1 Inhibition Assay

The enzyme preparation used in this assay is a membrane preparation from Sf9 cells overexpressing human (His)$_6$DGAT1. During all steps samples were chilled to 4° C. Sf9 cells expressing human (His)$_6$DGAT1 were thawed at room temperature and re-suspended at a 10:1 ratio (mL buffer/g of cells) in 50 mM HEPES, 1× Complete Protease Inhibitor, pH 7.5. The re-suspended pellet was homogenized for 1 min using a Brinkman PT 10/35 homogenizer with a 20 mm generator. Cells were lysed using Avestin Emulsiflex (chilled to 4° C.) at 10000-15000 psi. Lysate was centrifuged at 100,000×g for 1 h at 4° C. Supernatant was removed and pellets were re-suspended in 50 mM HEPES, 1× Complete Protease Inhibitor, pH 7.5 at ⅙ the volume of supernatant. Re-suspended pellets were pooled and homogenized with 10 strokes of a Glas-Col motor driven teflon pestle on setting 70. The protein concentration of the membrane preparation was quantified using BCA protein assay with 1% SDS. The membrane preparation was aliquoted, frozen on dry ice, and stored at −80° C.

For 50 mL, 25 mL of 0.2 M HEPES stock buffer, 0.5 mL of 1 M MgCl$_2$ (5 mM final concentration), and 24.5 mL of milli-Q H$_2$O are added to the 55 mL Wheaton Potter-Elvehjem homogenizer. Enzyme preparation (0.1 mL) is added to buffer and the mixture is homogenized with 5 strokes on ice using the Glas-Col variable speed homogenizer system on setting 70.

For 50 mL, 0.5 mL 10 mM diolein is added to 9.5 mL of EtOH in a 50 mL Falcon screw cap conical centrifuge tube. Five mL of 10 mM sodium acetate pH 4.5 is added followed by 0.5 mL of 10 mM oleoyl-CoA. Finally, the remaining 4.5 mL of 10 mM sodium acetate pH 4.5 is added followed by 30 mL of milli-Q H20. The solution should be gently agitated by hand to induce mixing. The final concentrations of EtOH and sodium acetate are 20% and 2 mM, respectively.

Dry compounds are dissolved in the appropriate volume of DMSO to a final concentration of 10 mM. A 10-point, 3-fold dose response is used to evaluate compound potency. All dilutions are performed in DMSO in a Greiner 384-well microplate.

1. 2 µL of compound in DMSO is added to the appropriate wells, 2 µL of DMSO is added to 100% activity and 100% inhibition controls.

2. 25 μL of enzyme mix is added to all wells and plate(s) are incubated for 10 min at RT.
3. 10 μL of 20% acetic acid quench is added to 100% inhibition control wells. Plate(s) are vortexed using Troemner multi-tube vortexer (setting 7 for 10 sec).
4. 25 μL of substrate mix is added to all wells. Plate(s) are vortexed using Troemner multi-tube vortexer (setting 7 for 10 sec). Plate(s) are incubated for 30 min at RT.
5. 10 μL of 20% acetic acid quench is added to all wells. Plate(s) are vortexed using Troemner multi-tube vortexer (setting 7 for 10 sec).
6. 50 μL of 1-butanol w/glyceryl tripalmitoleate internal standard is added to all wells.
7. Plate(s) are sealed with super pierce strong plate sealer using the thermo-sealer.
8. Plate(s) are vortexed using Troemner multi-tube vortexer (setting 10 for 5 min).
9. Plate(s) are centrifuged at 162×g (1000 rpm for GH-3.8 rotor) for 5 min using Beckman GS-6R tabletop centrifuge.

Samples were analyzed by LC/MS/MS using a Waters 1525μ LC and Quattro Micro API MS. Where indicated, tripalmitolein was used as an internal standard to control for instrument variation.

Data is converted to % inhibition prior to curve fitting using the following equation:

$$\% \text{ Inhibition} = \frac{(\text{response compound} - \text{reponse 100\% inhibition control})}{(\text{response 100\% activity control} - \text{response 100\% inhibition control})} \times 100$$

Using the method described above, the compounds of the present invention were shown to possess inhibitory activity with $IC_{50}$ values ranging from 0.001 μM to 100 μM.

Table 1 below shows the inhibitory activity ($IC_{50}$ values) of representative compounds to human DGAT1.

TABLE 1

Activities of compounds of the invention in the DGAT1 assay

| Example | Name | DGAT1 $IC_{50}$ (μM) |
|---|---|---|
| 1-1 | N-[1-(5-Benzyl-4-phenyl-thiazol-2-ylcarbamoyl)-1-methyl-ethyl]-3,4-diethoxy-benzamide | 0.0605333 |
| 1-6 | N-(5-Benzyl-4-phenyl-thiazol-2-yl)-2-(4-fluoro-benzenesulfonylamino)-2-methyl-propionamide | 0.24075 |
| 1-8 | N-[1-(5-Benzyl-4-phenyl-thiazol-2-ylcarbamoyl)-1-methyl-ethyl]-2-methoxy-benzamide | 0.0085 |
| 1-28 | Benzofuran-5-carboxylic acid [1-(5-benzyl-4-phenyl-thiazol-2-ylcarbamoyl)-1-methyl-ethyl]-amide | 0.011 |
| 1-29 | Pyridine-2-carboxylic acid [1-(5-benzyl-4-phenyl-thiazol-2-ylcarbamoyl)-1-methyl-ethyl]-amide | 0.0035 |
| 4-2 | Pyrrolidine-1,2-dicarboxylic acid 2-[(5-benzyl-4-phenyl-thiazol-2-yl)-amide] 1-o-tolylamide | 0.2315 |
| 4-9 | (S)-Pyrrolidine-1,2-dicarboxylic acid 2-[(5-benzyl-4-phenyl-thiazol-2-yl)-amide] 1-[(2-fluoro-4-trifluoromethyl-phenyl)-amide] | 0.473 |

TABLE 1-continued

Activities of compounds of the invention in the DGAT1 assay

| Example | Name | DGAT1 $IC_{50}$ (μM) |
|---|---|---|
| 6-1 | N-{1-[5-(4-Fluoro-phenoxy)-4-(4-fluoro-phenyl)-thiazol-2-ylcarbamoyl]-1-methyl-ethyl}-4-trifluoromethoxybenzamide | 0.91 |
| 6-2 | Morpholine-4-carboxylic acid {1-[5-(4-fluoro-phenoxy)-4-(4-fluoro-phenyl)-thiazol-2-ylcarbamoyl]-1-methyl-ethyl}-amide | 0.0525 |
| 6-9 | N-{1-[5-(4-Fluoro-phenoxy)-4-(4-fluoro-phenyl)-thiazol-2-ylcarbamoyl]-1-methyl-ethyl}-nicotinamide | 0.6225 |
| 6-14 | Thiazole-5-carboxylic acid {1-[5-(4-fluoro-phenoxy)-4-(4-fluoro-phenyl)-thiazol-2-ylcarbamoyl]-1-methyl-ethyl}-amide | 0.197 |
| 8-1 | (S)-1-(2-Cyclopentyl-acetyl)-pyrrolidine-2-carboxylic acid (4-phenyl-quinolin-2-yl)-amide | 0.0545 |
| 8-2 | (S)-2-(6-Phenyl-4-p-tolyl-pyridin-2-ylcarbamoyl)-pyrrolidine-1-carboxylic acid tert-butyl ester | 0.2395 |
| 12-3 | 1-Methyl-cyclopropanecarboxylic acid {1-[5-(4-fluoro-benzoyl)-4-trifluoromethyl-thiazol-2-ylcarbamoyl]-1-methyl-ethyl}-amide | 1.18 |
| 12-4 | [1,4]Oxazepane-4-carboxylic acid {1-[5-(4-fluoro-benzoyl)-4-trifluoromethyl-thiazol-2-ylcarbamoyl]-1-methyl-ethyl}-amide | 2.08 |
| 14-4 | Pyridine-2-carboxylic acid {1-[1-benzyl-5-(4-fluoro-phenyl)-1H-[1,2,4]triazol-3-ylcarbamoyl]-1-methyl-ethyl}-amide | 0.225 |
| 14-3 | (S)-1-Methyl-pyrrolidine-2-carboxylic acid {1-[1-benzyl-5-(4-fluoro-phenyl)-1H-[1,2,4]triazol-3-ylcarbamoyl]-1-methyl-ethyl}-amide | 2.3 |
| 14-24 | Oxazole-5-carboxylic acid {1-[1-benzyl-5-(4-fluoro-phenyl)-1H-[1,2,4]triazol-3-ylcarbamoyl]-1-methyl-ethyl}-amide | 1.75 |
| 14-28 | 5-Methyl-isoxazole-3-carboxylic acid {1-[1-benzyl-5-(4-fluoro-phenyl)-1H-[1,2,4]triazol-3-ylcarbamoyl]-1-methyl-ethyl}-amide | 6.13 |

CONCLUSIONS

It can be seen that the compounds of the invention are useful as inhibitors of DGAT1 and therefore useful in the treatment of diseases and conditions mediated by DGAT1 such as the metabolic disorders disclosed herein.

It will be understood that the invention has been described by way of example only and modifications may be made whilst remaining within the scope and spirit of the invention.

We claim:

1. A compound of formula (I):

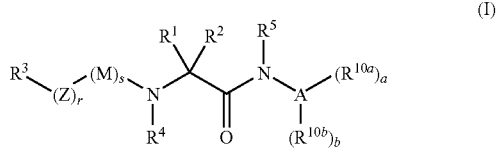

or a pharmaceutically acceptable salt thereof, wherein:

$R^3$ is H or optionally substituted $C_{1-10}$alkyl, $C_{1-10}$heteroalkyl, $-(Alk^b)_g-C_{3-10}$cycloalkyl, $-(Alk^b)_g-C_{3-10}$heterocycloalkyl, $C_{2-10}$alkenyl, $C_{2-10}$heteroalkenyl, -(Alk$^b$)$_g$-C$_{3-10}$cycloalkenyl, -(Alk$^b$)$_g$-C$_{3-10}$heterocycloalkenyl, $C_{2-10}$alkynyl, $C_{2-10}$heteroalkynyl, -(Alk$^b$)$_g$-C$_{6-14}$aryl, and -(Alk$^b$)$_g$-heteroaryl (where heteroaryl contains 5-13 ring members), wherein Alk$^b$ is optionally substituted $C_{1-6}$alkylene or $C_{1-6}$heteroalkylene, g is 0 or 1;

r is 0 or 1;

s is 1;

M is —C(O)

$R^4$ is H;

$R^1$ and $R^2$ are independently optionally substituted $C_{1-6}$alkyl or -(Alk$^c$)$_h$-phenyl, where Alk$^c$ is independently optionally substituted $C_{1-6}$alkylene or $C_{1-6}$heteroalkylene, h is independently 0 or 1;

$R^5$ is H;

A is a substituted triazole;

a is 1;

b is 1;

$R^{10a}$ is -Q-R$^{7a}$ and $R^{10b}$ is —R$^{7b}$, wherein

Q is independently optionally substituted $C_{1-6}$alkylene, $C_{1-6}$heteroalkylene, $C_{2-6}$alkenylene or $C_{2-6}$heteroalkenylene, or O, S, NR$^8$, or —C(O)—, wherein $R^8$ is H or optionally substituted $C_{1-6}$alkyl; and $R^{7a}$ is H or optionally substituted $C_{1-10}$alkyl, $C_{1-10}$heteroalkyl, $C_{3-10}$cycloalkyl, $C_{3-10}$heterocycloalkyl, $C_{6-14}$aryl or heteroaryl containing 5-13 ring members;

$R^{7b}$ is optionally substituted $C_{1-10}$alkyl, $C_{1-10}$heteroalkyl, $C_{3-10}$cycloalkyl, $C_{3-10}$heterocycloalkyl, $C_{6-14}$aryl or heteroaryl containing 5-13 ring members; and provided that at least one of $R^3$ and $R^4$ is not H.

2. The compound of claim 1 wherein

Q is independently $C_{1-6}$alkylene, $C_{1-6}$heteroalkylene, $C_{2-6}$alkenylene, $C_{2-6}$heteroalkenylene, O, S, NR$^8$, or —C(O)—, wherein $R^8$ is H or optionally substituted $C_{1-6}$alkyl; and $R^{7b}$ is optionally substituted $C_{3-10}$cycloalkyl, $C_{3-10}$heterocycloalkyl, $C_{6-14}$aryl or heteroaryl containing 5-13 ring members.

3. The compound according to claim 1, wherein $R^3$ is optionally substituted $C_{1-10}$alkyl, $C_{1-10}$heteroalkyl, -(Alk$^b$)$_g$-C$_{3-10}$cycloalkyl, -(Alk$^b$)$_g$-C$_{3-10}$heterocycloalkyl, $C_{2-10}$alkenyl, $C_{2-10}$heteroalkenyl, -(Alk$^b$)$_g$-C$_{3-10}$cycloalkenyl, -(Alk$^b$)$_g$-C$_{3-10}$heterocycloalkenyl, $C_{2-10}$alkynyl, $C_{2-10}$heteroalkynyl, -(Alk$^b$)$_g$-C$_{6-14}$aryl, and -(Alk$^b$)$_g$-heteroaryl (where heteroaryl contains 5-13 ring members).

4. The compound of claim 3 wherein $R^3$ is optionally substituted $C_{1-10}$alkyl, $C_{1-10}$heteroalkyl, -(Alk$^b$)$_g$-C$_{3-10}$cycloalkyl, -(Alk$^b$)$_g$-C$_{3-10}$heterocycloalkyl, -(Alk$^b$)$_g$-C$_{6-14}$aryl, and -(Alk$^b$)$_g$-heteroaryl (where heteroaryl contains 5, 6, 9 or 10 ring members).

5. The compound of claim 1, wherein $R^1$ and $R^2$ are independently optionally substituted $C_{1-6}$alkyl, or $R^1$ is optionally substituted $C_{1-6}$alkyl and $R^2$ is optionally substituted -(Alk$^c$)$_h$-phenyl.

6. The compound of claim 1, wherein Alk$^c$ is optionally substituted $C_{1-6}$alkylene and h=1.

7. The compound of claim 1, wherein $R^1$ and $R^2$ are both methyl.

8. The compound of claim 1 wherein A is

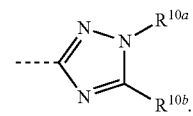

9. The compound of claim 1 wherein A is

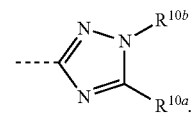

10. A pharmaceutical composition, comprising:

the compound according to claim 1, in combination with a pharmaceutically acceptable excipient.

11. A method for the treatment of a disease or condition mediated by DGAT1, comprising the step of:

administering a therapeutically effective amount of the compound according to claim 1, to a patient in need thereof.

12. The method of claim 11 wherein the disease or condition mediated by DGAT 1 is impaired glucose tolerance, Type II diabetes or obesity.

13. The compound of claim 1, wherein the compound is selected from:

N-{1-[1-Benzyl-5-(4-fluoro-phenyl)-1H-[1,2,4]triazol-3-ylcarbamoyl]-1-methyl-ethyl}-4-fluoro-benzamide;

{1-[1-Benzyl-5-(4-fluoro-phenyl)-1H-[1,2,4]triazol-3-ylcarbamoyl]-1-methyl-ethyl}-carbamic acid benzyl ester;

(S)-1-Methyl-pyrrolidine-2-carboxylic acid {1-[1-benzyl-5-(4-fluoro-phenyl)-1H-[1,2,4]triazol-3-ylcarbamoyl]-1-methyl-ethyl}-amide;

Pyridine-2-carboxylic acid {1-[1-benzyl-5-(4-fluoro-phenyl)-1H-[1,2,4]triazol-3-ylcarbamoyl]-1-methyl-ethyl}-amide;

N-[1-(1-Benzyl-5-phenyl-1H-[1,2,4]-triazol-3-ylcarbamoyl)-1-methyl-ethyl]-4-fluoro-benzamide;

N-{1-[1-(4-Chloro-benzyl)-5-(4-chloro-phenyl)-1H-[1,2,4]triazol-3-ylcarbamoyl]-1-methyl-ethyl}-4-fluoro-benzamide;

N-{1-[5-(4-Chloro-benzyl)-1-phenyl-1H-[1,2,4]triazol-3-ylcarbamoyl]-1-methyl-ethyl}-4-fluoro-benzamide;

N-{1-[1-Benzyl-5-(4-fluoro-phenyl)-1H-[1,2,4]triazol-3-ylcarbamoyl]-1-methyl-ethyl}-4-chloro-benzamide;

N-{1-[1-Benzyl-5-(4-fluoro-phenyl)-1H-[1,2,4]triazol-3-ylcarbamoyl]-1-methyl-ethyl}-4-trifluoromethyl-benzamide;

N-{1-[1-Benzyl-5-(2-fluoro-phenyl)-1H-[1,2,4]triazol-3-ylcarbamoyl]-1-methyl-ethyl}-4-fluoro-benzamide;

N-{1-[1-Benzyl-5-(2-chloro-phenyl)-1H-[1,2,4]triazol-3-ylcarbamoyl]-1-methyl-ethyl}-4-fluoro-benzamide;

2-Benzylamino-N-[1-benzyl-5-(4-fluoro-phenyl)-1H-[1,2,4]triazol-3-yl]-2-methyl-propionamide;

4-Chloro-pyridine-2-carboxylic acid{1-[1-benzyl-5-(4-fluoro-phenyl)-1H-[1,2,4]triazol-3-ylcarbamoyl]-1-methyl-ethyl}-amide;

1-Methyl-cyclopropanecarboxylic acid {1-[1-benzyl-5-(4-fluoro-phenyl)-1H-[1,2,4]triazol-3-ylcarbamoyl]-1-methyl-ethyl}-amide;

N-[1-Benzyl-5-(4-fluoro-phenyl)-1H-[1,2,4]triazol-3-yl]-2-methyl-2-phenylacetylamino-propionamide;

Tetrahydro-pyran-4-carboxylic acid {1-[1-benzyl-5-(4-fluoro-phenyl)-1H-[1,2,4]triazol-3-ylcarbamoyl]-1-methyl-ethyl}-amide;
N-[1-Benzyl-5-(4-fluoro-phenyl)-1H-[1,2,4]triazol-3-yl]-2-(2-cyclopentyl-acetylamino)-2-methyl-propionamide;
2-Methyl-2H-pyrazole-3-carboxylic acid {1-[1-benzyl-5-(4-fluoro-phenyl)-1H-[1,2,4]triazol-3-ylcarbamoyl]-1-methyl-ethyl}-amide;
Oxazole-4-carboxylic acid {1-[1-benzyl-5-(4-fluoro-phenyl)-1H-[1,2,4]triazol-3-ylcarbamoyl]-1-methyl-ethyl}-amide;
Oxazole-5-carboxylic acid {1-[1-benzyl-5-(4-fluoro-phenyl)-1H-[1,2,4]triazol-3-ylcarbamoyl]-1-methyl-ethyl}-amide;
Isoxazole-5-carboxylic acid {1-[1-benzyl-5-(4-fluoro-phenyl)-1H-[1,2,4]triazol-3-ylcarbamoyl]-1-methyl-ethyl}-amide;
1-Methyl-1H-pyrrole-2-carboxylic acid {1-[1-benzyl-5-(4-fluoro-phenyl)-1H-[1,2,4]triazol-3-ylcarbamoyl]-1-methyl-ethyl}-amide;
5-Methyl-isoxazole-3-carboxylic acid {1-[1-benzyl-5-(4-fluoro-phenyl)-1H-[1,2,4]triazol-3-ylcarbamoyl]-1-methyl-ethyl}-amide;
4-Methyl-oxazole-5-carboxylic acid {1-[1-benzyl-5-(4-fluoro-phenyl)-1H-[1,2,4]triazol-3-ylcarbamoyl]-1-methyl-ethyl}-amide;
N-{1-[5-Benzyl-1-(4-fluoro-phenyl)-1H-[1,2,4]triazol-3-ylcarbamoyl]-1-methyl-ethyl}-4-fluoro-benzamide;
6-Methyl-pyridine-2-carboxylic acid {1-[1-benzyl-5-(4-fluoro-phenyl)-1H-[1,2,4]triazol-3-ylcarbamoyl]-1-methyl-ethyl}-amide;
4-Methyl-pyridine-2-carboxylic acid {1-[1-benzyl-5-(4-fluoro-phenyl)-1H-[1,2,4]triazol-3-ylcarbamoyl]-1-methyl-ethyl}-amide;
4-Methoxy-pyridine-2-carboxylic acid {1-[1-benzyl-5-(4-fluoro-phenyl)-1H-[1,2,4]triazol-3-ylcarbamoyl]-1-methyl-ethyl}-amide;
6-Methoxy-pyridine-2-carboxylic acid {1-[1-benzyl-5-(4-fluoro-phenyl)-1H-[1,2,4]triazol-3-ylcarbamoyl]-1-methyl-ethyl}-amide;
(R)-1-Methyl-piperidine-2-carboxylic acid {1-[1-benzyl-5-(4-fluoro-phenyl)-1H-[1,2,4]triazol-3-ylcarbamoyl]-1-methyl-ethyl}-amide;
(S)-1-Methyl-piperidine-2-carboxylic acid {1-[1-benzyl-5-(4-fluoro-phenyl)-1H-[1,2,4]triazol-3-ylcarbamoyl]-1-methyl-ethyl}-amide;
(R)-1-Methyl-pyrrolidine-2-carboxylic acid {1-[1-benzyl-5-(4-fluoro-phenyl)-1H-[1,2,4]triazol-3-ylcarbamoyl]-1-methyl-ethyl}-amide;
(R)-1-Isopropyl-pyrrolidine-2-carboxylic acid {1-[1-benzyl-5-(4-fluoro -phenyl)-1H-[1,2,4]triazol-3-ylcarbamoyl]-1-methyl-ethyl}-amide;
(S)-1-Isopropyl-pyrrolidine-2-carboxylic acid {1-[1-benzyl-5-(4-fluoro-phenyl)-1H-[1,2,4]triazol-3-ylcarbamoyl]-1-methyl-ethyl}-amide;
3-Methyl-pyridine-2-carboxylic acid {1-[1-benzyl-5-(4-fluoro-phenyl)-1H-[1,2,4]triazol-3-ylcarbamoyl]-1-methyl-ethyl}-amide;
Pyrimidine-4-carboxylic acid {1-[1-benzyl-5-(4-fluoro-phenyl)-1H-[1,2,4]triazol-3-ylcarbamoyl]-1-methyl-ethyl}-amide;
Pyrazine-2-carboxylic acid {1-[1-benzyl-5-(4-fluoro-phenyl)-1H-[1,2,4]-triazol-3-ylcarbamoyl]-1-methyl-ethyl}-amide;
1-Methyl-1H-imidazole-2-carboxylic acid {1-[1-benzyl-5-(4-fluoro-phenyl)-1H-[1,2,4]triazol-3-ylcarbamoyl]-1-methyl-ethyl}-amide;
Pyrimidine-2-carboxylic acid {1-[1-benzyl-5-(4-fluoro-phenyl)-1H-[1,2,4]triazol-3-ylcarbamoyl]-1-methyl-ethyl}-amide;
1-Isopropyl-1H-pyrazole-4-carboxylic acid {1-[1-benzyl-5-(4-fluoro-phenyl)-1H-[1,2,4]triazol-3-ylcarbamoyl]-1-methyl-ethyl}-amide;
(R)-3-Phenyl-pyrrolidine-1-carboxylic acid {1-[1-benzyl-5-(4-fluoro-phenyl)-1H-[1,2,4]triazol-3-ylcarbamoyl]-1-methyl-ethyl}-amide;
N-[1-Benzyl-5-(4-fluoro-phenyl)-1H-[1,2,4]triazol-3-yl]-2-(3-cyclopentyl-ureido)-2-methyl-propionamide;
N-[1-Benzyl-5-(4-fluoro-phenyl)-1H-[1,2,4]triazol-3-yl]-2-(3-cyclohexyl-ureido)-2-methyl-propionamide;
[1,4]Oxazepane-4-carboxylic acid {1-[1-benzyl-5-(4-fluoro-phenyl)-1H-[1,2,4]triazol-3-ylcarbamoyl]-1-methyl-ethyl}-amide; and
(R)-2-Methoxymethyl-pyrrolidine-1-carboxylic acid {1-[1-benzyl-5-(4-fluoro-phenyl)-1H-[1,2,4]triazol-3-yl-carbamoyl]-1-methyl-ethyl}-amide, or a pharmaceutically acceptable salt thereof.

14. The compound, Oxazole-5-carboxylic acid {1-[1-benzyl-5-(4-fluoro-phenyl)-1H-[1,2,4]triazol-3-ylcarbamoyl]-1-methyl-ethyl}-amide, or a pharmaceutically acceptable salt thereof.

* * * * *